(12) United States Patent
Yoshida et al.

(10) Patent No.: US 8,470,859 B2
(45) Date of Patent: Jun. 25, 2013

(54) IMINOPYRIDINE DERIVATIVE AND USE THEREOF

(75) Inventors: Masato Yoshida, Osaka (JP); Tomohiko Suzaki, Osaka (JP); Yasuhisa Kohara, Osaka (JP); Haruhiko Kuno, Osaka (JP); Hiroshi Nagabukuro, Fanwood, NJ (US); Reiko Saikawa, Osaka (JP); Yuuichi Okabe, Osaka (JP); Shigemitsu Imai, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 600 days.

(21) Appl. No.: 12/446,960

(22) PCT Filed: Oct. 22, 2007

(86) PCT No.: PCT/JP2007/070581
§ 371 (c)(1),
(2), (4) Date: Jul. 30, 2009

(87) PCT Pub. No.: WO2009/050732
PCT Pub. Date: May 2, 2008

(65) Prior Publication Data
US 2010/0016315 A1 Jan. 21, 2010

(30) Foreign Application Priority Data

Oct. 23, 2006 (JP) .................................. 2006-287957

(51) Int. Cl.
C07D 213/78 (2006.01)
A61K 31/44 (2006.01)

(52) U.S. Cl.
USPC .......................................... 514/352; 546/310

(58) Field of Classification Search
None
See application file for complete search history.

(56) References Cited

U.S. PATENT DOCUMENTS

| | | | |
|---|---|---|---|
| 3,997,666 | A | 12/1976 | Witte et al. |
| 4,699,918 | A | 10/1987 | Maillard et al. |
| 5,250,498 | A | 10/1993 | Andree et al. |
| 5,688,795 | A | 11/1997 | Pfister et al. |
| 6,153,614 | A | 11/2000 | Meyer et al. |
| 6,156,757 | A | 12/2000 | Kennis et al. |
| 6,218,396 | B1 | 4/2001 | Kuo et al. |
| 6,488,922 | B1 | 12/2002 | Damm et al. |
| 7,288,549 | B2 | 10/2007 | Aszodi et al. |
| 2003/0031639 | A1 | 2/2003 | Damm et al. |
| 2004/0053908 | A1 | 3/2004 | Funahashi et al. |
| 2004/0062736 | A1 | 4/2004 | Damm et al. |
| 2005/0014763 | A1 | 1/2005 | Brown et al. |
| 2005/0215590 | A1 | 9/2005 | Brown et al. |
| 2008/0207689 | A1 | 8/2008 | Brown et al. |
| 2009/0005354 | A1 | 1/2009 | Allerton et al. |
| 2009/0023763 | A1 | 1/2009 | Vidal Juan et al. |
| 2009/0105239 | A1 | 4/2009 | Brimert et al. |
| 2009/0270393 | A1 | 10/2009 | Yoshida et al. |
| 2010/0003246 | A1 | 1/2010 | Hunag et al. |
| 2010/0016315 | A1 | 1/2010 | Yoshida et al. |
| 2010/0286135 | A1 | 11/2010 | Reddy et al. |
| 2011/0034464 | A1 | 2/2011 | Yoshida et al. |
| 2011/0039846 | A1 | 2/2011 | Yoshida et al. |
| 2011/0039892 | A1 | 2/2011 | Yoshida et al. |
| 2011/0098298 | A1 | 4/2011 | Vidal Juan et al. |
| 2011/0124874 | A1 | 5/2011 | Yoshida et al. |
| 2011/0124875 | A1 | 5/2011 | Yoshida et al. |
| 2011/0124876 | A1 | 5/2011 | Yoshida et al. |

FOREIGN PATENT DOCUMENTS

| | | |
|---|---|---|
| AR | 071392 | 6/2010 |
| AU | 2009238938 | 4/2009 |
| BD | 101/2009 | 4/2009 |
| BR | PI 0910737-1 | 4/2009 |
| CA | 2723216 | 4/2009 |
| CL | 1366-2004 | 5/2005 |
| CL | 1258-2005 | 6/2005 |
| CL | 839-2005 | 12/2005 |
| CL | 419-2007 | 9/2007 |
| CL | 802-2007 | 12/2007 |
| CL | 2131-2008 | 1/2009 |
| CL | 687-2009 | 3/2010 |
| CL | 964-2009 | 3/2010 |
| CN | 200980123875.8 | 4/2009 |

(Continued)

OTHER PUBLICATIONS

International Search Report, Dec. 2007.
Ruan, Hongmei et al., Effects of Cl⁻-channel blockers on $CA^{2+}$ influx induced α1-adrenoceptor subtypes, Chinese Pharmacological Bulletin, 2001, vol. 17, No. 2, pp. 147-150.
Szell E A et al., Smooth muscle and parasympathetic nerve terminals in the rat urinary bladder have different subtypes of α1 adrenoceptors, British Journal of Pharmacology, 2000, vol. 130, No. 7, pp. 1685-1691.
Pluske, I. et al., Γα, β-Butenolides. XII. Syntheses based on 2,4-pentadienoic acid derivatives, Latvijas PSR Zinatnu Akademijas Vestis, Kimijas Serija, 1986, No. 4, pp. 471-478.

(Continued)

Primary Examiner — Zinna Northington Davis
(74) Attorney, Agent, or Firm — Sughrue Mion, PLLC

(57) ABSTRACT

Provided are an iminopyridine derivative having a selective $\alpha_{1D}$ adrenergic receptor antagonistic action and useful as an agent for the prophylaxis or treatment of a lower urinary tract disease and the like, and a screening method for a compound having an $\alpha_{1D}$ adrenergic receptor antagonistic action. An $\alpha_{1D}$ adrenergic receptor antagonist containing a compound represented by the formula:

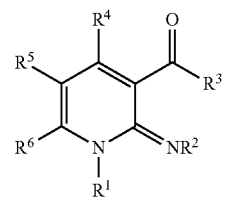

wherein each symbol is as defined in the specification, or a salt thereof, and a method of screening for an agent having an $\alpha_{1D}$ adrenergic receptor antagonistic action for the prophylaxis or treatment of a lower urinary tract disease, which includes measuring the bladder smooth muscle tension of rats with bladder outlet obstruction.

10 Claims, 2 Drawing Sheets

FOREIGN PATENT DOCUMENTS

| | | |
|---|---|---|
| CO | 10.145.079 | 4/2009 |
| CR | 11765 | 4/2009 |
| DE | 106 377 A1 | 6/1973 |
| DE | 263 759 A1 | 4/1986 |
| DO | P2010-0321 | 11/2010 |
| DZ | 100716 | 4/2009 |
| EA | 201071229 | 4/2009 |
| EC | SP-10-10626 | 4/2009 |
| EP | 0 047 977 A2 | 3/1982 |
| EP | 0 432 600 A2 | 6/1991 |
| EP | 0533352 A2 | 3/1993 |
| EP | 0 711 757 A1 | 5/1996 |
| EP | 2771624 | 1/2011 |
| GC | 13335 | 4/2009 |
| GE | AP 2009 012013 | 4/2009 |
| ID | W00201003644 | 4/2009 |
| IL | 208771 | 4/2009 |
| IN | 7546/DELNP/2010 | 4/2009 |
| JO | 146/2009 | 4/2009 |
| JP | 48-40544 B4 | 12/1973 |
| JP | 2002-503724 A | 2/2002 |
| JP | 2008/113135 | 5/2008 |
| JP | 8-208614 A | 8/2008 |
| JP | 2010-541619 | 4/2009 |
| KE | P/2010/001170 | 4/2009 |
| KR | 2010-130235 | 12/2010 |
| LB | 8596 | 8/2010 |
| MA | PV/33353 | 4/2009 |
| MX | MX/a/2010/011652 | 4/2009 |
| MY | PI2010004943 | 4/2009 |
| NG | C/2010/796 | 4/2009 |
| NZ | 588909 | 4/2009 |
| PE | 000559-2009/DIN | 12/2009 |
| PH | 1-2010-502392 | 4/2009 |
| PK | 346/2009 | 4/2009 |
| SG | 165762 | 11/2010 |
| TH | 0901001782 | 4/2009 |
| TN | 2010/0451 | 4/2009 |
| TW | 200948784 | 12/2009 |
| UA | 2010 13899 | 4/2009 |
| UY | 31.781 | 4/2009 |
| VE | 2009-000731 | 4/2009 |
| VN | 1-2010-03138 | 4/2009 |
| WO | 98/09948 A2 | 3/1998 |
| WO | 99/42448 A1 | 8/1999 |
| WO | 00/04012 | 1/2000 |
| WO | 00/04027 A1 | 1/2000 |
| WO | 00/19969 | 4/2000 |
| WO | 01/05765 A1 | 1/2001 |
| WO | 02/32872 A1 | 4/2002 |
| WO | 03/076405 A1 | 9/2003 |
| WO | 2005/026124 A1 | 3/2005 |
| WO | 2005/051301 A2 | 6/2005 |
| WO | 2008050732 A1 | 5/2008 |
| WO | PCT 1750/2010 | 4/2009 |
| WO | 2009/131135 A1 | 10/2009 |
| WO | 2009131196 A1 | 10/2009 |
| WO | 2009131245 A1 | 10/2009 |
| ZA | 2010/07643 | 4/2009 |

OTHER PUBLICATIONS

Pluske, I. et al., Γα, β-Butenolides. X. Reactions of halobutenolides with aliphatic amines, Latvijas PSR Zinatnu Akademijas Vestis, Kimijas Serija, 1985, No. 3, pp. 351-358.

A.-Z. A.-Z. Elassar, "A Facile and Efficient Synthesis of Bisazine Derivatives", Heteroatom Chemistry, vol. 15, No. 4, 2004, pp. 293-299, XP002662182.

Ammar, Y. A., et al., "Cyanoacetanilides Intermediates in Heterocyclic Synthesis. Part 1: A Facile Synthesis of Polysubstituted and Condensed Pyridones", Journal of the Chinese Chemical Society, 2004, 51, 975-981.

Ammar, Y. A., et al., Cyanoacetanilides Intermediates in Heterocyclic Synthesis. Part 2: Preparation of Some Hitherto Unknown Ketene Dithioacetal, Benzoazole and Pyridone Derivatives, Journal of the Chinese Chemical Society, 2005, 52, 553-558.

Ammar, Yousry A., et al., "Novel Pirfenidone Analogues:Synthesis of Pyridin-2-ones for the Treatment of Pulmonary Fibrosis", Arch. Pharm. Chem. Life Sci. 2006, 339, 429-436.

Database CAPLUS [Online] Chemical Abstracts Service, Columbus, 01-110, US; XP002660344, retrieved from STN Database accession No. 1996:694620 ; & A. Arklina et al: Latvijas Kimijas Zurnals, No. 3-4, 1995, pp. 109-113.

Database CAPLUS [Online] Chemical Abstracts Service, Columbus, 01-110, US; XP002660345, retrieved from STN Database accession No. 1986:68726 ; &I. Plukse et al: Latvijas PSR Zinatnu Akademijas Vestis,Kimijas Serija, No. 2, 1985, pp. 200-205.

Database CAPLUS [Online] Chemical Abstracts Service, Columbus, Ohio, US; XP002660249, retrieved from STN Database accession No. 2001:534681; & H. Ruan et al: Zhongguo Yaolixue Tongbao—Chinese Pharmacological Bulletin, Linchuang Yaoli Yanjiusuo, Hefei, CN, vol. 17, No. 2, (2001), pp. 147-150.

Database CAPLUS [Online] Chemical Abstracts Service, Columbus, Ohio, US; XP002660250, retrieved from STN Database accession No. 1986:148695 ; & Plukse I et al: Latvijas Psr Zinatnu Akademijas Vestis, Zinatne, Riga, Lv, No. 3, Jan. 1, 1985, pp. 351-358, XP003022389, ISSN: 0132-6422.

Database CAPLUS [Online] Chemical Abstracts Service, Columbus, Ohio, US; XP002660253, retrieved from STN Database accession No. 1990:118601; R. Bartroli et al: Revista Sobre Los Derivados de la Cana De Azucar, vol. 22, No. 3, 1998, pp. 44-49.

Database CAPLUS [Online] Chemical Abstracts Service, Columbus, Ohio, US; XP002660254, Database accession No. 1987:477578; & I. Plukse et al: Latvijas Psr Zinatnu Akademijas Vestis, Zinatne, Riga, LV, No. 4, Jan. 1, 1986, pp. 471-478, XP003022388, ISSN: 0132-6422.

Database CAPLUS [Online] Chemical Abstracts Service, Columbus, Ohio, US; XP002660343, Database accession No. 1989:57471; & P. Neelakantan et al: Indian Journal of Chemistry, Section B, vol. 26B, No. 11, 1987, pp. 1086-1087.

Database CAPLUS [Online] Chemical Abstracts Service, Columbus, Ohio, US; XP002662170, retrived from STN Database accession No. 1977:601331; & JP 52 083761 A (Yamanouchi Pharma Co Ltd) (1977).

Database CAPLUS [Online] Chemical Abstracts Service, Columbus, Ohio, US; XP002662178 retrieved from STN Database accession No. 1998:420841; & A.I. Osman et al., Indian Journal of Chemistry, Section B, vol. 37B, No. 4, 1998, pp. 399-403.

Database CAPLUS [Online] Chemical Abstracts Service, Columbus, Ohio, US; XP002662179, retrieved from STN Database accession No. 2001:730246 ; & E.I. Al-Afaleq: Synthetic Communications, vol. 31, No. 22, 2001, pp. 3557-3567.

Database CAPLUS [Online] Chemical Abstracts Service, Columbus, Ohio, US; XP002662180, retrieved from STN Database accession No. 2006:924833 ; & M.M. Ismail et al: Medicinal Chemistry Report, vol. 14, No. 7, 2006, pp. 382-403.

El-Rady, Eman A., et al., "2-Cyanoacetamide in the Synthesis of Heterocyclic Compounds: Synthesis of New Polysubstituted Pyrazole, Pyridine and Pyrimidine Derivatives", Journal of the Chinese Chemical Society, 2004, 51, 779-784.

Gewald Von K., et al., "Uber die Reaktion von 6-Aminothiopyranthionen-(2) mit Aminen", Journal f. prakt. Chemie. Band 315, Heft 4. 1978, S. 649-689.

Hehemann David G., et al., "Addition of Diamines to Methylthiopyridones"., J. Heterocyclic Chem., 31, 393 (1994).

Mohareb R.M. et al., Heterocyclic Synthesis with Enamines: Convenient Syntheses of Polyfunctionally Substituted Pyrazole, Pyridine, Pyrimidine and Pyrazolo[3,4-d]pyrimidine Derivatives: Journal of the Chinese Chemical Society, vol. 40, No. 2, 1993, pp. 181-187, XP002662181.

P. Hong et al, Synthesis of 2-OXO- and 2-Imino-1,2-Dihydropyridines by Cobalt-Catalyzed Cyclocotrimerization of acetylenes with isocyanates and carbodimides: Tetrahedron Letters, No. 15, 1977, pp. 1333-1336, XP002662183.

R. Gompper et al, "Cycloaddition to Diethyl 2, 4-Bis(diethylamino)-cyclobutadiene-1,3-dicarboxylate" Angewandte Chemie, International Edition in English, vol. 10, No. 1, 1971, pp. 68-70, XP002662184.

Schirok Hartmut, et al., "Efficient Synthesis of 6-Amino-Substituted Pyridin-2(1H)-ones Using in situ Generated Propiolic Acid Chloride", Synthesis 2005, 18, 99. 3085-3094.
Schirok, Hartmut, et at., "Efficient Regioselective Synthesis of 6-Amino-5-benzoyl-1-Substituted 2(1H)-Phridinones", Journal of Organic Chemistry, 2005, 70, pp. 9463-9469.
Schmitz, E.; et al., "Synthesis of Heterocyclic Compounds by C-C-bond Closure. V. A Novel Pyridone Synthesis", Journal f. prakt. Chemie. Band 324, Heft 1, 1982, S. 82-84.
Wardakhan, Wagnat, et al., "Reaction of Benzoyl Acetonitrile with Acetoace-tanilides: Synthesis of Some Pyrazole, Pyrimidine, Pyrazolo [3,4-b] Pyridine and Pyrido [2,3-d] Pyrimidine Derivatives", Egypt J. Chem. 44, No. 4-6, pp. 315-333 (2001).
Winnik Witold, et al., "Reactions of Polyfunctional Amines with 3-Amino-4-(anilinothio-methylidene)-2-cyano-2-pentenedioic Acid Diethyl Ester", J. Heterocyclic Chem. 32, 477 (1995).
European Search Report issued in Application No. 07830315.3-1521 dated Nov. 24, 2011.
Abstract of GE20084455, (Pfizer, Inc) Mar. 10, 2008 which corresponds to US 2005/215590 and US 2008/207689.
Abstract of GE 2002 2823, (Janssen Pharmaceutica N.V. (BE)) Oct. 25, 2002, which corresponds to US6156757.
Kondakova, M. S. and Gol'dfarb, Ya. L., "Action of alkyl halides on α- and α'-aminonicotines", Doklady Akademii Nauk SSSR (1949) vol. 66, pp. 647-650. Abstract at p. 38 of STN Search Result, AN 1949:38907 ZCAPLUS, STN Search Result, p. 38.
Extended European Search Report dated Nov. 22, 2012, issued in corresponding European Patent Application No. EP12179169.3.
A.K. Das et al., "Effect of Doxazosin on Rat Urinary Bladder Function After Partial Outlet Obstruction" Neurology and Urodynamics, vol. 21, 2002, pp. 160-166, XP002686625.
D.J. Martin, et al. "Comparative Alpha-1 Adrenoceptor Subtype Selectivity and Functional Uroselectivity of Alpha-1 Adrenoceptor Antagonists", Journal of Pharmacology and Experimental Therapeutics, vol. 282, No. 1, 1997, pp. 228-235, XP002686626.
Bartroli et al., "Relation of Furanic push-pull systems with CH acids," Abstract No. XP002660253, Revista Sobre Los Derivados de al Cana de Azucar, (1988). 22(3):44-49.
Gompper et al., "Cycloaddition to Diethyl 2, 4-Bis(diethylamino)-cyclobutadiene-1,3-dicarboxylate," Angewandte Chemie, International Edition in English, vol. 10, No. 1, 1971, pp. 68-70, XP002662184.
Wu et al., "Regulatory Perspectives of Type II prodrug development and time-dependent toxicity management: Nonclinical Pharm/Tox analysis and the role of comparative toxicology." Toxicology, 236, pp. 1-6. 2007.
Hong and Yamazaki, "Synthesis of 2-oxo and 2-imino-1, 2-dihydropyridines by cobalt-catalyzed cyclocotrimerization of acetylenes with isocyanates and carbodiimides," Tetrahedron Letters No. 15, pp. 1333-1336, 1977, XP-002662183.
International Search Report mailed Jul. 16, 2009 for International Application No. PCT/JP2009/058434.
International Search Report mailed Dec. 25, 2007 for International Application No. PCT/JP2007/070581.
International Search Report mailed May 26, 2009 for International Application No. PCT/JP2009/057961.
Goetz et al., "BMY 7378 is a selective antagonist of the D subtype of $a_1$-adrenoceptors." European Journal of Pharmacology, 272, pp .R5-R6 (1995).
Indra et al., "+Domesticine, a novel and selective $a_{1D}$-adrenoceptor antagonist in animal tissues and human a1-adrenoceptors," European Journal of Pharmacology, 445, pp. 21-29, (2002).
Examiner's report dated Oct. 21, 2011 for Chilean Office Action No. 1983-09.
Jones, Letter from foreign Associate dated Dec. 16, 2011 (redacted).
Beheshita et al., "DABCO as an efficient catalyst for the synthesis of 3-Cyano -2 (1H)-pyridinones and their 2-imino analogues," European Journal of Chemistry, 1 (3), pp. 2674-2687 (1997).
Chilean Office Action dated Jul. 12, 2011, issued in corresponding Chilean Patent Application No. 964-2009.
Doklady Akademii Nauk SSSR vol. 66 (1949), 66, pp. 647-650. Abstract at p. 38 of STN Search Result, AN 1949: 38907 ZCAPLUS.
Elworthy et al., "N-Arylpiperazinyl-N-propylamino Derivatives of Heteroaryl Amides as Functional Uroselective $a_1$-Adrenoceptor Antagonists", Journal of Medicinal Chemistry, 1997, pp. 2674-2687, vol. 40, 17.

Abdel-Zaher and Abdel-Aziz Elassar. "A Facile and Efficient Synthesis of Bisazine Derivatives."Heteroatom Chemistry, vol. 15, No. 4 (2004), pp. 293-299.
Latvijas Kimijas Zurnals (1995), Nr. 3-4, pp. 109-113. Abstract at p. 2 of STN Search Result, AN 1996:694620 ZCA, STN Search Result, p. 2.
A. Rampa et al. "Structure-Activity Relationship Studies in the Field of Calcium Antagonists, Xanthone 1,4-dihydropyridines bearing a 2,3-lactone ring."Arzneim-Forsch/Drug Res. 45 (II), Nr. 9 (1995), pp. 957-962.
Mohareb et al., "Heterocyclic Synthesis with Enamines: Convenient Syntheses of Polyfunctionally Substituted Pyrazole, Pyridine, Pyrimidine and Pyrazolo [3,4-d]pyrimidine Derivatives,"Journal of the Chinese Chemical Society (1993), 40, pp. 181-187.
Latvijas PSR Zinatnu Akademijas Vestis, Kimijas Serija (1985), No. 2, pp. 200-205. Abstract at p. 17 of STN Search Result, AN 1986:68726 ZCAPLUS, STN Search Result, p. 17.
Moracci et al., "Covalent Adducts From 1,3-Disubstituted Pyridinium Salts Piperdine."Tetrahedon, vol. 36, pp. 785-789. Pergamon Press Ltd., 1980 (Great Britain).
Moracci et al., "Reactivity of Pseudobases from Pyridinium Salts Competition Between Hydrogen Transfer and Ring-Opening Reactions."Tetrahedon, vol. 35, pp. 2591-2593. Pergamon Press Ltd., 1979 (Great Britain).
Franke et al., "Zur Reaktivitat des Methoxybutenons."Fette, Seifen, Anstrichmittel (1980), 82, Nr. 2, pp. 82-86. Abstract at p. 21 of STN Search Result, AN 1980:495102 ZCAPLUS, STN Search Result, p. 21.
Moracci et al. "Reactivity of 3-Cyano-1-Methylpyridinium Iodide in Aqueous Ammonia or Amine Solutions." Tetrahedon, vol. 35 pp. 809-812. Pergamon Press, 1979 (Great Britain).
Hong et al., "Syntheses of 2-Oxo- and 2-Imino-1,2-dihydropyridines by Cobalt-calalyzed Cyclocotrimerization of Acetylenes with Isocyanates and Carbodiimides." The Institute of Physical and Chemical Research (Japan). Nihon Kagaku Kaishi (1978), No. 5. pp. 730-736, Abstract p. 735-736.
Hong et al., Syntheses of 2-Oxo and 2-Imino-1,2-Dihropyridines by Cohalt-catalyzed Cyclocotrimerization of Acetylenes with Isocyanates and Carbodiimides. Tetrahedon Letters No. 15, pp. 1333-1336 (1977). Pergamon Press (Great Britain).
Liebscher et al., "Zur Chemie aktivierter Vinylhalogenide-Synthese and Reaktionsverhalten von 3-(β-Chlor-vinyl)-acrylnitrilen." Joumal fur Praktische Chemie, Band 318 (1976), No. 5, pp. 705-730. Abstract at p. 24 of STN Search Result, AN 1977:502127, STN Search Result, p. 24.
Liebscher et al., "Zeitschrift fuer Chemie" (1973), 13(9), pp. 342-343. Abstract at p. 33 of STN Search Result, AN 1974:27061, STN Search Result, p. 33.
Blanch et al., "Formation of 2-Methylaminopyridine-3-carbaldehyde and the Corresponding Methylimine by Ring-opening and Ring-closing Reactions of 3-Cyano-1-methlpyridinium Iodide in N-Sodium Hydroxide." J. Chem. Soc. (C) (1971) pp. 1892-1895.
Rudolf Gompper and Gunther Seybold, "Cycloaddition to Diethyl 2,4-Bis(diethylamino)-cyclobutadiene-1,3-dicarboxylate", Angewandte Chemie, International Edition, vol. 10, No. 1 (1971), pp. 68-70.
Ikuo Adachi, "Isoxazoles, XXI. Ring conversion Reactions of 2,3,4-Trisubstituted Isoxazolium Salts with Some Nucleophiles." Chem. Pharm. Bull., vol. 17, No. 11 (1969), pp. 2209-2216.
Eizo Hirai, "The Behavior of 4-Amino-5-carboxy-2-methylpyrimidine in Aqueous Solution." Chem. Pharm. Bull. vol. 14, No. 8, (1966), pp. 861-865.
Mumm, et al., "Pyridone Methide", Abstract, Ann. (1925), 443, pp. 272-309, AN 1925:19212 ZCAPLUS, STN Search Result, p. 38.
Belyakov et al., "Molecular, crystal, and electronic structure of 3-aminocarbonyl-1-phenyl-8-choloro-2-iminopyridone", Abstract, Zhurnal Strukturnoi Khimii (1988), vol. 29, No. 5 (1988), pp. 169-172, AN 1989:67326 ZCAPLUS, STN Search Result, p. 8.
Guendel, Wolf H., "Investigations of Quaternary Pyridinium Salts, X[1] A Condensation Reaction of 3-Cyanopyridinium Salts on Addition of Alcoxides", Abstract, Zeitschrift fuer Naturforschung, Tel B: Anorganische Cheime, Organische Chemie vol. 35B, No. 4, (1980), pp. 490-493, AN 1980:550146 ZCAPLUS, STN Search Result, p. 20.

Sham

BOO

SEQUENCE LISTING

<160> NUMBER OF SEQ ID NOS: 2

<210> SEQ ID NO 1
<211> LENGTH: 45
<212> TYPE: DNA
<213> ORGANISM: Artificial Sequence

```
<220> FEATURE:
<223> OTHER INFORMATION: Synthetic oligonucleotide primer for cloning
      alpha1D adrenaline receptor gene

<400> SEQUENCE: 1
ccgacggccg ctagcgagat gactttccgc gatctcctga gcgtc                    45

<210> SEQ ID NO 2
<211> LENGTH: 38
<212> TYPE: DNA
<213> ORGANISM: Artificial Sequence
<220> FEATURE:
<223> OTHER INFORMATION: Synthetic oligonucleotide primer for cloning
      alpha1D adrenaline receptor gene

<400> SEQUENCE: 2
gctctgggta ccttaaatat cggtctcccg taggttgc                            38
```

IMINOPYRIDINE DERIVATIVE AND USE THEREOF

TECHNICAL FIELD

The present invention relates to an iminopyridine derivative having a superior selective $\alpha_{1D}$ adrenergic receptor (hereinafter to be simply referred to as an $\alpha_{1D}$ receptor) antagonistic action and useful as an agent for the prophylaxis or treatment of a lower urinary tract disease and the like, and a screening method for a compound having an $\alpha_{1D}$ adrenergic receptor antagonistic action.

BACKGROUND OF THE INVENTION $\alpha_1$ adrenergic receptors (hereinafter to be abbreviated as an $\alpha_1$ receptor) are widely distributed in the cardiovascular system, lower urinary tracts and the like, and involved in sympathetic nerve response activities. Since the relationship with pathologies such as hypertension, cardiac hypertrophy and dysuria has been suggested, $\alpha_1$ receptors have attracted attention for some time, and many attempts have been made to develop therapeutic drugs. In recent years, it has been clarified that $\alpha_1$ blockers are effective for dysuria associated with benign prostatic hypertrophy (BPH). Coupled with the marketability thereof, extensive interests have been created again (non-patent document 1).

The $\alpha_1$ receptor gene was cloned from the late 1980s to the early 1990s, and the presence of three subtypes of $\alpha_{1A}$, $\alpha_{1B}$ and $\alpha_{1D}$ has been clarified. Among these, $\alpha_{1D}$ receptor has been confirmed to express in a number of tissues such as blood vessel, brain, spinal cord, gastrointestinal tract, bladder, kidney and the like. While the physiological function of $\alpha_{1D}$ receptor has not been elucidated, $\alpha_{1D}$ receptor antagonists may provide therapeutic drugs for various diseases since they are localized widely.

A greater distribution of $\alpha_{1D}$ receptors in the bladder, parasympathetic nerve nucleus of the sacral cord, and the like as compared to other subtypes has been confirmed (non-patent documents 2, 3), thus suggesting strong involvement in urine storage. In fact, there is a report on a significant increase in the bladder capacity and the single voided volume in $\alpha_{1D}$ knock-out mouse (non-patent document 4). Recent reports have documented that the expression amount of $\alpha_{1D}$ receptor mRNA increases in the bladder of BPH patients and BPH model animal (non-patent documents 5 and 6), the bladder muscle isolated from BPH patients may show a promoted contractile function via $\alpha_{1D}$ receptor (non-patent document 7) and the like, thus suggesting a possible involvement of an $\alpha_{1D}$ receptor expressed in the bladder in the pathology of BPH. From the foregoing, an $\alpha_{1D}$ receptor antagonist is promising as an agent for the prophylaxis or treatment of a lower urinary tract disease and the like.

As examples of the compound showing a selective $\alpha_{1D}$ receptor antagonistic action, non-patent document 8 describes a compound represented by the formula

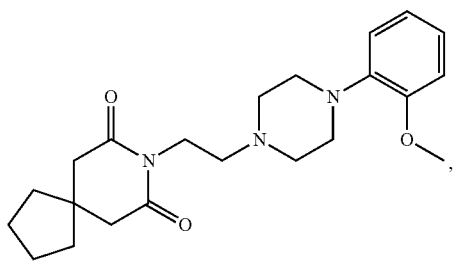 [SMILES: COc1ccccc1N1CCN(CCN2C(=O)CC3(CCCC3)CC2=O)CC1]

patent document 1 describes a compound represented by the formula

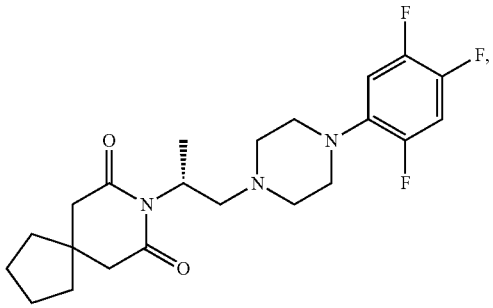 [SMILES: C[C@H](CN1CCN(c2cc(F)c(F)cc2F)CC1)N1C(=O)CC2(CCCC2)CC1=O]

patent document 2 describes a compound represented by the formula

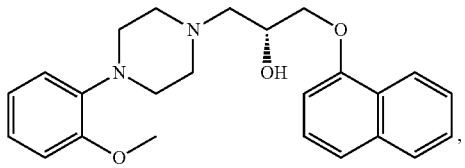 [SMILES: COc1ccccc1N1CCN(C[C@@H](O)COc2cccc3ccccc23)CC1]

patent document 3 describes a compound represented by the formula

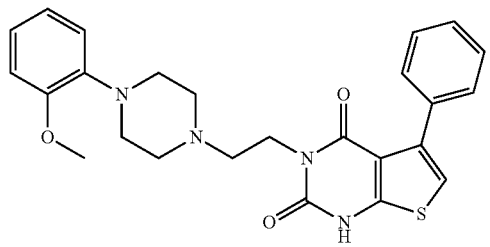 [SMILES: COc1ccccc1N1CCN(CCn2c(=O)[nH]c3scc(-c4ccccc4)c3c2=O)CC1]

and non-patent document 9 describes a compound represented by the formula

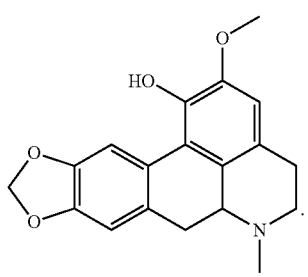 [SMILES: COc1cc2c3c(c1O)-c1cc4c(cc1CC3N(C)CC2)OCO4]

In addition, as iminopyridine derivatives, those described in patent documents 4-7 and non-patent documents 10-32 are known.
patent document 1: WO00/04012
patent document 2: U.S. Pat. No. 3,997,666
patent document 3: WO00/04027
patent document 4: DD 263759
patent document 5: EP47977
patent document 6: DD106377 patent document 7: JP-B-48-40544
non-patent document 1: Yakugaku Zasshi 126, 187-198, 2006
non-patent document 2: Molecular Brain Research 63, 254-261, 1999
non-patent document 3: J. Urol. 160: 937-943., 1998
non-patent document 4: J. Urol. 174: 370-4., 2005
non-patent document 5: J. Urol. 170: 649-653., 2003
non-patent document 6: J. Urol. 167: 1513-1521., 2002
non-patent document 7: J. Urol. 173: 657-61., 2005
non-patent document 8: Eur. J. Pharmacol., 272, (1995), R5-R6
non-patent document 9: Eur. J. Pharmacol., 445, (2002), 21-29
non-patent document 10: Heteroatom Chemistry (2004), 15(4), 293-299
non-patent document 11: Latvijas Kimijas Zurnals (1995), (3-4), 109-113
non-patent document 12: Arzneimittel-Forschung (1995), 45(9), 957-62
non-patent document 13: Journal of the Chinese Chemical Society (Taipei, Taiwan) (1993), 40(2), 181-7
non-patent document 14: Zhurnal Strukturnoi Khimii (1988), 29(5), 169-72
non-patent document 15: Latvijas PSR Zinatnu Akademijas Vestis, Kimijas Serija (1986), (4), 471-8
non-patent document 16: Latvijas PSR Zinatnu Akademijas Vestis, Kimijas Serija (1985), (3), 351-8
non-patent document 17: Latvijas PSR Zinatnu Akademijas Vestis, Kimijas Serija (1985), (2), 200-5
non-patent document 18: Tetrahedron (1980), 36(6), 785-9
non-patent document 19: Zeitschrift fuer Naturforschung, Teil B: Anorganische Chemie, Organische Chemie (1980), 35B(4), 490-3
non-patent document 20: Tetrahedron (1979), 35(21), 2591-3
non-patent document 21: Fette, Seifen, Anstrichmittel (1980), 82(2), 82-6
non-patent document 22: Tetrahedron (1979), 35(6), 809-12
non-patent document 23: Journal of Chemical Society of Japan (1978), (5), 730-6
non-patent document 24: Tetrahedron Letters (1977), (15), 1333-6
non-patent document 25: Journal fuer Praktische Chemie (Leipzig) (1976), 318(5), 705-30
non-patent document 26: Zeitschrift fuer Chemie (1973), 13(9), 342-3
non-patent document 27: Journal of Chemical Society [Section] C: Organic (1971), (10), 1892-5
non-patent document 28: Angewandte Chemie, International Edition in English (1971), 10(1), 68-70
non-patent document 29: Chemical & Pharmaceutical Bulletin (1969), 17(11), 2209-16
non-patent document 30: Chemical & Pharmaceutical Bulletin (1966), 14(8), 861-6
non-patent document 31: Doklady Akademii Nauk SSSR (1949), 66, 647-50
non-patent document 32: Ann. (1925), 443, 272-309

DISCLOSURE OF THE INVENTION

Problems to be Solved by the Invention

The present invention aims to develop a compound useful as an agent for the prophylaxis or treatment of a lower urinary tract disease and the like and a screening method therefor, and provide a means for the prophylaxis or treatment of a lower urinary tract disease using the compound.

Means of Solving the Problems

The present inventors have conducted intensive studies in view of the above-mentioned situation and found that a compound represented by the formula

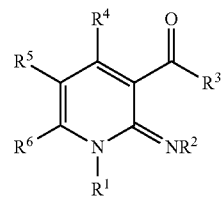

wherein $R^1$ is a hydrogen atom, a hydrocarbon group optionally having substituent(s), an acyl group or a heterocyclic group optionally having substituent(s);

$R^2$ is a hydrogen atom, a hydrocarbon group optionally having substituent(s), an acyl group or a heterocyclic group optionally having substituent(s);

$R^3$ is a hydrogen atom, a hydrocarbon group optionally having substituent(s), a heterocyclic group optionally having substituent(s), an amino group optionally having substituent(s), a hydroxyl group optionally having a substituent or a thiol group optionally having a substituent;

$R^4$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent;

$R^5$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent; and $R^6$ is a hydrogen atom, a halogen atom, a cyano group, a hydrocarbon group optionally having substituent(s), an acyl group or a heterocyclic group optionally having substituent(s), or a salt thereof has an $\alpha_{1D}$ adrenergic receptor antagonistic action based on its specific chemical structure. Based on the finding, they have completed the present invention.

Moreover, the present inventors have found that the bladder smooth muscle of bladder outlet obstruction rat, which is a BPH model animal, has promoted contractile function to $\alpha_1$ receptor stimulation, and the contractile function was mostly based on the functional changes of the $\alpha_{1D}$ receptor, since the contraction was completely inhibited by a pharmaceutical agent that selectively antagonizes the $\alpha_{1D}$ receptor. Based on the finding, they have completed the present invention.

Accordingly, the present invention relates to

[1] an $\alpha_{1D}$ adrenergic receptor antagonist comprising a compound represented by the formula

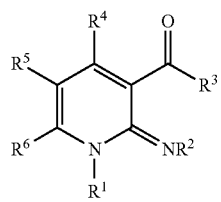

wherein

R¹ is a hydrogen atom, a hydrocarbon group optionally having substituent(s), an acyl group or a heterocyclic group optionally having substituent(s);

R² is a hydrogen atom, a hydrocarbon group optionally having substituent(s), an acyl group or a heterocyclic group optionally having substituent(s);

R³ is a hydrogen atom, a hydrocarbon group optionally having substituent(s), a heterocyclic group optionally having substituent(s), an amino group optionally having substituent(s), a hydroxyl group optionally having a substituent or a thiol group optionally having a substituent;

R⁴ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent;

R⁵ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent; and R⁶ is a hydrogen atom, a halogen atom, a cyano group, a hydrocarbon group optionally having substituent(s), an acyl group or a heterocyclic group optionally having substituent(s), or a salt thereof (hereinafter to be abbreviated as compound (I));

[2] the α$_{1D}$ adrenergic receptor antagonist of [1], which is an agent for the prophylaxis or treatment of a lower urinary tract disease;

[3] a method of preventing or treating a lower urinary tract disease, comprising administering an effective amount of a compound represented by the formula

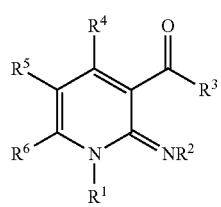

wherein

R¹ is a hydrogen atom, a hydrocarbon group optionally having substituent(s), an acyl group or a heterocyclic group optionally having substituent(s);

R² is a hydrogen atom, a hydrocarbon group optionally having substituent(s), an acyl group or a heterocyclic group optionally having substituent(s);

R³ is a hydrogen atom, a hydrocarbon group optionally having substituent(s), a heterocyclic group optionally having substituent(s), an amino group optionally having substituent(s), a hydroxyl group optionally having a substituent or a thiol group optionally having a substituent;

R⁴ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent;

R⁵ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent; and R⁶ is a hydrogen atom, a halogen atom, a cyano group, a hydrocarbon group optionally having substituent(s), an acyl group or a heterocyclic group optionally having substituent(s), or a salt thereof, to a mammal;

[4] use of a compound represented by the formula

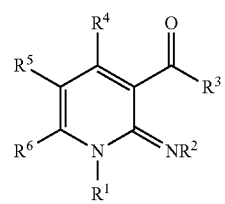

wherein

R¹ is a hydrogen atom, a hydrocarbon group optionally having substituent(s), an acyl group or a heterocyclic group optionally having substituent(s);

R² is a hydrogen atom, a hydrocarbon group optionally having substituent(s), an acyl group or a heterocyclic group optionally having substituent(s);

R³ is a hydrogen atom, a hydrocarbon group optionally having substituent(s), a heterocyclic group optionally having substituent(s), an amino group optionally having substituent(s), a hydroxyl group optionally having a substituent or a thiol group optionally having a substituent;

R⁴ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent;

R⁵ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent; and R⁶ is a hydrogen atom, a halogen atom, a cyano group, a hydrocarbon group optionally having substituent(s), an acyl group or a heterocyclic group optionally having substituent(s), or a salt thereof, for the production of an agent for the prophylaxis or treatment of a lower urinary tract disease;

[5] a compound represented by the formula

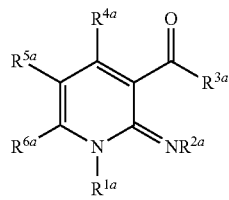

wherein
$R^{1a}$ is a benzyl group optionally having substituent(s);
$R^{2a}$ is a hydrogen atom, a hydrocarbon group optionally having substituent(s), an acyl group or a heterocyclic group optionally having substituent(s);
$R^{3a}$ is a hydrocarbon group optionally having substituent(s), a heterocyclic group optionally having substituent(s), an amino group optionally having substituent(s), a hydroxyl group optionally having a substituent or a thiol group optionally having a substituent;
$R^{4a}$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent;
$R^{5a}$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent; and
$R^{6a}$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent, excluding
5-chloro-1,2-dihydro-2-imino-1-phenylmethyl-3-pyridinecarboxamide,
5-bromo-1,2-dihydro-2-imino-1-phenylmethyl-3-pyridinecarboxamide,
5-aminocarbonyl-3-chloro-1,6-dihydro-6-imino-1-phenylmethyl-2-pyridinecarboxylic acid and
5-aminocarbonyl-3-bromo-1,6-dihydro-6-imino-1-phenylmethyl-2-pyridinecarboxylic acid, or a salt thereof;

[6] the compound of [5], wherein $R^{1a}$ is a benzyl group optionally having 1 to 3 substituents selected from (i) a halogen atom, (ii) a $C_{1-6}$ alkoxy group optionally substituted by halogen atom(s), (iii) a $C_{1-6}$ alkyl group optionally substituted by halogen atom(s), (iv) an aminosulfonyl group, (v) a di-N,N—$C_{1-6}$ alkylaminosulfonyl group, (vi) a sulfonyl group optionally substituted by a $C_{1-3}$ alkyl group, (vii) a cyano group and (viii) an acyl group optionally substituted by substituent(s) selected from an amino group, a hydroxyl group and a $C_{1-3}$ alkyl group;
$R^{2a}$ is a hydrogen atom;
$R^{3a}$ is an amino group;
$R^{4a}$ is a hydrogen atom;
$R^{5a}$ is a halogen atom, a hydrogen atom, methyl group, a cyano group or a methoxy group; and
$R^{6a}$ is a hydrogen atom;

[7] a compound represented by the formula

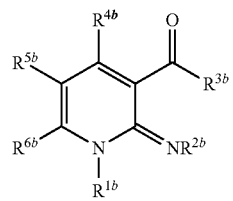

wherein
$R^{1b}$ is $C_{1-6}$ alkyl;
$R^{2b}$ is a hydrogen atom, a hydrocarbon group optionally having substituent(s), an acyl group or a heterocyclic group optionally having substituent(s);
$R^{3b}$ is a hydrocarbon group optionally having substituent(s), a heterocyclic group optionally having substituent(s), an amino group optionally having substituent(s) or a thiol group optionally having a substituent;
$R^{4b}$ is a hydrogen atom, a halogen atom, a cyano group, an acyl group, a heterocyclic group optionally having substituent(s), an amino group optionally having substituent(s), a hydroxyl group optionally having a substituent or a thiol group optionally having a substituent;
$R^{5b}$ is a hydrogen atom, a halogen atom, a cyano group, a hydrocarbon group optionally having substituent(s), an acyl group, an amino group optionally having substituent(s), a hydroxyl group optionally having a substituent or a thiol group optionally having a substituent; and
$R^{6b}$ is a hydrogen atom, a halogen atom, a cyano group, an acyl group, a heterocyclic group optionally having substituent(s), an amino group optionally having substituent(s), a hydroxyl group optionally having a substituent or a thiol group optionally having a substituent, excluding
5-(aminocarbonyl)-3-chloro-1,6-dihydro-6-imino-1-methyl-2-pyridinecarboxylic acid,
5-(aminocarbonyl)-3-bromo-1,6-dihydro-6-imino-1-methyl-2-pyridinecarboxylic acid,
5-(aminocarbonyl)-1-butyl-3-chloro-1,6-dihydro-6-imino-2-pyridinecarboxylic acid,
5-(aminocarbonyl)-3-bromo-1-butyl-1,6-dihydro-6-imino-2-pyridinecarboxylic acid and
5-chloro-1,2-dihydro-2-imino-1-methyl-3-pyridinecarboxamide, or a salt thereof;

[8] a compound represented by the formula

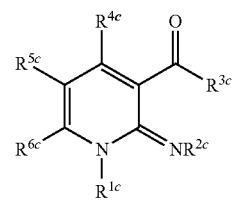

wherein
$R^{1c}$ is a phenyl group optionally having substituent(s);
$R^{2c}$ is a hydrogen atom, a hydrocarbon group optionally having substituent(s), an acyl group or a heterocyclic group optionally having substituent(s);
$R^{3c}$ is a hydrogen atom, a hydrocarbon group optionally having substituent(s), a heterocyclic group optionally having substituent(s), an amino group optionally having substituent(s), a hydroxyl group optionally having a substituent or a thiol group optionally having a substituent;

$R^{4c}$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent;

$R^{5c}$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent; and $R^{6c}$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent, excluding diethyl 1,1'-(1,4-phenylene)bis[2-imino-4,6-dimethyl-5-(phenyldiazenyl)-1,2-dihydropyridine-3-carboxylate], diethyl 1,1'-(1,4-phenylene)bis{5-[(4-chlorophenyl)diazenyl]-2-imino-4,6-dimethyl-1,2-dihydropyridine-3-carboxylate}, 5-(aminocarbonyl)-3-bromo-1,6-dihydro-6-imino-1-phenyl-2-pyridinecarboxylic acid, 5-bromo-1,2-dihydro-2-imino-1-phenyl-3-pyridinecarboxamide, ethyl 5-acetyl-1,2-dihydro-2-imino-4-methyl-1-phenyl-3-pyridinecarboxylate, ethyl 5-acetyl-1,2-dihydro-2-imino-1-phenyl-4-(2-phenylethenyl)-3-pyridinecarboxylate, ethyl 5-acetyl-1,2-dihydro-2-imino-1-phenyl-4-[(phenylhydrazono)methyl]-3-pyridinecarboxylate, 5-chloro-1,2-dihydro-2-imino-1-phenyl-3-pyridinecarboxamide, 5-chloro-1,2-dihydro-2-imino-1-(2-methylphenyl)-3-pyridinecarboxamide, 5-chloro-1,2-dihydro-2-imino-1-(3-methylphenyl)-3-pyridinecarboxamide, 5-chloro-1,2-dihydro-2-imino-1-(4-methylphenyl)-3-pyridinecarboxamide, 5-(aminocarbonyl)-3-chloro-1,6-dihydro-6-imino-1-(2-methylphenyl)-2-pyridinecarboxylic acid, 5-(aminocarbonyl)-3-chloro-1,6-dihydro-6-imino-1-(3-methylphenyl)-2-pyridinecarboxylic acid, 5-(aminocarbonyl)-3-chloro-1,6-dihydro-6-imino-1-(4-methylphenyl)-2-pyridinecarboxylic acid, 5-(aminocarbonyl)-3-chloro-1,6-dihydro-6-imino-1-phenyl-2-pyridinecarboxylic acid, dimethyl 1,2-dihydro-1,4,6-triphenyl-2-(phenylimino)-3,5-pyridinecarboxylate and diethyl 4,6-bis(diethylamino)-1,2-dihydro-1-phenyl-2-(phenylimino)-3,5-pyridinecarboxylate, or a salt thereof;

[9] the compound of [8], wherein $R^{1c}$ is a phenyl group having 1 to 3 substituents selected from (i) a halogen atom, (ii) a $C_{1-6}$ alkoxy group optionally substituted by halogen atom(s), (iii) a $C_{1-6}$ alkyl group substituted by halogen atom(s), (iv) a $C_{3-8}$ cycloalkyl group, (v) a $C_{6-14}$ aryl group, and (vi) a $C_{6-14}$ aryloxy group;

$R^{2c}$ is a hydrogen atom;

$R^{3c}$ is an amino group;

$R^{4c}$ is a hydrogen atom;

$R^{5c}$ is a halogen atom; and $R^{6c}$ is a hydrogen atom;

[10] a compound represented by the formula

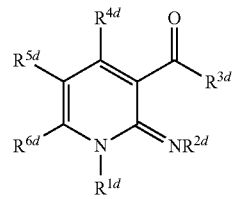

wherein
$R^{1d}$ is
(1) a heterocyclic group optionally having substituent(s),
(2) a cycloalkyl group optionally having substituent(s),
(3) the formula $—CR^{1da}R^{1db}R^{1dc}$ wherein $R^{1da}$ is a hydrogen atom, an alkyl group optionally having substituent(s) or an aryl group optionally having substituent(s); $R^{1db}$ is an alkyl group optionally having substituent(s) or an aryl group optionally having substituent(s); $R^{1dc}$ is an aryl group optionally having substituent(s) or a heterocyclic group optionally having substituent(s),
(4) the formula $—CH_2R^{1dd}$ wherein $R^{1dd}$ is cycloalkyl optionally having substituent(s), a cycloalkenyl group optionally having substituent(s), a naphthyl group optionally having substituent(s), an arylsulfonyl group optionally having substituent(s) or a heterocyclic group optionally having substituent(s),
(5) the formula $—(CH_2)_n—R^{1de}$ wherein n is an integer of 2 to 5, $R^{1de}$ is a cycloalkyl group optionally having substituent(s), a cycloalkenyl group optionally having substituent(s), an aryl group optionally having substituent(s), an acyl group, an amino group optionally having substituent(s), a thiol group optionally having a substituent or a hydroxyl group optionally having a substituent, and $(CH_2)_n$ optionally has substituent(s),
(6) an indenyl group optionally having substituent(s),
(7) a naphthyl group optionally having substituent(s) or
(8) a fluorenyl group optionally having substituent(s);

$R^{2d}$ is a hydrogen atom, a hydrocarbon group optionally having substituent(s), an acyl group or a heterocyclic group optionally having substituent(s);

$R^{3d}$ is a hydrogen atom, a hydrocarbon group optionally having substituent(s), a heterocyclic group optionally having substituent(s), an amino group optionally having substituent(s), a hydroxyl group optionally having a substituent or a thiol group optionally having a substituent;

$R^{4d}$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent;

$R^{5d}$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent; and $R^{6d}$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent, excluding 1,6-dihydro-1-(2-hydroxyethyl)-6-imino-[3,4'-bipyridine]-5-carboxamide, 1,6-dihydro-6-imino-1-(2-methoxyethyl)-[3,4'-bipyridine]-5-carboxamide, 1-[3-(diethylamino)propyl]-1,6-dihydro-6-imino-[3,4'-bipyridine]-5-carboxamide and 7-[[(5-amino-1,2,4-thiadiazol-3-yl)(methoxyimino)acetyl]amino]-3-[(3-carboxy-2-imino-1(2H)-pyridinyl)methyl]-8-oxo-5-thia-1-azabicyclo[4.2.0]oct-2-ene-2-carboxylic acid, or a salt thereof;

[11] the compound of [10], wherein $R^{1d}$ is (1) a 5- to 8-membered aromatic heterocyclic group containing, besides carbon atom, 1 to 4 hetero atoms selected from a nitrogen atom, a sulfur atom and an oxygen atom, which optionally has 1 to 3 substituents selected from a halogen atom and a $C_{6-14}$ aryl group, and is optionally condensed with a benzene ring, (2) a $C_{3-8}$ cycloalkyl group optionally condensed with a benzene ring, (3) the formula —$CR^{1da'}R^{1db'}R^{1dc'}$ wherein $R^{1da'}$ is a hydrogen atom; $R^{1db'}$ is a $C_{1-3}$ alkyl group; $R^{1dc'}$ is an aryl group optionally having 1 to 3 substituents selected from (i) a halogen atom, (ii) a $C_{1-6}$ alkoxy group optionally substituted by halogen atom(s), (iii) a $C_{1-6}$ alkyl group optionally substituted by halogen atom(s), (iv) an aminosulfonyl group, (v) a di-N,N—$C_{1-6}$ alkylaminosulfonyl group, (vi) a sulfonyl group optionally substituted by a $C_{1-3}$ alkyl group, (vii) a cyano group, and (viii) an acyl group, (4) the formula —$CH_2R^{1dd'}$ wherein $R^{1dd'}$ is (1) a cycloalkyl group optionally substituted by a hydroxyl group, or (2) a naphthyl group optionally having 1 to 3 substituents selected from (i) a halogen atom, (ii) a $C_{1-6}$ alkoxy group optionally substituted by halogen atom(s), (iii) a $C_{1-6}$ alkyl group optionally substituted by halogen atom(s), (iv) an aminosulfonyl group, (v) a di-N,N—$C_{1-6}$ alkylaminosulfonyl group, (vi) a sulfonyl group optionally having a $C_{1-3}$ alkyl group, (vii) a cyano group, and (viii) an acyl group, (5) the formula —$(CH_2)_n$—$R^{1de'}$ wherein n is an integer of 2 to 5, $R^{1de'}$ is 1) a cycloalkyl group optionally substituted by hydroxyl group(s), 2) a cycloalkenyl group optionally substituted by hydroxyl group(s), 3) an aryl group optionally having 1 to 3 substituents selected from (i) a halogen atom, (ii) a $C_{1-6}$ alkoxy group optionally substituted by halogen atom(s), (iii) a $C_{1-6}$ alkyl group optionally substituted by halogen atom(s), (iv) an aminosulfonyl group, (v) a di-N,N—$C_{1-6}$ alkylaminosulfonyl group, (vi) a sulfonyl group optionally substituted by a $C_{1-3}$ alkyl group, (vii) a cyano group, and (viii) an acyl group, 4) an aryloxy group optionally having 1 to 3 substituents selected from (i) a halogen atom, (ii) a $C_{1-6}$ alkoxy group optionally substituted by halogen atom(s), (iii) a $C_{1-6}$ alkyl group optionally substituted by halogen atom(s), (iv) an aminosulfonyl group, (v) a di-N,N—$C_{1-6}$ alkylaminosulfonyl group, (vi) a sulfonyl group optionally substituted by a $C_{1-3}$ alkyl group, (vii) a cyano group, and (viii) an acyl group, or 5) a thiol group optionally substituted by an aryl group optionally having 1 to 3 substituents selected from (i) a halogen atom, (ii) a $C_{1-6}$ alkoxy group optionally substituted by halogen atom(s), (iii) a $C_{1-6}$ alkyl group optionally substituted by halogen atom(s), (iv) an aminosulfonyl group, (v) a di-N,N—$C_{1-6}$ alkylaminosulfonyl group, (vi) a sulfonyl group optionally substituted by a $C_{1-3}$ alkyl group, (vii) a cyano group, and (viii) an acyl group, and $(CH_2)_n$ optionally has a $C_{1-3}$ alkyl group.), (6) an indenyl group optionally having substituent(s) selected from a halogen atom, a cyano group, a methylsulfonyl group and an acyl group, (7) a naphthyl group optionally having substituent(s) selected from a halogen atom, a cyano group, a methylsulfonyl group and an acyl group, or (8) a fluorenyl group optionally having substituent(s) selected from a halogen atom, a cyano group, a methylsulfonyl group and an acyl group;

$R^{2d}$ is a hydrogen atom;

$R^{3d}$ is an amino group;

$R^{4d}$ is a hydrogen atom;

$R^{5d}$ is a halogen atom, a hydrogen atom, a methyl group, a cyano group or a methoxy group; and $R^{6d}$ is a hydrogen atom;

[12] a compound selected from the group consisting of
5-chloro-1-(3-chlorobenzyl)-2-imino-1,2-dihydropyridine-3-carboxamide,
5-chloro-1-(3,4-dichlorobenzyl)-2-imino-1,2-dihydropyridine-3-carboxamide,
5-chloro-1-[(5-chloro-2-thienyl)methyl]-2-imino-1,2-dihydropyridine-3-carboxamide,
5-chloro-2-imino-1-(1-naphthyl)-1,2-dihydropyridine-3-carboxamide,
5-chloro-1-[(1R)-2,3-dihydro-1H-inden-1-yl]-2-imino-1,2-dihydropyridine-3-carboxamide,
5-chloro-2-imino-1-[(1R)-1-phenylethyl]-1,2-dihydropyridine-3-carboxamide,
5-chloro-1-[4-chloro-2-(methylsulfonyl)benzyl]-2-imino-1,2-dihydropyridine-3-carboxamide,
1-(3-chlorobenzyl)-5-cyano-2-imino-1,2-dihydropyridine-3-carboxamide,
5-chloro-1-(3-chloro-5-cyanobenzyl)-2-imino-1,2-dihydropyridine-3-carboxamide,
5-chloro-1-(5-cyano-2-fluorobenzyl)-2-imino-1,2-dihydropyridine-3-carboxamide,
5-chloro-1-(3-cyano-5-fluorobenzyl)-2-imino-1,2-dihydropyridine-3-carboxamide,
5-chloro-2-imino-1-(2,4,5-trifluorobenzyl)-1,2-dihydropyridine-3-carboxamide,
5-chloro-2-imino-1-[3-(methylsulfonyl)benzyl]-1,2-dihydropyridine-3-carboxamide and
5-chloro-1-(3-cyanobenzyl)-2-imino-1,2-dihydropyridine-3-carboxamide, or a salt thereof;

[13] a pharmaceutical agent comprising a compound of any of [5] to [12] or a salt thereof; and the like.

The present invention also relates to

[14] a screening method for an agent having an $\alpha_{1D}$ adrenergic receptor antagonistic action for the prophylaxis or treatment of a lower urinary tract disease, which comprises measuring the tension of the bladder smooth muscle of rats with bladder outlet obstruction;

[15] the screening method of [14], comprising adding a drug having an $\alpha_1$ adrenergic receptor agonistic activity to induce or enhance rhythmic contractile responses of the bladder smooth muscle of the rats with bladder outlet obstruction, administering, at predetermined time intervals, an agent having an $\alpha_{1D}$ adrenergic receptor antagonistic action for the prophylaxis or treatment of a lower urinary tract disease, measuring changes in the contraction tension in a given predetermined time for each administration, and evaluating an inhibitory effect of the agent on the rhythmic contractile responses in the bladder smooth muscle based on the inconsistency in the level of changes in the obtained contraction tension;

[16] the screening method of [15], comprising defining the time from the addition of the drug having an $\alpha_1$ adrenergic receptor agonistic activity to the start of the measurement of the changes in the contraction tension, or limiting the administration frequency of the agent having an $\alpha_{1D}$ adrenergic receptor antagonistic action for the prophylaxis or treatment of a lower urinary tract disease, so as to remove a contraction component irrelevant to the $\alpha_{1D}$ adrenergic receptor, which increases with the lapse of time after the addition of the drug; and the like.

Effect of the Invention

The compound (I) of the present invention has a superior selective $\alpha_{1D}$ receptor antagonistic action, and is useful as an agent for the prophylaxis or treatment of a lower urinary tract disease and the like. According to the screening method of the present invention, an agent for the prophylaxis or treatment of a lower urinary tract disease and the like antagonizing an $\alpha_{1D}$ adrenergic receptor, can be rapidly and conveniently screened for.

Figure 1:
FIG. 1 is a drawing showing phenylephrine-induced contraction of the bladder muscles isolated from pseudo-operation (Sham) and BOO model rats.

The present invention is explained in detail in the following.

In the present specification, as the "hydrocarbon group optionally having substituent(s)", an alkyl group optionally having substituent(s), an alkenyl group optionally having substituent(s), an alkynyl group optionally having substituent(s), an aralkyl group optionally having substituent(s), an aryl group optionally having substituent(s), a cycloalkyl group optionally having substituent(s), a cycloalkenyl group optionally having substituent(s) and the like can be mentioned.

In the present specification, as the "alkyl group optionally having substituent(s)", a $C_{1-6}$ alkyl group (e.g., methyl, ethyl, propyl, isopropyl, butyl, isobutyl, sec-butyl, tert-butyl, pentyl, neopentyl, hexyl etc.) optionally having substituent(s) selected from
(i) a halogen atom (e.g., fluorine atom, chlorine atom, bromine atom, iodine atom),
(ii) a cyano group,
(iii) a hydroxyl group,
(iv) a nitro group,
(v) a formyl group,
(vi) an amino group,
(vii) a mono- or di-$C_{1-6}$ alkylamino group (e.g., methylamino, ethylamino, propylamino, dimethylamino, diethylamino, dipropylamino etc.),
(viii) a $C_{1-6}$ alkyl-carbonylamino group (e.g., acetylamino, ethylcarbonylamino etc.),
(ix) a $C_{1-6}$ alkoxy-carbonylamino group (e.g., methoxycarbonylamino, ethoxycarbonylamino, propoxycarbonylamino etc.),
(x) a $C_{3-8}$ cycloalkyl group (e.g., cyclopropyl, cyclobutyl, cyclopentyl, cyclohexyl etc.) optionally condensed with a benzene ring,
(xi) a $C_{3-8}$ cycloalkenyl group (e.g., cyclopropenyl, cyclobutenyl, cyclopentenyl, cyclohexenyl etc.) optionally condensed with a benzene ring,
(xii) a $C_{6-14}$ aryl group (e.g., phenyl, 1-naphthyl, 2-naphthyl etc.) optionally substituted by substituent(s) selected from a halogen atom (e.g., fluorine atom, chlorine atom, bromine atom, iodine atom) and a $C_{1-6}$ alkoxy group (e.g., methoxy, ethoxy, propoxy etc.),
(xiii) a $C_{1-6}$ alkoxy group (e.g., methoxy, ethoxy, propoxy, isopropoxy, butoxy, isobutoxy, sec-butoxy, tert-butoxy etc.) optionally substituted by a halogen atom (e.g., fluorine atom, chlorine atom, bromine atom, iodine atom),
(xiv) a $C_{7-16}$ aralkyloxy group (e.g., benzyloxy etc.),
(xv) a $C_{6-14}$ aryloxy group (e.g., phenoxy etc.) optionally substituted by substituent(s) selected from a $C_{1-6}$ alkoxy group (e.g., methoxy etc.), a $C_{1-6}$ alkyl group (e.g., methyl etc.) and a halogen atom (e.g., fluorine atom, chlorine atom, bromine atom, iodine atom),
(xvi) a carboxyl group,
(xvii) a $C_{1-6}$ alkoxy-carbonyl group (e.g., methoxycarbonyl, ethoxycarbonyl, propoxycarbonyl, isopropoxycarbonyl, tert-butoxycarbonyl etc.),
(xviii) a $C_{7-16}$ aralkyloxy-carbonyl group (e.g., benzyloxycarbonyl etc.),
(xix) a $C_{6-14}$ aryloxy-carbonyl group (e.g., phenoxycarbonyl etc.),
(xx) a $C_{1-6}$ alkyl-carbonyl group (e.g., acetyl, ethylcarbonyl, propylcarbonyl, isopropylcarbonyl, 2,2-dimethylpropylcarbonyl etc.),
(xxi) a $C_{3-8}$ cycloalkyl-carbonyl group (e.g., cyclopropylcarbonyl, cyclobutylcarbonyl, cyclopentylcarbonyl, cyclohexylcarbonyl etc.),
(xxii) a $C_{7-16}$ aralkyl-carbonyl group (e.g., benzylcarbonyl etc.),
(xxiii) a carbamoyl group,
(xxiv) a thiocarbamoyl group,
(xxv) a mono- or di-$C_{1-6}$ alkyl-carbamoyl group (e.g., methylcarbamoyl, ethylcarbamoyl, propylcarbamoyl, isopropylcarbamoyl, dimethylcarbamoyl, diethylcarbamoyl, dipropylcarbamoyl etc.),
(xxvi) a mono- or di-$C_{7-16}$ aralkyl-carbamoyl group (e.g., benzylcarbamoyl, dibenzylcarbamoyl etc.),
(xxvii) a thiol group,
(xxviii) a $C_{1-6}$ alkylthio group (e.g., methylthio, ethylthio, propylthio etc.),
(xxix) a $C_{7-16}$ aralkylthio group (e.g., benzylthio etc.),
(xxx) a $C_{1-6}$ alkylsulfonyl group (e.g., methylsulfonyl, ethylsulfonyl, propylsulfonyl, isopropylsulfonyl etc.),
(xxxi) a $C_{3-8}$ cycloalkylsulfonyl group (e.g., cyclopropylsulfonyl, cyclobutylsulfonyl, cyclopentylsulfonyl etc.),
(xxxii) a $C_{6-14}$ arylsulfonyl group (e.g., phenylsulfonyl, 1-naphthylsulfonyl, 2-naphthylsulfonyl etc.),
(xxxiii) a $C_{7-16}$ aralkylsulfonyl group (e.g., benzylsulfonyl etc.),
(xxxiv) a 5- to 8-membered nonaromatic heterocyclic group (e.g., pyrrolidinyl, tetrahydrofuryl, tetrahydrothienyl, piperidyl, tetrahydropyranyl, morpholinyl, thiomorpholinyl, piperazinyl etc.) containing, besides carbon atom, 1 to 4 hetero atoms selected from a nitrogen atom, a sulfur atom and an oxygen atom, wherein the nonaromatic heterocyclic group is optionally substituted by a $C_{1-6}$ alkyl group (e.g., methyl etc.), (xxxv) a 5- to 8-membered aromatic heterocyclic group containing, besides carbon atom, 1 to 4 hetero atoms selected from a nitrogen atom, a sulfur atom and an oxygen atom (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl etc.), wherein the aromatic heterocyclic group is optionally substituted by halogen atom(s) (e.g., chlorine atom etc.) or a $C_{1-6}$ alkyl group (e.g., methyl etc.), and optionally condensed with a benzene ring (e.g., benzothienyl etc.), (xxxvi) a 5- to 8-membered non-aromatic heterocyclyl-carbonyl group (e.g., pyrrolidinylcarbonyl, tetrahydrofurylcarbonyl, tetrahydrothienylcarbonyl, piperidylcarbonyl, tetrahydropyranylcarbonyl, morpholinylcarbonyl, thiomorpholinylcarbonyl, piperazinylcarbonyl etc.) containing, besides carbon atom, 1 to 4 hetero atoms selected from a nitrogen atom, a sulfur atom and an oxygen atom, (xxxvii) a 5- to 8-membered aromatic heterocyclyl-carbonyl group (e.g., furylcarbonyl, thienylcarbonyl, pyrrolylcarbonyl, oxazolylcarbonyl, isooxazolylcarbonyl, thiazolylcarbonyl, isothiazolylcarbonyl, imidazolylcarbonyl, pyrazolylcarbonyl, 1,2,3-oxadiazolylcarbonyl, 1,2,4-oxadiazolylcarbonyl, 1,3,4-oxadiazolylcarbonyl, furazanylcarbonyl, 1,2,3-thiadiazolylcarbonyl, 1,2,4-thiadiazolylcarbonyl, 1,3,4-thiadiazolylcarbonyl, 1,2,3-triazolylcarbonyl, 1,2,4-triazolycarbonyl, tetrazolylcarbonyl, pyridylcarbonyl, pyridazinylcarbonyl, pyrimidinylcarbonyl, pyrazinylcarbonyl, triazinylcarbonyl etc.) containing, besides carbon atom, 1 to 4 hetero atoms selected from a nitrogen atom, a sulfur atom and an oxygen atom,
(xxxviii) a ureido group,
(xxxix) a $C_{1-6}$ alkyl-ureido group (e.g., methylureido, ethylureido, propylureido etc.),
(xxxx) a $C_{6-14}$ aryl-ureido group (e.g., phenylureido, 1-naphthylureido, 2-naphthylureido etc.),
(xxxxi) a $C_{1-4}$ alkylenedioxy group (e.g., methylenedioxy, ethylenedioxy, propylenedioxy etc.)
(xxxxii) an aminosulfonyl group,
(xxxxiii) a mono-N—$C_{1-6}$ alkylaminosulfonyl group (e.g., methylaminosulfonyl, ethylaminosulfonyl etc.),
(xxxxiv) a di-N,N—$C_{1-6}$ alkylaminosulfonyl group (e.g., dimethylaminosulfonyl, diethylaminosulfonyl etc.),
(xxxxv) bridged $C_{7-10}$ cycloalkyl group (e.g., bicyclo[3.1.1]heptyl, adamantyl etc.) optionally substituted by $C_{1-6}$ alkyl group(s) (e.g., methyl etc.),
(xxxxvi) a $C_{6-14}$ arylthio group (e.g., phenylthio etc.) and the like can be mentioned, wherein the number of the substituents is 1 to 4, preferably 1 to 3.

In the present specification, as the "alkenyl group optionally having substituent(s)", a $C_{2-6}$ alkenyl group (e.g., vinyl, 1-propenyl, allyl, isopropenyl, butenyl, isobutenyl etc.) optionally having 1 to 4, preferably 1 to 3, substituents that the alkyl group of the above-mentioned "alkyl group optionally having substituent(s)" may have and the like can be mentioned.

In the present specification, as the "alkynyl group optionally having substituent(s)", a $C_{2-6}$ alkynyl group (e.g., ethynyl, propargyl, butynyl, 1-hexynyl etc.) optionally having 1 to 4, preferably 1 to 3, substituents that the alkyl group of the above-mentioned "alkyl group optionally having substituent(s)" may have and the like can be mentioned.

In the present specification, as the "aralkyl group optionally having substituent(s)", a $C_{7-12}$ aralkyl group (e.g., benzyl, 2-phenylethyl, 1-phenylethyl, 3-phenylpropyl etc.) optionally having 1 to 4, preferably 1 to 3, from (i) the substituent that the alkyl group of the above-mentioned "alkyl group optionally having substituent(s)" may have,
(ii) a $C_{1-6}$ alkyl group (e.g., methyl, ethyl, propyl, isopropyl, butyl, isobutyl, sec-butyl, tert-butyl, pentyl, neopentyl, hexyl etc.) optionally substituted by substituent(s) selected from a halogen atom (e.g., fluorine atom, chlorine atom, bromine atom, iodine atom), a $C_{1-6}$ alkoxy group (e.g., methoxy, ethoxy, propoxy etc.), a $C_{6-14}$ arylsulfonyl group and a heterocyclic group (e.g., morpholinyl, pyridyl, imidazopyridyl, benzimidazolyl etc.),
(iii) a $C_{7-16}$ aralkyl group (e.g., benzyl, 2-phenylethyl, 1-phenylethyl, 3-phenylpropyl, 4-phenylbutyl etc.),
(iv) a 5- to 8-membered aromatic heterocyclyl-oxy group (e.g., furyloxy, thienyloxy, pyrrolyloxy, oxazolyloxy, isooxazolyloxy, thiazolyloxy, isothiazolyloxy, imidazolyloxy, pyrazolyloxy, 1,2,3-oxadiazolyloxy, 1,2,4-oxadiazolyloxy, 1,3,4-oxadiazolyloxy, furazanyloxy, 1,2,3-thiadiazolyloxy, 1,2,4-thiadiazolyloxy, 1,3,4-thiadiazolyloxy, 1,2,3-triazolyloxy, 1,2,4-triazolyloxy, tetrazolyloxy, pyridyloxy, pyridazinyloxy, pyrimidinyloxy, pyrazinyloxy, triazinyloxy etc.) containing, besides carbon atom, 1 to 4 hetero atoms selected from a nitrogen atom, a sulfur atom and an oxygen atom, and the like can be mentioned. The substituent of the "aralkyl group optionally having substituent(s)" in the present specification may be present at the aryl moiety and/or the alkylene moiety of the aralkyl group.

In the present specification, as the "aryl group optionally having substituent(s)", a $C_{6-14}$ aryl group (e.g., phenyl, naphthyl etc.) optionally having 1 to 4, preferably 1 to 3, substituents that the aralkyl group of the above-mentioned "aralkyl group optionally having substituent(s)" may have can be mentioned.

In the present specification, as the "cycloalkyl group optionally having substituent(s)", a $C_{3-8}$ cycloalkyl group (e.g., cyclopropyl, cyclobutyl, cyclopentyl, cyclohexyl) optionally having 1 to 4, preferably 1 to 3, substituents, that the aralkyl group of the above-mentioned "aralkyl group optionally having substituent(s)" may have can be mentioned. The substituents of the "cycloalkyl group optionally having substituent(s)" may be bonded to each other to form a ring (cycloalkane ring ($C_{3-6}$ cycloalkane ring such as cyclopropane ring, cyclobutane ring, cyclopentane ring, cyclohexane ring and the like), or an arene ring ($C_{6-10}$ arene ring such as benzene ring, naphthalene ring and the like)).

In the present specification, as the "cycloalkenyl group optionally having substituent(s)", a $C_{3-8}$ cycloalkenyl group (e.g., cyclopropenyl, cyclobutenyl, cyclopentenyl, cyclohexenyl etc.) optionally having 1 to 4, preferably 1 to 3, substituents, that the aralkyl group of the above-mentioned "aralkyl group optionally having substituent(s)" may have can be mentioned. The substituents of the "cycloalkenyl group optionally having substituent(s)" may be bonded to each other to form a ring (cycloalkane ring ($C_{3-6}$ cycloalkane ring such as cyclopropane ring, cyclobutane ring, cyclopentane ring, cyclohexane ring and the like), or an arene ring ($C_{6-10}$ arene ring such as benzene ring, naphthalene ring and the like).

In the present specification, as the "acyl group", there can be mentioned "alkylcarbonyl group optionally having substituent(s)", "alkenylcarbonyl group optionally having substituent(s)", "alkynylcarbonyl group optionally having substituent(s)", "aralkylcarbonyl group optionally having substituent(s)", "arylcarbonyl group optionally having substituent(s)", "cycloalkylcarbonyl group optionally having substituent(s)", "alkoxycarbonyl group optionally having substituent(s)", "alkenyloxycarbonyl group optionally having substituent(s)", "alkynyloxycarbonyl group optionally having substituent(s)", "aralkyloxycarbonyl group optionally having substituent(s)", "aryloxycarbonyl group optionally having substituent(s)", "cycloalkyloxycarbonyl group optionally having substituent(s)", "carboxyl group" and the like.

In the present specification, as the "alkylcarbonyl group optionally having substituent(s)", a $C_{1-6}$ alkyl-carbonyl group (e.g., methylcarbonyl, ethylcarbonyl, propylcarbonyl, isopropylcarbonyl, butylcarbonyl, isobutylcarbonyl, sec-butylcarbonyl, tert-butylcarbonyl, pentylcarbonyl, hexylcarbonyl etc.) optionally having 1 to 4, preferably 1 to 3, substituents that the alkyl group of the above-mentioned "alkyl group optionally having substituent(s)" may have can be mentioned.

In the present specification, as the "alkenylcarbonyl group optionally having substituent(s)", a $C_{2-6}$ alkenyl-carbonyl group (e.g., vinylcarbonyl, 1-propenylcarbonyl, allylcarbonyl, isopropenylcarbonyl, butenylcarbonyl, isobutenylcarbonyl etc.) optionally having 1 to 4, preferably 1 to 3, substituents that the alkyl group of the above-mentioned "alkyl group optionally having substituent(s)" may have, and the like can be mentioned.

In the present specification, as the "alkynylcarbonyl group optionally having substituent(s)", a $C_{2-6}$ alkynyl-carbonyl group (e.g., ethynylcarbonyl, propargylcarbonyl, butynylcarbonyl, 1-hexynylcarbonyl etc.) optionally having 1 to 4, preferably 1 to 3, substituents that the alkyl group of the above-mentioned "alkyl group optionally having substituent(s)" may have and the like can be mentioned.

In the present specification, as the "aralkylcarbonyl group optionally having substituent(s)", a $C_{7-12}$ aralkyl-carbonyl group (e.g., benzylcarbonyl, 2-phenylethylcarbonyl, 1-phenylethylcarbonyl, 3-phenylpropylcarbonyl etc.) optionally having 1 to 4, preferably 1 to 3, substituents, that the aralkyl group of the above-mentioned "aralkyl group optionally having substituent(s)" may have can be mentioned.

In the present specification, as the "arylcarbonyl group optionally having substituent(s)", a $C_{6-14}$ aryl-carbonyl group (e.g., phenylcarbonyl, naphthylcarbonyl etc.) optionally having 1 to 4, preferably 1 to 3, substituents, that the aralkyl group of the above-mentioned "aralkyl group optionally having substituent(s)" may have can be mentioned.

In the present specification, as the "cycloalkylcarbonyl group optionally having substituent(s)", a $C_{3-8}$ cycloalkyl-carbonyl group (e.g., cyclopropylcarbonyl, cyclobutylcarbonyl, cyclopentylcarbonyl, cyclohexylcarbonyl) optionally having 1 to 4, preferably 1 to 3, substituents, that the aralkyl group of the above-mentioned "aralkyl group optionally having substituent(s)" may have can be mentioned.

In the present specification, as the "alkoxycarbonyl group optionally having substituent(s)", a $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, hexyloxycarbonyl etc.) optionally having 1 to 4, preferably 1 to 3, substituents that the alkyl group of the above-mentioned "alkyl group optionally having substituent(s)" may have can be mentioned.

In the present specification, as the "alkenyloxycarbonyl group optionally having substituent(s)", a $C_{2-6}$ alkenyl-oxycarbonyl group (e.g., vinyloxycarbonyl, 1-propenyloxycarbonyl, allyloxycarbonyl, isopropenyloxycarbonyl, butenyloxycarbonyl, isobutenyloxycarbonyl etc.) optionally having 1 to 4, preferably 1 to 3, substituents that the alkyl group of the above-mentioned "alkyl group optionally having substituent(s)" may have, and the like can be mentioned.

In the present specification, as the "alkynyloxycarbonyl group optionally having substituent(s)", a $C_{2-6}$ alkynyl-oxycarbonyl group (e.g., ethynyloxycarbonyl, propargyloxycarbonyl, butynyloxycarbonyl, 1-hexynyloxycarbonyl etc.) optionally having 1 to 4, preferably 1 to 3, substituents that the alkyl group of the above-mentioned "alkyl group optionally having substituent(s)" may have, and the like can be mentioned.

In the present specification, as the "aralkyloxycarbonyl group optionally having substituent(s)", a $C_{7-12}$ aralkyl-oxycarbonyl group (e.g., benzyloxycarbonyl, 2-phenylethyloxycarbonyl, 1-phenylethyloxycarbonyl, 3-phenylpropyloxycarbonyl etc.) optionally having 1 to 4, preferably 1 to 3, substituents, that the aralkyl group of the above-mentioned "aralkyl group optionally having substituent(s)" may have can be mentioned.

In the present specification, as the "aryloxycarbonyl group optionally having substituent(s)", a $C_{6-14}$ aryl-oxycarbonyl group (e.g., phenyloxycarbonyl, naphthyloxycarbonyl etc.) optionally having 1 to 4, preferably 1 to 3, substituents, that the aralkyl group of the above-mentioned "aralkyl group optionally having substituent(s)" may have can be mentioned.

In the present specification, as the "cycloalkyloxycarbonyl group optionally having substituent(s)", a $C_{3-8}$ cycloalkyloxycarbonyl group (e.g., cyclopropyloxycarbonyl, cyclobutyloxycarbonyl, cyclopentyloxycarbonyl, cyclohexyloxycarbonyl) optionally having 1 to 4, preferably 1 to 3, substituents, that the aralkyl group of the above-mentioned "aralkyl group optionally having substituent(s)" may have can be mentioned.

In the present specification, as the "heterocyclic group optionally having substituent(s)", (1) a 5- to 8-membered nonaromatic heterocyclic group (e.g., pyrrolidinyl, tetrahydrofuryl, tetrahydrothienyl, piperidyl, tetrahydropyranyl, morpholinyl, thiomorpholinyl, piperazinyl, azepanyl, 1,4-diazepanyl etc.) containing, besides carbon atom, 1 to 4 hetero atoms selected from a nitrogen atom, a sulfur atom and an oxygen atom, which optionally has 1 to 3 substituents from those the aralkyl group of the aforementioned "aralkyl group optionally having substituent(s)" may have and is optionally condensed with a benzene ring, and (2) a 5- to 8-membered aromatic heterocyclic group (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl etc.) containing, besides carbon atom, 1 to 4 hetero atoms selected from a nitrogen atom, a sulfur atom and an oxygen atom, which optionally has 1 to 3 substituents from those the aralkyl group of the aforementioned "aralkyl group optionally having substituent(s)" may have and is optionally condensed with a benzene ring can be mentioned.

In the present specification, as the "amino group optionally having substituent(s)", an amino group and an amino group having substituent(s) can be mentioned.

In the present specification, as the "amino group having substituent(s)", an amino group having 1 or 2 substituents selected from the aforementioned "hydrocarbon group optionally having substituent(s)", "acyl group" and "heterocyclic group optionally having substituent(s)" can be mentioned.

In the present specification, as the "hydroxyl group optionally having a substituent", a hydroxyl group and a hydroxyl group having a substituent can be mentioned.

In the present specification, as the "hydroxyl group having substituent(s)", a hydroxyl group having the aforementioned "hydrocarbon group optionally having substituent(s)" or "an acyl group" can be mentioned.

In the present specification, as the "thiol group optionally having a substituent", a thiol group and a thiol group having a substituent can be mentioned.

In the present specification, as the "thiol group having a substituent", a thiol group having the aforementioned "hydrocarbon group optionally having substituent(s)" or "an acyl group" can be mentioned.

In the present specification, as the "halogen atom", fluorine atom, chlorine atom, bromine atom, and iodine atom can be mentioned.

In the present specification, as the substituent of the "indenyl group optionally having substituent(s)", "naphthyl group optionally having substituent(s)" and "fluorenyl group optionally having substituent(s)", those similar to the substituents that the aryl group of the above-mentioned "aryl group optionally having substituent(s)" may have can be mentioned, wherein the number of the substituents is 1 to 4, preferably 1 to 3.

In the present specification, $R^1$ is a hydrogen atom, a hydrocarbon group optionally having substituent(s), an acyl group or a heterocyclic group optionally having substituent(s).

As $R^1$, a hydrocarbon group optionally having substituent(s), an acyl group or a heterocyclic group optionally having substituent(s) is preferable, a hydrocarbon group optionally having substituent(s) or a heterocyclic group optionally having substituent(s) is more preferable, and an alkyl group optionally having substituent(s) or an aralkyl group optionally having substituent(s) is particularly preferable.

In the present specification, $R^2$ is a hydrogen atom, a hydrocarbon group optionally having substituent(s), an acyl group or a heterocyclic group optionally having substituent(s).

As $R^2$, a hydrogen atom is preferable.

In the present specification, $R^3$ is a hydrogen atom, a hydrocarbon group optionally having substituent(s), a heterocyclic group optionally having substituent(s), an amino group optionally having substituent(s), a hydroxyl group optionally having a substituent or a thiol group optionally having a substituent.

As $R^3$, an amino group optionally having substituent(s) is preferable, and an amino group is particularly preferable.

In the present specification, $R^4$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent.

As $R^4$, a hydrogen atom is preferable.

In the present specification, $R^5$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent.

As $R^5$, a halogen atom is preferable.

In the present specification, $R^6$ is a hydrogen atom, a halogen atom, a cyano group, a hydrocarbon group optionally having substituent(s), an acyl group or a heterocyclic group optionally having substituent(s).

As $R^6$, a hydrogen atom is preferable.

In the present invention, as compound (I), a compound wherein $R^1$ is a hydrocarbon group optionally having substituent(s), an acyl group or a heterocyclic group optionally having substituent(s);

$R^2$ is a hydrogen atom, a hydrocarbon group optionally having substituent(s), an acyl group or a heterocyclic group optionally having substituent(s);

$R^3$ is a hydrogen atom, a hydrocarbon group optionally having substituent(s), a heterocyclic group optionally having substituent(s), an amino group optionally having substituent(s), a hydroxyl group optionally having a substituent or a thiol group optionally having a substituent;

$R^4$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent;

$R^5$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent; and $R^6$ is a hydrogen atom, a halogen atom, a cyano group, a hydrocarbon group optionally having substituent(s), an acyl group or a heterocyclic group optionally having substituent(s) is preferable.

Of compounds (I), a compound represented by the formula

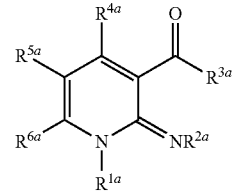

wherein $R^{1a}$ is a benzyl group optionally having substituent(s);

$R^{2a}$ is a hydrogen atom, a hydrocarbon group optionally having substituent(s), an acyl group or a heterocyclic group optionally having substituent(s);

$R^{3a}$ is a hydrocarbon group optionally having substituent(s), a heterocyclic group optionally having substituent(s), an amino group optionally having substituent(s), a hydroxyl group optionally having a substituent or a thiol group optionally having a substituent;

$R^{4a}$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent;

$R^{5a}$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent; and $R^{6a}$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent, excluding 5-chloro-1,2-dihydro-2-imino-1-phenylmethyl-3-pyridinecarboxamide, 5-bromo-1,2-dihydro-2-imino-1-phenylmethyl-3-pyridinecarboxamide, 5-aminocarbonyl-3-chloro-1,6-dihydro-6-imino-1-phenylmethyl-2-pyridinecarboxylic acid and 5-aminocarbonyl-3-bromo-1,6-dihydro-6-imino-1-phenylmethyl-2-pyridinecarboxylic acid, or a salt thereof (hereinafter to be abbreviated as compound (Ia));

a compound represented by the formula

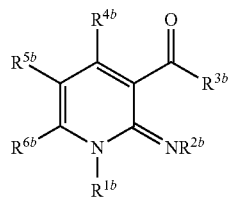

wherein

R$^{1b}$ is C$_{1-6}$ alkyl;

R$^{2b}$ is a hydrogen atom, a hydrocarbon group optionally having substituent(s), an acyl group or a heterocyclic group optionally having substituent(s);

R$^{3b}$ is a hydrocarbon group optionally having substituent(s), a heterocyclic group optionally having substituent(s), an amino group optionally having substituent(s) or a thiol group optionally having a substituent;

R$^{4b}$ is a hydrogen atom, a halogen atom, a cyano group, an acyl group, a heterocyclic group optionally having substituent(s), an amino group optionally having substituent(s), a hydroxyl group optionally having a substituent or a thiol group optionally having a substituent;

R$^{5b}$ is a hydrogen atom, a halogen atom, a cyano group, a hydrocarbon group optionally having substituent(s), an acyl group, an amino group optionally having substituent(s), a hydroxyl group optionally having a substituent or a thiol group optionally having a substituent; and R$^{6b}$ is a hydrogen atom, a halogen atom, a cyano group, an acyl group, a heterocyclic group optionally having substituent(s), an amino group optionally having substituent(s), a hydroxyl group optionally having a substituent or a thiol group optionally having a substituent, excluding 5-(aminocarbonyl)-3-chloro-1,6-dihydro-6-imino-1-methyl-2-pyridinecarboxylic acid, 5-(aminocarbonyl)-3-bromo-1,6-dihydro-6-imino-1-methyl-2-pyridinecarboxylic acid, 5-(aminocarbonyl)-1-butyl-3-chloro-1,6-dihydro-6-imino-2-pyridinecarboxylic acid, 5-(aminocarbonyl)-3-bromo-1-butyl-1,6-dihydro-6-imino-2-pyridinecarboxylic acid and 5-chloro-1,2-dihydro-2-imino-1-methyl-3-pyridinecarboxamide, or a salt thereof (hereinafter to be abbreviated as compound (Ib));

a compound represented by the formula

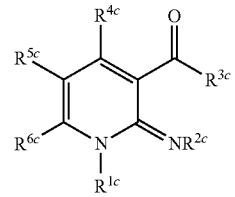

wherein

R$^{1c}$ is a phenyl group optionally having substituent(s);

R$^{2c}$ is a hydrogen atom, a hydrocarbon group optionally having substituent(s), an acyl group or a heterocyclic group optionally having substituent(s);

R$^{3c}$ is a hydrogen atom, a hydrocarbon group optionally having substituent(s), a heterocyclic group optionally having substituent(s), an amino group optionally having substituent(s), a hydroxyl group optionally having a substituent or a thiol group optionally having a substituent;

R$^{4c}$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent;

R$^{5c}$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent; and R$^{6c}$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent, excluding diethyl 1,1'-(1,4-phenylene)bis[2-imino-4,6-dimethyl-5-(phenyldiazenyl)-1,2-dihydropyridine-3-carboxylate], diethyl 1,1'-(1,4-phenylene)bis{5-[(4-chlorophenyl)diazenyl]-2-imino-4,6-dimethyl-1,2-dihydropyridine-3-carboxylate}, 5-(aminocarbonyl)-3-bromo-1,6-dihydro-6-imino-1-phenyl-2-pyridinecarboxylic acid, 5-bromo-1,2-dihydro-2-imino-1-phenyl-3-pyridinecarboxamide, ethyl 5-acetyl-1,2-dihydro-2-imino-4-methyl-1-phenyl-3-pyridinecarboxylate, ethyl 5-acetyl-1,2-dihydro-2-imino-1-phenyl-4-(2-phenylethenyl)-3-pyridinecarboxylate, ethyl 5-acetyl-1,2-dihydro-2-imino-1-phenyl-4-[(phenylhydrazono)methyl]-3-pyridinecarboxylate, 5-chloro-1,2-dihydro-2-imino-1-phenyl-3-pyridinecarboxamide, 5-chloro-1,2-dihydro-2-imino-1-(2-methylphenyl)-3-pyridinecarboxamide, 5-chloro-1,2-dihydro-2-imino-1-(3-methylphenyl)-3-pyridinecarboxamide, 5-chloro-1,2-dihydro-2-imino-1-(4-methylphenyl)-3-pyridinecarboxamide, 5-(aminocarbonyl)-3-chloro-1,6-dihydro-6-imino-1-(2-methylphenyl)-2-pyridinecarboxylic acid, 5-(aminocarbonyl)-3-chloro-1,6-dihydro-6-imino-1-(3-methylphenyl)-2-pyridinecarboxylic acid, 5-(aminocarbonyl)-3-chloro-1,6-dihydro-6-imino-1-(4-methylphenyl)-2-pyridinecarboxylic acid, 5-(aminocarbonyl)-3-chloro-1,6-dihydro-6-imino-1-phenyl-2-pyridinecarboxylic acid, dimethyl 1,2-dihydro-1,4,6-triphenyl-2-(phenylimino)-3,5-pyridinecarboxylate and diethyl 4,6-bis(diethylamino)-1,2-dihydro-1-phenyl-2-(phenylimino)-3,5-pyridinecarboxylate, or a salt thereof (hereinafter to be abbreviated as compound (Ic)); and a compound represented by the formula

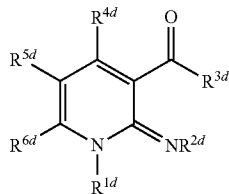

wherein $R^{1d}$ is (1) a heterocyclic group optionally having substituent(s),
(2) a cycloalkyl group optionally having substituent(s),
(3) the formula —$CR^{1da}R^{1db}R^{1dc}$ wherein $R^{1da}$ is a hydrogen atom, an alkyl group optionally having substituent(s) or an aryl group optionally having substituent(s); $R^{1db}$ is an alkyl group optionally having substituent(s) or an aryl group optionally having substituent(s); $R^{1dc}$ is an aryl group optionally having substituent(s) or a heterocyclic group optionally having substituent(s),
(4) the formula —$CH_2R^{1dd}$ wherein $R^{1dd}$ is a cycloalkyl group optionally having substituent(s), a cycloalkenyl group optionally having substituent(s), a naphthyl group optionally having substituent(s), an arylsulfonyl group optionally having substituent(s) or a heterocyclic group optionally having substituent(s),
(5) the formula —$(CH_2)_n$—$R^{1de}$ wherein n is an integer of 2 to 5, $R^{1de}$ is a cycloalkyl group optionally having substituent(s), a cycloalkenyl group optionally having substituent(s), an aryl group optionally having substituent(s), an acyl group, an amino group optionally having substituent(s), a thiol group optionally having a substituent or a hydroxyl group optionally having a substituent, and $(CH_2)_n$ optionally has substituent(s),
(6) an indenyl group optionally having substituent(s),
(7) a naphthyl group optionally having substituent(s) or
(8) a fluorenyl group optionally having substituent(s);

$R^{2d}$ is a hydrogen atom, a hydrocarbon group optionally having substituent(s), an acyl group or a heterocyclic group optionally having substituent(s);

$R^{3d}$ is a hydrogen atom, a hydrocarbon group optionally having substituent(s), a heterocyclic group optionally having substituent(s), an amino group optionally having substituent(s), a hydroxyl group optionally having a substituent or a thiol group optionally having a substituent;

$R^{4d}$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent;

$R^{5d}$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent; and $R^{6d}$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent, excluding 1,6-dihydro-1-(2-hydroxyethyl)-6-imino-[3,4'-bipyridine]-5-carboxamide, 1,6-dihydro-6-imino-1-(2-methoxyethyl)-[3,4'-bipyridine]-5-carboxamide, 1-[3-(diethylamino)propyl]-1,6-dihydro-6-imino-[3,4'-bipyridine]-5-carboxamide and 7-[[(5-amino-1,2,4-thiadiazol-3-yl)(methoxyimino)acetyl]amino]-3-[(3-carboxy-2-imino-1(2H)-pyridinyl)methyl]-8-oxo-5-thia-1-azabicyclo[4.2.0]oct-2-ene-2-carboxylic acid, or a salt thereof (hereinafter to be abbreviated as compound (Id)) are novel compounds. Compound (Ia)-compound (Id) are explained in detail in the following.

1. Compound (Ia)

$R^{1a}$ is a benzyl group optionally having substituent(s). As the substituent of the "benzyl group optionally having substituent (s)", (i) substituents that the above-mentioned "alkyl group optionally having substituent(s)" may have, (ii) a $C_{1-6}$ alkyl group (e.g., methyl, ethyl, propyl, isopropyl, butyl, isobutyl, sec-butyl, tert-butyl, pentyl, neopentyl, hexyl etc.) optionally substituted by substituent(s) selected from a halogen atom (e.g., fluorine atom, chlorine atom, bromine atom, iodine atom), a $C_{1-6}$ alkoxy group (e.g., methoxy, ethoxy, propoxy etc.), a $C_{6-14}$ arylsulfonyl group and a heterocyclic group (e.g., morpholinyl, pyridyl, imidazopyridyl, benzimidazolyl etc.), (iii) a $C_{7-16}$ aralkyl group (e.g., benzyl, 2-phenylethyl, 1-phenylethyl, 3-phenylpropyl, 4-phenylbutyl etc.) and the like can be mentioned, wherein the number of the substituents is 1 to 4, preferably 1 to 3. The substituent of the "benzyl group optionally having substituent(s)" may be present in the benzene ring part and/or the methylene part of the benzyl group.

As $R^{1a}$, a benzyl group optionally having 1 to 3 substituents selected from (i) a halogen atom (e.g., fluorine atom, chlorine atom, bromine atom, iodine atom), (ii) a $C_{1-6}$ alkoxy group (e.g., methoxy, ethoxy, propoxy, isopropoxy, butoxy, isobutoxy, sec-butoxy, tert-butoxy etc.) optionally substituted by halogen atom(s) (e.g., fluorine atom, chlorine atom, bromine atom, iodine atom), (iii) $C_{1-6}$ alkyl group (e.g., methyl, ethyl, propyl, isopropyl, butyl, isobutyl, sec-butyl, tert-butyl, pentyl, neopentyl, hexyl etc.) optionally substituted by halogen atom(s) (e.g., fluorine atom, chlorine atom, bromine atom, iodine atom), (iv) an aminosulfonyl group, (v) a di-N,N—$C_{1-6}$ alkylaminosulfonyl group (e.g., dimethylaminosulfonyl, diethylaminosulfonyl etc.), (vi) a sulfonyl group optionally substituted by a $C_{1-3}$ alkyl group, (vii) a cyano group, and (viii) an acyl group optionally substituted by substituent(s) selected from an amino group, a hydroxyl group and a $C_{1-3}$ alkyl group is preferable, and a benzyl group optionally having 1 to 3 substituents selected from (i) a halogen atom (e.g., fluorine atom, chlorine atom, bromine atom, iodine atom), (ii) $C_{1-6}$ alkoxy group (e.g., methoxy, ethoxy, propoxy, isopropoxy, butoxy, isobutoxy, sec-butoxy, tert-butoxy etc.) optionally substituted by halogen atom(s) (e.g., fluorine atom, chlorine atom, bromine atom, iodine atom), (iii) a $C_{1-6}$ alkyl group (e.g., methyl, ethyl, propyl, isopropyl, butyl, isobutyl, sec-butyl, tert-butyl, pentyl, neopentyl, hexyl etc.) optionally substituted by halogen atom(s) (e.g., fluorine atom, chlorine atom, bromine atom, iodine atom), (iv) an aminosulfonyl group and (v) a di-N,N—$C_{1-6}$ alkylaminosulfonyl group (e.g., dimethylaminosulfonyl, diethylaminosulfonyl etc.) is more preferable.

$R^{2a}$ is a hydrogen atom, a hydrocarbon group optionally having substituent(s), an acyl group or a heterocyclic group optionally having substituent(s).

$R^{2a}$ is preferably a hydrogen atom.

$R^{3a}$ is a hydrocarbon group optionally having substituent(s), a heterocyclic group optionally having substituent(s), an amino group optionally having substituent(s), a hydroxyl group optionally having a substituent or a thiol group optionally having a substituent.

As $R^{3a}$, an amino group optionally having substituent(s) is preferable, and an amino group is particularly preferable.

$R^{4a}$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent.

$R^{4a}$ is more preferably a hydrogen atom.

$R^{5a}$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent.

As $R^{5a}$, a halogen atom, a hydrogen atom, a methyl group, a cyano group or a methoxy group is preferable, particularly a halogen atom, especially a chlorine atom, is preferable.

$R^{6a}$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent.

$R^{6a}$ is preferably a hydrogen atom.

As compound (Ia), a compound wherein $R^{1a}$ is a benzyl group optionally having 1 to 3 substituents selected from (i) a halogen atom (e.g., fluorine atom, chlorine atom, bromine atom, iodine atom), (ii) a $C_{1-6}$ alkoxy group (e.g., methoxy, ethoxy, propoxy, isopropoxy, butoxy, isobutoxy, sec-butoxy, tert-butoxy etc.) optionally substituted by halogen atom(s) (e.g., fluorine atom, chlorine atom, bromine atom, iodine atom), (iii) a $C_{1-6}$ alkyl group (e.g., methyl, ethyl, propyl, isopropyl, butyl, isobutyl, sec-butyl, tert-butyl, pentyl, neopentyl, hexyl etc.) optionally substituted by halogen atom(s) (e.g., fluorine atom, chlorine atom, bromine atom, iodine atom), (iv) an aminosulfonyl group, (v) a di-N,N—$C_{1-6}$ alkylaminosulfonyl group (e.g., dimethylaminosulfonyl, diethylaminosulfonyl etc.), (vi) a sulfonyl group optionally substituted by a $C_{1-3}$ alkyl group, (vii) a cyano group, and (viii) an acyl group optionally substituted by substituent(s) selected from an amino group, a hydroxyl group and a $C_{1-3}$ alkyl group;

$R^{2a}$ is a hydrogen atom;
$R^{3a}$ is an amino group;
$R^{4a}$ is a hydrogen atom;
$R^{5a}$ is a halogen atom (particularly chlorine atom), a hydrogen atom, a methyl group, a cyano group or a methoxy group; and
$R^{6a}$ is a hydrogen atom is preferable, and a compound wherein $R^{1a}$ is a benzyl group optionally having 1 to 3 substituents selected from (i) a halogen atom (e.g., fluorine atom, chlorine atom, bromine atom, iodine atom), (ii) a $C_{1-6}$ alkoxy group (e.g., methoxy, ethoxy, propoxy, isopropoxy, butoxy, isobutoxy, sec-butoxy, tert-butoxy etc.) optionally substituted by halogen atom(s) (e.g., fluorine atom, chlorine atom, bromine atom, iodine atom), (iii) a $C_{1-6}$ alkyl group (e.g., methyl, ethyl, propyl, isopropyl, butyl, isobutyl, sec-butyl, tert-butyl, pentyl, neopentyl, hexyl etc.) optionally substituted by halogen atom(s) (e.g., fluorine atom, chlorine atom, bromine atom, iodine atom), (iv) an aminosulfonyl group and (v) a di-N,N—$C_{1-6}$ alkylaminosulfonyl group (e.g., dimethylaminosulfonyl, diethylaminosulfonyl etc.);

$R^{2a}$ is a hydrogen atom;
$R^{3a}$ is an amino group;
$R^{4a}$ is a hydrogen atom;
$R^{5a}$ is a halogen atom (particularly chlorine atom); and
$R^{6a}$ is a hydrogen atom is more preferable.

Particularly,
5-chloro-1-(3-chlorobenzyl)-2-imino-1,2-dihydropyridine-3-carboxamide;
5-chloro-1-(3,4-dichlorobenzyl)-2-imino-1,2-dihydropyridine-3-carboxamide;
5-chloro-2-imino-1-(3-methoxybenzyl)-1,2-dihydropyridine-3-carboxamide;
5-chloro-1-(2,5-difluorobenzyl)-2-imino-1,2-dihydropyridine-3-carboxamide;
5-chloro-1-(3,5-difluorobenzyl)-2-imino-1,2-dihydropyridine-3-carboxamide;
5-chloro-2-imino-1-[3-(trifluoromethyl)benzyl]-1,2-dihydropyridine-3-carboxamide;
5-chloro-1-(2,4-dichlorobenzyl)-2-imino-1, 2-dihydropyridine-3-carboxamide; and
5-chloro-1-[3-fluoro-5-(trifluoromethyl)benzyl]-2-imino-1,2-dihydropyridine-3-carboxamide and a salt thereof and the like are preferable.

2. Compound (Ib)

$R^{1b}$ is $C_{1-6}$ alkyl (e.g., methyl, ethyl, propyl, isopropyl, butyl, isobutyl, sec-butyl, tert-butyl, pentyl, neopentyl, hexyl etc.).

As $R^{1b}$, butyl, neopentyl and the like are preferable.

$R^{2b}$ is a hydrogen atom, a hydrocarbon group optionally having substituent(s), an acyl group or a heterocyclic group optionally having substituent(s).

$R^{2b}$ is preferably a hydrogen atom.

$R^{3b}$ is a hydrocarbon group optionally having substituent(s), a heterocyclic group optionally having substituent(s), an amino group optionally having substituent(s) or a thiol group optionally having a substituent.

As $R^{3b}$, an amino group optionally having substituent(s) is preferable, and an amino group is particularly preferable.

$R^{4b}$ is a hydrogen atom, a halogen atom, a cyano group, an acyl group, a heterocyclic group optionally having substituent(s), an amino group optionally having substituent(s), a hydroxyl group optionally having a substituent or a thiol group optionally having a substituent.

As $R^{4b}$, a hydrogen atom is preferable.

$R^{5b}$ is a hydrogen atom, a halogen atom, a cyano group, hydrocarbon group optionally having substituent(s), an acyl group, an amino group optionally having substituent(s), a hydroxyl group optionally having a substituent or a thiol group optionally having a substituent.

In one embodiment, $R^{5b}$ is a hydrogen atom, a cyano group, a hydrocarbon group optionally having substituent(s), an acyl group, an amino group optionally having substituent(s), a hydroxyl group optionally having a substituent or a thiol group optionally having a substituent.

In another embodiment, as $R^{5b}$, a halogen atom is preferable, and a chlorine atom is particularly preferable.

$R^{6b}$ is a hydrogen atom, a halogen atom, a cyano group, an acyl group, a heterocyclic group optionally having substituent(s), an amino group optionally having substituent(s), a hydroxyl group optionally having a substituent or a thiol group optionally having a substituent.

As $R^{6b}$, a hydrogen atom is preferable.

As compound (Ib), a compound wherein $R^{1b}$ is butyl or neopentyl;
$R^{2b}$ is a hydrogen atom;
$R^{3b}$ is an amino group;
$R^{4b}$ is a hydrogen atom;
$R^{5b}$ is a halogen atom (particularly chlorine atom); and
$R^{6b}$ is a hydrogen atom is preferable, and a compound wherein
$R^{1b}$ is neopentyl;
$R^{2b}$ is a hydrogen atom;
$R^{3b}$ is an amino group;
$R^{4b}$ is a hydrogen atom;
$R^{5b}$ is a halogen atom (particularly chlorine atom); and
$R^{6b}$ is a hydrogen atom is particularly preferable.

Particularly, 5-chloro-1-(2,2-dimethylpropyl)-2-imino-1,2-dihydropyridine-3-carboxamide and a salt thereof and the like are preferable.

3. Compound (Ic)

$R^{1c}$ is a phenyl group optionally having substituent(s). The "phenyl group optionally having substituent(s)" is, for example, a phenyl group optionally having 1 to 4, preferably 1 to 3, substituents that the aforementioned "aryl group optionally having substituent(s)" may have.

As $R^{1c}$, a phenyl group optionally having 1 to 3 substituents selected from (i) a halogen atom (e.g., fluorine atom, chlorine atom, bromine atom, iodine atom), (ii) a $C_{1-6}$ alkoxy group (e.g., methoxy, ethoxy, propoxy, isopropoxy, butoxy, isobutoxy, sec-butoxy, tert-butoxy etc.) optionally substituted by halogen atom(s) (e.g., fluorine atom, chlorine atom, bromine atom, iodine atom), (iii) a $C_{1-6}$ alkyl group (e.g., methyl, ethyl, propyl, isopropyl, butyl, isobutyl, sec-butyl, tert-butyl, pentyl, neopentyl, hexyl etc.) optionally substituted by halogen atom(s) (e.g., fluorine atom, chlorine atom, bromine atom, iodine atom), (iv) a $C_{3-8}$ cycloalkyl group, (v) a $C_{6-14}$ aryl group and (vi) a $C_{6-14}$ aryloxy group is preferable, and a phenyl group having 1 to 3 substituents selected from (i) a halogen atom (e.g., fluorine atom, chlorine atom, bromine atom, iodine atom), (ii) a $C_{1-6}$ alkoxy group (e.g., methoxy, ethoxy, propoxy, isopropoxy, butoxy, isobutoxy, sec-butoxy, tert-butoxy etc.) optionally substituted by halogen atom(s) (e.g., fluorine atom, chlorine atom, bromine atom, iodine atom), (iii) a $C_{1-6}$ alkyl group (e.g., methyl, ethyl, propyl, isopropyl, butyl, isobutyl, sec-butyl, tert-butyl, pentyl, neopentyl, hexyl etc.) substituted by halogen atom(s) (e.g., fluorine atom, chlorine atom, bromine atom, iodine atom), (iv) a $C_{3-8}$ cycloalkyl group, (v) a $C_{6-14}$ aryl group, and (vi) a $C_{6-14}$ aryloxy group is more preferable.

$R^{2c}$ is a hydrogen atom, a hydrocarbon group optionally having substituent(s), an acyl group or a heterocyclic group optionally having substituent(s).

As $R^{2c}$, a hydrogen atom is preferable.

$R^{3c}$ is a hydrogen atom, a hydrocarbon group optionally having substituent(s), a heterocyclic group optionally having substituent(s), an amino group optionally having substituent(s), a hydroxyl group optionally having a substituent or a thiol group optionally having a substituent.

As $R^{3c}$, an amino group optionally having substituent(s) is preferably, and an amino group is particularly preferable.

$R^{4c}$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent.

As $R^{4c}$, a hydrogen atom is preferable.

$R^{5c}$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent.

As $R^{5c}$, a halogen atom is preferable, and a chlorine atom is particularly preferable.

$R^{6c}$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent.

As $R^{6c}$, a hydrogen atom is preferable.

As compound (Ic), a compound wherein $R^{1c}$ is a phenyl group optionally having 1 to 3 substituents selected from (i) a halogen atom (e.g., fluorine atom, chlorine atom, bromine atom, iodine atom), (ii) a $C_{1-6}$ alkoxy group (e.g., methoxy, ethoxy, propoxy, isopropoxy, butoxy, isobutoxy, sec-butoxy, tert-butoxy etc.) optionally substituted by halogen atom(s) (e.g., fluorine atom, chlorine atom, bromine atom, iodine atom), (iii) a $C_{1-6}$ alkyl group (e.g., methyl, ethyl, propyl, isopropyl, butyl, isobutyl, sec-butyl, tert-butyl, pentyl, neopentyl, hexyl etc.) optionally substituted by halogen atom(s) (e.g., fluorine atom, chlorine atom, bromine atom, iodine atom), (iv) a $C_{3-8}$ cycloalkyl group, (v) a $C_{6-14}$ aryl group and (vi) a $C_{6-14}$ aryloxy group;

$R^{2c}$ is a hydrogen atom;
$R^{3c}$ is an amino group;
$R^{4c}$ is a hydrogen atom;
$R^{5c}$ is a halogen atom (particularly chlorine atom); and
$R^{6c}$ is a hydrogen atom is preferable, and a compound wherein $R^{1c}$ is a phenyl group having 1 to 3 substituents selected from (i) a halogen atom (e.g., fluorine atom, chlorine atom, bromine atom, iodine atom), (ii) a $C_{1-6}$ alkoxy group (e.g., methoxy, ethoxy, propoxy, isopropoxy, butoxy, isobutoxy, sec-butoxy, tert-butoxy etc.) optionally substituted by halogen atom(s) (e.g., fluorine atom, chlorine atom, bromine atom, iodine atom), (iii) a $C_{1-6}$ alkyl group (e.g., methyl, ethyl, propyl, isopropyl, butyl, isobutyl, sec-butyl, tert-butyl, pentyl, neopentyl, hexyl etc.) substituted by halogen atom(s) (e.g., fluorine atom, chlorine atom, bromine atom, iodine atom), (iv) a $C_{3-8}$ cycloalkyl group, (v) a $C_{6-14}$ aryl group, and (vi) a $C_{6-14}$ aryloxy group;

$R^{2c}$ is a hydrogen atom;
$R^{3c}$ is an amino group;
$R^{4c}$ is a hydrogen atom;
$R^{5c}$ is a halogen atom (particularly chlorine atom); and
$R^{6c}$ is a hydrogen atom is more preferable.

Particularly, 1-(4-butylphenyl)-5-chloro-2-imino-1,2-dihydropyridine-3-carboxamide;

5-chloro-1-(2-chlorophenyl)-2-imino-1,2-dihydropyridine-3-carboxamide; and 5-chloro-1-(3,4-dichlorophenyl)-2-imino-1,2-dihydropyridine-3-carboxamide and a salt thereof and the like are preferable.

4. Compound (Id)

$R^{1d}$ is (1) a heterocyclic group optionally having substituent(s), (2) a cycloalkyl group optionally having substituent(s), (3) the formula —$CR^{1da}R^{1db}R^{1dc}$ wherein $R^{1da}$ is a hydrogen atom, an alkyl group optionally having substituent(s) or an aryl group optionally having substituent(s); $R^{1db}$ is an alkyl group optionally having substituent(s) or an aryl group optionally having substituent(s); $R^{1dc}$ is an aryl group optionally having substituent(s) or a heterocyclic group optionally having substituent(s), (4) the formula —$CH_2R^{1dd}$ wherein $R^{1dd}$ is a cycloalkyl group optionally having substituent(s), a cycloalkenyl group optionally having substituent(s), a naphthyl group optionally having substituent(s) (the substituents are similar to the substituents that the above-mentioned "aryl group optionally having substituent(s)" may have), an arylsulfonyl group optionally having substituent(s) or a heterocyclic group optionally having substituent(s)), (5) the formula —$(CH_2)_n$—$R^{1de}$ wherein n is an integer of 2 to 5, $R^{1de}$ is a cycloalkyl group optionally having substituent(s), a cycloalkenyl group optionally having substituent(s), an aryl group optionally having substituent(s), an acyl group, an amino group optionally having substituent(s), a thiol group optionally having a substituent or a hydroxyl group optionally having a substituent, and $(CH_2)_n$ optionally has substituent(s), (6) an indenyl group optionally having substituent(s), (7) a naphthyl group optionally having substituent(s) or (8) a fluorenyl group optionally having substituent(s).

As $R^{1d}$,
(1) a 5- to 8-membered aromatic heterocyclic group containing, besides carbon atom, 1 to 4 hetero atoms selected from a nitrogen atom, a sulfur atom and an oxygen atom (e.g., furyl, thienyl, pyrrolyl, oxazolyl, isoxazolyl, thiazolyl, 5 isothiazolyl, imidazolyl, pyrazolyl, 1,2,3-oxadiazolyl, 1,2, 4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl etc.), which optionally has 1 to 3 lo substituents selected from a halogen atom (e.g., fluorine atom, chlorine atom, bromine atom, iodine atom) and a $C_{6-14}$ aryl group, and is optionally condensed with a benzene ring,
(2) a $C_{3-8}$ cycloalkyl group optionally condensed with a benzene ring,
(3) the formula —$CR^{1da'}R^{1db'}R^{1dc'}$ wherein $R^{1da'}$ is a hydrogen atom; $R^{1db'}$ is an alkyl group optionally having substituent(s); and
$R^{1dc'}$ is an aryl group optionally having substituent(s),
(4) the formula —$CH_2R^{1dd'}$ wherein $R^{1dd'}$ is a cycloalkyl group optionally having substituent(s) or a naphthyl group optionally having substituent(s),
(5) the formula —$(CH_2)_n$—$R^{1de'}$ wherein n is an integer of 2 to 5, $R^{1de'}$ is a cycloalkyl group optionally having substituent(s), a cycloalkenyl group optionally having substituent(s), an aryl group optionally having substituent(s) or a thiol group optionally having a substituent, and $(CH_2)_n$ optionally has substituent(s),
(6) an indenyl group optionally having substituent(s),
(7) a naphthyl group optionally having substituent(s) or
(8) a fluorenyl group optionally having substituent(s) is preferable.

As $R^{1d}$,
(1) a 5- to 8-membered aromatic heterocyclic group containing, besides carbon atom, 1 to 4 hetero atoms selected from a nitrogen atom, a sulfur atom and an oxygen atom (e.g., furyl, thienyl, pyrrolyl, oxazolyl, isoxazolyl, thiazolyl, isothiazolyl, imidazolyl, pyrazolyl, 1,2,3-oxadiazolyl, 1,2, 4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl etc.), which optionally has 1 to 3 substituents selected from a halogen atom (e.g., fluorine atom, chlorine atom, bromine atom, iodine atom) and a $C_{6-14}$ aryl group, and is optionally condensed with a benzene ring,
(2) a $C_{3-8}$ cycloalkyl group optionally condensed with a benzene ring,
(3) the formula —$CR^{1da'}R^{1db'}R^{1dc'}$ wherein $R^{1da'}$ is a hydrogen atom; $R^{1db'}$ is a $C_{1-3}$ alkyl group; $R^{1dc'}$ is an aryl group optionally having 1 to 3 substituents selected from (i) a halogen atom, (ii) a $C_{1-6}$ alkoxy group optionally substituted by halogen atom(s), (iii) a $C_{1-6}$ alkyl group optionally substituted by halogen atom(s), (iv) an aminosulfonyl group, (v) a di-N,N—$C_{1-6}$ alkylaminosulfonyl group, (vi) a sulfonyl group optionally substituted by a $C_{1-3}$ alkyl group, (vii) a cyano group, and (viii) an acyl group,
(4) the formula —$CH_2R^{1dd'}$ wherein $R^{1dd'}$ is (1) a cycloalkyl group optionally substituted by hydroxyl group(s), or (2) a naphthyl group optionally having 1 to 3 substituents selected from (i) a halogen atom, (ii) a $C_{1-6}$ alkoxy group optionally substituted by halogen atom(s), (iii) a $C_{1-6}$ alkyl group optionally substituted by halogen atom(s), (iv) an aminosulfonyl group, (v) a di-N,N—$C_{1-6}$ alkylaminosulfonyl group, (vi) a sulfonyl group optionally having a $C_{1-3}$ alkyl group, (vii) a cyano group, and (viii) an acyl group,
(5) the formula —$(CH_2)_n$—$R^{1de'}$ wherein n is an integer of 2 to 5, $R^{1de'}$ is
1) a cycloalkyl group optionally substituted by hydroxyl group(s),
2) a cycloalkenyl group optionally substituted by hydroxyl group(s),
3) an aryl group optionally having 1 to 3 substituents selected from (i) a halogen atom, (ii) a $C_{1-6}$ alkoxy group optionally substituted by halogen atom(s), (iii) a $C_{1-6}$ alkyl group optionally substituted by halogen atom(s), (iv) an aminosulfonyl group, (v) a di-N,N—$C_{1-6}$ alkylaminosulfonyl group, (vi) a sulfonyl group optionally substituted by a $C_{1-3}$ alkyl group, (vii) a cyano group, and (viii) an acyl group,
4) an aryloxy group optionally having 1 to 3 substituents selected from (i) a halogen atom, (ii) a $C_{1-6}$ alkoxy group optionally substituted by halogen atom(s), (iii) a $C_{1-6}$ alkyl group optionally substituted by halogen atom(s), (iv) an aminosulfonyl group, (v) a di-N,N—$C_{1-6}$ alkylaminosulfonyl group, (vi) a sulfonyl group optionally substituted by a $C_{1-3}$ alkyl group, (vii) a cyano group, and (viii) an acyl group, or
5) a thiol group optionally substituted by an aryl group optionally having 1 to 3 substituents selected from (i) a halogen atom, (ii) a $C_{1-6}$ alkoxy group optionally substituted by halogen atom(s), (iii) a $C_{1-6}$ alkyl group optionally substituted by halogen atom(s), (iv) an aminosulfonyl group, (v) a di-N,N—$C_{1-6}$ alkylaminosulfonyl group, (vi) a sulfonyl group optionally substituted by a $C_{1-3}$ alkyl group, (vii) a cyano group, and (viii) an acyl group, and
$(CH_2)_n$ optionally has a $C_{1-3}$ alkyl group,
(6) an indenyl group optionally having substituent(s) selected from a halogen atom, a cyano group, a methylsulfonyl group and an acyl group,
(7) a naphthyl group optionally having substituent(s) selected from a halogen atom, a cyano group, a methylsulfonyl group and an acyl group, or
(8) a fluorenyl group optionally having substituent(s) selected from a halogen atom, a cyano group, a methylsulfonyl group and an acyl group is also preferable.

$R^{2d}$ is a hydrogen atom, a hydrocarbon group optionally having substituent(s), an acyl group or a heterocyclic group optionally having substituent(s).

As $R^{2d}$, a hydrogen atom is preferable.

$R^{3d}$ is a hydrogen atom, a hydrocarbon group optionally having substituent(s), a heterocyclic group optionally having substituent(s), an amino group optionally having substituent(s), a hydroxyl group optionally having a substituent or a thiol group optionally having a substituent.

As $R^{3d}$, an amino group optionally having substituent(s) is preferable, and an amino group is particularly preferable.

$R^{4d}$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent.

As $R^{4d}$, a hydrogen atom is preferable.

$R^{5d}$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent.

As $R^{5d}$, a halogen atom, a hydrogen atom, a methyl group, a cyano group or a methoxy group is preferable, a halogen atom is more preferable, and a chlorine atom is particularly preferable.

$R^{6d}$ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent.

As $R^{6d}$, a hydrogen atom is preferable.

As compound (Id), a compound wherein $R^{1d}$ is (1) a 5- to 8-membered aromatic heterocyclic group containing, besides carbon atom, 1 to 4 hetero atoms selected from a nitrogen atom, a sulfur atom and an oxygen atom (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl etc.), which optionally has 1 to 3 substituents selected from a halogen atom (e.g., fluorine atom, chlorine atom, bromine atom, iodine atom) and a $C_{6-14}$ aryl group, and is optionally condensed with a benzene ring, (2) a $C_{3-8}$ cycloalkyl group optionally condensed with a benzene ring, (3) the formula —$CR^{1da'}R^{1db'}R^{1dc'}$ wherein $R^{1da'}$ is a hydrogen atom; $R^{1db'}$ is an alkyl group optionally having substituent(s); and $R^{1dc'}$ is an aryl group optionally having substituent(s), (4) the formula —$CH_2R^{1dd'}$ wherein $R^{1dd'}$ is a cycloalkyl group optionally having substituent(s) or a naphthyl group optionally having substituent(s), (5) the formula —$(CH_2)_n$—$R^{1de'}$ wherein n is an integer of 2 to 5, $R^{1de'}$ is a cycloalkyl group optionally having substituent(s), a cycloalkenyl group optionally having substituent(s), an aryl group optionally having substituent(s) or a thiol group optionally having a substituent, and $(CH_2)_n$ optionally has substituent(s), (6) an indenyl group optionally having substituent(s), (7) a naphthyl group optionally having substituent(s) or (8) a fluorenyl group optionally having substituent(s);

$R^{2d}$ is a hydrogen atom;

$R^{3d}$ is an amino group;

$R^{4d}$ is a hydrogen atom;

$R^{5d}$ is a halogen atom (particularly chlorine atom); and $R^{6d}$ is a hydrogen atom is preferable.

As compound (Id), a compound wherein $R^{1d}$ is (1) a 5- to 8-membered aromatic heterocyclic group containing, besides carbon atom, 1 to 4 hetero atoms selected from a nitrogen atom, a sulfur atom and an oxygen atom (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl etc.), which optionally has 1 to 3 substituents selected from a halogen atom (e.g., fluorine atom, chlorine atom, bromine atom, iodine atom) and a $C_{6-14}$ aryl group, and is optionally condensed with a benzene ring, (2) a $C_{3-8}$ cycloalkyl group optionally condensed with a benzene ring, (3) the formula —$CR^{1da'}R^{1db'}R^{1dc'}$ wherein $R^{1da'}$ is a hydrogen atom; $R^{1db'}$ is a $C_{1-3}$ alkyl group; $R^{1dc'}$ is an aryl group optionally having 1 to 3 substituents selected from (i) a halogen atom, (ii) a $C_{1-6}$ alkoxy group optionally substituted by halogen atom(s), (iii) a $C_{1-6}$ alkyl group optionally substituted by halogen atom(s), (iv) an aminosulfonyl group, (v) a di-N,N—$C_{1-6}$ alkylaminosulfonyl group, (vi) a sulfonyl group optionally substituted by a $C_{1-3}$ alkyl group, (vii) a cyano group, and (viii) an acyl group, (4) the formula —$CH_2R^{1dd'}$ wherein $R^{1dd'}$ is (1) a cycloalkyl group optionally substituted by hydroxyl group(s), or (2) a naphthyl group optionally having 1 to 3 substituents selected from (i) a halogen atom, (ii) a $C_{1-6}$ alkoxy group optionally substituted by halogen atom(s), (iii) a $C_{1-6}$ alkyl group optionally substituted by halogen atom(s), (iv) an aminosulfonyl group, (v) a di-N,N—$C_{1-6}$ alkylaminosulfonyl group, (vi) a sulfonyl group optionally having a $C_{1-3}$ alkyl group, (vii) a cyano group, and (viii) an acyl group, (5) the formula —$(CH_2)_n$—$R^{1de'}$ wherein n is an integer of 2 to 5, $R^{1de'}$ is 1) a cycloalkyl group optionally substituted by hydroxyl group(s), 2) a cycloalkenyl group optionally substituted by hydroxyl group(s), 3) an aryl group optionally having 1 to 3 substituents selected from (i) a halogen atom, (ii) a $C_{1-6}$ alkoxy group optionally substituted by halogen atom(s), (iii) a $C_{1-6}$ alkyl group optionally substituted by halogen atom(s), (iv) an aminosulfonyl group, (v) a di-N,N—$C_{1-6}$ alkylaminosulfonyl group, (vi) a sulfonyl group optionally substituted by a $C_{1-3}$ alkyl group, (vii) a cyano group, and (viii) an acyl group, 4) an aryloxy group optionally having 1 to 3 substituents selected from (i) a halogen atom, (ii) a $C_{1-6}$ alkoxy group optionally substituted by halogen atom(s), (iii) a $C_{1-6}$ alkyl group optionally substituted by halogen atom(s), (iv) an aminosulfonyl group, (v) a di-N,N—$C_{1-6}$ alkylaminosulfonyl group, (vi) a sulfonyl group optionally substituted by a $C_{1-3}$ alkyl group, (vii) a cyano group, and (viii) an acyl group, or 5) a thiol group optionally substituted by an aryl group optionally having 1 to 3 substituents selected from (i) a halogen atom, (ii) a $C_{1-6}$ alkoxy group optionally substituted by halogen atom(s), (iii) a $C_{1-6}$ alkyl group optionally substituted by halogen atom(s), (iv) an aminosulfonyl group, (v) a di-N,N—$C_{1-6}$ alkylaminosulfonyl group, (vi) a sulfonyl group optionally substituted by a $C_{1-3}$ alkyl group, (vii) a cyano group, and (viii) an acyl group, and
$(CH_2)_n$ optionally has a $C_{1-3}$ alkyl group,
(6) an indenyl group optionally having substituent(s) selected from a halogen atom, a cyano group, a methylsulfonyl group and an acyl group,
(7) a naphthyl group optionally having substituent(s) selected from a halogen atom, a cyano group, a methylsulfonyl group and an acyl group, or
(8) a fluorenyl group optionally having substituent(s) selected from a halogen atom, a cyano group, a methylsulfonyl group and an acyl group;
$R^{2d}$ is a hydrogen atom;
$R^{3d}$ is an amino group;
$R^{4d}$ is a hydrogen atom;
$R^{5d}$ is a halogen atom (particularly chlorine atom), a hydrogen atom, a methyl group, a cyano group or a methoxy group; and
$R^{6d}$ is a hydrogen atom is also preferable.
Particularly,
5-chloro-2-imino-1-(1-naphthylmethyl)-1,2-dihydropyridine-3-carboxamide;
5-chloro-1-(cyclohexylmethyl)-2-imino-1,2-dihydropyridine-3-carboxamide;
5-chloro-1-(2-furylmethyl)-2-imino-1,2-dihydropyridine-3-carboxamide;
5-chloro-1-(2,3-dihydro-1H-inden-1-yl)-2-imino-1,2-dihydropyridine-3-carboxamide;
5-chloro-2-imino-1-(2-phenylethyl)-1,2-dihydropyridine-3-carboxamide;
5-chloro-2-imino-1-(3-phenylpropyl)-1,2-dihydropyridine-3-carboxamide;
5-chloro-2-imino-1-(4-phenylbutyl)-1,2-dihydropyridine-3-carboxamide;
5-chloro-2-imino-1-(1-naphthyl)-1,2-dihydropyridine-3-carboxamide: and
5-chloro-2-imino-1-(2-phenylpropyl)-1,2-dihydropyridine-3-carboxamide and a salt thereof and the like are preferable.

When compound (I) is a salt, examples of such salt include salt with inorganic base, ammonium salt, salt with organic base, salt with inorganic acid, salt with organic acid, salt with basic or acidic amino acid and the like.

Preferable examples of the salt with inorganic base include alkali metal salts such as sodium salt, potassium salt and the like; alkaline earth metal salts such as calcium salt, magnesium salt, barium salt and the like; aluminum salt and the like.

Preferable examples of the salt with organic base include salts with trimethylamine, triethylamine, pyridine, picoline, ethanolamine, diethanolamine, triethanolamine, dicyclohexylamine, N,N'-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

Of these salts, pharmaceutically acceptable salts are preferable.

Compound (I) encompasses solvate, e.g., hydrate, within the scope thereof. In addition, compound (I) may be labeled with an isotope (e.g., $^3H$, $^{14}C$, $^{35}S$, $^{125}I$ etc.) and the like. Compound (I) may be a deuterium converted form.

When compound (I) has an asymmetric center, isomers such as enantiomer, diastereomer and the like can be present. Such isomers and a mixture thereof are all encompassed in the scope of the present invention. When a conformational isomer is produced, such isomer and a mixture thereof are also encompassed in compound (I).

Now, the production methods of compound (I) of the present invention or a salt thereof are explained.

Of the compounds (I), a compound represented by the formula (I-A)

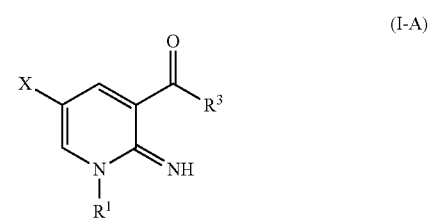

wherein X is a halogen atom, and other symbols are as defined above (hereinafter to be abbreviated as compound (I-A)) can be produced by Method A shown below or a method analogous thereto. Compound (I) can be produced by the production method of compound (I-A) shown below or a method analogous thereto. In each step of the following production methods, a starting material compound may be used in the form of a salt, and as such salt, those exemplified as the salts of compound (I) can be used.

[Method A]

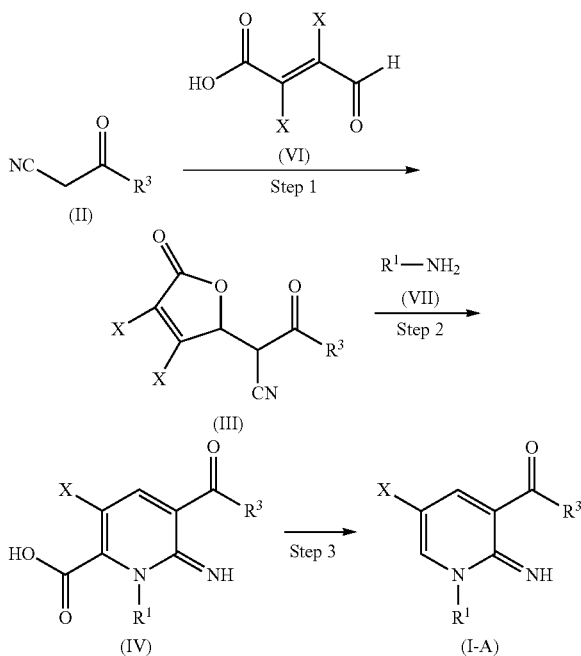

A compound represented by the formula (II) and a compound represented by the formula (VII), which are used as starting materials in the this method, may be commercially available products, or can be produced by a method known per se or a method analogous thereto.

Also, the compound represented by the formula (VI) to be used as a starting material in this method can be produced by a method known per se or a method analogous thereto. The compound can be produced, for example, by the method described in J. Am. Chem. Soc., 1953, 75, 1909 and the like.
(Step 1)

In this step, compound (III) is produced by reacting compound (II) with a compound represented by (VI) wherein X is a halogen atom, which is an aldehyde, in the presence of a base.

Examples of the halogen atom for X include chlorine atom, bromine atom, iodine atom and the like.

This reaction can be generally performed by reacting the above-mentioned aldehydes (VI) in the presence of a base in an inert solvent.

Examples of the base to be used in this reaction include alkali metal salts such as potassium hydroxide, sodium hydroxide, sodium carbonate, potassium carbonate and the like, amines such as pyridine, trimethylamine, N,N-dimethylaniline, 1,8-diazabicyclo[5.4.0]undec-7-ene (DBU) and the like, metal alkoxides such as sodium methoxide, sodium ethoxide, potassium tert-butoxide and the like, metal hydrides such as sodium hydride, potassium hydride, etc., and the like.

The amount of the base to be used is about 1-20 molar equivalents per 1 mol of compound (II), and particularly about 1-3 molar equivalents is preferable.

The amount of (VI) (aldehyde) to be used is, for example, 1-5, preferably about 1-3, molar equivalents per 1 mol of compound (II).

The solvent in this reaction is not particularly limited as long as the reaction proceeds. Examples of the solvent include aromatic hydrocarbons such as benzene, toluene, xylene and the like, ethers such as tetrahydrofuran, dimethoxyethane, dioxane, diethyl ether and the like, amides such as N,N-dimethylformamide (DMF), dimethylacetamide (DMA), 1-methyl-2-pyrrolidone and the like, alcohols such as methanol, ethanol, propanol, tert-butanol, methoxyethanol and the like, sulfoxides such as dimethyl sulfoxide (DMSO) and the like, water and a mixed solvent thereof.

This reaction is generally performed at −50° C. to 200° C., preferably −10° C. to 100° C. The reaction time of this reaction is generally 0.5 hr-60 hr.

The thus-obtained compound (III) can be isolated and purified by known separation and purification means, for example, concentration, concentration under reduced pressure, solvent extraction, crystallization, recrystallization, phase transfer, chromatography and the like.
(Step 2)

In this step, compound (IV) is produced by cyclizing compound (III) with (VII) (amine) in the presence of a base in an inert solvent.

The amount of (VII) (amine) to be used is, for example, 1-10, preferably about 1-3, molar equivalents per 1 mol of compound (III).

Examples of the base to be used in this reaction include alkali metal salts such as potassium hydroxide, sodium hydroxide, sodium carbonate, potassium carbonate and the like, amines such as pyridine, trimethylamine, triethylamine, N,N-dimethylaniline, 1,8-diazabicyclo[5.4.0]undec-7-ene (DBU) and the like, metal alkoxides such as sodium methoxide, sodium ethoxide, potassium tert-butoxide and the like, organic metals such as n-butyllithium, lithium diisopropylamide (LDA) and the like, metal hydrides such as sodium hydride, potassium hydride, etc., and the like.

The amount of the base to be used is about 1-10 molar equivalents per 1 mol of compound (III), and about 1-3 equivalents is preferable.

The solvent for this reaction is not particularly limited as long as the reaction proceeds. Examples of the solvent include aromatic hydrocarbons such as benzene, toluene, xylene and the like, ethers such as tetrahydrofuran, dimethoxyethane, dioxane, diethyl ether and the like, amides such as N,N-dimethylformamide (DMF), dimethylacetamide (DMA), 1-methyl-2-pyrrolidone and the like, alcohols such as methanol, ethanol, propanol, tert-butanol, methoxyethanol and the like, ketones such as acetone and the like, nitriles such as acetonitrile and the like, sulfoxides such as dimethyl sulfoxide (DMSO) and the like, water and a mixed solvent thereof.

This reaction is generally performed at −50° C. to 200° C., preferably −10° C. to 100° C. The reaction time of this reaction is generally 0.1 hr -60 hr.

The thus-obtained compound (IV) can be isolated and purified by known separation and purification means, for example, concentration, concentration under reduced pressure, solvent extraction, crystallization, recrystallization, phase transfer, chromatography and the like. In addition, compound (IV) may be used for the next step (Step 3) directly in the form of a reaction mixture without isolation and purification.
(Step 3)

In this step, compound (I-A) is produced by subjecting a compound represented by the formula (IV) to a decarboxylation reaction. For this decarboxylation reaction, known decarboxylation reaction can be used. For example, a heating reaction or a reaction using an acid or base may be employed. The solvent for this reaction is not particularly limited as long as the reaction proceeds. Examples of the solvent include aromatic hydrocarbons such as benzene, toluene, xylene and the like, ethers such as tetrahydrofuran, dimethoxyethane, dioxane, diethyl ether and the like, amides such as N,N-dimethylformamide (DMF), dimethylacetamide (DMA), 1-methyl-2-pyrrolidone and the like, alcohols such as methanol, ethanol, propanol, tert-butanol, methoxyethanol and the like, sulfoxides such as dimethyl sulfoxide (DMSO) and the like, nitriles such as acetonitrile and the like, organic acids such as acetic acid, trifluoroacetic acid and the like, water and a mixed solvent thereof.

Examples of the base to be used in this reaction include alkali metal salts such as potassium hydroxide, sodium hydroxide, sodium carbonate, potassium carbonate and the like, amines such as pyridine, trimethylamine, N,N-dimethylaniline, 1,8-diazabicyclo[5.4.0]undec-7-ene (DBU) and the like, metal alkoxides such as sodium methoxide, sodium ethoxide, potassium tert-butoxide and the like, metal hydrides such as sodium hydride, potassium hydride, etc. and the like. Examples of the acid include inorganic acids such as hydrochloric acid, sulfuric acid, hydrobromic acid and the like; organic acids such as acetic acid, trifluoroacetic acid, etc. and the like.

The amount of the base or acid to be used is, for example, 1-100, preferably about 1-10, molar equivalents per 1 mol of compound (IV).

This reaction is generally performed at −50° C. to 200° C., preferably −10° C. to 100° C. The reaction time of this reaction is generally 0.1 hr -60 hr.

The thus-obtained compound (I-A) can be isolated and purified by known separation and purification means, for example, concentration, concentration under reduced pressure, solvent extraction, crystallization, recrystallization, phase transfer, chromatography and the like.

In addition, of compounds (I), a compound represented by the formula (I-B)

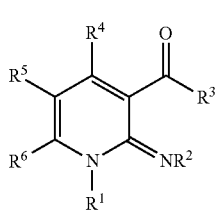

(I-B)

wherein each symbol is as defined above (hereinafter to be abbreviated as compound (I-B)) can be produced by Method B or a method analogous thereto.
[Method B]

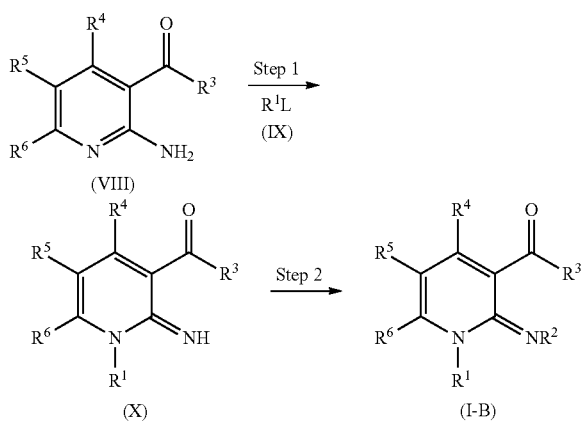

A compound represented by the formula (VIII) to be used as a starting material in this method can be produced by a method known per se or a method analogous thereto. For example, it can be produced according to the method described in J. Org. Chem., (1954), 19, 1633, Tetrahedron. Lett., (1994), 35(32), 5775 and the like.

In addition, a compound represented by the formula (IX) wherein L is a leaving group and $R^1$ is as defined above, to be used as a starting material in this method may be a commercially available product or can be produced by a method known per se or a method analogous thereto.
(Step 1)

For example, compound (X) can be produced by reacting compound (VIII) with a compound represented by the formula (IX) wherein $R^1$ is a hydrocarbon group optionally having substituent(s).

As the leaving group for L, a halogen atom (e.g., chlorine atom, bromine atom, iodine atom, etc.), a substituted sulfonyloxy group (e.g., $C_{1-6}$ alkylsulfonyloxy group such as methanesulfonyloxy, ethanesulfonyloxy, etc.; $C_{6-14}$ arylsulfonyloxy group such as benzenesulfonyloxy, p-toluenesulfonyloxy, etc.; $C_{7-16}$ aralkylsulfonyloxy group such as benzylsulfonyloxy group, etc. and the like) and the like can be used, and a halogen atom can be used particularly preferably.

This reaction is generally performed by reacting the above-mentioned compound (IX) with compound (VIII) in a solvent inert to the reaction.

The solvent for this reaction is not particularly limited as long as the reaction proceeds. Examples of the solvent include aromatic hydrocarbons such as benzene, toluene, xylene and the like, ethers such as tetrahydrofuran, dimethoxyethane, dioxane, diethyl ether and the like, amides such as N,N-dimethylformamide (DMF), dimethylacetamide (DMA) and the like, alcohols such as methanol, ethanol, propanol, tert-butanol, methoxyethanol and the like, ketones such as acetone and the like, nitriles such as acetonitrile and the like, sulfoxides such as dimethyl sulfoxide (DMSO) and the like and a mixed solvent thereof.

The amount of compound (IX) to be used is, for example, 1-5, preferably about 1-3, molar equivalents per 1 mol of compound (VIII).

This reaction is generally performed at 0° C. to 200° C., preferably 20° C. to 150° C. The reaction time of this reaction is generally 0.5 hr -60 hr.

The thus-obtained compound (X) can be isolated and purified by known separation and purification means, for example, concentration, concentration under reduced pressure, solvent extraction, crystallization, recrystallization, phase transfer, chromatography and the like. In addition, compound (X) may be used for the next step (Step 2) directly in the form of a reaction mixture without isolation and purification.
(Step 2)

In this step, compound (I-B) is produced from compound (X).

For example, of compounds (I-B), a compound wherein $R^2$ is a hydrocarbon group optionally having substituent(s) can be produced by subjecting compound (X) to a known substitution reaction and the like. For example, this reaction can be generally performed be reacting electrophile in the presence of a base in a solvent inert to the reaction, using a catalyst where necessary.

The solvent for this reaction is not particularly limited as long as the reaction proceeds. Examples of the solvent include aromatic hydrocarbons such as benzene, toluene, xylene and the like, ethers such as tetrahydrofuran, dimethoxyethane, dioxane, diethyl ether and the like, amides such as N,N-dimethylformamide (DMF), dimethylacetamide (DMA) and the like, alcohols such as methanol, ethanol, propanol, tert-butanol, methoxyethanol and the like, ketones such as acetone and the like, nitrites such as acetonitrile and the like, sulfoxides such as dimethyl sulfoxide (DMSO) and the like and a mixed solvent thereof.

Examples of the base include organic bases such as trimethylamine, triethylamine, N-methylmorpholine, pyridine, picoline, N,N-dimethylaniline and the like, and inorganic bases such as potassium carbonate, sodium carbonate, potassium hydroxide, sodium hydroxide and the like. The amount of the base to be used is for example, about 1-about 100, preferably about 1-about 10, molar equivalents per 1 mol of compound (X).

The amount of the electrophile to be used is, for example, 1-5 molar equivalents, preferably about 1-3 molar equivalents, per 1 mol of compound (X). The amount of the catalyst to be used varies depending on the kind thereof, and is generally about 0.0001-about 1 molar equivalent, preferably about 0.01-about 0.5 molar equivalent, per 1 mol of a substrate (compound (X)).

This reaction is generally performed at 0° C. to 200° C., preferably 20° C. to 150° C. The reaction time of this reaction is generally 0.5 hr -60 hr.

In addition, of compounds (I-B), a compound wherein $R^2$ is an acyl group can be produced by subjecting compound (X) to a known acylation reaction and the like. This reaction can be generally performed by reacting an acylating agent in the presence of a base in a solvent inert to the reaction.

Examples of the solvent include hydrocarbons such as benzene, toluene and the like, ethers such as ethyl ether, dioxane, tetrahydrofuran and the like, esters such as ethyl acetate and the like, halogenated hydrocarbons such as chloroform, dichloromethane and the like, esters such as ethyl acetate and the like, amides such as N,N-dimethylformamide and the like, aromatic amines such as pyridine and the like, water and the like, and the solvent may be used in an appropriate mixture. In addition, examples of the base include alkali metal hydroxides such as sodium hydroxide, potassium hydroxide and the like, hydrogen carbonates such as sodium hydrogen carbonate, potassium hydrogen carbonate and the like, carbonates such as sodium carbonate, potassium carbonate and the like, acetates such as sodium acetate and the like, tertiary amines such as trimethylamine, triethylamine, N-methylmorpholine and the like, aromatic amines such as pyridine, picoline, N,N-dimethylaniline, 4-dimethylaminopyridine, etc. and the like. The amount of the base to be used is, for example, about 1-about 100, preferably about 1-about 10, molar equivalents per 1 mol of compound (X).

Examples of the acylating agent include carboxylic acid, sulfonic acid, phosphoric acid, carbonic acid, a reactive derivative thereof (e.g., acid halide, acid anhydride, mixed acid anhydride, active ester, etc.), isocyanate ester, isothiocyanate ester and the like.

The amount of the acylating agent to be used is generally, 1-10, preferably 1-3, molar equivalents per 1 mol of compound (X).

The reaction temperature is generally at –10° C. to 150° C., preferably about 0° C. to 100° C. The reaction time is generally 5 min-48 hr, preferably about 10 min-16 hr.

In addition, of compounds (I-B), a compound wherein $R^2$ is a heterocyclic group optionally having substituent(s) can be produced by subjecting compound (X) to a known substitution reaction and the like.

The thus-obtained compound (I-B) can be isolated and purified by known separation and purification means, for example, concentration, concentration under reduced pressure, solvent extraction, crystallization, recrystallization, phase transfer, chromatography and the like.

Of compounds (I), a compound represented by the formula (I-C)

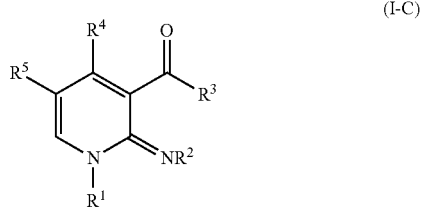

(I-C)

wherein each symbol is as defined above (hereinafter to be abbreviated as compound (I-C)) can be produced by, for example, Method C shown below or a method analogous thereto. In each step of the following production methods, a starting compound may be used in the form of a salt, and as such salt, those exemplified as the salts of compound (I) can be used. In each step, moreover, the starting compound may be protected as necessary by a protecting group generally used. In this case, the protecting group is removed as necessary after the reaction to give the object compound.

[Method C]

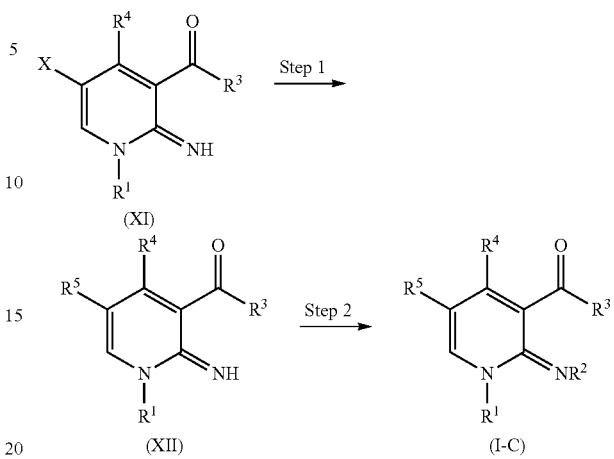

A compound represented by the formula (XI) wherein X is a halogen atom and other symbols are as defined above, to be used as a starting material in this method can be produced, for example, by the above-mentioned Method A, Method B or a method analogous thereto.

(Step 1)

In this step, compound (XII) is produced by subjecting compound (XI) to a known substitution reaction. As the substitution reaction to be used here, an insertion reaction of carbon monoxide using a transition metal catalyst or Suzuki coupling reaction, a cyanation reaction using a cyanating agent such as zinc cyanide and the like, and the like can be mentioned.

The insertion reaction of carbon monoxide or Suzuki coupling reaction can be performed by a method known per se [e.g., Chemical Reviews, 1995, vol. 95, page 2457 and the like] or a method analogous thereto. For example, the reaction can be performed in the presence of a transition metal catalyst and a base in a solvent that does not adversely influence the reaction.

Examples of the transition metal catalyst to be used include palladium catalysts (e.g., palladium (II) acetate, tris(dibenzylideneacetone)dipalladium (0), palladium (II) chloride, tetrakis(triphenylphosphine)palladium (0) and the like), nickel catalysts (e.g., nickel chloride and the like) and the like. Where necessary, a ligand (e.g., triphenylphosphine, tri-tert-butylphosphine and the like) may be added, and metal oxide (e.g., copper oxide, silver oxide and the like) and the like may be used as a cocatalyst. While the amount of the catalyst to be used varies depending on the kind of the catalyst, it is generally about 0.0001-about 1 molar equivalent, preferably about 0.01-about 0.5 molar equivalent, per 1 mol of a substrate (compound (XI)), and the amount of the ligand to be used is generally about 0.0001-about 4 molar equivalents, preferably about 0.01-about 2 molar equivalents per 1 mol of the substrate (compound (XI)). The amount of the cocatalyst to be used is about 0.0001-about 4 molar equivalents, preferably about 0.01-about 2 molar equivalents, per 1 mol of the substrate (compound (XI)).

Examples of the base to be used include organic amines (e.g., trimethylamine, triethylamine, diisopropylamine, N-methylmorpholine, 1,8-diazabicyclo[5.4.0]undec-7-ene, pyridine, N,N-dimethylaniline and the like), alkali metal salts (e.g., sodium hydrogen carbonate, potassium hydrogen carbonate, sodium carbonate, potassium carbonate, cesium carbonate, sodium phosphate, potassium phosphate, sodium hydroxide, potassium hydroxide and the like), metal hydrides (potassium hydride, sodium hydride and the like), alkali metal alkoxides (sodium methoxide, sodium ethoxide, sodium-tert-butoxide, potassium-tert-butoxide and the like), alkali disilazides (e.g., lithium disilazide, sodium disilazide, potassium disilazide and the like) and the like. Among these, alkali metal salts such as potassium carbonate, cesium carbonate, sodium phosphate, potassium phosphate and the like; alkali metal alkoxides such as sodium-tert-butoxide, potassium-tert-butoxide and the like; organic amines such as triethylamine, diisopropylamine and the like; and the like are preferable. The amount of the base to be used is about 0.1-about 10 molar equivalents, preferably about 1-about 5 molar equivalents, per 1 mol of the substrate (compound (XI)).

The solvent for this reaction is not particularly limited as long as it does not adversely influence the reaction. Examples of the solvent include hydrocarbons (e.g., benzene, toluene, xylene and the like), halogenated hydrocarbons (e.g., chloroform, 1,2-dichloroethane and the like), nitrites (e.g., acetonitrile and the like), ethers (e.g., dimethoxyethane, tetrahydrofuran and the like), alcohols (e.g., methanol, ethanol and the like), aprotic polar solvents (e.g., N,N-dimethylformamide, dimethyl sulfoxide, hexamethylphosphoramide and the like), water or a mixture thereof and the like.

The reaction temperature is generally about −10° C. to about 200° C., preferably about 0° C. to about 150° C. The reaction time is generally about 0.5-about 48 hr, preferably about 0.5-about 16 hr.

The cyanation reaction can be performed by a method known per se [e.g., the method described in Synth. Commun., 24. 6. 1994. 887-890 and the like] or a method analogous thereto. For example, the reaction can be performed by a reaction with a cyanating agent in the presence of a transition metal catalyst and a base as necessary in a solvent that does not adversely influence the reaction.

As the cyanating agent to be used here, zinc cyanide, copper cyanide, sodium cyanide, potassium cyanide, trimethylsilyl cyanide and the like can be mentioned. While the amount of the cyanating agent to be used varies depending on the kind of the cyanating agent, it is generally about 1-about 10 molar equivalents, preferably about 1-about 5 molar equivalents, per 1 mol of the substrate (compound (XI)).

Examples of the transition metal catalyst to be used include palladium catalysts (e.g., palladium (II) acetate, tris(dibenzylideneacetone)dipalladium (0), palladium (II) chloride, tetrakis(triphenylphosphine)palladium (0) and the like), nickel catalysts (e.g., nickel chloride and the like) and the like. While the amount of the catalyst to be used varies depending on the kind of the catalyst, it is generally about 0.0001-about 1 molar equivalent, preferably about 0.01-about 0.5 molar equivalent, per 1 mol of the substrate (compound (XI)).

Examples of the base to be used include organic amines (e.g., trimethylamine, triethylamine, diisopropylamine, N-methylmorpholine, 1,8-diazabicyclo[5.4.0]undec-7-ene, pyridine, N,N-dimethylaniline and the like), alkali metal salts (e.g., sodium hydrogen carbonate, potassium hydrogen carbonate, sodium carbonate, potassium carbonate, cesium carbonate, sodium phosphate, potassium phosphate, sodium hydroxide, potassium hydroxide and the like), metal hydrides (potassium hydride, sodium hydride and the like), alkali metal alkoxides (sodium methoxide, sodium ethoxide, sodium-tert-butoxide, potassium-tert-butoxide and the like), alkali disilazides (e.g., lithium disilazide, sodium disilazide, potassium disilazide and the like) and the like. Of these, alkali metal salts such as potassium carbonate, cesium carbonate, sodium phosphate, potassium phosphate and the like; alkali metal alkoxides such as sodium-tert-butoxide, potassium-tert-butoxide and the like; organic amines such as triethylamine, diisopropylamine and the like; and the like are preferable. The amount of the base to be used is about 0.1-about 10 molar equivalents, preferably about 1-about 5 molar equivalents, per 1 mol of the substrate (compound (XI)).

The solvent to be used is not particularly limited as long as it does not adversely influence the reaction. Examples of the solvent include hydrocarbons (e.g., benzene, toluene, xylene and the like), halogenated hydrocarbons (e.g., chloroform, 1,2-dichloroethane and the like), nitrites (e.g., acetonitrile and the like), ethers (e.g., dimethoxyethane, tetrahydrofuran and the like), alcohols (e.g., methanol, ethanol and the like), aprotic polar solvents (e.g., N,N-dimethylformamide, dimethyl sulfoxide, hexamethylphosphoramide and the like), water or a mixture thereof.

The reaction temperature is generally about −10° C. to about 200° C., preferably about 0° C. to about 150° C. The reaction time is generally about 0.5-about 48 hr, preferably about 0.5-about 16 hr.

The thus-obtained compound (XII) can be isolated and purified by known separation and purification means, for example, concentration, concentration under reduced pressure, solvent extraction, crystallization, recrystallization, phase transfer, chromatography and the like. In addition, compound (XII) may be used for the next step (Step 2) directly in the form of a reaction mixture without isolation and purification.

(Step 2)

In this step, compound (I-C) is produced by subjecting compound (XII) to a known addition reaction.

For example, of compounds (I-C), a compound wherein $R^2$ is a hydrocarbon group optionally having substituent(s) can be produced by subjecting compound (XII) to a known substitution reaction. This reaction can be generally performed by reacting an electrophile in a solvent inert to the reaction in the presence of a base, where necessary, a catalyst.

The solvent to be used for this reaction is not particularly limited as long as the reaction proceeds. Examples of the solvent include aromatic hydrocarbons such as benzene, toluene, xylene and the like, ethers such as tetrahydrofuran, dimethoxyethane, dioxane, diethyl ether and the like, amides such as N,N-dimethylformamide (DMF), dimethylacetamide (DMA) and the like, alcohols such as methanol, ethanol, propanol, tert-butanol, methoxyethanol and the like, ketones such as acetone and the like, nitriles such as acetonitrile and the like, sulfoxides such as dimethyl sulfoxide (DMSO) and the like; and a mixed solvent thereof.

Examples of the base include organic bases such as trimethylamine, triethylamine, N-methylmorpholine, pyridine, picoline, N,N-dimethylaniline and the like, inorganic bases such as potassium carbonate, sodium carbonate, potassium hydroxide, sodium hydroxide and the like; and the like. The amount of the base to be used is, for example, about 1-about 100 molar equivalents, preferably about 1-about 10 molar equivalents, per 1 mol of compound (XII).

The amount of the electrophile to be used is, for example, 1-5 molar equivalents, preferably 1-3 molar equivalents, per 1 mol of compound (XII). While the amount of the catalyst to be used varies depending on the kind of the catalyst, it is generally about 0.0001-about 1 molar equivalent, preferably about 0.01-about 0.5 molar equivalent, per 1 mol of the substrate (compound (XII)).

This reaction is generally performed at 0° C. to 200° C., preferably 20° C. to 150° C. The reaction time of this reaction is generally 0.5 hr -60 hr.

For example, of compounds (I-C), a compound wherein $R^2$ is an acyl group can be produced by subjecting compound (XII) to a known acylation reaction and the like. This reaction can be generally performed by reacting an acylating agent in a solvent inert to the reaction in the presence of a base and the like.

Examples of the solvent include hydrocarbons such as benzene, toluene and the like, ethers such as ethyl ether, dioxane, tetrahydrofuran and the like, esters such as ethyl acetate and the like, halogenated hydrocarbons such as chloroform, dichloromethane and the like, esters such as ethyl acetate and the like, amides such as N,N-dimethylformamide and the like, aromatic amines such as pyridine and the like, water and the like, which may be used in an appropriate mixture. Examples of the base include alkali metal hydroxides such as sodium hydroxide, potassium hydroxide and the like, hydrogen carbonates such as sodium hydrogen carbonate, potassium hydrogen carbonate and the like, carbonates such as sodium carbonate, potassium carbonate and the like, acetates such as sodium acetate and the like, tertiary amines such as trimethylamine, triethylamine, N-methylmorpholine and the like, aromatic amines such as pyridine, picoline, N,N-dimethylaniline, 4-dimethylaminopyridine and the like; and the like. The amount of the base to be used is, for example, about 1-about 100 molar equivalents, preferably about 1-about 10 molar equivalents, per 1 mol of the substrate (compound (XII)).

Examples of the acylating agent include carboxylic acid, sulfonic acid, phosphoric acid, carbonic acid or reactive derivatives thereof (e.g., acid halide, acid anhydride, mixed acid anhydride, active ester and the like), isocyanate ester, isothiocyanate ester and the like.

The amount of the acylating agent to be used is generally 1-10 molar equivalents, preferably 1-3 molar equivalents, per 1 mol of the substrate (compound (XII)).

The reaction temperature is generally $-10°$ C. to $150°$ C., preferably about $0°$ C. to $100°$ C. The reaction time generally 5 min-48 hr, preferably 10 min-16 hr.

Moreover, of compounds (I-C), a compound wherein $R^2$ is a heterocyclic group optionally having substituent(s) can be produced by subjecting compound (XII) to a known substitution reaction and the like.

The thus-obtained compound (I-C) can be isolated and purified by known separation and purification means, for example, concentration, concentration under reduced pressure, solvent extraction, crystallization, recrystallization, phase transfer, chromatography and the like.

The compound (I-A) obtained by the above-mentioned Method A, compounds (X) and (I-B) obtained by the above-mentioned Method B, and compounds (XII) and (I-C) obtained by the above-mentioned Method C may be further derivatized by subjecting them, after isolation and purification, or directly in the form of a reaction mixture without isolation and purification, to various condensation reactions such as acylation reaction, alkylation reaction and the like, or a known reaction such as oxidation reaction, reduction reaction and the like. These reactions can be performed according to a method known per se.

In each of the reactions for the synthesis of the objective compounds and the starting materials, when the starting compounds have an amino group, a carboxyl group or a hydroxyl group as a substituent, such groups may be protected with the protecting groups which are generally used in peptide chemistry etc. In such a case, if necessary, such protecting groups can be removed to obtain the objective compounds after the reactions.

Such a protecting group includes, for example, protecting groups described in "Protective Groups in Organic Synthesis, $3^{rd}$ Ed. (1999)", edited by Theodara W. Greene, Peter G. M. Wuts, published by Wiley-Interscience.

Examples of the protecting group for the amino group include a formyl group, a $C_{1-6}$ alkyl-carbonyl group (e.g., an acetyl group, a propionyl group etc.), a phenylcarbonyl group, a $C_{1-6}$ alkyl-oxycarbonyl group (e.g., methoxycarbonyl group, an ethoxycarbonyl group etc.), an aryloxycarbonyl group (e.g., a phenyloxycarbonyl group etc.), a $C_{7-10}$ aralkyl-carbonyl group (e.g., a benzyloxycarbonyl group etc.), a benzyl group, a benzhydryl group, a trityl group, a phthaloyl etc., each of which may have substituent(s). Examples of such substituent include a halogen atom (e.g., a fluorine atom, a chlorine atom, a bromine atom, an iodine atom etc.), a $C_{1-6}$ alkyl-carbonyl group (e.g., an acetyl group, a propionyl group, a butylcarbonyl group etc.), a nitro group and the like. The number of substituent(s) is 1 to 3.

Examples of the protecting group for the carboxyl group include a $C_{1-6}$ alkyl group (e.g., a methyl group, an ethyl group, a n-propyl group, an i-propyl group, a n-butyl group, a tert-butyl group etc.), a phenyl group, a trityl group, a silyl group and the like, each of which may have substituent(s). Examples of these substituents include a halogen atom (a fluorine atom, a chlorine atom, a bromine atom, an iodine atom), a formyl group, a $C_{1-6}$ alkyl-carbonyl group (e.g., an acetyl group, a propionyl group, a butylcarbonyl group etc.), a nitro group and the like. The number of substituent(s) is 1 to 3.

Examples of the hydroxyl-protecting group include a $C_{1-6}$ alkyl group (e.g., a methyl group, an ethyl group, a n-propyl group, an i-propyl group, a n-butyl group, a tert-butyl group etc.), a phenyl group, a $C_{7-10}$ aralkyl group (e.g., a benzyl group etc.), a formyl group, $C_{1-6}$ alkyl-carbonyl group (e.g., an acetyl group, a propionyl group etc.), an aryloxycarbonyl group (e.g., a phenyloxycarbonyl group etc.), a $C_{7-10}$ aralkyl-carbonyl group (e.g., a benzyloxycarbonyl group etc.), a pyranyl group, a furanyl group, a silyl group and the like, each of which may have substituent(s). Examples of these substituents include a halogen atom (a fluorine atom, a chlorine atom, a bromine atom, an iodine atom), a $C_{1-6}$ alkyl group, a phenyl group, a $C_{7-10}$ aralkyl group, a nitro group and the like. The number of substituent(s) is 1 to 4.

Such protecting groups can be removed by a known method or the method described in "Protective Groups in Organic Synthesis, $3^{rd}$ Ed. (1999)", edited by Theodora W. Greene, Peter G. M. Wuts, published by Wiley-Interscience, or the like, or an analogous method thereto. For example, treatment with an acid, a base, reduction, ultraviolet radiation, hydrazine, phenylhydrazine, sodium N-methyldithiocarbamate, tetrabutylammonium fluoride, palladium acetate or the like, can be used.

In the above-mentioned methods, when compound (I-A), compound (I-B), compound (I-C), compound (X) or compound (XII) is obtained as a free compound, it can form a salt with, for example, inorganic acid (e.g., hydrochloric acid, sulfuric acid, hydrobromic acid and the like), organic acid (e.g., methanesulfonic acid, benzenesulfonic acid, toluenesulfonic acid, oxalic acid, fumaric acid, maleic acid, tartaric acid and the like), inorganic base (e.g., alkali metals such as sodium, potassium and the like, alkaline earth metals such as calcium, magnesium and the like, aluminum, ammonium and the like) or organic base (e.g., trimethylamine, triethylamine, pyridine, picoline, ethanolamine, diethanolamine, triethanolamine, dicyclohexylamine, N,N'-dibenzylethylenediamine and the like) and the like according to a conventional method.

When compound (I) is obtained in the form of a salt, it can also be converted to a free compound or other salt according to a conventional method.

In addition, when the starting compound forms a salt in each of the above-mentioned reactions, the compound may be used as a salt. Such salt includes, for example, those exemplified as the salt of compound (I).

Compound (I) thus prepared by such methods, can be isolated and purified by a typical separation means such as recrystallization, distillation, chromatography and the like.

When compound (I) includes an optical isomer, a stereoisomer, a regioisomer and a rotamer, these are also included in the scope of compound (I), and can be obtained as single products according to synthesis and separation methods known per se (e.g., concentration, solvent extraction, column chromatography, recrystallization etc.). For example, when compound (I) has an optical isomer, the optical isomer resolved from this compound is also encompassed in compound (I).

The optical isomer can be prepared by a method known per se. To be specific, an optically active synthetic intermediate is used, or the final racemate product is subjected to optical resolution according to a conventional method to give an optical isomer.

The method of optical resolution may be a method known per se, such as a fractional recrystallization method, a chiral column method, a diastereomer method etc.

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallization method, and if desired, a neutralization step to give a free optical isomer.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer, etc.) and organic solvents (e.g., ethanol, methanol, isopropanol, acetonitrile, trifluoroacetic acid, diethylamine etc.) solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method etc.) and the like, and is subjected to a chemical treatment such as hydrolysis and the like to separate an optically active reagent moiety, whereby an optical isomer is obtained. For example, when compound (I) contains hydroxy, or primary or secondary amino group within a molecule, the compound and an optically active organic acid (e.g., MTPA [α-methoxy-α-(trifluoromethyl)phenylacetic acid], (−)-menthoxyacetic acid etc.) and the like are subjected to condensation reaction to give diastereomers of the ester compound or the amide compound, respectively. When compound (I) has a carboxyl group, this compound and an optically active amine or an optically active alcohol are subjected to condensation reaction to give diastereomers of the amide compound or the ester compound, respectively. The separated diastereomer is converted to an optical isomer of the original compound by acid hydrolysis or base hydrolysis.

Compound (I) may be in the form of crystals.

The crystal of compound (I) can be prepared by crystallization of compound (I) by a crystallization method known per se.

Examples of the crystallization method include a method of crystallization from a solution, a method of crystallization from vapor, a method of crystallization from the melts and the like.

The "crystallization from a solution" is typically a method of shifting a non-saturated state to supersaturated state by varying factors involved in solubility of compounds (solvent composition, pH, temperature, ionic strength, redox state etc.) or the amount of solvent. To be specific, for example, a concentration method, a cold removing method, a reaction method (a diffusion method, an electrolysis method), a hydrothermal growth method, a flux method and the like can be mentioned. Examples of the solvent to be used include aromatic hydrocarbons (e.g., benzene, toluene, xylene etc.), halogenated hydrocarbons (e.g., dichloromethane, chloroform etc.), saturated hydrocarbons (e.g., hexane, heptane, cyclohexane etc.), ethers (e.g., diethyl ether, diisopropyl ether, tetrahydrofuran, dioxane etc.), nitriles (e.g., acetonitrile etc.), ketones (e.g., acetone etc.), sulfoxides (e.g., dimethyl sulfoxide etc.), acid amides (e.g., N,N-dimethylformamide etc.), esters (e.g., ethyl acetate etc.), alcohols (e.g., methanol, ethanol, isopropyl alcohol etc.), water and the like. These solvents are used alone or in a combination of two or more at a suitable ratio (e.g., 1:1 to 1:100 (a volume ratio)). Where necessary, a seed crystal can also be used.

The "crystallization from vapor" is, for example, a vaporization method (a sealed tube method, a gas stream method), a gas phase reaction method, a chemical transportation method and the like.

The "crystallization from the melts" is, for example, a normal freezing method (a Czochralski method, a temperature gradient method and a Bridgman method), a zone melting method (a zone leveling method and a floating zone method), a special growth method (a VLS method and a liquid phase epitaxy method) and the like.

Preferable examples of the crystallization method include a method of dissolving compound (I) in a suitable solvent (e.g., alcohols such as methanol, ethanol etc. and the like) at a temperature of 20 to 120° C., and cooling the resulting solution to a temperature not higher than the temperature of dissolution (e.g., 0 to 50° C., preferably 0 to 20° C.) and the like.

The thus obtained crystals of compound (I) can be isolated, for example, by filtration and the like.

As an analysis method of the obtained crystal, crystal analysis by powder X-ray diffraction is generally employed. Moreover, as a method for determining the crystal orientation, a mechanical method, an optical method and the like can also be mentioned.

The crystals of compound (I) obtained in the above-mentioned production method (hereinafter to be abbreviated as "crystal of the present invention") has high purity, high quality and low hygroscopicity, is free of denaturation even after a long-term preservation under normal conditions, and is extremely superior in stability. The crystal is also superior in biological properties (e.g., in vivo kinetics (absorbability, distribution, metabolism, excretion), efficacy expression etc.), and is extremely useful as a pharmaceutical agent.

In the present specification, the melting point means that measured using, for example, a micromelting point apparatus (Yanako, MP-500D) or a DSC (differential scanning calorimetry) device (SEIKO, EXSTAR 6000) and the like.

The prodrug of compound (I) means a compound which is converted to the compound of the present invention with a reaction due to an enzyme, gastric acid, etc. under the physiological condition in the living body, that is, a compound which is converted to the compound of the present invention by enzymatic oxidation, reduction, hydrolysis, etc.; a compound which is converted to the compound of the present invention by hydrolysis etc. due to gastric acid, and the like. A prodrug of compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation, dimethylaminomethylcarbonylation, etc.); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like. Any of these compounds can be produced from compound (I) by a method known per se.

A prodrug for compound (I) may also be one which is converted into compound (I) under a physiological condition, such as those described in IYAKUHIN no KAIHATSU (Development of Pharmaceuticals), Vol.7, Design of Molecules, p.163-198, 1990, Published by HIROKAWA SHOTEN.

Compound (I) has a superior $\alpha_{1D}$ adrenergic receptor antagonistic action. Of compounds (I), a compound having a selective $\alpha_{1D}$ adrenergic receptor antagonistic action is preferable. The selective $\alpha_{1D}$ adrenergic receptor antagonistic action here means the presence of an antagonistic activity at least 10-fold or above for $\alpha_{1A}$ adrenergic receptor, and at least 10-fold or above for $\alpha_{1B}$ adrenergic receptor. Since compound (I) has a selective $\alpha_{1D}$ adrenergic receptor antagonistic action, it decreases a blood pressure lowering effect and the like considered to be based on the antagonistic S action on the $\alpha_{1A}$ receptor or $\alpha_{1B}$ receptor. Therefore, compound (I) is considered to provide a pharmaceutical agent with a few side effects.

Based on the $\alpha_{1D}$ adrenergic receptor antagonistic action, compound (I) is useful as a drug for the prophylaxis or treatment of any $\alpha_{1D}$ adrenergic receptor associated diseases in mammals (e.g., mouse, rat, hamster, rabbit, cat, dog, bovine, sheep, monkey, human etc.), for example, (1) lower urinary tract diseases (including all diseases having lower urinary tract symptom as described in the following, e.g., overactive bladder, benign prostatic hyperplasia, interstitial cystitis, chronic prostatitis etc.) storage symptom (daytime urinary frequency, nocturia, urinary urgency, urinary incontinence, stress urinary incontinence, urge urinary incontinence, mixed urinary incontinence, enuresis, nocturnal enuresis, continuous urinary incontinence, other urinary incontinence, enhanced, decreased or missing bladder sensation etc.), voiding symptom (weak urinary stream (or slow stream), split urinary stream (or splitting stream), spraying stream, intermittent urinary stream (or intermittent stream), voiding postponement (or hesitancy), straining at urination (or straining), terminal dribbling (or terminal dribble) etc.), post-micturition symptom (sense of residual urine, post-micturition dribble etc.), symptom due to sexual intercourse (coital pain, vaginal dryness, urinary incontinence etc.), symptom due to pelvic organ prolapse (foreign body sensation, lumbago etc.), genital organ pain or lower urinary tract pain (cystalgia, urethral pain, pudendalgia, vaginodynia, scrotal pain, perineal pain, pelvic pain etc.), genital organ or urinary tract pain syndrome (cystalgia syndrome, urethral pain syndrome, pudendalgia syndrome, vaginal syndrome, scrotal pain syndrome, perineal pain syndrome, pelvic pain syndrome etc.), symptom syndrome suggesting lower urinary tract dysfunction (overactive bladder syndrome, lower urinary tract symptom suggesting bladder outlet obstruction etc.), polyuria, urolithiasis (urinary duct, urethra) and the like]

(2) metabolic diseases [for example, diabetes (insulin dependent diabetes, diabetic complications, diabetic retinopathy, diabetic microangiopathy, diabetic neuropathy etc.), impaired glucose tolerance, obesity, benign prostatic hyperplasia, sexual dysfunction and the like]

(3) central nervous system diseases [for example, neurodegenerative diseases (e.g., Alzheimer's disease, Down's disease, Parkinson's disease, Creutzfeldt-Jakob disease, amyotrophic lateral sclerosis (ALS), Huntington chorea, diabetic neuropathy, multiple sclerosis etc.), mental diseases (e.g., schizophrenia, depression, mania, anxiety neurosis, obsessive-compulsive neurosis, panic disorder, epilepsy, alcohol dependence, drug dependence, anxiety, anxious mental state, emotional abnormality, cyclothymia, nervous erethism, autism, faint, addiction, low sex drive etc.), disorders such as central nervous system and peripheral nerve disorders (e.g., head trauma, spinal trauma, brain edema, disorders of sensory function, abnormality of sensory function, disorders of autonomic nervous function, abnormality of autonomic nervous function, whiplash injury etc.), memory disorders (e.g., senile dementia, amnesia, cerebrovascular dementia etc.), cerebrovascular disorder (e.g., cerebral hemorrhage, cerebral infarction and the like and sequelae or complication thereof, asymptomatic cerebrovascular accident, transient cerebral ischemic attack, hypertensive encephalopathia, blood-brain barrier disorder, etc.), recurrence and sequelae of cerebrovascular disorders (e.g., neural symptoms, mental symptoms, subjective symptoms, disorders of daily living activities etc.), central nervous system hypofunction after brain blood vessel occlusion, disorder or abnormality of autoregulation ability of brain circulation or renal circulation etc.], sleep disorder (4) genital insufficiency diseases [for example, male erectile dysfunction, dysspermia, female genital insufficiency etc.]

(5) gastrointestinal diseases [for example, irritable bowel syndrome, inflammatory bowel disease, ulcerative colitis, Crohn's disease, abnormality (e.g., gastritis, gastric ulcer etc.) caused by urease positive herical gram negative bacteria (e.g., *Helicobacter pylori* etc.), gastric cancer, postgastrostomy disorder, dyspepsia, esophageal ulcer, pancreatitis, colon polyp, cholelithiasis, hemorrhoids, peptic ulcer, situational ileitis, gluttony, constipation, diarrhea, borborygmus etc.], (6) inflammatory or allergic diseases [for example, allergic rhinitis, conjunctivitis, gastrointestinal allergy, pollinosis, anaphylaxis, dermatitis, herpes, psoriasis, bronchitis, expectoration, retinopathy, postoperative and posttraumatic inflammation, regression of puffiness, pharyngitis, cystitis, meningitidis, inflammatory ophthalmic diseases etc.], (7) osteoarthropathy diseases [for example, rheumatoid arthritis (chronic rheumatoid arthritis), arthritis deformans, rheumatoid myelitis, osteoporosis, abnormal growth of cells, bone fracture, bone refracture, osteomalacia, osteopenia, osseous Behcet's disease, rigid myelitis, articular tissue destruction by gonarthrosis deformans and similar diseases thereto etc.], (8) respiratory diseases [for example, cold syndrome, pneumonia, asthma, pulmonary hypertension, pulmonary thrombi/pulmonary obliteration, pulmonary sarcoidosis, pulmonary tuberculosis, interstitial pneumonia, silicosis, adult respiratory distress syndrome, chronic obliterative pulmonary diseases, cough etc.], (9) infectious diseases [HIV infectious diseases, virus infectious diseases due to cytomegalo virus, influenza virus, herpes virus and the like, rickettsia infectious diseases, bacterial infectious diseases, sexually-transmitted diseases, carinii pneumonia, *helicobacter pylori* infectious disease, systemic fungal infectious diseases, tuberculosis, invasive *staphylococcal* infectious diseases, acute viral encephalitis, acute bacterial meningitidis, AIDS encephalitis, septicemia, sepsis, sepsis gravis, septic shock, endotoxin shock, toxic shock syndromes etc.],

(10) cancers [for example, primary, metastatic or recurrent breast cancer, prostatic cancer, pancreatic cancer, gastric cancer, lung cancer, colorectal cancer (colon cancer, rectal cancer, anal cancer), esophagus cancer, duodenal cancer, head and neck cancer (cancer of the tongue, pharynx cancer, laryngeal cancer), brain tumor, schwannoma, non-small cell lung cancer, small cell lung cancer, liver cancer, kidney cancer, cancer of the bile duct, uterus cancer (endometrial cancer, cancer of the uterine cervix ), ovarian cancer, urinary bladder cancer, skin cancer, Hemangioma, malignant lymphoma, malignant melanoma, thyroid cancer, bone tumor, Hemangioma, vascular fibroma, retinosarcoma, penile cancer, solid cancer in childhood, Kaposi's sarcoma, Kaposi's sarcoma caused by AIDS, maxillary tumor, fibrous histiocytoma, leiomyosarcoma, rhabdomyosarcoma, liposarcoma, fibroid tumors of the uterus, osteoblastoma, osteosarcoma, chondrosarcoma, cancerous mesothelioma, tumors such as leukemia, Hodgkin's disease etc.],

(11) circulatory diseases [for example, acute coronary artery syndromes (e.g., acute myocardial infarction, unstable angina etc.), peripheral arterial obstruction, Raynaud's disease; Buerger disease; restenosis after coronary-artery intervention (percutaneous transluminal coronary angioplasty (PTCA), directional coronary atherectomy (DCA), stenting etc.), restenosis after coronary-artery bypass operation, restenosis after intervention (angioplasty, atherectomy, stenting etc.) or bypass operation in other peripheral artery, ischemic cardiac diseases (e.g., myocardial infarction, angina etc.), myocarditis, intermittent claudication, lacunar infarction, arteriosclerosis (e.g., atherosclerosis etc.), cardiac failure (acute cardiac failure, chronic cardiac failure accompanied by congestion), arrhythmia, progress of atherosclerotic plaque, thrombosis, hypertension, hypertensive tinnitus; hypotension etc.],

(12) pain [for example, headache, migraine, neuralgia and pelvic visceral pain including cystalgia etc.],

(13) autoimmune diseases [for example, collagen disease, systemic lupus erythematosus, scleroderma, polyarteritis, myasthenia gravis, multiple sclerosis, Sjogren's syndrome, Behcet's disease etc.],

(14) hepatic diseases [e.g., hepatitis (including chronic hepatitis), cirrhosis, interstitial hepatic diseases etc.],

(15) pancreatic diseases [e.g., pancreatitis (including chronic pancreatitis) etc.],

(16) renal diseases [e.g., nephritis, glomerulonephritis, glomerulosclerosis, renal failure, thrombotic microangiopathy, dialysis complications, organ disorders including nephropathia by radiation, diabetic nephropathy etc.],

(17) endocrine diseases [e.g., Addison's disease, Cushing's syndrome, melanocytoma, primary aldosteronism etc.],

(18) other diseases such as (a) transplant rejection [e.g., posttransplantational rejection, posttransplantational polycythemia, hypertension, organ disorder and/or vascular hypertrophy, graft-versus-host disease etc.], (b) abnormality in characteristic of blood and/or blood components [e.g., enhancement in platelet aggregation, abnormality of erythrocyte deformability, enhancement in leukocyte adhesiveness, increase in blood viscosity, polycythemia, vascular peliosis, autoimmune hemolytic anemia, disseminated intravascular coagulation syndrome (DIC), multiple myelopathy etc.], (c) gynecologic diseases [e.g., climacteric disorder, gestational toxicosis, endometriosis, hysteromyoma, ovarian disease, mammary disease, premenstrual syndrome, pelvic organ prolapse (e.g., prolapse of anterior wall of the vagina, prolapse of vaginal apex, prolapse of posterior wall of vagina, prolapse of uterus etc.), other diseases where organ is prolapsed from the normal position due to weakened pelvic floor muscle (e.g., rectal prolapse etc.) and the like]

(d) dermatic diseases [e.g., keloid, Hemangioma, psoriasis, pruritus, etc.]

(e) ophthalmic diseases [e.g., glaucoma, ocular hypertension disease etc.], (f) otolaryngological diseases [e.g., Menuel syndrome, tinnitus, gustation disorder, dizziness, disequilibrium, dysphagia etc.], (g) diseases due to environmental and/or occupational factors (e.g., radiation disorder, disorders by ultraviolet ray~infrared ray•laser ray, altitude sickness etc.), (h) ataxia, rigidity, tremor, motion impairment, akinesia, (i) chronic fatigue syndrome, (j) sudden infant death syndrome, (k) hiccup, (l) diseases causing palpitation, vertigo, heartburn and the like.

Among these diseases, compound (I) is particularly useful as an improving agent of lower urinary tract diseases such as hyperactive bladder, stress urinary incontinence of urine and the like, as well as a drug for the prophylaxis or treatment of these lower urinary tract diseases.

A preparation comprising compound (I) may be any of solid preparations such as powder, granule, tablet, capsule, orally disintegrable films and the like and liquids such as syrup, emulsion, injection and the like.

An agent for the prophylaxis or treatment of the present invention can be produced by any conventional method, for example, blending, kneading, granulation, tabletting, coating, sterilization, emulsification etc., in accordance with the form of the preparation to be produced. For the production of such pharmaceutical preparations, for example, reference can be made to each of the items in General principles for pharmaceutical preparations in the Japanese Pharmacopeia. In addition, the preparation of the present invention may be formulated into a sustained release preparation containing an active ingredient and a biodegradable polymer compound. The sustained release preparation can be produced according to the method described in JP-A-9-263545.

In the preparations of the present invention, the content of compound (I) varies depending on the forms of the preparations, but is generally 0.01 to 100% by weight, preferably 0.1 to 50% by weight, more preferably 0.5 to 20% by weight, relative to the whole preparation.

When compound (I) is used in the above-mentioned pharmaceutical product, it may be used alone, or in admixture with a suitable, pharmaceutically acceptable carrier, for example, excipients (e.g., starch, lactose, sucrose, calcium carbonate, calcium phosphate etc.), binders (e.g., starch, arabic gum, carboxymethyl cellulose, hydroxypropyl cellulose, crystalline cellulose, alginic acid, gelatin, polyvinyl pyrrolidone etc.), lubricants (e.g., stearic acid, magnesium stearate, calcium stearate, talc etc.), disintegrants (e.g., calcium carboxymethylcellulose, talc etc.), diluents (e.g., water for injection, physiological saline etc.) and if desired, with the additives (e.g., a stabilizer, a preservative, a colorant, a fragrance, a solubilizing agent, an emulsifier, a buffer, an isotonic agent etc.) and the like, by ordinary methods. It can be formulated into the solid preparations such as powders, fine granules, granules, tablets, capsules etc., or into the liquid preparations such as injections etc., and can be administered orally or parenterally. In this case, injection is preferably prepared. It can also be administered as a parenteral agent for topical administration (e.g., intramuscular, subcutaneous, organ or joint injection etc., solid preparation such as implant agent, granules, powder and the like, liquid such as suspension and the like, ointment etc.) and the like.

For example, to produce an injection, compound (I) is prepared into an aqueous suspension together with a dispersing agent (e.g., surfactant such as Tween 80, HCO-60 and the like, polysaccharides such as carboxymethylcellulose, sodium alginate, hyaluronic acid and the like, polysorbate etc.), a preservative (e.g., methylparaben, propylparaben etc.), an isotonicity agent (e.g., sodium chloride, mannitol, sorbitol, glucose etc.), a buffering agent (e.g., calcium carbonate etc.), a pH adjuster (e.g., sodium phosphate, potassium phosphate etc.) and the like, whereby a practical preparation for injection is obtained. In addition, compound (I) is dispersed together with a vegetable oil such as sesame oil, corn oil and the like or a mixture thereof with a phospholipid such as lecithin and the like, or medium-chain fatty acid triglyceride (e.g., miglyol 812 etc.) to give an oily suspension for practical injection.

The prophylactic or therapeutic agent of the present invention can also be used together with other pharmaceutical agents.

A drug which is mixed or combined with compound (I) (hereinafter briefly referred to as a combination drug) includes the following:

(1) Agent for the prophylaxis or treatment of other lower urinary tract diseases (including any disease having a symptom represented by lower urinary tract symptoms), adrenaline α1 receptor blocker (e.g., tamsulosin, urapidil, Naftopidil, silodosin, doxazosin, alfuzosin etc.), anti-choline drug (e.g., oxybutynin, propiverine, darifenacin, tolterodine, solifenacin, temiverine, trospium chloride and salts thereof etc.), NK-1 receptor antagonist (e.g., aprepitant, casopitant, LY686017 etc.), adrenaline β3 receptor agonist (e.g., solabegron, YM-178, KRP-204, KUC-7483, MN-246, CL-316243 etc.), TRPV1 receptor agonist (e.g., resiniferatoxin, capsaicin preparation etc.), TRPV1 receptor antagonist (e.g., SB-705498, NGD-8243 etc.), Botulinus toxin preparation (e.g., BTX-A etc.), adrenaline $\alpha_1$ receptor agonist (e.g., ephedrine hydrochloride, midodrine hydrochloride etc.), adrenaline β2 receptor agonist (e.g., clenbuterol etc.), noradrenaline uptake inhibitory substance, noradrenaline and serotonin uptake inhibitory substance (e.g., duloxetine etc.), tricyclic antidepressant (e.g., imipramine hydrochloride etc.), smooth muscle stimulant (e.g., celimeverine hydrochloride etc.), female sex hormone drug (e.g., binding type estrogen (premarin), estriol etc.) and the like.

(2) Agent for Treating Diabetes

Insulin preparations (e.g., animal insulin preparations extracted from the bovine or swine pancreas; human insulin preparations synthesized by a genetic engineering technique using *Escherichia coli* or a yeast; insulin zinc; protamine zinc insulin; a fragment or a derivative of insulin (e.g., INS-1 etc.), and the like), agents for potentiating insulin sensitivity (e.g., pioglitazone hydrochloride, troglitazone, rosiglitazone or its maleate, JTT-501, MCC-555, YM-440, GI-262570, KRP-297, FK-614, CS-011 etc.), α-glucosidase inhibitors (e.g., voglibose, acarbose, miglitol, emiglitate etc.), biguanides (e.g., phenformin, metformin, buformin etc.), sulfonylureas (e.g., tolbutamide, glibenclamide, gliclazide, chlorpropamide, tolazamide, acetohexamide, glyclopyramide, glimepiride etc.) and other insulin secretagogues (e.g., repaglinide, senaglinide, mitiglinide or its calcium salt hydrate, GLP-1, nateglinide etc.), dipeptidyl peptidase IV inhibitor (e.g., NVP-DPP-278, PT-100, P32/98 etc.), β3 agonists (e.g., CL-316243, SR-58611-A, UL-TG-307, AJ-9677, AZ40140 etc.), amylin agonists (e.g., pramlintide etc.), phosphotyrosine phosphatase inhibitors (e.g., vanadic acid etc.), gluconeogenesis inhibitors (e.g., glycogen phosphorylase inhibitors, glucose-6-phosphatase inhibitors, glucagon antagonists etc.), SGLT (sodium-glucose cotransporter) inhibitors (e.g., T-1095 etc.) and the like.

(3) Agent for Treating Diabetic Complications

Aldose reductase inhibitors (e.g., tolrestat, epalrestat, zenarestat, zopolrestat, fidarestat (SNK-860), minalrestat (ARI-509), CT-112 etc.), neurotrophic factors (e.g., NGF, NT-3 etc.), AGE inhibitors (e.g., ALT-945, pimagedine, pyratoxathine, N-phenacylthiazolium bromide (ALT-766), EXO-226 etc.), active oxygen scavengers (e.g., thioctic acid etc.), cerebral vasodilators (e.g., tiapuride etc.) and the like.

(4) Antihyperlipidemic Agent

Statin compounds inhibiting cholesterol synthesis (e.g., pravastatin, simvastatin, lovastatin, atorvastatin, fluvastatin, cerivastatin or their salt (e.g., sodium salt etc.) and the like), squalene synthase inhibitors or fibrate compounds having triglyceride lowering action (e.g., bezafibrate, clofibrate, simfibrate, clinofibrate etc.) and the like.

(5) Hypotensive Agent

Angiotensin converting enzyme inhibitors (e.g., captopril, enalapril, delapril etc.), angiotensin II antagonists (e.g., losartan, candesartan cilexetil etc.), calcium antagonists (e.g., manidipine, nifedipine, amlodipine, efonidipine, nicardipine etc.), clonidine, and the like.

(6) Antiobesity Agent

Antiobesity drugs acting on the central nervous system (e.g. dexfenfluramine, fenfluramine, phentermine, sibutramine, anfepramone, dexamphetamine, mazindol, phenylpropanolamine, clobenzorex etc.), pancreatic lipase inhibitors (e.g. orlistat etc.), $\beta_3$ agonists (e.g. CL-316243, SR-58611-A, UL-TG-307, AJ-9677, AZ40140 etc.), anorectic peptides (e.g. leptin, CNTF (Ciliary Neurotrophic Factor) etc.), cholecystokinin agonists (e.g. lintitript, FPL-15849 etc.), and the like.

(7) Diuretic Agent

Xanthine derivatives (e.g., theobromine sodium salicylate, theobromine calcium salicylate etc.), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide etc.), antialdosterone preparations (e.g., spironolactone, triamterene etc.), carbonic anhydrase inhibitors (e.g., acetazolamide etc.), chlorobenzenesulfonamide preparations (e.g., chlorthalidone, mefruside, indapamide etc.), azosemide, isosorbide, ethacrynic acid, piretanide, bumetanide, furosemide etc.

(8) Chemotherapeutic Agent

Alkylating agents (e.g., cyclophosphamide, ifosfamide etc.), metabolic antagonists (e.g., methotrexate, 5-fluorouracil etc.), antitumor antibiotics (e.g., mitomycin, adriamycin etc.), plant-derived antitumor agents (e.g., vincristine, vindesine, taxol etc.), cisplatin, carboplatin, etoposide etc. Among these, 5-fluorouracil derivatives such as Furtulon and Neo-Furtulon are preferred.

(9) Immunotherapeutic Agent

Microorganism- or bacterium-derived components (e.g., muramyl dipeptide derivatives, Picibanil etc.), immunopotentiator polysaccharides (e.g., lentinan, schizophyllan, krestin etc.), genetically engineered cytokines (e.g., interferons, interleukins (IL) etc.), colony stimulating factors (e.g., granulocyte colony stimulating factor, erythropoietin etc.) and the like. Among these, IL-1, IL-2, IL-12 etc. are preferred.

(10) Therapeutic Agent Recognized to Ameliorate Cachexia in Animal Models or Clinical Practice Progesterone derivatives (e.g., megestrol acetate) [Journal of Clinical Oncology, vol. 12, pp. 213-225, 1994], metoclopramide pharmaceuticals, tetrahydrocannabinol pharmaceuticals (the above reference is applied to both), fat metabolism ameliorating agents (e.g., eicosapentanoic acid) [British Journal of Cancer, vol. 68, pp. 314-318, 1993], growth hormones, IGF-1, and antibodies to the cachexia-inducing factors such as TNF-A, LIF, IL-6 and oncostatin M.

(11) Antiinflammatory Agent

Steroids (e.g., dexamethasone etc.), sodium hyaluronate, cyclooxygenase inhibitors (e.g., indomethacin, ketoprofen, loxoprofen, meloxicam, ampiroxicam, celecoxib, rofecoxib etc.) and the like.

(12) Miscellaneous

Glycosylation inhibitors (e.g., ALT-711 etc.), nerve regeneration promoting drugs (e.g., Y-128, VX853, prosaptide etc.), drugs acting on the central nervous system (e.g., antidepressants such as desipramine, amitriptyline, imipramine, fluoxetine, paroxetine, doxepin etc.), anticonvulsants (e.g., lamotrigine, carbamazepine), antiarrhythmic drugs (e.g., mexiletine), acetylcholine receptor ligands (e.g., ABT-594), endothelin receptor antagonists (e.g., ABT-627), monoamine uptake inhibitors (e.g., tramadol), indoleamine uptake inhibitors (e.g., fluoxetine, paroxetine), narcotic analgesics (e.g., morphine), GABA receptor agonists (e.g., gabapentin), GABA uptake inhibitors (e.g., tiagabine), $\alpha_2$ receptor agonists (e.g., clonidine), local analgesics (e.g., capsaicin), protein kinase C inhibitors (e.g., LY-333531), antianxiety drugs (e.g., benzodiazepines), phosphodiesterase inhibitors (e.g., sildenafil), dopamine receptor agonists (e.g., apomorphine), dopamine receptor antagonists (e.g., haloperidol), serotonin receptor agonists (e.g., tandospirone citrate, sumatryptan), serotonin receptor antagonists (e.g., cyproheptadine hydrochloride, ondansetron), serotonin uptake inhibitors (e.g., fluvoxamine maleate, fluoxetine, paroxetine), sleep-inducing drugs (e.g., triazolam, zolpidem), anticholinergic agents, $\alpha_1$ receptor blocking agents (e.g., tamsulosin), muscle relaxants (e.g., baclofen etc.), potassium channel openers (e.g., nicorandil), calcium channel blocking agents (e.g., nifedipine), agents for preventing and/or treating Alzheimer's disease (e.g., donepezil, rivastigmine, galanthamine), agents for treating Parkinson's disease (e.g., L-dopa), agents for preventing and/or treating multiple sclerosis (e.g., interferon β-1a), histamine $H_1$ receptor inhibitors (e.g., promethazine hydrochloride), proton pump inhibitors (e.g., lansoprazole, omeprazole), antithrombotic agents (e.g., aspirin, cilostazol), NK-2 receptor antagonists, agents of treating HIV infection (saquinavir, zidovudine, lamivudine, nevirapine), agents of treating chronic obstructive pulmonary diseases (salmeterol, thiotropium bromide, cilomilast) and the like.

Anticholinergic agents include, for example, atropine, scopolamine, homatropine, tropicamide, cyclopentolate, butyl scopolamine bromide, propantheline bromide, methylbenactyzium bromide, mepenzolate bromide, flavoxate, pirenzepine, ipratropium bromide, trihexyphenidyl, oxybutynin, propiverine, darifenacin, tolterodine, temiverine, trospium chloride or a salt thereof (e.g., atropine sulfate, scopolamine hydrobromide, homatropine hydrobromide, cyclopentolate hydrochloride, flavoxate hydrochloride, pirenzepine hydrochloride, trihexyphenidyl hydrochloride, oxybutynin hydrochloride, tolterodine tartrate etc.) and the like, preferably, oxybutynin, propiverine, darifenacin, tolterodine, temiverine, trospium chloride or a salt thereof (e.g., oxybutynin hydrochloride, tolterodine tartrate etc.). In addition, acetylcholine esterase inhibitors (e.g., distigmine etc.) and the like can be used.

NK-2 receptor antagonists include, for example, a piperidine derivative such as $GR^{159897}$, $GR^{149861}$, $SR^{48968}$ (saredutant), $SR^{144190}$, YM35375, YM38336, ZD7944, L-743986, MDL105212A, ZD6021, MDL105172A, SCH205528, SCH62373, R-113281 etc., a perhydroisoindole derivative such as RPR-106145 etc., a quinoline derivative such as SB-414240 etc., a pyrrolopyrimidine derivative such as ZM-253270 etc., a pseudopeptide derivative such as MEN11420 (nepadutant), SCH217048, L-659877, PD-147714 (CAM-2291), MEN10376, S16474 etc., and others such as $GR^{100679}$, DNK333, $GR^{94800}$, UK-224671, MEN10376, MEN10627, or a salt thereof, and the like.

For a combined use, the administration time of compound (I) and the concomitant drug is not restricted, and compound (I) or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the concomitant drug is not particularly limited, and compound (I) and the concomitant drug only need to be combined on administration. Examples of such administration mode include the following:

(1) administration of a single preparation obtained by simultaneously processing compound (I) or a pharmaceutical composition thereof and the concomitant drug, (2) simultaneous administration of two kinds of preparations of compound (I) or a pharmaceutical composition thereof and the concomitant drug or a pharmaceutical composition thereof, which have been separately produced, by the same administration route, (3) administration of two kinds of preparations of compound (I) or a pharmaceutical composition thereof and the concomitant drug or a pharmaceutical composition thereof, which have been separately produced, by the same administration route in a staggered manner, (4) simultaneous administration of two kinds of preparations of compound (I) or a pharmaceutical composition thereof and the concomitant drug or a pharmaceutical composition thereof, which have been separately produced, by different administration routes, (5) administration of two kinds of preparations of compound (I) or a pharmaceutical composition thereof and the concomitant drug or a pharmaceutical composition thereof, which have been separately produced, by different administration routes in a staggered manner (e.g., administration in the order of compound (I) or a pharmaceutical composition thereof and the concomitant drug or a pharmaceutical composition thereof, or in the reverse order) and the like.

The compounding ratio of compound (I) to the concomitant drug in the combination agent of the present invention can be appropriately selected depending on the administration subject, administration route, diseases and the like.

For example, the content of compound (I) in the combination agent of the present invention varies depending on the form of a preparation, and usually from about 0.01 to 100 wt %, preferably from about 0.1 to 50 wt %, further preferably from about 0.5 to 20 wt %, based on the whole preparation.

While the content of the concomitant drug in the combination agent of the present invention varies depending on the form of a preparation, it is usually from about 0.01 to 100 wt %, preferably from about 0.1 to 50 wt %, further preferably from about 0.5 to 20 wt %, based on the whole preparation.

While the content of the additives such as carrier and the like in the combination agent of the present invention varies depending on the form of a preparation, it is generally about 1 to 99.99 wt %, preferably about 10 to 90 wt %, based on the whole preparation.

Similar contents can be employed for individual preparations of compound (I) and the concomitant drug.

While the dose varies depending on the kind of compound (I) or a pharmaceutically acceptable salt thereof, administration route, symptom, age of patient and the like, it is, for example, about 0.005-50 mg/kg body weight/day, preferably about 0.05-10 mg/kg body weight/day, more preferably about 0.2-4 mg/kg body weight/day, as compound (I) for oral administration to an adult patient with stress urinary incontinence, which can be administered in about 1 to 3 portions.

When the pharmaceutical composition of the present invention is a sustained-release preparation, the dose varies depending on the kind and content of compound (I), dosage form, duration of drug release, subject animal of administration (e.g., mammal such as human, rat, mouse, cat, dog, rabbit, cow, pit and the like), and administration object. For parenteral administration, for example, about 0.1 to about 100 mg of compound (I) is designed to be released from the administered preparation in one week.

The dose of the combination drug may be set such that it causes no problems of side effects. The daily dose as the combination drug varies depending on severity of symptoms, age, sex, weight and sensitivity of the subject to be administered, time and interval of administration, property, formulation and kinds of pharmaceutical preparation, kinds of active ingredients, etc., and is not particularly limited. In the case of oral administration, a daily dosage in terms of the concomitant drug is generally in the order of about 0.001 to 2000 mg, preferably about 0.01 to 500 mg, and more preferably about 0.1 to 100 mg, per 1 kg body weight of mammals, which may be administered once a day or in two to four divided portions a day.

In administering the combination drug of the present invention, it may be administered at the same time or, the combination drugs may be administered before administering compound (I), and vice versa. In case of staggered administration, the time interval varies depending on the active ingredients to be administered, a formulation and an administration route. For example, if the combination drugs are administered first, compound (I) may be administered 1 minute to 3 days, preferably 10 min to 1 day, more preferably 15 min to 1 hr. after administering the combination drugs. If compound (I) is administered first, the combination drugs may be administered 1 minute to 1 day, preferably 10 min to 6 hr, more preferably 15 min to 1 hr. after administering compound (I).

The pharmaceutical composition of the present invention has low toxicity and can be used safely. Particularly, since the Example compounds shown below are superior in the absorbability by oral administration, they can be advantageously used for oral preparation.

The present invention also provides a screening method of a compound having an $\alpha_{1D}$ adrenergic receptor antagonistic action useful as an agent for the prophylaxis or treatment of a lower urinary tract disease and the like.

The screening method of the present invention is characterized by the measurement of the bladder smooth muscle tension of rats with bladder outlet obstruction. The measurement method of the tension (contraction tension) of the bladder smooth muscle is not particularly limited and any known method can be used. For example, a method using a Magnus bath, which is described in the below-mentioned Experimental Examples 2, 3 and 4, and the like can be preferably used. An $\alpha_1$ receptor stimulant (a drug having an $\alpha_1$ adrenergic receptor agonistic activity) to be used for inducing contraction of the bladder smooth muscle is not particularly limited. For example, norepinephrine, phenylephrine and the like can be used.

As an evaluation method of the contraction tension of bladder smooth muscle in the present invention, any known method can be used. For example, a method of evaluating an average value and the maximum value (both including the absolute value or changes from a value before $\alpha_1$ receptor stimulation) of contraction tension in a given time, a method of evaluating area under curve and the like on a chart recording the changes in the contraction tension and the like are preferably used. Since the contractile responses induced by $\alpha_1$ receptor stimulation characteristically show rhythmic variations in the tension with repeated contraction and relaxation, a method including inducing or enhancing rhythmic contractile responses of the bladder smooth muscle of rats with bladder outlet obstruction by the addition of an $\alpha_1$ receptor stimulant, administering an agent having an $\alpha_{1D}$ adrenergic receptor antagonistic action for the prophylaxis or treatment of a lower urinary tract disease at predetermined time intervals, measuring changes in the contraction tension in a given time for each administration, and evaluating the level of displacement of rhythmic changes in the tension based on the variation in the level of changes in the obtained contraction tension is useful. As a specific method, for example, a method of evaluating the standard deviation, standard error and the like of the level of changes in the contraction tension is preferably used. Based on the above-mentioned evaluation of the contraction tension of the bladder smooth muscle, the inhibitory effect (inhibition rate) of various concentrations of test compound (prophylactic or therapeutic drug having $\alpha_{1D}$ adrenergic receptor antagonistic action for lower urinary tract disease) on the $\alpha_1$ receptor stimulation-induced contraction (rhythmic contractile response) is measured, and the test compound is screened for according to the obtained inhibitory effect (inhibition rate) values, that is, $\alpha_{1D}$ adrenergic receptor antagonistic action of the test compound can be evaluated.

In the above-mentioned rhythmic tension changes with repeated contraction and relaxation of contractile response induced by $\alpha_1$ receptor stimulation, since contraction components not related to the $\alpha_{1D}$ adrenergic receptor increase with the progress of time after the addition of $\alpha_1$ receptor stimulant, it is preferable for an accurate evaluation of the $\alpha_{1D}$ adrenergic receptor antagonistic action of a test compound to define the time from the start of stimulation of the $\alpha_1$ receptor (from addition of $\alpha_1$ receptor stimulant) to the measurement of changes of the contraction tension, or when the test compound is accumulatively administered, limit the number thereof. As a result, contraction components not related to the $\alpha_{1D}$ adrenergic receptor which increase with the progress of time after the addition of an $\alpha_1$ receptor stimulant can be eliminated.

EXAMPLES

The present invention is explained in detail in the following by referring to Reference Examples, Examples, Formulation Examples and Experimental Examples. However, the present invention is not limited to the Examples, and may be modified without departing from the scope of the invention. (LC-MS measurement conditions)

In the following Examples, HPLC-mass spectrum (LC-MS) was measured under the following conditions.

Measurement device: Micromass Quattro Micro and Agilent Technologies HP1100, or SHIMADZU Corporation high-speed liquid chromatograph mass spectrometer LCMS-2010A, or Waters MUX system (Micromass ZQ)

Column: Shiseido Co., Ltd. Capcelpak C18 UG-120, 1.5× 35 mm, or Nomura Chemical Co., Ltd. Develosil Combi-RP-5, 2.0×35 mm Solvent: Solution A; 5 mM ammonium acetate/2% acetonitrile/water, Solution B; 5 mM ammonium acetate/95% acetonitrile/water Gradient cycle: 0.00 min (Solution A 100%), 2.00 min (Solution B 100%), 3.00 min (Solution B 100%), 3.01 min (Solution A 100%), 3.80 min (Solution A 100%)

Flow rate: 0.5 ml/min

Detection method: UV 220 nm

Ionization method: electron impact ionization method (Electron Spray Ionization: ESI)
(Preparative HPLC Conditions)

In the following Examples, purification by preparative HPLC was performed under the following conditions.

Measurement: Gilson Company Inc., High Throughput Purification System

Column: Shiseido Co., Ltd. Capcelpak C18 UG-120, S-5 µM, 20×50 mm, or YMC CombiPrep Hydrosphere C18 HS-340-CC, S-5 µM, 20×50 mm Solvent: Solution A; 0.1% trifluoroacetic acid containing water, Solution B; 0.1% trifluoroacetic acid containing acetonitrile Gradient cycle: 0.00 min (Solution A/Solution B=95/5), 1.10 min (Solution A/Solution B=95/5), 5.00 min (Solution A/Solution B=0/100), 6.40 min (Solution A/Solution B=0/100), 6.50 min (Solution A/Solution B=95/5)

Flow rate: 20 ml/min

Detection method: UV 220 nm
(Other Conditions)

$^1$H-NMR spectrum was measured using tetramethylsilane as the internal standard and AV-400M (400 MHz), AVANCE 300 (300 MHz) and AVANCE II 300 (300 MHz) manufactured by Bruker, and all δ values were shown by ppm. Unless otherwise specified, the numerical values shown for mixed solvents are volume mixing ratios of respective solvents. Unless otherwise specified, % means weight %. The room temperature (ambient temperature) in the present specification is a temperature of about 10° C. to about 35° C.

Reference Example 1

2-cyano-2-(3,4-dichloro-5-oxo-2,5-dihydrofuran-2-yl)acetamide

Mucochloric acid (15.1 g) and 2-cyanoacetamide (7.53 g) were dissolved in methanol (53.6 ml), and 2.5N aqueous sodium hydroxide solution (53.6 ml) was added dropwise with stirring under ice-cooling. The mixture was allowed to warm to room temperature and further stirred at room temperature for 3 hr. The reaction mixture was poured into 1N hydrochloric acid containing ice water, methanol was evaporated under reduced pressure, and the residue was extracted with ethyl acetate. The extract was washed with saturated brine, dried over anhydrous magnesium sulfate, and the solvent was evaporated under reduced pressure. Crystallization from ethanol-diisopropyl ether gave the title compound (3.74 g) as pale-brown crystals.

$^1$H-NMR (DMSO-d$_6$) δ ppm 4.84 (1 H, d, J=3.2 Hz), 5.91 (1 H, d, J=4.0 Hz), 7.85 (1 H, br. s.), 8.03 (1 H, br. s.).

Example 1

5-chloro-2-imino-1-(3-methylbenzyl)-1,2-dihydropyridine-3-carboxamide trifluoroacetate To a solution (0.10 M, 1.0 ml) of 2-cyano-2-(3,4-dichloro-5-oxo-2,5-dihydrofuran-2-yl)acetamide in ethanol was added a solution (0.50 ml) of 3-methylbenzylamine (0.24 M) (Table 1-1, amine 1) and triethylamine (0.36 M) in ethanol at room temperature, and the mixture was stirred at room temperature for 18 hr. The reaction mixture was purified by preparative HPLC to give the title compound (2 mg).

HPLC purity 83%. MS m/z 276 (M+H$^+$).

According to the method of Example 1 and using the corresponding amines 2-18 shown in Table 1-1, the compounds of Examples 2-18 shown below were obtained.

Example 2

5-chloro-2-imino-1-(4-methylbenzyl)-1,2-dihydropyridine-3-carboxamide trifluoroacetate HPLC purity 100%. MS m/z 276 (M+H$^+$).

Example 3

5-chloro-2-imino-1-[(5-methylpyrazin-2-yl)methyl]-1,2-dihydropyridine-3-carboxamide ditrifluoroacetate HPLC purity 100%. MS m/z 278 (M+H$^+$).

Example 4

5-chloro-1-(3-fluorobenzyl)-2-imino-1,2-dihydropyridine-3-carboxamide trifluoroacetate HPLC purity 100%. MS m/z 280 (M+H$^+$).

Example 5

5-chloro-2-imino-1-(2-methoxybenzyl)-1,2-dihydro-pyridine-3-carboxamide trifluoroacetate HPLC purity 90%. MS m/z 292 (M+H$^+$).

Example 6

5-chloro-2-imino-1-(3-methoxybenzyl)-1,2-dihydro-pyridine-3-carboxamide trifluoroacetate HPLC purity 100%. MS m/z 292 (M+H$^+$).

Example 7

5-chloro-1-(2-chlorobenzyl)-2-imino-1,2-dihydropyridine-3-carboxamide trifluoroacetate HPLC purity 100%. MS m/z 296 (M+H$^+$).

Example 8

5-chloro-1-(4-chlorobenzyl)-2-imino-1,2-dihydropyridine-3-carboxamide trifluoroacetate HPLC purity 100%. MS m/z 296 (M+H$^+$).

Example 9

5-chloro-1-(2,3-difluorobenzyl)-2-imino-1,2-dihydropyridine-3-carboxamide trifluoroacetate HPLC purity 100%. MS m/z 298 (M+H$^+$).

Example 10

5-chloro-1-(2,5-difluorobenzyl)-2-imino-1,2-dihydropyridine-3-carboxamide trifluoroacetate HPLC purity 100%. MS m/z 298 (M+H$^+$).

Example 11

5-chloro-1-(3,5-difluorobenzyl)-2-imino-1,2-dihydropyridine-3-carboxamide trifluoroacetate HPLC purity 100%. MS m/z 298 (M+H$^+$).

Example 12

5-chloro-2-imino-1-(1-naphthylmethyl)-1,2-dihydro-pyridine-3-carboxamide trifluoroacetate HPLC purity 91%. MS m/z 312 (M+H$^+$).

Example 13

5-chloro-2-imino-1-[2-(trifluoromethyl)benzyl]-1,2-dihydropyridine-3-carboxamide trifluoroacetate HPLC purity 100%. MS m/z 330 (M+H$^+$).
$^1$H-NMR (CD$_3$OD) δ ppm 5.67 (2 H, s), 7.11 (1 H, d, J=8.0 Hz), 7.63-7.70 (2 H, m), 7.91 (1 H, d, J=8.0 Hz), 8.27 (1 H, d, J=4.0 Hz), 8.64 (1 H, d, J=1.0 Hz).

Example 14

5-chloro-2-imino-1-[3-(trifluoromethyl)benzyl]-1,2-dihydropyridine-3-carboxamide trifluoroacetate HPLC purity 100%. MS m/z 330 (M+H$^+$).

Example 15

5-chloro-1-(2,4-dichlorobenzyl)-2-imino-1,2-dihydropyridine-3-carboxamide trifluoroacetate HPLC purity 100%. MS m/z 330 (M+H$^+$)

Example 16

5-chloro-2-imino-1-[4-(trifluoromethoxy)benzyl]-1,2-dihydropyridine-3-carboxamide trifluoroacetate HPLC purity 100%. MS m/z 346 (M+H$^+$).

Example 17

5-chloro-1-[3-fluoro-5-(trifluoromethyl)benzyl]-2-imino-1,2-dihydropyridine-3-carboxamide trifluoroacetate HPLC purity 100%. MS m/z 348 (M+H$^+$).

Example 18

1-[3,5-bis(trifluoromethyl)benzyl]-5-chloro-2-imino-1,2-dihydropyridine-3-carboxamide trifluoroacetate HPLC purity 96%. MS m/z 398 (M+H$^+$)

Example 19

5-chloro-1-(3-chlorobenzyl)-2-imino-1,2-dihydropyridine-3-carboxamide

To a solution of 2-cyano-2-(3,4-dichloro-5-oxo-2,5-dihydrofuran-2-yl)acetamide (0.5 g) in tetrahydrofuran (10 ml) was added a solution of 3-chlorobenzylamine (0.45 g) (Table 1-1, amine 19) and triethylamine (0.32 g) in tetrahydrofuran (3 ml) under ice-cooling, and the mixture was allowed to warm to room temperature and stirred for 18 hr. The reaction mixture was concentrated, and the crystals were collected by filtration. The obtained crystals were added to a mixture of dimethylsulfoxide (5 ml)-water (5 ml), and the mixture was stirred at 80° C. for 1 hr. The reaction mixture was concentrated, the residue was purified by preparative HPLC, and the obtained fraction was treated with PL-HCO$_3$MP (200 mg cartridge, Polymer Laboratories) to give the title compound (0.33 g).

HPLC purity 100%. MS m/z 297 (M+H$^+$).
$^1$H-NMR (CDCl$_3$) δ ppm 4.87 (2 H, s), 5.82 (1 H, br. s.), 6.31 (1 H, br. s.), 7.07-7.12 (1 H, m), 7.19 (1 H, s), 7.25 (1 H, d, J=2.6 Hz), 7.33 7.39 (2 H, m), 8.25 (1 H, d, J=2.3 Hz), 10.80 (1 H, br. s.).

According to the method of Example 19 and using the corresponding amines 20-68 shown in Table 1-1 to Table 1-2, the compounds of Examples 20-68 shown below were obtained.

Example 20

5-chloro-1-(3,4-dichlorobenzyl)-2-imino-1,2-dihydropyridine-3-carboxamide

HPLC purity 100%. MS m/z 331 (M+H$^+$)
$^1$H-NMR (CD$_3$OD) δ ppm 5.09 (2 H, s), 7.19 (1 H, dd, J=8.3, 1.5 Hz), 7.46 (1 H, d, J=1.5 Hz), 7.51 (1 H, d, J=8.5 Hz), 7.75 (2 H, d, J=1.9 Hz).

Example 21

5-chloro-1-(2-chloro-6-phenoxybenzyl)-2-imino-1,2-dihydropyridine-3-carboxamide

HPLC purity 99%. MS m/z 388 (M+H$^+$).

Example 22

5-chloro-2-imino-1-(tetrahydrofuran-2-ylmethyl)-1,2-dihydropyridine-3-carboxamide HPLC purity 90%. MS m/z 256 (M+H$^+$).

Example 23

5-chloro-2-imino-1-(2-phenylethyl)-1,2-dihydropyridine-3-carboxamide HPLC purity 99%. MS m/z 276 (M+H$^+$)

$^1$H-NMR (CD$_3$OD) δ ppm 3.03 (2 H, t, J=7.2 Hz), 3.95 (2 H, t, J=7.2 Hz), 6.80 (1 H, d, J=2.6 Hz), 7.12-7.17 (2 H, m), 7.29-7.38 (3 H, m), 8.14 (1 H, d, J=2.4 Hz).

Example 24

5 5-chloro-2-imino-1-(3-phenylpropyl)-1,2-dihydropyridine-3-carboxamide

HPLC purity 99%. MS m/z 290 (M+H$^+$).
$^1$H-NMR (CDCl$_3$) δ ppm 2.05-2.15 (2 H, m), 2.74 (2 H, t, J=7.3 Hz), 3.67 (2 H, d, J=7.0 Hz), 5.86 (1 H, br. s.), 7.06 (1 H, d, J=2.6 Hz), 7.20 (2 H, d, J=7.2 Hz), 7.23-7.28 (1 H, m), 7.30-7.37 (2 H, m), 8.18 (1 H, d, J=2.6 Hz), 10.97 (1 H, br. s.).

Example 25

5-chloro-2-imino-1-(4-phenylbutyl)-1,2-dihydropyridine-3-carboxamide

HPLC purity 88%. MS m/z 304 (M+H$^+$).
$^1$H-NMR (CDCl$_3$) δ ppm 1.65-1.83 (4 H, m), 2.68 (2 H, t, J=7.1 Hz), 3.68 (2 H, t, J=7.2 Hz), 5.88 (1 H, br. s.), 7.11 (1 H, d, J=2.6 Hz), 7.15-7.19 (2 H, m), 7.19-7.25 (1 H, m), 7.28-7.34 (2 H, m), 8.20 (1 H, d, J=2.6 Hz), 10.98 (1 H, br. s.).

Example 26

5-chloro-1-(cyclohexylmethyl)-2-imino-1,2-dihydropyridine-3-carboxamide

HPLC purity 100%. MS m/z 268 (M+H$^+$).

$^1$H-NMR (CDCl$_3$) δ ppm 0.92-1.06 (2 H, m), 1.10-1.33 (4 H, m), 1.69-1.89 (5H, m), 3.51 (2 H, d, J=7.2 Hz), 5.86 (1 H, br. s.), 6.15 (1 H, br. s.), 7.09 (1H, d, J=2.6 Hz), 8.21 (1 H, d, J=2.3 Hz), 11.11 (1 H, br. s.).

Example 27

5-chloro-2-imino-1-{2-[3-(trifluoromethyl)phenyl]ethyl}-1,2-dihydropyridine-3-carboxamide HPLC purity 97%. MS m/z 344 (M+H$^+$).

Example 28

5-chloro-1-(2,2-dimethylpropyl)-2-imino-1,2-dihydropyridine-3-carboxamide

HPLC purity 95%. MS m/z 242 (M+H$^+$).
$^1$H-NMR (CDCl$_3$) δ ppm 1.05 (9 H, s), 3.54 (2 H, s), 5.82 (1 H, br. s.), 6.36 (1 H, br. s.), 7.08 (1 H, d, J=2.8 Hz), 8.20 (1 H, d, J=2.6 Hz), 11.09 (1 H, br. s.).

Example 29

5-chloro-2-imino-1-(2-phenylpropyl)-1,2-dihydropyridine-3-carboxamide

HPLC purity 99%. MS m/z 290 (M+H$^+$).
$^1$H-NMR (CDCl$_3$) δ ppm 1.41 (3 H, d, J=7.2 Hz), 3.20-3.31 (1 H, m), 3.65 (1 H, dd, J=14.5, 8.5 Hz), 3.92 (1 H, dd, J=14.5, 6.6 Hz), 5.86 (1 H, br. s.), 6.62 (1H, d, J=2.6 Hz), 7.13-7.16 (2 H, m), 7.28-7.31 (1 H, m), 7.32-7.38 (2 H, m), 8.14 (1 H, d, J=2.6 Hz), 10.99 (1 H, br. s.).

Example 30

5-chloro-1-(2,2-diphenylethyl)-2-imino-1,2-dihydropyridine-3-carboxamide

HPLC purity 99%. MS m/z 352 (M+H$^+$).
$^1$H-NMR (CDCl$_3$) δ ppm 4.30 (2 H, d, J=8.0 Hz), 4.40 (1 H, t, J=7.5 Hz), 5.87 (1 H, br. s.), 6.42 (1 H, d, J=2.6 Hz), 7.17-7.22 (4 H, m), 7.27-7.31 (2 H, m), 7.32-7.38 (4 H, m), 8.12 (1 H, d, J=2.6 Hz), 10.95 (1 H, br. s.).

Example 31

5-chloro-1-(3,3-diphenylpropyl)-2-imino-1,2-dihydropyridine-3-carboxamide

HPLC purity 92%. MS m/z 366 (M+H$^+$).
$^1$H-NMR (CDCl$_3$) δ ppm 2.49 (2 H, q, J=7.9 Hz), 3.66 (2 H, t, J=7.5 Hz), 3.93 (1 H, t, J=8.0 Hz), 5.85 (1 H, br. s.), 6.92 (1 H, d, J=2.6 Hz), 7.20-7.28 (6 H, m), 7.30-7.37 (4 H, m), 8.19 (1 H, d, J=2.6 Hz), 10.97 (1 H, br. s.).

Example 32

5-chloro-1-(2,3-dihydro-1H-inden-1-yl)-2-imino-1,2-dihydropyridine-3-carboxamide HPLC purity 99%. MS m/z 288 (M+H$^+$).
$^1$H-NMR (CDCl$_3$) δ ppm 2.11 (1 H, br. s.), 2.70-2.80 (1 H, m), 2.99-3.18 (2 H, m), 5.63 (1 H, br. s.), 5.92 (1 H, br. s.), 6.78 (1 H, br. s.), 7.19 (1 H, d, J=7.5 Hz), 7.30-7.37 (1 H, m), 7.39-7.43 (2 H, m), 8.18 (1 H, d, J=2.1 Hz), 10.94 (1 H, br. s.).

Example 33

5-chloro-1-(2,3-dihydro-1H-inden-2-yl)-2-imino-1,2-dihydropyridine-3-carboxamide HPLC purity 99%. MS m/z 288 (M+H$^+$).
$^1$H-NMR (CDCl$_3$) δ ppm 3.14 (2 H, dd, J=17.1, 3.0 Hz), 3.59 (2 H, dd, J=17.0, 7.9 Hz), 5.11 (1 H, br. s.), 6.17 (1 H, br. s.), 7.07 (1 H, d, J=2.6 Hz), 7.25-7.34 (4 H, m), 7.39 (1 H, s), 8.00 (1 H, br. s.).

Example 34

1-[(3S,5S,7S)-1-adamantylmethyl]-5-chloro-2-imino-1,2-dihydropyridine-3-carboxamide HPLC purity 98%. MS m/z 320 (M+H$^+$).
$^1$H-NMR (CDCl$_3$) δ ppm 1.59 (6 H, d, J=2.6 Hz), 1.61-1.77 (6 H, m), 2.05 (3 H, br. s.), 3.42 (2 H, s), 5.85 (1 H, br. s.), 7.05 (1 H, d, J=2.8 Hz), 8.22 (1 H, d, J=2.4 Hz), 11.12 (1 H, br. s.).

Example 35

5-chloro-1-{[(1S,2R,5S)-6,6-dimethylbicyclo[3.1.1]hept-2-yl]methyl}-2-imino-1,2-dihydropyridine-3-carboxamide HPLC purity 99%. MS m/z 308. (M+H$^+$).
$^1$H-NMR (CDCl$_3$) δ ppm 0.92 (1 H, d, J=10.0 Hz), 1.14 (3 H, s), 1.25 (3 H, s), 1.46-1.59 (1 H, m), 1.86-2.08 (5 H, m), 2.36-2.45 (1 H, m), 2.47-2.58 (1 H, m), 3.63-3.77 (2 H, m), 5.85 (1 H, br. s.), 7.09 (1 H, d, J=2.8 Hz), 8.21 (1 H, d, J=2.6 Hz), 11.05 (1 H, br. s.).

Example 36

5-chloro-1-(2-furylmethyl)-2-imino-1,2-dihydropyridine-3-carboxamide

HPLC purity 99%. MS m/z 252 (M+H$^+$).
$^1$H-NMR (CDCl$_3$) δ ppm 4.82 (2 H, s), 5.83 (1 H, br. s.), 6.40-6.42 (1 H, m), 6.43-6.46 (1 H, m), 7.21 (1 H, d, J=2.6 Hz), 7.46 (1 H, d, J=1.3 Hz), 8.18 (1 H, d, J=2.4 Hz), 10.81 (1 H, br. s.).

Example 37

5-chloro-1-[2-(2-chlorophenyl)ethyl]-2-imino-1,2-dihydropyridine-3-carboxamide

HPLC purity 99%. MS m/z 310 (M+H$^+$).

Example 38

5-chloro-1-[2-(3-chlorophenyl)ethyl]-2-imino-1,2-dihydropyridine-3-carboxamide

HPLC purity 96%. MS m/z 310 (M+H$^+$).

Example 39

5-chloro-1-[2-(4-chlorophenyl)ethyl]-2-imino-1,2-dihydropyridine-3-carboxamide

HPLC purity 98%. MS m/z 310 (M+H$^+$).
$^1$H-NMR (CDCl$_3$) δ ppm 3.00 (2 H, t, J=7.2 Hz), 3.92 (2 H, t, J=7.2 Hz), 5.86 (1 H, br. s.), 6.81 (1 H, d, J=2.8 Hz), 7.08 (2 H, d, J=8.3 Hz), 7.32 (2 H, d, J=8.3 Hz), 8.16 (1 H, d, J=2.1 Hz), 10.87 (1H, br. s.).

Example 40

5-chloro-1-[2-(2,4-dichlorophenyl)ethyl]-2-imino-1,2-dihydropyridine-3-carboxamide HPLC purity 97%. MS m/z 344 (M+H$^+$).

Example 41

5-chloro-1-[2-(3,4-dichlorophenyl)ethyl]-2-imino-1,2-dihydropyridine-3-carboxamide HPLC purity 99%. MS m/z 344 (M+H$^+$)

Example 42

5-chloro-2-imino-1-[2-(3-methoxyphenyl)ethyl]-1,2-dihydropyridine-3-carboxamide

HPLC purity 95%. MS m/z 306 (M+H$^+$).

Example 43

5-chloro-1-[2-(3,4-dimethoxyphenyl)ethyl]-2-imino-1,2-dihydropyridine-3-carboxamide HPLC purity 94%. MS m/z 336 (M+H$^+$).

Example 44

1-[2-(4-bromophenyl)ethyl]-5-chloro-2-imino-1,2-dihydropyridine-3-carboxamide

HPLC purity 97%. MS m/z 354 (M+H$^+$).

Example 45

5-chloro-1-[2-(3-fluorophenyl)ethyl]-2-imino-1,2-dihydropyridine-3-carboxamide

HPLC purity 90%. MS m/z 294 (M+H$^+$).

Example 46

5-chloro-1-(2-cyclohex-1-en-1-ylethyl)-2-imino-1,2-dihydropyridine-3-carboxamide HPLC purity 95%. MS m/z 280 (M+H$^+$).

Example 47

5-chloro-1-[(5-chloro-2-thienyl)methyl]-2-imino-1,2-dihydropyridine-3-carboxamide HPLC purity 98%. MS m/z 302 (M+H$^+$).

Example 48

5-chloro-1-[2-(5-chloro-2-thienyl)ethyl]-2-imino-1,2-dihydropyridine-3-carboxamide HPLC purity 98%. MS m/z 316 (M+H$^+$).

Example 49

5-chloro-2-imino-1-[2-(1H-inden-3-yl)ethyl]-1,2-dihydropyridine-3-carboxamide

HPLC purity 90%. MS m/z 314 (M+H$^+$).

Example 50

5-chloro-2-imino-1-[2-(2-naphthyl)ethyl]-1,2-dihydropyridine-3-carboxamide

HPLC purity 84%. MS m/z 326 (M+H$^+$)

Example 51

1-(1-benzothien-2-ylmethyl)-5-chloro-2-imino-1,2-dihydropyridine-3-carboxamide

HPLC purity 94%. MS m/z 318 (M+H$^+$).

Example 52

5-chloro-2-imino-1-(4-phenoxybenzyl)-1,2-dihydropyridine-3-carboxamide

HPLC purity 97%. MS m/z 354 (M+H$^+$).

Example 53

1-(biphenyl-4-ylmethyl)-5-chloro-2-imino-1,2-dihydropyridine-3-carboxamide

HPLC purity 96%. MS m/z 338 (M+H$^+$).

Example 54

1-(biphenyl-2-ylmethyl)-5-chloro-2-imino-1,2-dihydropyridine-3-carboxamide

HPLC purity 99%. MS m/z 338 (M+H$^+$).

Example 55

1-(biphenyl-3-ylmethyl)-5-chloro-2-imino-1,2-dihydropyridine-3-carboxamide

HPLC purity 99%. MS m/z 338 (M+H$^+$).

Example 56

5-chloro-1-[(31,51-dichlorobiphenyl-4-yl)methyl]-2-imino-1,2-dihydropyridine-3-carboxamide HPLC purity 99%. MS m/z 406 (M+H$^+$).

Example 57

5-chloro-1-[(3',4'-dichlorobiphenyl-4-yl)methyl]-2-imino-1,2-dihydropyridine-3-carboxamide HPLC purity 98%. MS m/z 406 (M+H$^+$).
$^1$H-NMR (CDCl$_3$) δ ppm 4.94 (2 H, s), 5.83 (1 H, br. s.), 7.29 (2 H, d, J=3.0 Hz), 7.30 (1 H, d, J=1.7 Hz), 7.39 (1 H, dd, J=8.3, 2.1 Hz), 7.52 (1 H, d, J=8.0 Hz), 7.58 (2 H, d, J=8.1 Hz), 7.65 (1 H, d, J=2.1 Hz), 8.27 (1 H, d, J=2.4 Hz), 10.79 (1 H, br. s.).

Example 58

5-chloro-1-(3-cyclohexylpropyl)-2-imino-1,2-dihydropyridine-3-carboxamide

HPLC purity 94%. MS m/z 296 (M+H$^+$).

Example 59

5-chloro-1-{4-[(dimethylamino)sulfonyl]benzyl}-2-imino-1,2-dihydropyridine-3-carboxamide HPLC purity 99%. MS m/z 369 (M+H$^+$).

Example 60

5-chloro-1-[2-(2-chlorophenyl)-2-morpholin-4-ylethyl]-2-imino-1,2-dihydropyridine-3-carboxamide HPLC purity 91%. MS m/z 395 (M+H$^+$).

Example 61

5-chloro-2-imino-1-(2-phenoxypropyl)-1,2-dihydropyridine-3-carboxamide

HPLC purity 95%. MS m/z 306 (M+H$^+$)

Example 62

5-chloro-1-[2-(3,5-dichlorophenyl)-2-phenylethyl]-2-imino-1,2-dihydropyridine-3-carboxamide HPLC purity 90%. MS m/z 420 (M+H$^+$).

Example 63

5-chloro-1-[2-(3,4-dichlorophenyl)-2-phenylethyl]-2-imino-1,2-dihydropyridine-3-carboxamide HPLC purity 99%. MS m/z 420 (M+H$^+$).

Example 64

5-chloro-2-imino-1-[(1-methylpiperidin-2-yl)methyl]-1,2-dihydropyridine-3-carboxamide HPLC purity 80%. MS m/z 283 (M+H$^+$).

Example 65

5-chloro-2-imino-1-[4-(morpholin-4-ylmethyl)benzyl]-1,2-dihydropyridine-3-carboxamide HPLC purity 91%. MS m/z 361 (M+H$^+$).

Example 66

5-chloro-2-imino-1-[4-(pyrazin-2-yloxy)benzyl]-1,2-dihydropyridine-3-carboxamide HPLC purity 97%. MS m/z 356 (M+H$^+$).

Example 67

5-chloro-2-imino-1-[2-(4-methoxyphenoxy)ethyl]-1,2-dihydropyridine-3-carboxamide HPLC purity 93%. MS m/z 322 (M+H$^+$).

Example 68

5-chloro-2-imino-1-[2-(phenylthio)ethyl]-1,2-dihydropyridine-3-carboxamide

HPLC purity 94%. MS m/z 308 (M+H$^+$).

Example 69

1-(4-butylphenyl)-5-chloro-2-imino-1,2-dihydropyridine-3-carboxamide

To a solution of 2-cyano-2-(3,4-dichloro-5-oxo-2,5-dihydrofuran-2-yl)acetamide (0.5 g) in ethanol (10 ml) was added 4-butylaniline (0.95 g) (Table 1-2, amine 69), and the mixture was stirred at room temperature for 17 hr. Triethylamine (0.65 g) was added, and the mixture was further stirred at room temperature for 5 hr. The reaction mixture was concentrated and dissolved in a mixture of dimethyl sulfoxide (5 ml)-water (5 ml), and the mixture was stirred at 80° C. for 3 hr. The reaction mixture was concentrated, the residue was purified by preparative HPLC, and the obtained fraction was treated with PL-HCO$_3$ MP (200 mg cartridge, Polymer Laboratories) to give the title compound (0.15 g). HPLC purity 94%. MS m/z 304 (M+H$^+$).

$^1$H-NMR (CDCl$_3$) δ ppm 0.96 (3 H, t, J=7.3 Hz), 1.32-1.45 (2 H, m), 1.60-1.69 (2 H, m), 2.70 (2 H, d, J=8.0 Hz), 5.84 (1 H, br. s.), 6.18 (1 H, br. s.), 7.18-7.23 (3 H, m), 7.39 (2 H, d, J=8.1 Hz), 8.28 (1 H, d, J=2.8 Hz), 10.97 (1 H, br. s.).

According to the method of Example 69 and using the corresponding amines 70-118 shown in Table 1-2 to Table 1-4, the compounds of Examples 70-118 shown below were obtained.

Example 70

5-chloro-2-imino-1-(4-phenoxyphenyl)-1,2-dihydropyridine-3-carboxamide

HPLC purity 95%. MS m/z 340 (M+H$^+$).
$^1$H-NMR (CDCl$_3$) δ ppm 5.84 (1 H, br. s.), 6.19 (1 H, br. s.), 7.08-7.17 (4 H, m), 7.18-7.29 (4 H, m), 7.40-7.45 (2 H, m), 8.28 (1 H, d, J=2.6 Hz), 10.94 (1 H, br. s.).

Example 71

5-chloro-1-(2,3-dihydro-1H-inden-5-yl)-2-imino-1,2-dihydropyridine-3-carboxamide HPLC purity 96%. MS m/z 288 (M+H$^+$).
$^1$H-NMR (CDCl$_3$) δ ppm 2.09-2.25 (2 H, m), 2.89-3.09 (4 H, m), 5.85 (1 H, br. s.), 6.19 (1 H, br. s.), 7.04 (1 H, dd, J=7.9, 1.5 Hz), 7.14 (1 H, s), 7.19 (1 H, d, J=2.6 Hz), 7.40 (1H, d, J=7.7 Hz), 8.27 (1 H, d, J=2.6 Hz), 11.02 (1 H, br. s.).

Example 72

5-chloro-2-imino-1-(1-naphthyl)-1,2-dihydropyridine-3-carboxamide

HPLC purity 99%. MS m/z 298 (M+H$^+$).
$^1$H-NMR (CDCl$_3$) δ ppm 5.84 (1 H, br. s.), 5.95 (1 H, br. s.), 7.22 (1 H, d, J=2.6 Hz), 7.51 (1 H, d, J=6.4 Hz), 7.54-7.68 (4 H, m), 7.99-8.03 (1 H, m), 8.07 (1 H, d, J=8.3 Hz), 8.39 (1 H, d, J=2.8 Hz), 10.91 (1 H, br. s.).

Example 73

5-chloro-1-(2-chlorophenyl)-2-imino-1,2-dihydropyridine-3-carboxamide

HPLC purity 98%. MS m/z 282 (M+H$^+$).
$^1$H-NMR (CDCl$_3$) δ ppm 5.87 (1 H, br. s.), 6.04 (1 H, br. s.), 7.07 (1 H, d, J=2.4 Hz), 7.38-7.42 (1 H, m), 7.51-7.57 (2 H, m), 7.68 (1 H, dd, J=7.2, 2.3 Hz), 8.30 (1 H, d, J=2.6 Hz), 10.89 (1 H, br. s.).

Example 74

5-chloro-1-(4-chlorophenyl)-2-imino-1,2-dihydropyridine-3-carboxamide

HPLC purity 96%. MS m/z 282 (M+H$^+$).
$^1$H-NMR (CDCl$_3$) δ ppm 5.83 (1 H, br. s.), 6.16 (1 H, br. s.), 7.14 (1 H, d, J=2.6 Hz), 7.29 (2 H, d, J=8.5 Hz), 7.59 (2 H, d, J=8.5 Hz), 8.28 (1 H, d, J=2.6 Hz), 10.84 (1 H, br. s.).

Example 75

5-chloro-1-(3,4-dichlorophenyl)-2-imino-1,2-dihydropyridine-3-carboxamide

HPLC purity 95%. MS m/z 316 (M+H$^+$).
$^1$H-NMR (CDCl$_3$) δ ppm 5.82 (1 H, br. s.), 6.25 (1 H, br. s.), 7.12 (1 H, d, J=2.6 Hz), 7.23 (1 H, dd, J=8.7, 2.4 Hz), 7.50 (1 H, d, J=2.3 Hz), 7.70 (1 H, d, J=8.5 Hz), 8.27 (1 H, d, J=2.6 Hz), 10.76 (1H, br. s.).

Example 76

5-chloro-1-(3,5-dichlorophenyl)-2-imino-1,2-dihydropyridine-3-carboxamide

HPLC purity 96%. MS m/z 316 (M+H$^+$).
$^1$H-NMR (CDCl$_3$) δ ppm 5.84 (1 H, br. s.), 6.23 (1 H, br. s.), 7.12 (1 H, d, J=2.8 Hz), 7.30 (2 H, d, J=1.9 Hz), 7.57 (1 H, t, J=1.8 Hz), 8.27 (1 H, d, J=2.6 Hz), 10.74 (1 H, br. s.).

Example 77

5-chloro-1-(9H-fluoren-2-yl)-2-imino-1,2-dihydropyridine-3-carboxamide

HPLC purity 97%. MS m/z 336 (M+H$^+$).
$^1$H-NMR (CDCl$_3$) δ ppm 3.99 (2 H, s), 5.84 (1 H, br. s.), 6.25 (1 H, br. s.), 7.25-7.28 (1 H, m), 7.32 (1 H, dd, J=8.0, 1.2 Hz), 7.37-7.51 (3 H, m), 7.61 (1 H, d, J=7.3 Hz), 7.86 (1 H, d, J=7.3 Hz), 7.97 (1 H, d, J=8.1 Hz), 8.30 (1 H, d, J=2.6 Hz), 10.97 (1H, br. s.).

Example 78

5-chloro-1-(4-cyclohexylphenyl)-2-imino-1,2-dihydropyridine-3-carboxamide

HPLC purity 98%. MS m/z 330 (M+H$^+$)
$^1$H-NMR (CDCl$_3$) δ ppm 1.23-1.34 (1 H, m), 1.35-1.50 (4 H, m), 1.75-1.83 (1 H, m), 1.86-1.94 (4 H, m), 2.59 (1 H, t, J=10.6 Hz), 5.82 (1 H, br. s.), 6.19 (1 H, br. s.), 7.19 (1 H, d, J=2.8 Hz), 7.22 (2 H, d, J=8.3 Hz), 7.41 (2 H, d, J=8.5 Hz), 8.27 (1 H, d, J=2.6 Hz), 10.99 (1 H, br. s.).

Example 79

1-biphenyl-3-yl-5-chloro-2-imino-1,2-dihydropyridine-3-carboxamide

HPLC purity 99%. MS m/z 324 (M+H$^+$)
$^1$H-NMR (CDCl$_3$) δ ppm 5.84 (1 H, br. s.), 6.28 (1 H, br. s.), 7.24-7.27 (1 H, m), 7.28-7.33 (1 H, m), 7.39-7.45 (1 H, m), 7.49 (2 H, t, J=7.3 Hz), 7.54 (1 H, s), 7.60 (2 H, d, J=7.2 Hz), 7.67 (1 H, t, J=7.9 Hz), 7.78 (1 H, d, J=7.9 Hz), 8.30 (1 H, d, J=2.6 Hz), 10.95 (1 H, br. s.).

Example 80

5-chloro-2-imino-1-(1-phenylethyl)-1,2-dihydropyridine-3-carboxamide

HPLC purity 98%. MS m/z 276 (M+H$^+$).
$^1$H-NMR (CDCl$_3$) δ ppm 1.79 (3 H, d, J=7.0 Hz), 5.35 (1 H, q, J=6.9 Hz), 5.85 (1 H, br. s.), 7.21-7.26 (3 H, m), 7.34-7.46 (3 H, m), 8.19 (1 H, d, J=2.4 Hz), 10.88 (1 H, br. s.).

Example 81

5-chloro-2-imino-1-(1,2,3,4-tetrahydronaphthalen-1-yl)-1,2-dihydropyridine-3-carboxamide HPLC purity 99%. MS m/z 302 (M+H$^+$).

$^1$H-NMR (CDCl$_3$) δ ppm 1.76-1.99 (2 H, m), 2.03-2.31 (2 H, m), 2.76-3.08 (2 H, m), 5.42 (1 H, br. s.), 5.89 (1 H, br. s.), 6.85 (1 H, d, J=1.9 Hz), 6.97 (1 H, d, J=7.7 Hz), 7.19-7.33 (4 H, m), 8.17 (1 H, d, J=1.9 Hz), 10.90 (1 H, br. s.).

Example 82

5-chloro-2-imino-1-(5,6,7,8-tetrahydronaphthalen-1-yl)-1,2-dihydropyridine-3-carboxamide HPLC purity 100%. MS m/z 302 (M+H$^+$)
$^1$H-NMR (CDCl$_3$) δ ppm 1.75-1.86 (4 H, m), 2.45 (2 H, br. s.), 2.86 (2 H, br. s.), 5.83 (1 H, br. s.), 5.92 (1 H, br. s.), 7.03 (1 H, d, J=7.2 Hz), 7.11 (1 H, d, J=2.4 Hz), 7.25-7.33 (2 H, m), 8.30 (1 H, d, J=1.1 Hz), 10.98 (1 H, br. s.).

Example 83

1-biphenyl-2-yl-5-chloro-2-imino-1,2-dihydropyridine-3-carboxamide

HPLC purity 99%. MS m/z 324 (M+H$^+$).
$^1$H-NMR (CDCl$_3$) δ ppm 5.77 (1 H, br. s.), 6.19 (1 H, br. s.), 6.94 (1 H, d, J=2.6 Hz), 7.22 (2 H, dd, J=2.0, 7.1 Hz), 7.33-7.40 (4 H, m), 7.54-7.59 (1 H, m), 7.61-7.63 (2 H, m), 8.14 (1 H, d, J=2.1 Hz), 10.90 (1 H, br. s.).

Example 84

5-chloro-1-(3-fluorobenzyl)-2-imino-1,2-dihydropyridine-3-carboxamide

HPLC purity 99%. MS m/z 280 (M+H$^+$).
$^1$H-NMR (CDCl$_3$) δ ppm 4.89 (2 H, s), 5.84 (1 H, br. s.), 6.91 (1 H, d, J=9.2 Hz), 7.00 (1 H, d, J=7.5 Hz), 7.03-7.11 (1 H, m), 7.25 (1 H, d, J=2.6 Hz), 7.35-7.44 (1 H, m), 8.25 (1 H, d, J=2.4 Hz), 10.73 (1 H, br. s.).

Example 85

5-chloro-1-(3,5-difluorobenzyl)-2-imino-1,2-dihydropyridine-3-carboxamide

HPLC purity 99%. MS m/z 298 (M+H$^+$).
$^1$H-NMR (CDCl$_3$) δ ppm 4.88 (2 H, s), 5.84 (1 H, br. s.), 6.74 (2 H, d, J=5.8 Hz), 6.78-6.86 (1 H, m), 7.23 (1 H, d, J=2.4 Hz), 8.22 (1 H, d, J=2.1 Hz), 10.56 (1 H, br. s.).

Example 86

5-chloro-1-(3,4-difluorobenzyl)-2-imino-1,2-dihydropyridine-3-carboxamide

HPLC purity 99%. MS m/z 298 (M+H$^+$)
$^1$H-NMR (CDCl$_3$) δ ppm 4.87 (2 H, s), 5.87 (1 H, br. s.), 6.93-6.99 (1 H, m), 7.00-7.07 (1 H, m), 7.17-7.26 (2 H, m), 8.22 (1 H, d, J=2.4 Hz), 10.57 (1 H, br. s.).

Example 87

5-chloro-1-(2-ethylphenyl)-2-imino-1,2-dihydropyridine-3-carboxamide

HPLC purity 98%. MS m/z 276 (M+H$^+$)
1H-NMR (CDCl$_3$) δ ppm 1.20 (3 H, t, J=7.6 Hz), 2.49 (2 H, q, J=7.5 Hz), 5.85 (1 H, br. s.), 5.92 (1 H, br. s.), 7.13 (1 H, d, J=2.1 Hz), 7.21 (1 H, d, J=7.7 Hz), 7.38-7.45 (1 H, m), 7.46-7.55 (2 H, m), 8.31 (1 H, d, J=2.4 Hz), 10.95 (1 H, br. s.).

Example 88

5-chloro-2-imino-1-(2-isopropylphenyl)-1,2-dihydropyridine-3-carboxamide

HPLC purity 92%. MS m/z 290 (M+H$^+$)
$^1$H-NMR (CDCl$_3$) δ ppm 1.18 (3 H, d, J=7.0 Hz), 1.22 (3 H, d, J=6.8 Hz), 2.71-2.85 (1 H, m), 5.83 (1 H, br. s.), 5.91 (1 H, br. s.), 7.12 (1 H, d, J=2.4 Hz), 7.18 (1 H, d, J=7.7 Hz), 7.36-7.44 (1 H, m), 7.54 (2 H, d, J=4.1 Hz), 8.30 (1 H, d, J=2.3 Hz), 10.95 (1 H, br. s.).

Example 89

5-chloro-1-(2,3-dihydro-1H-inden-4-yl)-2-imino-1,2-dihydropyridine-3-carboxamide HPLC purity 99%. MS m/z 288 (M+H$^+$)
$^1$H-NMR (CDCl$_3$) δ ppm 2.08-2.19 (2 H, m), 2.76 (2 H, t, J=7.4 Hz), 2.98-3.10 (2 H, m), 5.84 (1 H, br. s.), 6.01 (1 H, br. s.), 7.05 (1 H, d, J=7.5 Hz), 7.16 (1 H, d, J=2.6 Hz), 7.31-7.42 (2 H, m), 8.28 (1 H, d, J=2.6 Hz), 10.98 (1 H, br. s.).

Example 90

5-chloro-1-(2,3-dichlorophenyl)-2-imino-1,2-dihydropyridine-3-carboxamide

HPLC purity 100%. MS m/z 316 (M+H$^+$)
$^1$H-NMR (CDCl$_3$) δ ppm 5.84 (1 H, br. s.), 5.98 (1 H, br. s.), 7.04 (1 H, d, J=2.4 Hz), 7.34 (1 H, dd, J=1.2, 7.8 Hz), 7.47 (1 H, t, J=8.0 Hz), 7.70 (1 H, dd, J=1.2, 8.2 Hz), 8.29 (1 H, d, J=2.4 Hz), 10.76 (1 H, br. s.).

Example 91

5-chloro-1-[2-(2-chlorophenoxy)propyl]-2-imino-1,2-dihydropyridine-3-carboxamide HPLC purity 98%. MS m/z 340 (M+H$^+$).
$^1$H-NMR (CDCl$_3$) δ ppm 1.46 (3 H, d, J=6.2 Hz), 3.86 (1 H, dd, J=8.9, 15.0 Hz), 4.13-4.23 (1 H, m), 4.63-4.83 (1 H, m), 6.85 (1 H, d, J=8.1 Hz), 6.90-6.96 (1 H, m), 7.14-7.20 (1 H, m), 7.36 (1 H, dd, J=1.5, 7.9 Hz), 7.43 (1 H, d, J=2.6 Hz), 8.03 (1 H, br. s.).

Example 92

5-chloro-2-imino-1-[(1S,2R)-2-phenylcyclopropyl]-1,2-dihydropyridine-3-carboxamide HPLC purity 94%. MS m/z 288 (M+H$^+$).
$^1$H-NMR (CDCl$_3$) δ ppm 1.59-1.66 (1 H, m), 1.74 (1 H, q, J=6.8 Hz), 2.26-2.34 (1 H, m), 2.96-3.03 (1 H, m), 5.87 (1 H, br. s.), 6.73 (1 H, br. s.), 7.19 (2 H, d, J=7.2 Hz), 7.28-7.34 (2 H, m), 7.35-7.41 (2 H, m), 8.20 (1 H, d, J=2.4 Hz), 11.01 (1 H, br. s.).

Example 93

5-chloro-2-imino-1-(1-phenylpropyl)-1,2-dihydropyridine-3-carboxamide

HPLC purity 100%. MS m/z 290 (M+H$^+$).
$^1$H-NMR (CDCl$_3$) δ ppm 1.04 (3 H, t, J=7.3 Hz), 2.06-2.28 (2 H, m), 5.13 (1 H, br. s.), 5.92 (1 H, br. s.), 7.24-7.28 (2 H, m), 7.30 (1 H, d, J=2.4 Hz), 7.33-7.47 (3 H, m), 8.23 (1 H, d, J=2.3 Hz), 10.80 (1 H, br. s.).

Example 94

5-chloro-2-imino-1-[(5-methylpyrazin-2-yl)methyl]-1,2-dihydropyridine-3-carboxamide HPLC purity 98%. MS m/z 278 (M+H$^+$).
$^1$H-NMR (CDCl$_3$) δ ppm 2.61 (3 H, s), 4.97 (2 H, s), 5.81 (1 H, br. s.), 6.61 (1 H, br. s.), 7.39 (1 H, d, J=2.6 Hz), 8.18 (1 H, br. s.), 8.46 (1 H, s), 8.50 (1 H, s), 10.89 (1 H, br. s.).

Example 95

5-chloro-2-imino-1-(pyridin-3-ylmethyl)-1,2-dihydropyridine-3-carboxamide HPLC purity 96%. MS m/z 263 (M+H$^+$).

$^1$H-NMR (CDCl$_3$) δ ppm 4.95 (2 H, s), 5.84 (1 H, br. s.), 6.22 (1 H, br. s.), 7.26-7.28 (1 H, m), 7.36 (1 H, dd, J=4.7, 7.9 Hz), 7.52 (1 H, d, J=7.3 Hz), 8.23 (1 H, br. s.), 8.58 (1 H, d, J=2.3 Hz), 8.62-8.65 (1 H, m), 10.84 (1 H, br. s.).

Example 96

5-chloro-2-imino-1-(2-pyridin-3-ylethyl)-1,2-dihydropyridine-3-carboxamide

HPLC purity 98%. MS m/z 277 (M+H$^+$).
$^1$H-NMR (CDCl$_3$) δ ppm 3.06 (2 H, t, J=7.3 Hz), 3.96 (2 H, t, J=7.3 Hz), 5.87 (1 H, br. s.), 6.31 (1 H, br. s.), 6.84 (1 H, d, J=2.6 Hz), 7.27-7.30 (1 H, m), 7.43-7.48 (1 H, br. s.), 8.14 (1 H, br. s.), 8.50 (1 H, d, J=2.1 Hz), 8.57 (1 H, dd, J=1.5, 4.9 Hz), 11.09 (1 H, br. s.).

Example 97

5-chloro-1-[(6-chloropyridin-3-yl)methyl]-2-imino-1,2-dihydropyridine-3-carboxamide HPLC purity 99%. MS m/z 298 (M+H$^+$).
$^1$H-NMR (CD$_3$OD) δ ppm 5.14 (2 H, s), 7.44 (1 H, d, J=8.3 Hz), 7.68 (1 H, br. s.), 7.74 (1 H, dd, J=2.2, 8.3 Hz), 7.80 (1 H, d, J=2.4 Hz), 8.33 (1 H, d, J=2.4 Hz).

Example 98

5-chloro-2-imino-1-(pyridin-2-ylmethyl)-1,2-dihydropyridine-3-carboxamide

HPLC purity 94%. MS m/z 263 (M+H$^+$).
$^1$H-NMR (CDCl$_3$) δ ppm 4.98 (2 H, s), 5.79 (1 H, br. s.), 6.59 (1 H, br. s.), 7.22 (1 H, d, J=7.8 Hz), 7.30 (1 H, dd, J=5.0, 7.5 Hz), 7.39 (1 H, d, J=2.4 Hz), 7.70-7.78 (1 H, m), 8.24 (1 H, br. s.), 8.63 (1 H, d, J=4.9 Hz), 10.94 (1 H, br. s.).

Example 99

5-chloro-2-imino-1-(pyridin-4-ylmethyl)-1,2-dihydropyridine-3-carboxamide

HPLC purity 89%. MS m/z 263 (M+H$^+$).
$^1$H-NMR (CDCl$_3$) δ ppm 4.92 (2 H, s), 5.82 (1 H, br. s.), 6.10 (1 H, br. s.), 7.13 (2 H, d, J=5.9 Hz), 7.25 (1 H, d, J=2.7 Hz), 8.29 (1 H, br. s.), 8.66 (2 H, d, J=6.1 Hz), 10.83 (1 H, br. s.).

Example 100

5-chloro-1-[3-(cyclopropylmethoxy)benzyl]-2-imino-1,2-dihydropyridine-3-carboxamide HPLC purity 94%. MS m/z 332 (M+H$^+$).
$^1$H-NMR (CDCl$_3$) δ ppm 0.35 (2 H, q, J=4.9 Hz), 0.61-0.71 (2 H, m), 1.20-1.33 (1 H, m), 3.79 (2 H, d, J=7.1 Hz), 4.83 (2 H, s), 5.79 (1 H, br. s.), 6.25 (1 H, br. s.), 6.72 (1 H, s), 6.78 (1 H, d, J=7.6 Hz), 6.87 (1 H, dd, J=2.2, 8.3 Hz), 7.24 (1 H, d, J=2.7 Hz), 7.32 (1 H, t, J=7.9 Hz), 8.25 (1 H, br. s.), 10.95 (1 H, br. s.).

Example 101

5-chloro-2-imino-1-[3-(2,2,2-trifluoroethoxy)benzyl]-1,2-dihydropyridine-3-carboxamide HPLC purity 97%. MS m/z 360 (M+H$^+$).
$^1$H-NMR (CDCl$_3$) δ ppm 4.36 (2 H, q, J=8.1 Hz), 4.87 (2 H, s), 5.77 (1 H, br. s.), 6.22 (1 H, br. s.), 6.80 (1 H, s), 6.87-6.94 (2 H, m), 7.24 (1 H, d, J=2.7 Hz), 7.38 (1 H, t, J=8.1 Hz), 8.26 (1 H, br. s.), 10.88 (1 H, br. s.).

Example 102

1-(3-tert-butylbenzyl)-5-chloro-2-imino-1,2-dihydropyridine-3-carboxamide

HPLC purity 91%. MS m/z 318 (M+H$^+$)
$^1$H-NMR (CDCl$_3$) δ ppm 1.32 (9 H, s), 4.87 (2 H, s), 5.80 (1 H, br. s.), 6.26 (1 H, br. s.), 6.96 (1 H, d, J=7.3 Hz), 7.23 (1 H, s), 7.25 (1 H, d, J=2.7 Hz), 7.34 (1 H, t, J=7.7 Hz), 7.38-7.42 (1 H, m), 8.26 (1 H, br. s.), 10.99 (1 H, br. s.).

Example 103

1-(1-benzothien-7-ylmethyl)-5-chloro-2-imino-1,2-dihydropyridine-3-carboxamide

HPLC purity 97%. MS m/z 318 (M+H⁺)
¹H-NMR (CDCl₃) δ ppm 5.09 (2 H, s), 5.78 (1 H, br. s.), 6.27 (1 H, br. s.), 7.12 (1 H, d, J=7.1 Hz), 7.31 (1 H, d, J=2.7 Hz), 7.42 (1 H, d, J=4.0 Hz), 7.46 (1 H, d, J=5.4 Hz), 7.52 (1 H, d, J=4.0 Hz), 7.87 (1 H, d, J=7.8 Hz), 8.29 (1 H, br. s.), 10.94 (1 H, br. s.).

Example 104

5-chloro-1-[(5-chloro-1-benzothien-2-yl)methyl]-2-imino-1,2-dihydropyridine-3-carboxamide HPLC purity 97%. MS m/z 352 (M+H⁺).
¹H-NMR (CDCl₃) δ ppm 5.11 (2 H, br. s.), 5.82 (1 H, br. s.), 6.41 (1 H, br. s.), 7.18 (1 H, s), 7.29 (1 H, d, J=2.7 Hz), 7.33 (1 H, dd, J=2.2, 8.6 Hz), 7.69-7.74 (2 H, m), 8.26 (1 H, br. s.), 10.89 (1 H, br. s.).

Example 105

1-(1-benzothien-4-ylmethyl)-5-chloro-2-imino-1,2-dihydropyridine-3-carboxamide

HPLC purity 98%. MS m/z 318 (M+H⁺).
¹H-NMR (CDCl₃) δ ppm 5.19 (2 H, s), 5.81 (1 H, br. s.), 6.30 (1 H, br. s.), 7.07 (1 H, d, J=7.3 Hz), 7.20 (1 H, d, J=2.7 Hz), 7.34-7.41 (2 H, m), 7.64 (1 H, d, J=5.6 Hz), 7.93 (1 H, d, J=8.3 Hz), 8.27 (1 H, br. s.), 10.95 (1 H, br. s.).

Example 106

5-chloro-2-imino-1-(1-methyl-1H-indazol-4-yl)-1,2-dihydropyridine-3-carboxamide

HPLC purity 88%. MS m/z 302 (M+H⁺).
¹H-NMR (CDCl₃) δ ppm 4.18 (3 H, s), 5.84 (1 H, br. s.), 6.21 (1 H, s), 7.14 (1 H, dd, J=0.9, 6.8 Hz), 7.25 (1 H, d, J=2.6 Hz), 7.53-7.63 (2 H, m), 7.86 (1 H, s), 8.34 (1 H, d, J=2.6 Hz), 10.91 (1 H, br. s.).

Example 107

1-(1-benzofuran-4-yl)-5-chloro-2-imino-1,2-dihydropyridine-3-carboxamide

HPLC purity 98%. MS m/z 288 (M+H⁺).
¹H-NMR (CDCl₃) δ ppm 5.84 (1 H, br. s.), 6.18 (1 H, br. s.), 6.66 (1 H, d, J=1.5 Hz), 7.22-7.26 (2 H, m), 7.50 (1 H, t, J=7.9 Hz), 7.71 (1 H, d, J=8.3 Hz), 7.75 (1 H, d, J=2.2 Hz), 8.31-8.35 (1 H, m), 10.92 (1 H, br. s.).

Example 108

1-(1-benzothien-4-yl)-5-chloro-2-imino-1,2-dihydropyridine-3-carboxamide

HPLC purity 98%. MS m/z 304 (M+H⁺).
¹H-NMR (CDCl₃) δ ppm 5.84 (1 H, br. s.), 6.07 (1 H, s), 7.13 (1 H, d, J=5.4 Hz), 7.24 (1 H, d, J=2.7 Hz), 7.35 (1 H, d, J=7.6 Hz), 7.54 (1 H, t, J=7.9 Hz), 7.63 (1 H, d, J=5.4 Hz), 8.07 (1 H, d, J=8.1 Hz), 8.35 (1 H, dd, J=1.3, 2.6 Hz), 10.91 (1 H, br. s.)

Example 109

1-(1-benzothien-3-ylmethyl)-5-chloro-2-imino-1,2-dihydropyridine-3-carboxamide

HPLC purity 99%. MS m/z 318 (M+H⁺).
¹H-NMR (CDCl₃) δ ppm 5.07 (2 H, s), 5.82 (1 H, br. s.), 6.39 (1 H, br. s.), 7.21 (1 H, d, J=2.7 Hz), 7.26 (1 H, s), 7.43-7.50 (2 H, m), 7.65-7.69 (1 H, m), 7.90-7.96 (1 H, m), 8.25 (1 H, br. s.), 10.97 (1 H, br. s.).

Example 110

5-chloro-1-[2-(3-fluorophenoxy)propyl]-2-imino-1,2-dihydropyridine-3-carboxamide HPLC purity 96%. MS m/z 324 (M+H⁺).
¹H-NMR (CDCl₃) δ ppm 1.42 (3 H, d, J=6.1 Hz), 3.79 (1 H, br. s.), 4.03 (1 H, br. s.), 4.71 (1 H, br. s.), 5.85 (1 H, br. s.), 6.32 (1 H, br. s.), 6.53-6.59 (1 H, m), 6.62 (1 H, dd, J=2.0, 8.3 Hz), 6.65-6.71 (1 H, m), 7.16-7.24 (1 H, m), 7.25 (1 H, d, J=2.7 Hz), 8.12 (1 H, br. s.), 11.01 (1 H, br. s.).

Example 111

5-chloro-1-[2-(3-chlorophenoxy)propyl]-2-imino-1,2-dihydropyridine-3-carboxamide HPLC purity 96%. MS m/z 340 (M+H⁺).
¹H-NMR (CDCl₃) δ ppm 1.42 (3 H, d, J=6.1 Hz), 3.78 (1 H, dd, J=8.8, 14.9 Hz), 4.03-4.15 (1 H, m), 4.72 (1 H, br. s.), 5.84 (1 H, br. s.), 6.72 (1 H, dd, J=2.3, 8.3 Hz), 6.85 (1 H, t, J=2.2 Hz), 6.95 (1 H, dd, J=1.0, 7.8 Hz), 7.18 (1 H, t, J=8.2 Hz), 7.24 (1 H, d, J=2.9 Hz), 8.03 (1 H, br. s.), 10.99 (1 H, br. s.).

Example 112

5-chloro-1-[2-(3,4-dichlorophenoxy)propyl]-2-imino-1,2-dihydropyridine-3-carboxamide HPLC purity 100%. MS m/z 374 (M+H⁺).
¹H-NMR (CDCl₃) δ ppm 1.41 (3 H, d, J=6.4 Hz), 3.78 (1 H, br. s.), 3.98-4.17 (1 H, m), 4.69 (1 H, br. s.), 5.81 (1 H, br. s.), 6.31 (1 H, br. s.), 6.70 (1 H, dd, J=2.9, 8.8 Hz), 6.96 (1 H, d, J=2.9 Hz), 7.22 (1 H, d, J=2.7 Hz), 7.31 (1 H, d, J=8.8 Hz), 10.94 (1 H, br. s.).

Example 113

5-chloro-2-imino-1-(pyrazolo[1,5-a]pyridin-2-ylmethyl)-1,2-dihydropyridine-3-carboxamide HPLC purity 99%. MS m/z 302 (M+H⁺).
¹H-NMR (CDCl₃) δ ppm 5.04 (2 H, s), 5.80 (1 H, br. s.), 6.43 (1 H, s), 6.64-6.76 (1 H, m), 6.79-6.86 (1 H, m), 7.11-7.20 (1 H, m), 7.39 (1 H, d, J=2.7 Hz), 7.48-7.52 (1 H, m), 8.22 (1 H, br. s.), 8.42 (1 H, dd, J=1.0, 7.1 Hz), 11.01 (1 H, br. s.).

Example 114

1-(1-benzofuran-2-ylmethyl)-5-chloro-2-imino-1,2-dihydropyridine-3-carboxamide

HPLC purity 97%. MS m/z 302 (M+H⁺).
¹H-NMR (CDCl₃) δ ppm 4.97 (2 H, s), 5.79 (1 H, br. s.), 6.55 (1 H, br. s.), 6.79 (1 H, s), 7.24-7.29 (1 H, m), 7.32 (1 H, d, J=2.7 Hz), 7.34-7.36 (1 H, m), 7.49 (1 H, d, J=8.8 Hz), 7.57 (1 H, d, J=7.8 Hz), 8.23 (1 H, br. s.), 10.98 (1 H, br. s.).

Example 115

5-chloro-2-imino-1-(3-pyridin-2-ylbenzyl)-1,2-dihydropyridine-3-carboxamide

HPLC purity 95%. MS m/z 339 (M+H$^+$).
$^1$H-NMR (CDCl$_3$) δ ppm 4.97 (2 H, s), 5.78 (1 H, br. s.), 6.31 (1 H, br. s.), 7.22 (1 H, d, J=7.6 Hz), 7.27-7.31 (1 H, m), 7.31 (1 H, d, J=2.7 Hz), 7.52 (1 H, t, J=7.8 Hz), 7.70-7.74 (1 H, m), 7.77-7.82 (1 H, m), 7.91-7.96 (2 H, m), 8.27 (1 H, br. s.), 8.70-8.73 (1 H, m), 10.98 (1 H, br. s.).

Example 116

5-chloro-1-[3-(1-hydroxy-1-methylethyl)benzyl]-2-imino-1,2-dihydropyridine-3-carboxamide HPLC purity 98%. MS m/z 320 (M+H$^+$).
$^1$H-NMR (CDCl$_3$) δ ppm 1.58 (6 H, s), 4.89 (2 H, s), 5.79 (1 H, br. s.), 6.29 (1 H, br. s.), 7.04 (1 H, d, J=7.8 Hz), 7.25-7.27 (1 H, m), 7.35-7.40 (1 H, m), 7.42-7.46 (2 H, m), 8.25 (1 H, br. s.), 11.06 (1 H, br. s.).

Example 117

5-chloro-1-[(2-ethoxypyridin-4-yl)methyl]-2-imino-1,2-dihydropyridine-3-carboxamide HPLC purity 98%. MS m/z 307 (M+H$^+$).
$^1$H-NMR (CDCl$_3$) δ ppm 1.39 (3 H, t, J=7.1 Hz), 4.36 (2 H, q, J=7.0 Hz), 4.82 (2 H, s), 5.81 (1 H, br. s.), 6.12 (1 H, br. s.), 6.49 (1 H, s), 6.67-6.72 (1 H, m), 7.23 (1 H, d, J=2.6 Hz), 8.17 (1 H, d, J=5.3 Hz), 8.29 (1 H, br. s.), 10.88 (1 H, br. s.).

Example 118

5-chloro-2-imino-1-[(1S)-1-phenylethyl]-1,2-dihydropyridine-3-carboxamide

HPLC purity 97%. MS m/z 276 (M+H$^+$).
$^1$H-NMR (CDCl$_3$) δ ppm 1.79 (3 H, d, J=7.0 Hz), 5.39 (1 H, d, J=6.6 Hz), 5.87 (1 H, br. s.), 7.21-7.26 (3 H, m), 7.33-7.46 (3 H, m), 8.20 (1 H, d, J=2.4 Hz), 10.81 (1 H, br. s.).

Example 119

5-chloro-1-(3-chlorobenzyl)-2-imino-1,2-dihydropyridine-3-carboxamide hydrochloride 5-Chloro-1-(3-chlorobenzyl)-2-imino-1,2-dihydropyridine-3-carboxamide (0.1 g) obtained in Example 19 was dissolved in ethyl acetate (2 ml), and 4N hydrochloric acid-ethyl acetate solution (0.5 ml) was added. The precipitated crystals were collected by filtration to give the title compound (85 mg).
HPLC purity 100%. MS m/z 297 (M+H$^+$).
$^1$H-NMR (DMSO-d$_6$) δ ppm 5.61 (2 H, s), 7.22-7.29 (1 H, m), 7.39-7.53 (4 H, m), 8.22 (1 H, s), 8.71 (1 H, d, J=2.1 Hz), 8.73 (1 H, br. s.), 8.85 (1 H, d, J=2.1 Hz), 9.56 (2 H, br. s.).

Example 120

1-benzyl-5-bromo-2-imino-1,2-dihydropyridine-3-carboxamide

Mucobromic acid (2.5 g) and 2-cyanoacetamide (0.82 g) were dissolved in methanol (10 ml), and 1.5N aqueous sodium hydroxide solution (10 ml) was added dropwise with stirring under ice-cooling. The mixture was allowed to warm to room temperature and further stirred at room temperature for 4 hr. The reaction mixture was poured into 1N hydrochloric acid containing ice water, methanol was evaporated under reduced pressure, and the residue was extracted with ethyl acetate. The extract was washed with saturated brine and dried over anhydrous magnesium sulfate, and the solvent was evaporated under reduced pressure. A solution of the obtained candy-like compound, benzylamine (3.12 g) and triethylamine (5.9 g) in ethanol (50 ml) was stirred at room temperature for 8 hr. The reaction mixture was concentrated, a mixture of dimethyl sulfoxide (5 ml)-water (5 ml) was added, and the mixture was stirred at 80° C. for 1 hr. The reaction mixture was concentrated, the residue was purified by preparative HPLC, and the obtained fraction was treated with PL-HCO$_3$MP (200 mg cartridge, Polymer Laboratories) to give the title compound (10 mg).
HPLC purity 96%. MS m/z 307 (M+H$^+$).
$^1$H-NMR (CDCl$_3$) δ ppm 4.90 (2 H, s), 5.84 (1 H, br. s.), 7.21 (1 H, d, J=7.2 Hz), 7.30-7.46 (5 H, m), 8.33 (1 H, br. s.), 10.83 (1 H, br. s.).

Example 121

1-(3-chlorobenzyl)-2-imino-1,2-dihydropyridine-3-carboxamide hydrobromide

To a solution of 2-aminonicotinamide (0.1 g) in N,N-dimethylformamide (3 ml) was added 1-(bromomethyl)-3-chlorobenzene (0.3 g), and the mixture was stirred at 80° C. for 15 hr. The precipitated crystals were collected by filtration and washed with ethyl acetate to give the title compound (90 mg).
HPLC purity 99%. MS m/z 262 (M+H$^+$).
$^1$H-NMR (DMSO-d$_6$) δ ppm 5.57 (2 H, s), 7.14 (1 H, t, J=7.1 Hz), 7.18 (1 H, d, J=5.6 Hz), 7.41-7.49 (3 H, m), 8.11 (1 H, s), 8.42 (1 H, d, J=6.6 Hz), 8.50 (1 H, d, J=7.1 Hz), 8.56 (1 H, br. s.), 9.33 (2 H, br. s.).

Example 122

1-(2,5-dichlorobenzyl)-2-imino-1,2-dihydropyridine-3-carboxamide hydrobromide

To a solution of 2-aminonicotinamide (0.2 g) in N,N-dimethylformamide (5 ml) was added 2,5-dichlorobenzylbromide (0.39 g) (Table 2, bromide 122), and the mixture was stirred at 80° C. for 14 hr. The reaction mixture was diluted with ethyl acetate. The precipitate was collected by filtration and washed with ethyl acetate. The obtained precipitate was recrystallized from methanol-ethyl acetate to give the title compound (0.21 g).
$^1$H-NMR (DMSO-d$_6$) d ppm 5.52 (2 H, s) 6.95 (1 H, d, J=2.27 Hz) 7.06-7.17 (1 H, m) 7.50-7.59 (1 H, m) 7.63-7.71 (1 H, m) 8.13 (1 H, s) 8.23 (1 H, d, J=5.30 Hz) 8.52 (1 H, d, J=6.82 Hz) 8.59 (1 H, s) 9.45 (2 H, s).

According to the method of Example 122 and using the corresponding bromides 123-133 shown in Table 2, the compounds of Examples 123-133 shown below were obtained.

Example 123

1-(3,4-dichlorobenzyl)-2-imino-1,2-dihydropyridine-3-carboxamide hydrobromide $^1$H-NMR (DMSO-d$_6$) d ppm 5.54 (2 H, s) 7.08-7.17 (1 H, m) 7.22 (1 H, dd, J=8.52, 2.08 Hz) 7.66 (1 H, d, J=1.89 Hz)

7.70 (1 H, d, J=8.33 Hz) 8.09 (1 H, s) 8.40 (1 H, d, J=6.82 Hz) 8.49 (1 H, d, J=6.44 Hz) 8.55 (1 H, s) 9.33 (2 H, s).

Example 124

1-(2,3-dichlorobenzyl)-2-imino-1,2-dihydropyridine-3-carboxamide hydrobromide $^1$H-NMR (DMSO-d$_6$) d ppm 5.57 (2 H, s) 6.70 (1 H, d, J=6.82 Hz) 7.09-7.19 (1 H, m) 7.37 (1 H, t, J=7.95 Hz) 7.70 (1 H, dd, J=8.14, 1.33 Hz) 8.13 (1 H, s) 8.29 (1 H, dd, J=6.63, 1.33 Hz) 8.55 (1 H, dd, J=7.57, 1.14 Hz) 8.59 (1 H, s) 9.42 (2 H, s).

Example 125

1-(3-cyanobenzyl)-2-imino-1,2-dihydropyridine-3-carboxamide hydrobromide $^1$H-NMR (DMSO-d$_6$) d ppm 5.62 (2 H, s) 7.14 (1 H, dd, J=7.54, 6.78 Hz) 7.53-7.69 (2 H, m) 7.79 (1 H, s) 7.83-7.92 (1 H, m) 8.09 (1 H, s) 8.42 (1 H, dd, J=6.69, 1.41 Hz) 8.52 (1 H, d, J=7.54 Hz) 8.56 (1 H, s) 9.34 (2 H, s).

Example 126

1-(3-chloro-4-fluorobenzyl)-2-imino-1,2-dihydropyridine-3-carboxamide hydrobromide $^1$H-NMR (DMSO-d$_6$) d ppm 5.52 (2 H, s) 7.12 (1 H, t, J=7.06 Hz) 7.30 (1 H, s) 7.49 (1 H, t, J=8.85 Hz) 7.64 (1 H, d, J=6.59 Hz) 8.09 (1 H, s) 8.39 (1 H, s) 8.49 (1 H, d, J=7.35 Hz) 8.55 (1 H, s) 9.34 (2 H, s).

Example 127

1-(3-chloro-2-fluorobenzyl)-2-imino-1,2-dihydropyridine-3-carboxamide hydrobromide $^1$H-NMR (DMSO-d$_6$) d ppm 5.66 (2 H, s) 6.93 (1 H, t, J=7.06 Hz) 7.11-7.18 (1 H, m) 7.19-7.29 (1 H, m) 7.60-7.69 (1 H, m) 8.12 (1 H, s) 8.33 (1 H, d, J=6.59 Hz) 8.54 (1 H, d, J=7.53 Hz) 8.58 (1 H, s) 9.38 (2 H, s).

Example 128

1-[3-(4-fluorophenoxy)benzyl]-2-imino-1,2-dihydropyridine-3-carboxamide hydrobromide $^1$H-NMR (DMSO-d$_6$) d ppm 5.54 (2 H, s) 6.90-7.01 (3 H, m) 7.04-7.16 (3 H, m) 7.19-7.30 (2 H, m) 7.41 (1 H, t, J=7.82 Hz) 8.09 (1 H, s) 8.39 (1 H, d, J=6.59 Hz) 8.49 (1 H, d, J=6.97 Hz) 8.55 (1 H, s) 9.29 (2 H, s).

Example 129

1-(3-bromobenzyl)-2-imino-1,2-dihydropyridine-3-carboxamide hydrobromide $^1$H-NMR (DMSO-d$_6$) d ppm 5.55 (2 H, s) 7.09-7.17 (1 H, m) 7.20 (1 H, t, J=7.72 Hz) 7.38 (1 H, t, J=7.91 Hz) 7.52-7.64 (2 H, m) 8.09 (1 H, s) 8.41 (1 H, dd, J=6.69, 1.22 Hz) 8.45-8.51 (1 H, m) 8.55 (1 H, s) 9.31 (2 H, s).

Example 130

1-[3-chloro-4-(trifluoromethoxy)benzyl]-2-imino-1,2-dihydropyridine-3-carboxamide hydrobromide $^1$H-NMR (DMSO-d$_6$) d ppm 5.58 (2 H, s) 7.09-7.18 (1 H, m) 7.30 (1 H, dd, J=8.52, 2.08 Hz) 7.63 (1 H, dd, J=8.52, 1.33 Hz) 7.69 (1 H, d, J=2.27 Hz) 8.09 (1 H, s) 8.41 (1 H, dd, J=6.82, 1.14 Hz) 8.50 (1 H, dd, J=7.57, 1.14 Hz) 8.55 (1 H, s) 9.34 (2 H, s).

Example 131

1-(3-chloro-5-fluorobenzyl)-2-imino-1,2-dihydropyridine-3-carboxamide hydrobromide $^1$H-NMR (DMSO-d$_6$) d ppm 5.57 (2 H, s) 7.07-7.21 (2 H, m) 7.27 (1 H, s) 7.45-7.54 (1 H, m) 8.09 (1 H, s) 8.41 (1 H, dd, J=6.63, 1.33 Hz) 8.51 (1 H, dd, J=7.57, 1.14 Hz) 8.55 (1 H, s) 9.34 (2 H, s).

Example 132

1-(biphenyl-3-ylmethyl)-2-imino-1,2-dihydropyridine-3-carboxamide hydrobromide $^1$H-NMR (DMSO-d$_6$) d ppm 5.63 (2 H, s) 7.10-7.18 (1 H, m) 7.22 (1 H, d, J=7.91 Hz) 7.36-7.44 (1 H, m) 7.45-7.56 (3 H, m) 7.67 (4 H, dd, J=8.10, 6.78 Hz) 8.09 (1 H, s) 8.45-8.52 (2 H, m) 8.53-8.59 (1 H, m) 9.34 (2 H, s).

Example 133

2-imino-1-(3-phenoxybenzyl)-1,2-dihydropyridine-3-carboxamide hydrobromide $^1$H-NMR (DMSO-d$_6$) d ppm 5.54 (2 H, s) 6.89-7.06 (5 H, m) 7.07-7.22 (2 H, m) 7.36-7.46 (3 H, m) 8.09 (1 H, s) 8.39 (1 H, dd, J=6.59, 1.13 Hz) 8.48 (1 H, d, J=7.54 Hz) 8.54 (1 H, s) 9.29 (2 H, s).

Example 134

1-(3,5-dichlorobenzyl)-2imino-1,2-dihydropyridine-3-carboxamide hydrochloride

To a solution of 2-aminonicotinamide (0.18 g) in N,N-dimethylformamide (3 ml) was added 3,5-dichlorobenzyl chloride (0.31 g), and the mixture was stirred at 80° C. for 14 hr. The reaction mixture was diluted with ethyl acetate. The precipitate was collected by filtration and washed with ethyl acetate. The obtained precipitate was recrystallized from methanol-ethyl acetate to give the title compound (0.10 g).

$^1$H-NMR (DMSO-d$_6$) d ppm 5.62 (2 H, s) 7.12 (1 H, t, J=7.19 Hz) 7.42 (2 H, d, J=1.51 Hz) 7.66 (1 H, s) 8.09 (1 H, s) 8.44 (1 H, d, J=6.06 Hz) 8.55 (1 H, d, J=7.57 Hz) 8.64 (1 H, s) 9.49 (2 H, s).

Example 135

5-bromo-1-(3-chlorobenzyl)-2-imino-1,2-dihydropyridine-3-carboxamide hydrobromide To a solution of 2-amino-5-bromonicotinamide (0.15 g) in N,N-dimethylformamide (3 ml) was added 3-chlorobenzylbromide (0.17 g), and the mixture was stirred at 80° C. for 4 hr. The reaction mixture was diluted with ethyl acetate. The precipitate was collected by filtration and washed with ethyl acetate. The obtained precipitate was recrystallized from methanol-ethyl acetate to give the title compound (0.05 g).

$^1$H-NMR (DMSO-$d_6$) d ppm 5.53 (2 H, s) 7.12-7.26 (1 H, m) 7.39-7.52 (3 H, m) 8.20 (1 H, s) 8.57 (1 H, s) 8.66 (1 H, d, J=2.20 Hz) 8.83 (1 H, d, J=2.20 Hz) 9.41 (2 H, s).

Example 136

5-chloro-1-(3-cyanobenzyl)-2-imino-1,2-dihydropyridine-3-carboxamide hydrobromide (Step 1) To a solution of 2-aminonicotinamide (0.5 g) in concentrated hydrochloric acid (3 ml) was added dropwise 30% aqueous hydrogen peroxide (0.3 ml). After stirring at 60° C. for 1 hr, the reaction mixture was diluted with water and basified with 1N aqueous sodium hydroxide solution. The mixture was extracted with a mixed solution of ethyl acetate and THF, washed with saturated brine and dried over magnesium sulfate. The reaction solvent was concentrated under reduced pressure, and the residue was purified by silica gel chromatography (ethyl acetate) to give 2-amino-5-chloronicotinamide as crystals (0.25 g).

$^1$H-NMR (DMSO-$d_6$) d ppm 7.36 (2 H, s) 7.46 (1 H, s) 7.99-8.07 (2 H, m) 8.10 (1 H, d, J=2.65 Hz).

(Step 2) To a solution of 2-amino-5-chloronicotinamide (0.14 g) obtained in Step 1 in N,N-dimethylformamide (3 ml) was added 3-cyanobenzylbromide (0.19 g), and the mixture was stirred at 105° C. for 5 hr. The reaction mixture was diluted with ethyl acetate. The precipitate was collected by filtration and washed with ethyl acetate. The obtained precipitate was recrystallized from methanol-ethyl acetate to give the title compound (85 mg).

$^1$H-NMR (DMSO-$d_6$) d ppm 5.60 (2 H, s) 7.64 (2 H, d, J=4.92 Hz) 7.79-7.90 (2 H, m) 8.21 (1 H, s) 8.60 (1 H, s) 8.65 (1 H, d, J=2.27 Hz) 8.80 (1 H, d, J=2.27 Hz) 9.44 (2 H, s).

According to the method of Example 136 and using the corresponding bromides 137-148 shown in Table 2, the compounds of Examples 137-148 shown below were obtained.

Example 137

5-chloro-1-(3-fluoro-4-methoxybenzyl)-2-imino-1,2-dihydropyridine-3-carboxamide hydrobromide $^1$H-NMR (DMSO-$d_6$) d ppm 3.84 (3 H, s) 5.44 (2 H, s) 7.13-7.34 (3H, m) 8.18 (1 H, s) 8.55 (1 H, s) 8.58 (1 H, dd, J=1.8 Hz) 8.74 (1 H, d, J=2.1 Hz) 9.38 (2 H, s).

Example 138

5-chloro-1-(5-fluoro-2-methoxybenzyl)-2-imino-1,2-dihydropyridine-3-carboxamide hydrobromide 1H-NMR (DMSO-$d_6$) d ppm 3.83 (3 H, s) 5.40 (2 H, s) 7.03 (1 H, dd, J=9.09, 3.03 Hz) 7.09-7.16 (1 H, m) 7.19-7.29 (1 H, m) 8.20 (1 H, s) 8.57 (1 H, s) 8.62 (2 H, dd, J=9.66, 2.08 Hz) 9.38 (2 H, s).

Example 139

5-chloro-2-imino-1-(3-methylbenzyl)-1,2-dihydropyridine-3-carboxamide hydrobromide $^1$H-NMR (DMSO-$d_6$) d ppm 2.31 (3 H, s) 5.50 (2 H, s) 7.00-7.24 (3 H, m) 7.31 (1 H, t, J=7.57 Hz) 8.20 (1 H, s) 8.58 (1 H, s) 8.62 (1 H, d, J=1.89 Hz) 8.76 (1 H, d, J=1.89 Hz) 9.38 (2 H, s).

Example 140

5-chloro-1-[(3-chloro-2-thienyl)methyl]-2-imino-1,2-dihydropyridine-3-carboxamide hydrobromide $^1$H-NMR (DMSO-$d_6$) d ppm 5.67 (2 H, s) 7.20 (1 H, d, J=5.46 Hz) 7.80 (1 H, d, J=5.46 Hz) 8.23 (1 H, s) 8.53 (1 H, d, J=2.26 Hz) 8.55-8.62 (2 H, m) 9.59 (2 H, s).

Example 141

5-chloro-1-(2,5-dimethoxybenzyl)-2-imino-1,2-dihydropyridine-3-carboxamide hydrochloride $^1$H-NMR (DMSO-$d_6$) d ppm 3.70 (3 H, s) 3.77 (3 H, s) 5.38 (2 H, s) 6.74-7.09 (3 H, m) 8.18 (1 H, s) 8.48-8.66 (3 H, m) 9.35 (2 H, s).

Example 142

5-chloro-1-(3-ethoxybenzyl)-2-imino-1,2-dihydropyridine-3-carboxamide hydrobromide $^1$H-NMR (DMSO-$d_6$) d ppm 1.32 (3 H, t, J=6.97 Hz) 4.02 (2 H, q, J=6.97 Hz) 5.48 (2 H, s) 6.81 (1 H, d, J=8.10 Hz) 6.87-6.98 (2 H, m) 7.33 (1 H, t, J=8.01 Hz) 8.19 (1 H, s) 8.56 (1 H, s) 8.60 (1 H, d, J=2.26 Hz) 8.76 (1 H, d, J=2.26 Hz) 9.36 (2 H, s).

Example 143

5-chloro-1-(3,5-dimethoxybenzyl)-2-imino-1,2-dihydropyridine-3-carboxamide hydrobromide $^1$H-NMR (DMSO-$d_6$) d ppm 3.74 (6 H, s) 5.45 (2 H, s) 6.48 (2 H, d, J=1.89 Hz) 6.53 (1 H, t, J=2.08 Hz) 8.20 (1 H, s) 8.58 (1 H, s) 8.61 (1 H, d, J=2.27 Hz) 8.76 (1 H, d, J=2.27 Hz) 9.34 (2 H, s).

Example 144

5-chloro-2-imino-1-[3-(trifluoromethoxy)benzyl]-1,2-dihydropyridine-3-carboxamide hydrobromide $^1$H-NMR (DMSO-$d_6$) d ppm 5.60 (2 H, s) 7.26 (1 H, d, J=7.57 Hz) 7.36-7.46 (2 H, m) 7.56 (1 H, t, J=7.76 Hz) 8.21 (1 H, s) 8.59 (1 H, s) 8.64 (1 H, s) 8.83 (1 H, s) 9.44 (2 H, s).

Example 145 methyl 3-{[3-(aminocarbonyl)-5-chloro-2-iminopyridin-1(2H)-yl]methyl}benzoate hydrobromide $^1$H-NMR (DMSO-$d_6$) d ppm 3.87 (3 H, s) 5.61 (2 H, s) 7.46-7.63 (2 H, m) 7.92-8.00 (2 H, m) 8.20 (1 H, s) 8.56 (1 H, d) 8.61 (1 H, d, J=1.89 Hz) 8.83 (1 H, d, J=1.89 Hz) 9.42 (2 H, s).

Example 146

5-chloro-1-[3-(difluoromethoxy)benzyl]-2-imino-1,2-dihydropyridine-3-carboxamide hydrobromide $^1$H-NMR (DMSO-d$_6$) d ppm 5.61 (2 H, s) 6.93-7.57 (5 H, m) 8.20 (1 H, s) 8.70 (2 H, s) 8.83 (1 H, s) 9.55 (2 H, s).

Example 147

5-chloro-1-(2-fluoro-5-methoxybenzyl)-2-imino-1,2-dihydropyridine-3-carboxamide hydrobromide $^1$H-NMR (DMSO-d$_6$) d ppm 3.73 (3 H, s) 5.56 (2 H, s) 6.77 (1 H, dd, J=6.12, 2.92 Hz) 6.96-7.04 (1 H, m) 7.21-7.30 (1 H, m) 8.21 (1 H, s) 8.59 (1 H, s) 8.63 (1 H, d, J=1.88 Hz) 8.68 (1 H, d, J=0.75 Hz) 9.45 (2 H, s).

Example 148

1-[3-(aminocarbonyl)benzyl]-5-chloro-2-imino-1,2-dihydropyridine-3-carboxamide hydrobromide $^1$H-NMR (DMSO-d$_6$) d ppm 5.59 (2 H, s) 7.39-7.55 (3 H, m) 7.76 (1 H, s) 7.88 (1 H, d, J=7.95 Hz) 8.03 (1 H, s) 8.20 (1 H, s) 8.59 (1 H, s) 8.64 (1 H, d, J=2.27 Hz) 8.81 (1 H, d, J=2.27 Hz) 9.40 (2 H, s).

Example 149

5-chloro-1-[4-chloro-2-(methylsulfonyl)benzyl]-2-imino-1,2-dihydropyridine-3-carboxamide hydrobromide To a solution of 2-amino-5-chloronicotinamide (0.15 g) in N,N-dimethylformamide (3 ml) was added 1-(bromomethyl)-4-chloro-2-(methylsulfonyl)benzene (0.37 g), and the mixture was stirred at 100° C. for 14 hr. The reaction mixture was diluted with ethyl acetate. The precipitate was collected by filtration and washed with ethyl acetate. The obtained precipitate was recrystallized from methanol-ethyl acetate to give the title compound (50 mg).

$^1$H-NMR (DMSO-d$_6$) d ppm 3.46 (3 H, s) 5.82 (2 H, s) 7.04 (1 H, d, J=8.33 Hz) 7.76 (1 H, dd, J=8.33, 2.27 Hz) 8.08 (1 H, d, J=2.27 Hz) 8.24 (1 H, s) 8.63 (1 H, s) 8.67 (2 H, d, J=4.16 Hz) 9.58 (2 H, s).

Example 150

5-chloro-2-imino-1-[4-(methylsulfonyl)benzyl]-1,2-dihydropyridine-3-carboxamide hydrobromide To a solution of 2-amino-5-chloronicotinamide (0.15 g) in N,N-dimethylformamide (3 ml) was added 1-(bromomethyl)-4-(methylsulfonyl)benzene (0.33 g), and the mixture was stirred at 100° C. for 8 hr. The reaction mixture was diluted with ethyl acetate. The precipitate was collected by filtration and washed with ethyl acetate. The obtained precipitate was recrystallized from methanol-ethyl acetate to give the title compound (126 mg).

$^1$H-NMR (DMSO-d$_6$) d ppm 3.23 (3 H, s) 5.66 (2 H, s) 7.52 (2 H, d, J=8.33 Hz) 7.96 (2 H, d, J=8.33 Hz) 8.21 (1 H, s) 8.59 (1 H, s) 8.64 (1 H, d, J=1.89 Hz) 8.82 (1 H, d, J=2.27 Hz) 9.42 (2 H, s).

Example 151

1-(3-chlorobenzyl)-5-cyano-2-imino-1,2-dihydropyridine-3-carboxamide hydrobromide To a solution of 2-amino-5-cyanonicotinamide (0.15 g) in N,N-dimethylformamide (3 ml) was added 3-chlorobenzylbromide (0.29 g), and the mixture was stirred at 100° C. for 8 hr. The reaction mixture was diluted with ethyl acetate. The precipitate was filtered and washed with ethyl acetate. The obtained precipitate was recrystallized from methanol-ethyl acetate to give the title compound (0.09 g).

$^1$H-NMR (DMSO-d$_6$) d ppm 5.56 (2 H, s) 7.28 (1 H, d, J=5.68 Hz) 7.38-7.55 (3 H, m) 8.25 (1 H, s) 8.56 (1 H, s) 8.75 (1 H, s) 9.20 (1 H, s) 9.53 (1 H, s) 10.35 (1 H, s).

Example 152

5-chloro-2-imino-1-[2-methoxy-5-(methylsulfonyl)benzyl]-1,2-dihydropyridine-3-carboxamide hydrobromide To a solution of 2-amino-5-chloronicotinamide (0.15 g) in N,N-dimethylformamide (3 ml) was added 2-(bromomethyl)-1-methoxy-4-(methylsulfonyl)benzene (0.29 g), and the mixture was stirred at 100° C. for 4 hr. The reaction mixture was diluted with ethyl acetate. The precipitate was collected by filtration and washed with ethyl acetate. The obtained precipitate was recrystallized from methanol-ethyl acetate to give the title compound (110 mg).

$^1$H-NMR (DMSO-d$_6$) d ppm 3.17 (3 H, s) 3.92 (3 H, s) 5.47 (2 H, s) 7.74 (1 H, s) 7.98 (1 H, dd, J=8.67, 2.26 Hz) 8.21 (1 H, s) 8.59-8.66 (3 H, m) 9.40 (2 H, s).

Example 153

5-chloro-2-imino-1-{[5-(trifluoromethyl)-2-furyl]methyl}-1,2-dihydropyridine-3-carboxamide hydrochloride To a solution of 2-amino-5-chloronicotinamide (0.15 g) in N,N-dimethylformamide (3 ml) was added 2-(bromomethyl)-5-(trifluoromethyl)furan (0.30 g), and the mixture was stirred at 100° C. for 4 hr. The reaction mixture was diluted with ethyl acetate. The precipitate was collected by filtration and washed with ethyl acetate. The obtained precipitate was recrystallized from methanol-ethyl acetate. The obtained crystals were dissolved in aqueous sodium hydrogen carbonate solution, and the mixture was extracted with ethyl acetate, washed with saturated brine and dried over anhydrous magnesium sulfate. The solvent was evaporated under reduced pressure and the obtained residue was treated by silica gel chromatography (ethyl acetate 100%→ethyl acetate:methanol=5:1) to give a yellow solid. The obtained solid was dissolved in methanol, and 2N hydrochloric acid-methanol solution (0.3 ml) was added. The solvent was concentrated under reduced pressure and the residue was crystallized from methanol-ethyl acetate to give the title compound (45 mg).

$^1$H-NMR (DMSO-d$_6$) d ppm 5.67 (2 H, s) 6.91 (1 H, d, J=2.65 Hz) 7.28 (1 H, d, J=2.27 Hz) 8.19 (1 H, s) 8.61 (2 H, d, J=1.89 Hz) 8.80 (1 H, d, J=1.89 Hz) 9.65 (2 H, s).

Example 154

5-chloro-1-[2-chloro-4-(methylsulfonyl)benzyl]-2-imino-1,2-dihydropyridine-3-carboxamide hydrobromide To a solution of 2-amino-5-chloronicotinamide (0.15 g) in N,N-dimethylformamide (3 ml) was added 1-(bromomethyl)-2-chloro-4-(methylsulfonyl)benzene (0.37 g), and the mixture was stirred at 100° C. for 14 hr. The reaction mixture was diluted with ethyl acetate. The precipitate was collected by filtration and washed with ethyl acetate. The obtained precipitate was recrystallized from methanol-ethyl acetate to give the title compound (90 mg).

$^1$H-NMR (DMSO-$d_6$) d ppm 3.31 (3 H, s) 5.61 (2 H, s) 7.04-7.21 (1 H, m) 7.73-7.89 (1 H, m) 8.10-8.18 (1 H, m) 8.20-8.30 (1 H, m) 8.59-8.65 (1 H, m) 8.66-8.74 (2 H, m) 9.59 (2 H, s).

Example 155

1-(3-chlorobenzyl)-2-imino-5-methyl-1,2-dihydropyridine-3-carboxamide hydrobromide To a solution of 2-amino-5-methylnicotinamide (0.15 g) in N,N-dimethylformamide (3 ml) was added 3-chlorobenzylbromide (0.31 g), and the mixture was stirred at 100° C. for 6 hr. The reaction mixture was diluted with ethyl acetate. The precipitate was collected by filtration and washed with ethyl acetate. The obtained precipitate was recrystallized from methanol-ethyl acetate to give the title compound (0.15 g).

$^1$H-NMR (DMSO-$d_6$) d ppm 2.24 (3 H, s) 5.51 (2 H, s) 7.13-7.22 (1 H, m) 7.38-7.48 (3 H, m) 8.07 (1 H, s) 8.31 (1 H, s) 8.44 (1 H, s) 8.49 (1 H, s) 9.11 (2 H, s).

Example 156

5-chloro-1-(5-cyano-2-fluorobenzyl)-2-imino-1,2-dihydropyridine-3-carboxamide hydrobromide To a solution of 2-amino-5-chloronicotinamide (0.15 g) in N,N-dimethylformamide (3 ml) was added 3-(bromomethyl)-4-fluorobenzonitrile (0.29 g), and the mixture was stirred at 100° C. for 14 hr. The reaction mixture was diluted with ethyl acetate. The precipitate was collected by filtration and washed with ethyl acetate. The obtained precipitate was recrystallized from methanol-ethyl acetate to give the title compound (60 mg).

$^1$H-NMR (DMSO-$d_6$) d ppm 5.59 (2H, s), 7.59 (1H, dd, J=10.2, 8.7 Hz), 7.71 (1H, dd, J=7.2, 1.9 Hz), 7.94-8.06 (1H, m), 8.23 (1H, s), 8.61 (1H, s), 8.64-8.70 (2H, m), 9.29-9.77 (2H, m).

Example 157

5-chloro-1-{3-chloro-5-[(methylamino)carbonyl]benzyl}-2-imino-1,2-dihydropyridine-3-carboxamide hydrobromide (Step 1) To a mixed solution of methyl 3-chloro-5-[(methylamino)carbonyl]benzoate (2.5 g) in tetrahydrofuran:ethanol=10:1 (110 ml) was added lithium tetrahydroborate (0.36 g) at room temperature. After stirring at 60° C. for 4 hr, the reaction solution was quenched with ice and extracted with ethyl acetate. The extract was washed with 1N hydrochloric acid and then with saturated brine, and dried over anhydrous magnesium sulfate. The solvent was evaporated under reduced pressure, and the obtained residue was treated by silica gel chromatography (ethyl acetate) to give 3-chloro-5-(hydroxymethyl)-N-methylbenzamide (1.2 g).

$^1$H-NMR (CDCl$_3$) d ppm 2.98 (3 H, t, J=5.49 Hz) 3.15 (1 H, s) 4.65 (2 H, s) 6.50 (1 H, s) 7.42 (1 H, s) 7.56 (2 H, d, J=9.84 Hz).

(Step 2) Triphenylphosphine (1.45 g) was suspended in acetonitrile (50 ml), bromine (0.29 ml) was added, and the suspension was stirred at 40° C. for 30 min. A solution (10 ml) of 3-chloro-5-(hydroxymethyl)-N-methylbenzamide (1.1 g) obtained in Step 1 in acetonitrile was added to the reaction mixture, and the mixture was stirred at 90° C. for 5 hr. The reaction solution was quenched with aqueous sodium hydrogen carbonate solution and extracted with ethyl acetate. The extract was washed with saturated brine and dried over anhydrous magnesium sulfate. The solvent was evaporated under reduced pressure, and the obtained residue was treated by basic silica gel chromatography (ethyl acetate:hexane=2:3) to give 3-(bromomethyl)-5-chloro-N-methylbenzamide (0.44 g).

$^1$H-NMR (CDCl$_3$) δ ppm 2.91-3.14 (3 H, m) 4.43 (2 H, s) 6.39 (1 H, s) 7.44-7.54 (1 H, m) 7.67 (2 H, d, J=1.88 Hz).

(Step 3) To a solution of 2-amino-5-chloronicotinamide (0.15 g) in N,N-dimethylformamide (3 ml) was added 3-(bromomethyl)-5-chloro-N-methylbenzamide (0.28 g), and the mixture was stirred at 100° C. for 12 hr. The reaction mixture was diluted with ethyl acetate. The solvent was removed, and the obtained precipitate was dissolved in methanol and crystallized from ethyl acetate. The obtained crystals were recrystallized from methanol-ethyl acetate to give the title compound (0.11 g).

$^1$H-NMR (DMSO-$d_6$) d ppm 2.77 (3 H, d, J=4.52 Hz) 5.57 (2 H, s) 7.60 (1 H, s) 7.66 (1 H, s) 7.89 (1 H, s) 8.21 (1 H, s) 8.52-8.69 (3 H, m) 8.81 (1 H, d, J=1.70 Hz) 9.41 (2 H, s).

Example 158

5-chloro-1-[2-chloro-5-(methylsulfonyl)benzyl]-2-imino-1,2-dihydropyridine-3-carboxamide hydrochloride To a solution of 2-amino-5-chloronicotinamide (0.15 g) in N,N-dimethylformamide (3 ml) was added 2-(bromomethyl)-1-chloro-4-(methylsulfonyl)benzene (0.30 g), and the mixture was stirred at 100° C. for 4 hr. The reaction mixture was quenched with aqueous sodium hydrogen carbonate solution and extracted with ethyl acetate. The extract was washed with saturated brine and dried over anhydrous magnesium sulfate. The solvent was evaporated under reduced pressure, and the obtained residue was treated by silica gel chromatography (ethyl acetate100%→ethyl acetate:methanol=4:1) to give a yellow solid. The obtained solid was dissolved in methanol, and 2N hydrochloric acid-methanol solution (0.1 ml) was added. The solvent was concentrated under reduced pressure and the residue was crystallized from methanol-ethyl acetate to give the title compound (5 mg).

$^1$H-NMR (DMSO-$d_6$) d ppm 3.25 (3 H, s) 5.62 (2 H, s) 7.88-7.95 (1 H, m) 7.96-8.03 (1 H, m) 8.27 (1 H, s) 8.67 (1 H, d, J=2.07 Hz) 8.75 (2 H, s) 9.62 (2 H, s).

Example 159

1-[3-(aminocarbonyl)-5-chlorobenzyl]-5-chloro-2-imino-1,2-dihydropyridine-3-carboxamide hydrobromide (Step 1) To a mixed solution of methyl 3-(aminocarbonyl)-5-chlorobenzoate (2.2 g) in tetrahydrofuran:ethanol=10:1 (33 ml) was added lithium tetrahydroborate (0.34 g) at room temperature. After stirring at 60° C. for 2 hr, the reaction solution was quenched with ice and extracted with ethyl acetate. The extract was washed with 1N hydrochloric acid and then with saturated brine, and dried over anhydrous magnesium sulfate. The solvent was evaporated under reduced pressure, and the obtained residue was treated by silica gel chromatography (ethyl acetate:hexane=5:1) to give 3-chloro-5-(hydroxymethyl)benzamide (0.95 g).

$^1$H-NMR (DMSO-$d_6$) d ppm 4.54 (2 H, d, J=5.84 Hz) 5.41 (1 H, t, J=5.75 Hz) 7.48 (1 H, s) 7.51 (1 H, s) 7.78 (2 H, s) 8.06 (1 H, s).

(Step 2) Triphenylphosphine (1.27 g) was suspended in acetonitrile (50 ml), bromine (0.25 ml) was added, and the suspension was stirred for 30 min. 3-Chloro-5-(hydroxymethyl)benzamide (0.90 g) obtained in Step 1 was added to the reaction mixture, and the mixture was stirred at 85° C. for 2 hr. The reaction solution was quenched with water and extracted with ethyl acetate. The extract was washed with aqueous sodium hydrogen carbonate solution and then with saturated brine, and dried over anhydrous magnesium sulfate. The solvent was evaporated under reduced pressure, and the obtained residue was treated by silica gel chromatography (ethyl acetate:hexane=1:1) to give 3-(bromomethyl)-5-chlorobenzamide (0.54 g).

$^1$H-NMR (DMSO-$d_6$) d ppm 4.74 (2 H, s) 7.57 (1 H, s) 7.71 (1 H, t, J=1.70 Hz) 7.86 (1 H, t, J=1.70 Hz) 7.91 (1 H, t, J=1.51 Hz) 8.11 (1 H, s).

(Step 3) To a solution of 2-amino-5-chloronicotinamide (0.15 g) in N,N-dimethylformamide (3 ml) was added 3-(bromomethyl)-5-chlorobenzamide (0.26 g) obtained in Step 2, and the mixture was stirred at 100° C. for 3 hr. The reaction mixture was diluted with ethyl acetate. The precipitate was collected by filtration and washed with ethyl acetate. The obtained precipitate was recrystallized from methanol-ethyl acetate to give the title compound (110 mg).

$^1$H-NMR (DMSO-$d_6$) d ppm 5.57 (2 H, s) 7.61 (2 H, s) 7.67 (1 H, s) 7.94 (1 H, s) 8.14 (1 H, s) 8.20 (1 H, s) 8.59 (1 H, s) 8.63 (1 H, d, J=1.51 Hz) 8.81 (1 H, d, J=1.14 Hz) 9.42 (2 H, s).

Example 160

5-chloro-2-imino-1-(3-methoxybenzyl)-1,2-dihydropyridine-3-carboxamide hydrochloride To a solution of 2-cyano-2-(3,4-dichloro-5-oxo-2,5-dihydrofuran-2-yl)acetamide (0.5 g) in ethanol (5 ml) was added a solution (3 ml) of 3-methoxybenzylamine (410 μl) and triethylamine (450 μl) in ethanol at 0° C., and the mixture was stirred at room temperature for 24 hr. The reaction solvent was evaporated under reduced pressure, and the residue was purified by preparative HPLC. 4N Hydrochloric acid-ethyl acetate solution (1 ml) was added to the obtained yellow oil at room temperature, and the precipitated crystals were filtered and recrystallized to give the title compound (110 mg).

$^1$H-NMR (DMSO-$d_6$) d ppm 3.76 (3H, s), 5.53 (2H, s), 6.79-6.87 (1H, m), 6.92-7.00 (2H, m), 7.28-7.39 (1H, m), 8.19 (1H, s), 8.66 (2H, d, J=2.1 Hz), 8.79 (1H, d, J=2.1 Hz), 9.47 (2H, br-s).

Example 161

5-chloro-2-imino-1-[3-(trifluoromethyl)benzyl]-1,2-dihydropyridine-3-carboxamide hydrochloride According to the method of Example 160, 2-cyano-2-(3,4-dichloro-5-oxo-2,5-dihydrofuran-2-yl)acetamide was reacted with 1-[3-(trifluoromethyl)phenyl]methanamine to give the title compound.

$^1$H-NMR (DMSO-$d_6$) d ppm 5.71 (2H, s), 7.52-7.59 (1H, m), 7.65 (1H, t, J=7.8 Hz), 7.72-7.79 (1H, m), 7.86 (1H, s), 8.21 (1H, s), 8.73 (2H, d, J=1.9 Hz), 8.89 (1H, d, J=1.9 Hz), 9.41-9.81 (2H, m).

Example 162

5-chloro-1-(2,5-difluorobenzyl)-2-imino-1,2-dihydropyridine-3-carboxamide hydrochloride According to the method of Example 160, 2-cyano-2-(3,4-dichloro-5-oxo-2,5-dihydrofuran-2-yl)acetamide was reacted with 1-(2,5-difluorophenyl)methanamine to give the title compound.

$^1$H-NMR (DMSO-$d_6$) d ppm 5.66 (2H, s), 7.05-7.49 (3H, m), 8.22 (1H, s), 8.65-8.84 (3H, m), 9.67 (2H, br-s).

Example 163

5-chloro-2-imino-1-(2,4,5-trifluorobenzyl)-1,2-dihydropyridine-3-carboxamide hydrochloride According to the method of Example 160, 2-cyano-2-(3,4-dichloro-5-oxo-2,5-dihydrofuran-2-yl)acetamide was reacted with 1-(2,4,5-trifluorophenyl)methanamine to give the title compound.

$^1$H-NMR (DMSO-$d_6$) d ppm 5.59 (2H, s), 7.44-7.61 (1H, m), 7.64-7.78 (1H, m), 8.22 (1H, s), 8.59-8.80 (3H, m), 9.63 (2H, br-s).

Example 164

5-chloro-2-imino-1-(3,4,5-trifluorobenzyl)-1,2-dihydropyridine-3-carboxamide hydrochloride According to the method of Example 160, 2-cyano-2-(3,4-dichloro-5-oxo-2,5-dihydrofuran-2-yl)acetamide was reacted with 1-(3,4,5-trifluorophenyl)methanamine to give the title compound.

$^1$H-NMR (DMSO-$d_6$) d ppm 5.67 (2H, s), 7.04-7.21 (1H, m), 7.27-7.43 (1H, m), 8.22 (1H,s), 8.61-8.81 (3H, m), 9.47-9.83 (2H, m).

Example 165

5-chloro-2-imino-1-(2,3,6-trifluorobenzyl)-1,2-dihydropyridine-3-carboxamide hydrochloride According to the method of Example 160, 2-cyano-2-(3,4-dichloro-5-oxo-2,5-dihydrofuran-2-yl)acetamide was reacted with 1-(2,3,6-trifluorophenyl)methanamine to give the title compound.

$^1$H-NMR (DMSO-$d_6$) d ppm 5.71 (2H, s), 7.18-7.35 (1H, m), 7.53-7.75 (1H, m), 8.24 (1H, s), 8.62 (1H, d, J=2.2 Hz), 8.68 (1 H, d, J=2.2 Hz), 8.74 (1H, s), 9.67 (2H, s).

Example 166

5-chloro-1-[(2R)-3,4-dihydro-2H-chromen-2-ylmethyl]-2-imino-1,2-dihydropyridine-3-carboxamide hydrochloride According to the method of Example 160, 2-cyano-2-(3,4-dichloro-5-oxo-2,5-dihydrofuran-2-yl)acetamide was reacted with 1-[(2R)-3,4-dihydro-2H-chromen-2-yl]methanamine hydrochloride to give the title compound.

$^1$H-NMR (DMSO-$d_6$) d ppm 1.62-1.82 (1H, m), 2.17-2.32 (1H, m), 2.69-2.93 (2H, m), 4.29-4.64 (2H, m), 4.68-4.82 (1H, m), 6.63 (1H, d, J=8.1 Hz), 6.79-6.89 (1H, m), 7.00-7.13 (2H, m), 8.20 (1H, s), 8.57-8.76 (3 H, m), 9.53-9.80 (2 H, m).

Example 167

5-chloro-1-(2,3-dihydro-1,4-benzodioxin-2-ylmethyl)-2-imino-1,2-dihydropyridine-3-carboxamide hydrochloride According to the method of Example 160, 2-cyano-2-(3,4-dichloro-5-oxo-2,5-dihydrofuran-2-yl)acetamide was reacted with 1-(2,3-dihydro-1,4-benzodioxin-2-yl) methanamine to give the title compound.
$^1$H-NMR (DMSO-$d_6$) d ppm 4.16 (1H, dd, J=11.4, 5.9 Hz), 4.43-4.91 (4H, m), 6.74-6.99 (4H, m), 8.20 (1H, s), 8.44 (1 H, d, J=2.3 Hz), 8.58-8.76 (2H, m), 9.59-9.93 (2H, m).

Example 168

5-chloro-2-imino-1-[(1R)-1-phenylethyl]-1,2-dihydropyridine-3-carboxamide hydrochloride To a solution of 2-cyano-2-(3,4-dichloro-5-oxo-2,5-dihydrofuran-2-yl)acetamide (1.0 g) in methanol (10 ml) was added a solution (5 ml) of (R)-(+)-phenylethylamine (1.6 ml) and triethylamine (1.8 ml) in ethanol at room temperature, and the mixture was stirred at 50° C. for 24 hr. The reaction solvent was evaporated under reduced pressure, DMSO (10 ml) was added, and the mixture was stirred at 80° C. for 3 hr. The solvent was evaporated under reduced pressure, and the residue was partitioned between ethyl acetate and water. The organic layer was dried over magnesium sulfate, and the solvent was evaporated under reduced pressure. The residue was purified by silica gel column chromatography (ethyl acetate/hexane=1/1-4/1). 4N Hydrochloric acid-ethyl acetate solution (1 ml) was added to the obtained yellow oil, and the precipitated crystals were filtered and recrystallized to give the title compound (260 mg).
$^1$H-NMR (DMSO-$d_6$) d ppm 1.90 (3H, d, J=6.5 Hz), 6.20 (1H, q, J=6.5 Hz), 7.30-7.57 (5H, m), 8.22 (1H, s), 8.37 (1 H, d, J=2.3 Hz), 8.54-8.73 (2H, m), 9.80 (2H, s).
$[\alpha]^{25}_D$=+136.0 (c 1.0, MeOH).

Example 169

5-chloro-1-[(1R)-2,3-dihydro-1H-inden-1-yl]-2-imino-1,2-dihydropyridine-3-carboxamide hydrochloride According to the method of Example 168, 2-cyano-2-(3,4-dichloro-5-oxo-2,5-dihydrofuran-2-yl)acetamide was reacted with (R)-(−)-aminoindane to give the title compound.
$^1$H-NMR (DMSO-$d_6$) d ppm 2.15-2.31 (1H, m), 2.67-3.04 (2H, m), 3.08-3.23 (1H, m), 6.20 (1H, t, J=6.5 Hz), 7.31-7.51 (4H, m), 7.56 (1 H, s), 8.23 (1 H, s), 8.52-8.59 (1 H, m), 8.66 (1 H, s), 9.79 (2 H, br-s).

Example 170

5-chloro-1-[(1S)-2,3-dihydro-1H-inden-1-yl]-2-imino-1,2-dihydropyridine-3-carboxamide hydrochloride According to the method of Example 168, 2-cyano-2-(3,4-dichloro-5-oxo-2,5-dihydrofuran-2-yl)acetamide was reacted with (S)-(+)-aminoindane to give the title compound.
$^1$H-NMR (DMSO-$d_6$) d ppm 2.13-2.32 (1H, m), 2.70-3.03 (2H, m), 3.07-3.22 (1H, m), 6.15-6.31 (1H, m), 7.31-7.51 (4H, m), 7.52-7.61 (1H, m), 8.23 (1H, s), 8.59 (1H, d, J=1.9 Hz), 8.69 (1H, s), 9.64-10.04 (2H, m).

Example 171

5-chloro-1-(4-cyano-2-fluorobenzyl)-2-imino-1,2-dihydropyridine-3-carboxamide hydrochloride A solution of 2-amino-5-chloronicotinamide (150 mg) and 4-(bromomethyl)-3-fluorobenzonitrile (282 mg) in DMF (3 ml) was stirred at 100° C. for 24 hr. After cooling to room temperature, ethyl acetate was added, and the precipitated crystals were filtered. The obtained crystals were dissolved in methanol (3 ml) and partitioned between ethyl acetate and aqueous sodium hydrogen carbonate solution. The organic layer was dried over magnesium sulfate and filtered. The solvent was evaporated under reduced pressure, and the residue was purified by silica gel column chromatography (ethyl acetate/methanol=1/0-9/1). 4N Hydrochloric acid-ethyl acetate solution was added to the obtained yellow oil, and the precipitated crystals were filtered and recrystallized to give the title compound (47 mg).
$^1$H-NMR (DMSO-$d_6$) d ppm 5.70 (2H, s), 7.27 (1H, t, J=7.9 Hz), 7.72 (1H, dd, J=7.9, 1.2 Hz), 8.00 (1H, dd, J=10.4, 1.2 Hz), 8.23 (1H, s), 8.67-8.77 (3H, m), 9.62 (2H, br-s).

Example 172

5-chloro-1-(3-fluoro-5-methylbenzyl)-2-imino-1,2-dihydropyridine-3-carboxamide hydrobromide A solution of 2-amino-5-chloronicotinamide (150 mg) and 1-(bromomethyl)-3-fluoro-5-methylbenzene (270 mg) in DMF (3 ml) was stirred at 100° C. for 24 hr. After cooling to room temperature, ethyl acetate was added, and the precipitated crystals were filtered and recrystallized to give the title compound (139 mg).
$^1$H-NMR (DMSO-$d_6$) d ppm 2.32 (3H, s), 5.49 (2H, s), 6.90-7.12 (3H, m), 8.20 (1H, s), 8.57 (1H, s), 8.62 (1H, d, J=2.3 Hz), 8.75 (1H, d, J=2.3 Hz), 9.19-9.61 (2H, m).

Example 173

5-chloro-1-(2-fluoro-5-methylbenzyl)-2-imino-1,2-dihydropyridine-3-carboxamide hydrobromide According to the method of Example 172, 2-amino-5-chloronicotinamide was reacted with 2-(bromomethyl)-1-fluoro-4-methylbenzene to give the title compound.
$^1$H-NMR (DMSO-$d_6$) d ppm 2.25 (3H, s), 5.54 (2H, s), 6.91 (1H, d, J=7.2 Hz), 7.13-7.31 (2H, m), 8.23 (1H, s), 8.54-8.71 (3H, m), 9.26-9.65 (2H, m).

Example 174

5-chloro-1-(3,5-difluoro-2-methoxybenzyl)-2-imino-1,2-dihydropyridine-3-carboxamide hydrobromide According to the method of Example 172, 2-amino-5-chloronicotinamide was reacted with 1-(bromomethyl)-3,5-difluoro-2-methoxybenzene to give the title compound.

¹H-NMR (DMSO-d₆) d ppm 3.87-3.92 (3H, m), 5.40-5.53 (2H, m), 6.85-6.96 (1H, m), 7.27-7.51 (1H, m), 8.21 (1H, s), 8.52-8.70 (3H, m), 9.17-9.71 (2H, m).

Example 175

5-chloro-1-(3-fluoro-4-methylbenzyl)-2-imino-1,2-dihydropyridine-3-carboxamide hydrobromide According to the method of Example 172, 2-amino-5-chloronicotinamide was reacted with 4-(bromomethyl)-2-fluoro-1-methylbenzene to give the title compound.
¹H-NMR (DMSO-d₆) d ppm 2.23 (3H, s), 5.49 (2H, s), 6.99-7.07 (1H, m), 7.14-7.22 (1H, m), 7.29-7.38 (1H, m), 8.19 (1H, s), 8.53-8.62 (2H, m), 8.77 (1H, d, J=2.1 Hz), 9.21-9.58 (2H, m).

Example 176

5-chloro-1-(2,4-difluorobenzyl)-2-imino-1,2-dihydropyridine-3-carboxamide hydrobromide According to the method of Example 172, 2-amino-5-chloronicotinamide was reacted with 1-(bromomethyl)-2,4-difluorobenzene to give the title compound.
¹H-NMR (DMSO-d₆) d ppm 5.54 (2H, s), 7.06-7.29 (2H, m), 7.35-7.47 (1H, m), 8.21 (1H, s), 8.52-8.71 (3H, m), 9.32-9.61 (2 H, m).

Example 177

5-chloro-1-(5-fluoro-2-methylbenzyl)-2-imino-1,2-dihydropyridine-3-carboxamide hydrobromide According to the method of Example 172, 2-amino-5-chloronicotinamide was reacted with 2-(bromomethyl)-4-fluoro-1-methylbenzene to give the title compound.
¹H-NMR (DMSO-d₆) d ppm 2.29 (3H, s), 5.44 (2H, s), 6.47-6.60 (1H, m), 7.05-7.18 (1H, m), 7.30-7.42 (1H, m), 8.22 (1H, s), 8.53-8.70 (3H, m), 9.08-9.74 (2H, m).

Example 178

5-chloro-1-(4-fluoro-3-methylbenzyl)-2-imino-1,2-dihydropyridine-3-carboxamide hydrochloride According to the method of Example 171, 2-amino-5-chloronicotinamide was reacted with 4-(bromomethyl)-1-fluoro-2-methylbenzene to give the title compound.
¹H-NMR (DMSO-d₆) d ppm 2.23 (3 H, d, J=1.5 Hz), 5.48 (2 H, s), 7.16-7.22 (2H, m), 7.29 (1H, d, J=7.2 Hz), 8.19 (1 H, s), 8.56-8.66 (2H, m), 8.74 (1H, d, J=2.3 Hz), 9.22-9.68 (2H, m).

Example 179

5-chloro-2-imino-1-[3-(methylsulfonyl)benzyl]-1,2-dihydropyridine-3-carboxamide hydrochloride To a solution of 2-cyano-2-(3,4-dichloro-5-oxo-2,5-dihydrofuran-2-yl)acetamide (0.5 g) in methanol (5 ml) was added a solution (3 ml) of 1-[3-(methylsulfonyl)phenyl]methanamine hydrochloride (1.4 g) and triethylamine (0.9 ml) in ethanol at room temperature, and the mixture was stirred for 24 hr. The reaction solvent was evaporated under reduced pressure, DMSO (5 ml) was added, and the mixture was stirred at 80° C. for 4 hr. The solvent was evaporated under reduced pressure and partitioned between ethyl acetate and water. The organic layer was dried over magnesium sulfate, and the solvent was evaporated under reduced pressure. The residue was purified by silica gel column chromatography (ethyl acetate/hexane=4/1-1/0). 2N Hydrochloric acid-methanol solution (1 ml) was added to the obtained yellow oil at room temperature, and the precipitated crystals were filtered and recrystallized to give the title compound (78 mg).
¹H-NMR (DMSO-d₆) d ppm 3.24 (3H, s), 5.66 (2H, s), 7.57 (1H, d, J=7.9 Hz), 7.69 (1H, t, J=7.9 Hz), 7.88-8.05 (2H, m), 8.20 (1H, s), 8.55-8.70 (2H, m), 8.85 (1H, d, J=2.3 Hz), 9.33-9.68 (2H, m).

Example 180

5-chloro-2-imino-1-(3-morpholin-4-ylbenzyl)-1,2-dihydropyridine-3-carboxamide hydrochloride According to the method of Example 179, 2-amino-5-chloronicotinamide was reacted with 1-(3-morpholin-4-ylphenyl)methanamine to give the title compound.
¹H-NMR (DMSO-d₆) d ppm 3.08-3.18 (4H, m), 3.70-3.79 (4H, m), 5.49 (2H, s), 6.66 (1H, d, J=7.2 Hz), 6.93-7.13 (2H, m), 7.26 (1H, t, J=8.0 Hz), 8.19 (1H, s), 8.60-8.69 (2H, m), 8.73-8.79 (1H, m), 9.48 (2H, br-s).

Example 181

5-chloro-1-(3-cyano-5-fluorobenzyl)-2-imino-1,2-dihydropyridine-3-carboxamide hydrobromide (Step 1) To a solution of 3-cyano-5-fluorobenzoic acid (1.0 g) in methanol (20 ml) was added TMS diazomethane (2M diethyl ether solution, 5 ml) at 0° C., and the mixture was stirred for 1 hr. The reaction solution was quenched with water and diluted with ethyl acetate. The organic layer was washed with aqueous sodium hydrogen carbonate solution and then with saturated brine, and dried over anhydrous magnesium sulfate. The solvent was evaporated under reduced pressure to give methyl 3-cyano-5-fluorobenzoate (0.58 g).
¹H-NMR (CDCl₃) δ ppm 3.98 (3 H, s) 7.55 (1 H, d, J=7.57 Hz) 7.97 (1 H, d, J=8.33 Hz) 8.14 (1 H, s).

(Step 2) To a mixed solution of methyl 3-cyano-5-fluorobenzoate (0.55 g) obtained in Step 1 in tetrahydrofuran:ethanol=10:1 (22 ml) was added lithium tetrahydroborate (0.10 g) at 0° C. After stirring at 55° C. for 1 hr, the reaction solution was quenched with ice and extracted with ethyl acetate. The extract was washed with 1N hydrochloric acid and then with saturated brine, and dried over anhydrous magnesium sulfate. The solvent was evaporated under reduced pressure to give 3-fluoro-5-(hydroxymethyl)benzonitrile (0.29 g).
¹H-NMR (CDCl₃) δ ppm 1.94 (1 H, s) 4.77 (2 H, s) 7.21-7.31 (1 H, m) 7.36 (1 H, dd, J=9.14, 0.85 Hz) 7.47 (1 H, s).

(Step 3) Triphenylphosphine (1.91 g) was suspended in acetonitrile (50 ml), bromine (0.38 ml) was added, and the suspension was stirred for 30 min. 3-Fluoro-5-(hydroxymethyl)benzonitrile (1.1 g) synthesized by the method of Steps 1 and 2 was added to the reaction mixture, and the mixture was stirred at 85° C. for 2 hr. The reaction solution was quenched with water and extracted with ethyl acetate. The extract was washed with aqueous sodium hydrogen carbonate solution and then with saturated brine, and dried over anhydrous magnesium sulfate. The solvent was evaporated under reduced pressure, and the obtained residue was treated by basic silica gel chromatography (ethyl acetate:hexane=1:5) to give 3-(bromomethyl)-5-fluorobenzonitrile (0.69 g).

¹H-NMR (CDCl₃) δ ppm 4.44 (2 H, s) 7.28-7.33 (1 H, m) 7.34-7.41 (1 H, m) 7.49 (1 H, s).

(Step 4) To a solution of 2-amino-5-chloronicotinamide (0.15 g) in N,N-dimethylformamide (3 ml) was added 3-(bromomethyl)-5-fluorobenzonitrile (0.29 g) obtained in Step 3, and the mixture was stirred at 100° C. for 14 hr. The reaction mixture was diluted with ethyl acetate. The precipitate was collected by filtration and washed with ethyl acetate. The obtained precipitate was recrystallized from methanol-ethyl acetate to give the title compound (69 mg).

¹H-NMR (DMSO-d₆) d ppm 5.58 (2H, s), 7.60-7.67 (1H, m), 7.69 (1H, s), 7.86-7.95 (1H, m), 8.21 (1H, s), 8.59 (1H, s), 8.64 (1H, d, J=2.1 Hz), 8.75 (1H, d, J=2.1 Hz), 9.44 (2H, br-s).

Example 182

5-chloro-1-(3-chloro-5-cyanobenzyl)-2-imino-1,2-dihydropyridine-3-carboxamide hydrobromide (Step 1) To a solution of methyl 3-(aminocarbonyl)-5-chlorobenzoate (2.2 g) in N,N-dimethylformamide (15 ml) was added thionyl chloride (2 ml) at 0° C., and the mixture was stirred at 80° C. for 1 hr. The reaction solution was quenched with ice and extracted with ethyl acetate. The extract was washed with aqueous sodium hydrogen carbonate solution and then with saturated brine, and dried over anhydrous magnesium sulfate. The solvent was evaporated under reduced pressure, and the obtained residue was treated by silica gel chromatography (ethyl acetate:hexane=1:1) to give methyl 3-chloro-5-cyanobenzoate (1.15 g) as a white solid.

¹H-NMR (CDCl₃) δ ppm 3.97 (3 H, s) 7.80-7.84 (1 H, m) 8.21 (1 H, t, J=1.41 Hz) 8.23-8.26 (1 H, m).

(Step 2) To a mixed solution of 3-chloro-5-cyanobenzoate (1.13 g) obtained in Step 1 in tetrahydrofuran:ethanol=10:1 (33 ml) was added lithium tetrahydroborate (0.19 g) at 0° C. After stirring at 60° C. for 2 hr, the reaction solution was quenched with ice and extracted with ethyl acetate. The extract was washed with 1N hydrochloric acid and then with saturated brine, and dried over anhydrous magnesium sulfate. The solvent was evaporated under reduced pressure, and the obtained residue was treated by silica gel chromatography (ethyl acetate:hexane=1:1) to give 3-chloro-5-(hydroxymethyl)benzonitrile (0.60 g) as a white solid.

¹H-NMR (CDCl₃) δ ppm 1.97 (1 H, t, J=5.65 Hz) 4.75 (2 H, d, J=5.84 Hz) 7.56 (2 H, s) 7.61 (1 H, s).

(Step 3) Triphenylphosphine (0.94 g) was suspended in acetonitrile (20 ml), bromine (0.19 ml) was added, and the mixture was stirred for 30 min. A solution (10 ml) of 3-chloro-5-(hydroxymethyl)benzonitrile (0.60 g) obtained in Step 2 in acetonitrile was added to the reaction mixture, and the mixture was stirred at 80° C. for 4 hr. The reaction solution was quenched with water, and the mixture was extracted with ethyl acetate. The extract was washed with aqueous sodium hydrogen carbonate solution and then with saturated brine, and dried over anhydrous magnesium sulfate. The solvent was evaporated under reduced pressure, and the obtained residue was treated by basic silica gel chromatography (ethyl acetate:hexane=1:2) to give 3-(bromomethyl)-5-chlorobenzonitrile (0.31 g) as a white solid.

¹H-NMR (CDCl₃) δ ppm 4.42 (2 H, s) 7.58 (2 H, d, J=1.70 Hz) 7.62 (1 H, t, J=1.79 Hz).

(Step 4) To a solution of 2-amino-5-chloronicotinamide (0.15 g) in N,N-dimethylformamide (3 ml) was added 3-(bromomethyl)-5-chlorobenzonitrile (0.29 g) obtained in Step 3, and the mixture was stirred at 100° C. for 14 hr. The reaction mixture was diluted with ethyl acetate. The precipitate was collected by filtration and washed with ethyl acetate. The obtained precipitate was recrystallized from methanol-ethyl acetate to give the title compound (80 mg).

¹H-NMR (DMSO-d₆) d ppm 5.56 (2H, s), 7.74-7.80 (1H, m), 7.81-7.88 (1H, m), 8.02-8.14 (1H, m), 8.21 (1H, s), 8.53-8.70 (2H, m), 8.71-8.81 (1H, m), 9.21-9.66 (2H, m).

Example 183

5-chloro-1-(3-cyano-4-fluorobenzyl)-2-imino-1,2-dihydropyridine-3-carboxamide hydrobromide To a solution of 2-amino-5-chloronicotinamide (0.15 g) in N,N-dimethylformamide (3 ml) was added 5-(bromomethyl)-2-fluorobenzonitrile (0.29 g), and the mixture was stirred at 100° C. for 14 hr. The reaction mixture was diluted with ethyl acetate. The precipitate was collected by filtration and washed with ethyl acetate. The obtained precipitate was recrystallized from methanol-ethyl acetate to give the title compound (71 mg).

¹H-NMR (DMSO-d₆) d ppm 5.56 (2H, s), 7.61 (1H, t, J=9.0 Hz), 7.74-7.84 (1H, m), 7.94 (1H, dd, J=2.3, 6.0 Hz), 8.21 (1H, s), 8.56-8.67 (2H, m), 8.78 (1H, d, J=2.3 Hz), 9.44 (2H, br-s).

Example 184

5-chloro-1-(3-chloro-4-cyanobenzyl)-2-imino-1,2-dihydropyridine-3-carboxamide hydrobromide To a solution of 2-amino-5-chloronicotinamide (0.14 g) in N,N-dimethylformamide (3 ml) was added 4-(bromomethyl)-2-chlorobenzonitrile (0.28 g), and the mixture was stirred at 100° C. for 14 hr. The reaction mixture was diluted with ethyl acetate. The precipitate was collected by filtration and washed with ethyl acetate. The obtained precipitate was recrystallized from methanol-ethyl acetate to give the title compound (85 mg).

¹H-NMR (DMSO-d₆) d ppm 5.60 (2H, s), 7.39 (1H, dd, J=8.0, 1.6 Hz), 7.75 (1H, d, J=1.6 Hz), 8.03 (1H, d, J=8.0 Hz), 8.20 (1H, s), 8.52-8.67 (2H, m), 8.74 (1H, s), 9.24-9.64 (2H, m).

Example 185

5-chloro-1-(4-chloro-3-cyanobenzyl)-2-imino-1,2-dihydropyridine-3-carboxamide hydrobromide To a solution of 2-amino-5-chloronicotinamide (0.15 g) in N,N-dimethylformamide (3 ml) was added 5-(bromomethyl)-2-chlorobenzonitrile (0.31 g), and the mixture was stirred at 100° C. for 14 hr. The reaction mixture was diluted with ethyl acetate. The precipitate was collected by filtration and washed with ethyl acetate. The obtained precipitate was recrystallized from methanol-ethyl acetate to give the title compound (93 mg).

¹H-NMR (DMSO-d₆) d ppm 5.57 (2H, s), 7.69 (1H, dd, J=8.5, 2.3 Hz), 7.78-7.86 (1H, m), 7.97 (1H, d, J=2.3 Hz), 8.21 (1H, s), 8.55-8.67 (2H, m), 8.77 (1H, d, J=2.3 Hz), 9.44 (2H, br-s).

Example 186

5-chloro-1-(5-chloro-2-cyanobenzyl)-2-imino-1,2-dihydropyridine-3-carboxamide hydrochloride To a solution of 2-amino-5-chloronicotinamide (0.15 g) in N,N-dimethylformamide (3 ml) was added 2-(bromomethyl)-4-chlorobenzonitrile (0.31 g), and the mixture was stirred at 100° C. for 14 hr. The reaction mixture was quenched with saturated aqueous sodium hydrogen carbonate solution and extracted with ethyl acetate. The extract was washed with saturated brine and dried over anhydrous magnesium sulfate. The solvent was evaporated under reduced pressure, and the obtained residue was purified by silica gel chromatography (ethyl acetate:hexane=3:2-4:1). 2N Hydrochloric acid-methanol solution (1 ml) was added to the obtained yellow oil at room temperature, and the obtained precipitate was recrystallized from methanol-ethyl acetate to give the title compound (2 mg).

$^1$H-NMR (DMSO-d$_6$) d ppm 5.76 (2H, s), 7.04 (1H, d, J=8.5 Hz), 7.74 (1H, dd, J-8.5, 2.3 Hz), 8.20-8.28 (2H, m), 8.62-8.81 (3H, m), 9.38-9.85 (2H, m).

Example 187

5-chloro-1-(4-chloro-2-cyanobenzyl)-2-imino-1,2-dihydropyridine-3-carboxamide hydrochloride To a solution of 2-amino-5-chloronicotinamide (0.16 g) in N,N-dimethylformamide (3 ml) was added 2-(bromomethyl)-5-chlorobenzonitrile (0.32 g), and the mixture was stirred at 100° C. for 14 hr. The reaction mixture was quenched with saturated aqueous sodium hydrogen carbonate solution and extracted with ethyl acetate. The extract was washed with saturated brine and dried over anhydrous magnesium sulfate. The solvent was evaporated under reduced pressure, and the obtained residue was purified by silica gel chromatography (ethyl acetate:hexane=3:2-4:1). 2N Hydrochloric acid-methanol solution (1 ml) was added to the obtained yellow oil at room temperature, and the obtained precipitate was recrystallized from methanol-ethyl acetate to give the title compound (3 mg).

$^1$H-NMR (DMSO-d$_6$) d ppm 5.75 (2H, s), 7.24 (1H, d, J=2.0 Hz), 7.68 (1H, dd, J=8.3, 2.0 Hz), 8.05 (1H, d, J=8.3 Hz), 8.23 (1H, s), 8.60-8.78 (3H, m), 9.38-9.81 (2H, m).

Example 188

5-chloro-1-(2-chloro-5-cyanobenzyl)-2-imino-1,2-dihydropyridine-3-carboxamide hydrochloride (Step 1) To a solution of 4-chloro-3-methylbenzonitrile (1 g) in t-butylacetic acid (10 ml) were added N-bromosuccinimide (1.5 g) and azobisisobutyronitrile (0.05 g), and the mixture was stirred at 90° C. for 12 hr. The reaction mixture was quenched with saturated aqueous sodium hydrogen carbonate solution and extracted with ethyl acetate. The extract was washed with saturated brine and dried over anhydrous magnesium sulfate. The solvent was evaporated under reduced pressure, and the obtained residue was purified by silica gel column chromatography (ethyl acetate:hexane=0:1-1:9) to give 3-(bromomethyl)-4-chlorobenzonitrile (1.5 g) as a white solid.

(Step 2) To a solution of 2-amino-5-chloronicotinamide (0.15 g) in N,N-dimethylformamide (3 ml) was added 3-(bromomethyl)-4-chlorobenzonitrile (0.31 g), and the mixture was stirred at 100° C. for 14 hr. The reaction mixture was quenched with saturated aqueous sodium hydrogen carbonate solution and extracted with ethyl acetate. The extract was washed with saturated brine and dried over anhydrous magnesium sulfate. The solvent was evaporated under reduced pressure, and the obtained residue was purified by silica gel chromatography (ethyl acetate:hexane=3:2-19:1). 2N Hydrochloric acid-methanol solution (1 ml) was added to the obtained yellow oil at room temperature, and the obtained precipitate was recrystallized from methanol-ethyl acetate to give the title compound (43 mg).

$^1$H-NMR (DMSO-d$_6$) d ppm 5.65 (2H, s), 7.41 (1H, dd, J=8.2, 1.5 Hz), 7.78 (1H, d, J=1.5 Hz), 8.02 (1H, d, J=8.2 Hz), 8.21 (1H, s), 8.61-8.71 (2H, m), 8.78 (1H, d, J=2.1 Hz), 9.37-9.69 (2H, m).

Example 189

5-chloro-1-(2-cyano-5-fluorobenzyl)-2-imino-1,2-dihydropyridine-3-carboxamide hydrochloride To a solution of 2-amino-5-chloronicotinamide (0.15 g) in N,N-dimethylformamide (3 ml) was added 2-(bromomethyl)-4-fluorobenzonitrile (0.29 g), and the mixture was stirred at 100° C. for 14 hr. The reaction mixture was quenched with saturated aqueous sodium hydrogen carbonate solution and extracted with ethyl acetate. The extract was washed with saturated brine and dried over anhydrous magnesium sulfate. The solvent was evaporated under reduced pressure, and the obtained residue was purified by silica gel chromatography (ethyl acetate:hexane=3:2-19:1). 2N Hydrochloric acid-methanol solution (1 ml) was added to the obtained yellow oil at room temperature, and the obtained precipitate was recrystallized from methanol-ethyl acetate to give the title compound (34 mg).

$^1$H-NMR (DMSO-d$_6$) d ppm 5.76 (2H, s), 7.07 (1H, dd, J=9.6, 2.3 Hz), 7.40-7.51 (1H, m), 8.12 (1H, dd, J=8.7, 5.5 Hz), 8.23 (1H, s), 8.58-8.77 (3H, m), 9.40-9.81 (2H, m).

TABLE 1

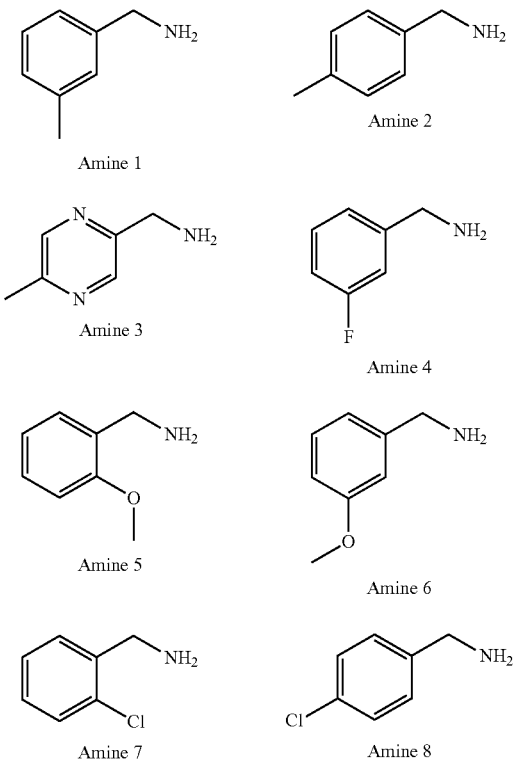

TABLE 1-continued

| Amine 9: 2,3-difluorobenzylamine | Amine 10: 2,5-difluorobenzylamine |
| Amine 11: 3,5-difluorobenzylamine | Amine 12: 1-naphthylmethylamine |
| Amine 13: 2-(trifluoromethyl)benzylamine | Amine 14: 3-(trifluoromethyl)benzylamine |
| Amine 15: 2,4-dichlorobenzylamine | Amine 16: 4-(trifluoromethoxy)benzylamine |
| Amine 17: 3-fluoro-5-(trifluoromethyl)benzylamine | Amine 18: 3,5-bis(trifluoromethyl)benzylamine |
| Amine 19: 3-chlorobenzylamine | Amine 20: 2,4-dichlorobenzylamine |
| Amine 21: 2-chloro-6-phenoxybenzylamine | Amine 22: (tetrahydrofuran-2-yl)methylamine |
| Amine 23: 2-phenylethylamine | Amine 24: 3-phenylpropylamine |
| Amine 25: 4-phenylbutylamine | Amine 26: cyclohexylmethylamine |
| Amine 27: 2-(3-(trifluoromethyl)phenyl)ethylamine | Amine 28: neopentylamine |
| Amine 29: 2-phenylpropylamine | Amine 30: 2,2-diphenylethylamine |
| Amine 31: 3,3-diphenylpropylamine | Amine 32: 1-aminoindane |
| Amine 33: 2-aminoindane | Amine 34: 1-adamantylmethylamine |
| Amine 35: bornylamine/norbornane derivative | Amine 36: furfurylamine |
| Amine 37: 2-(2-chlorophenyl)ethylamine | Amine 38: 2-(3-chlorophenyl)ethylamine |
| Amine 39: 2-(4-chlorophenyl)ethylamine | Amine 40: 2-(2,4-dichlorophenyl)ethylamine |

TABLE 1-continued
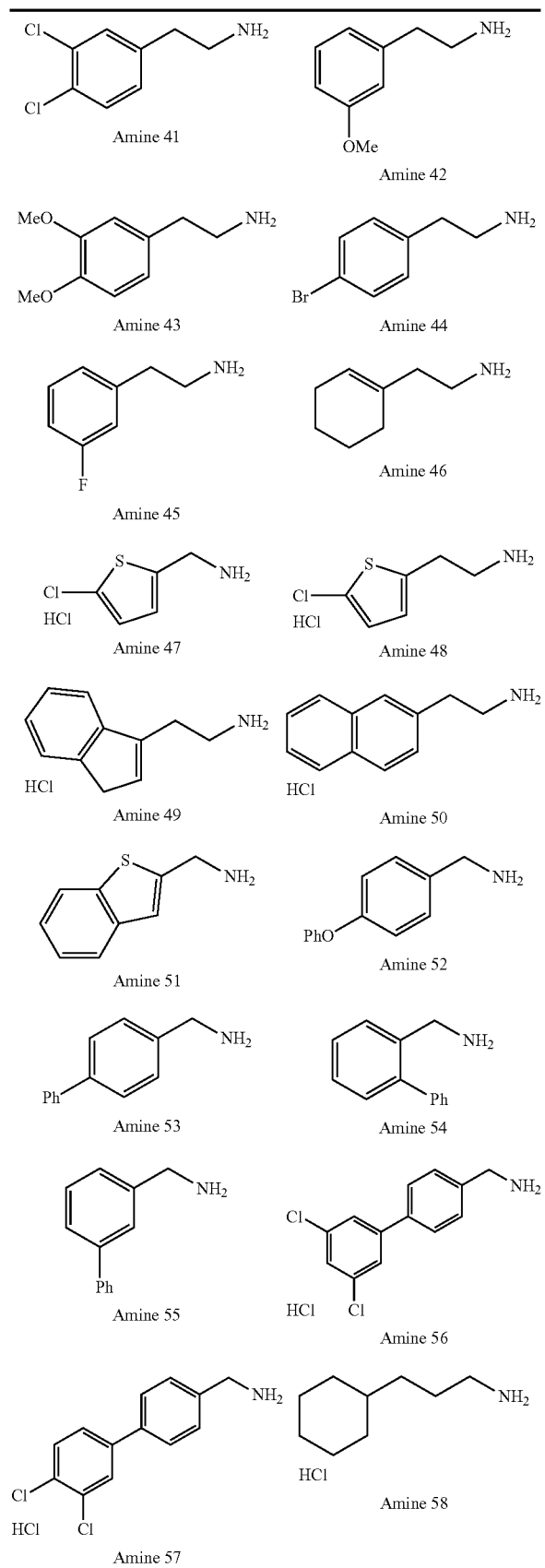
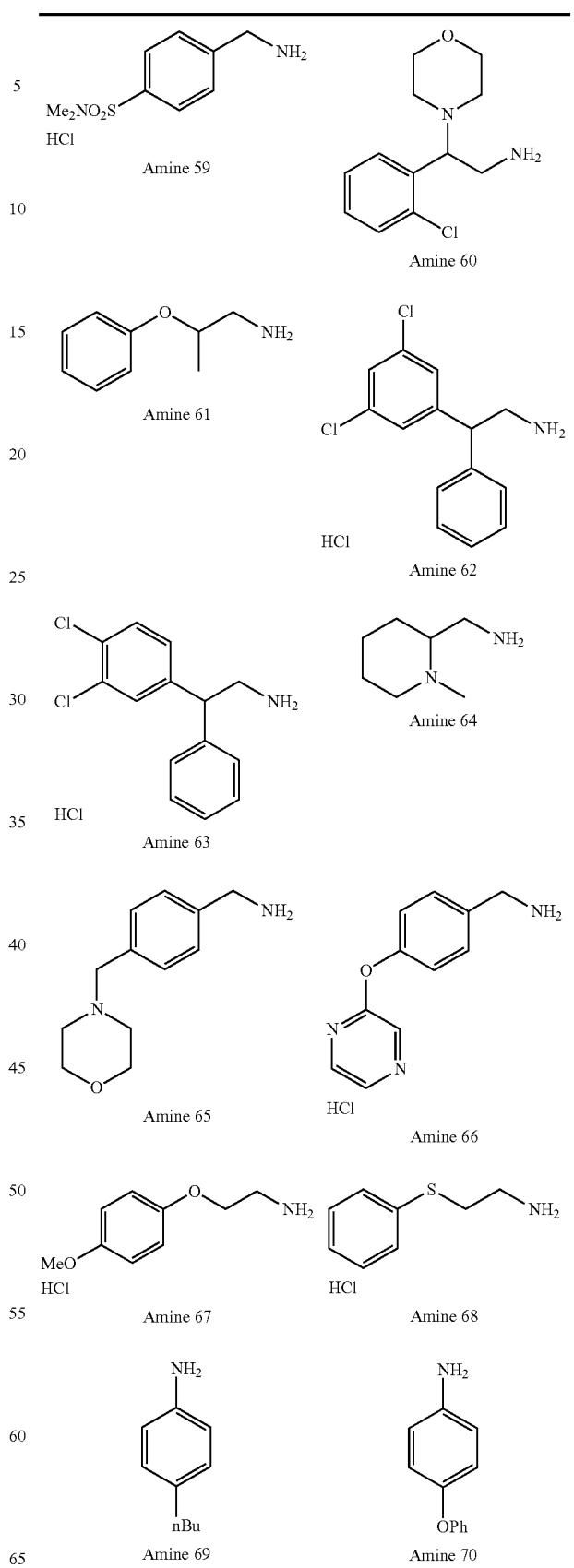

TABLE 1-continued
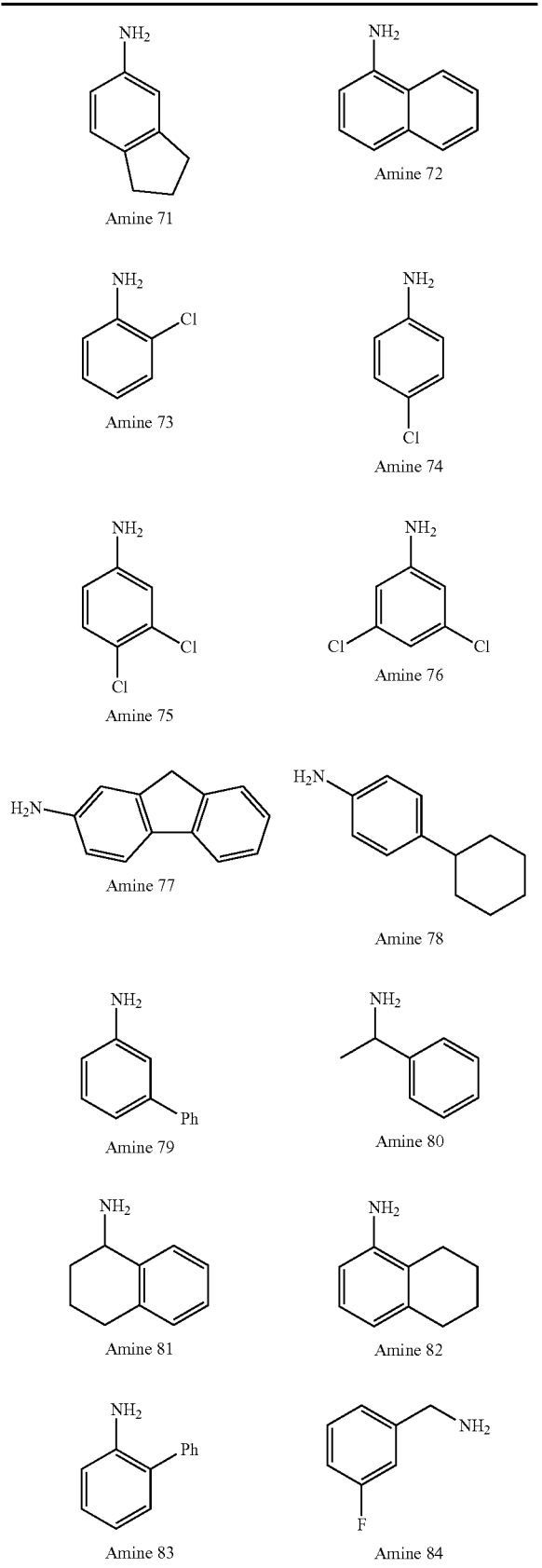
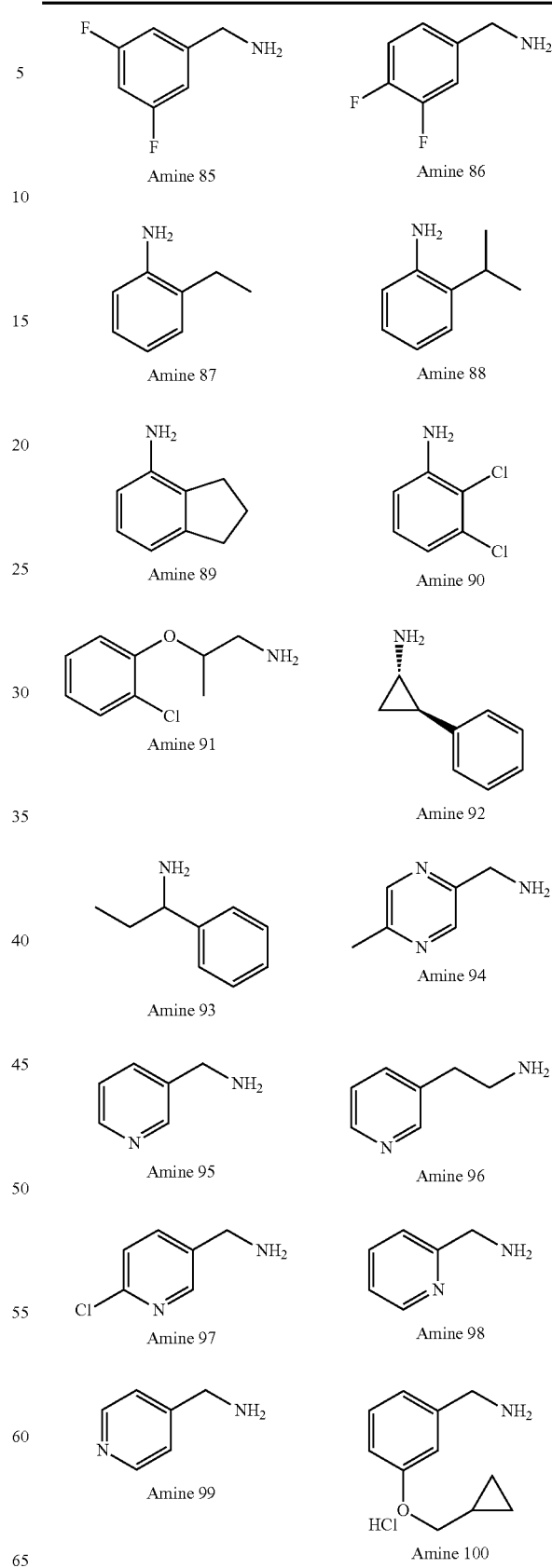

TABLE 1-continued
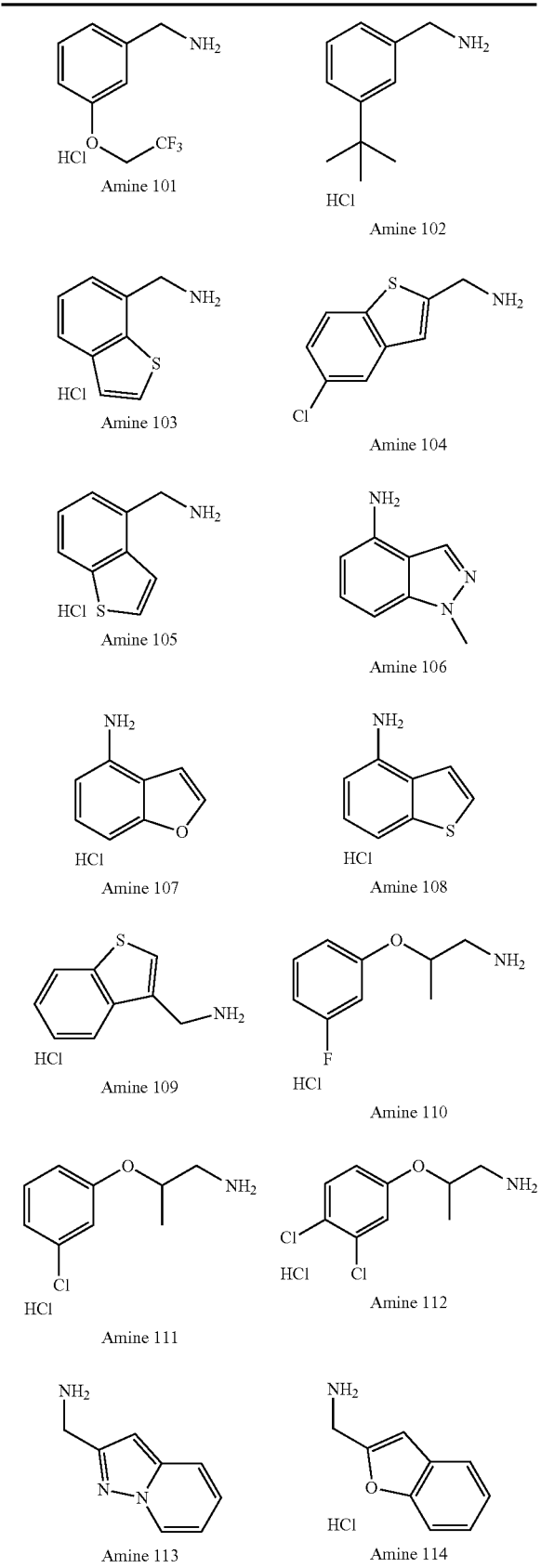
TABLE 1-continued
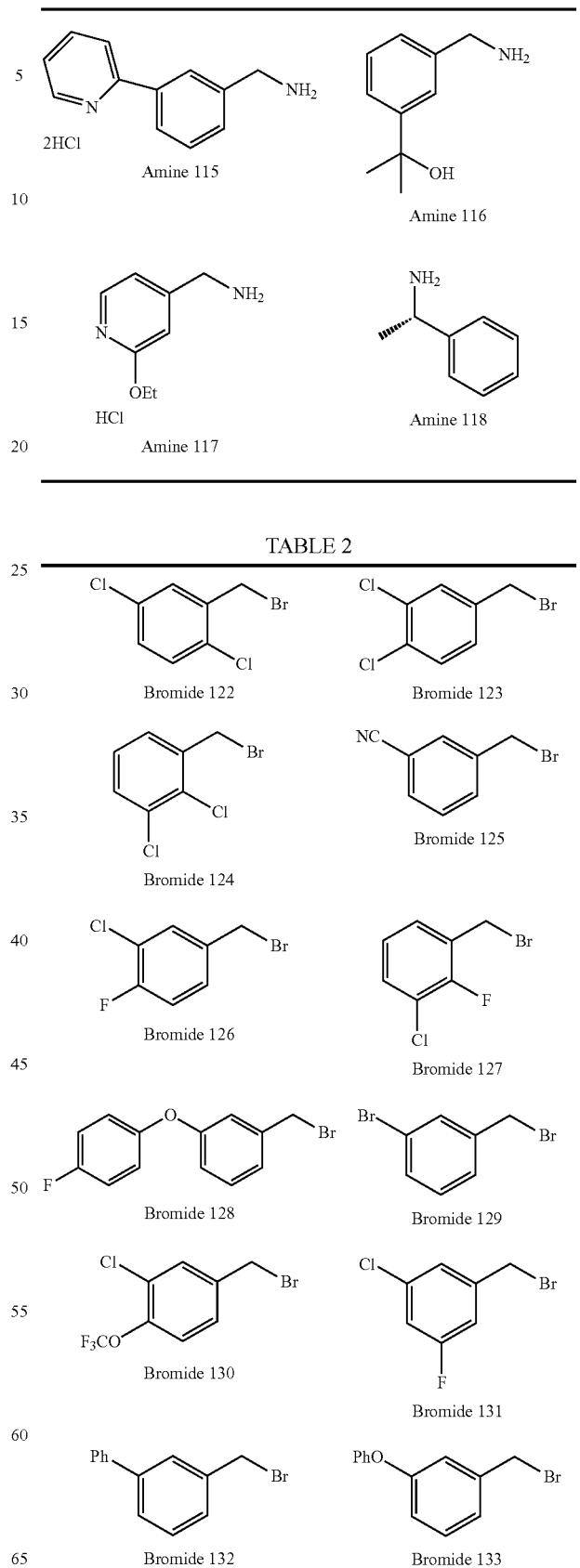

TABLE 2-continued
| | |
|---|---|
| Bromide 134 | Bromide 135 |
| Bromide 136 | Bromide 137 |
| Bromide 138 | Bromide 139 |
| Bromide 140 | Bromide 141 |
| Bromide 142 | Bromide 143 |
| Bromide 144 | Bromide 145 |
The structural formulas of the compounds of Reference Example 1 and Examples 1-189 are shown in Table 3-1 to Table 3-13 below.
TABLE 3
Reference Example 1
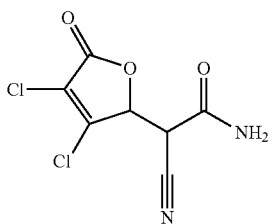 [SMILES: N#CC(C(N)=O)C1OC(=O)C(Cl)=C1Cl]
TABLE 3-continued
Example 1
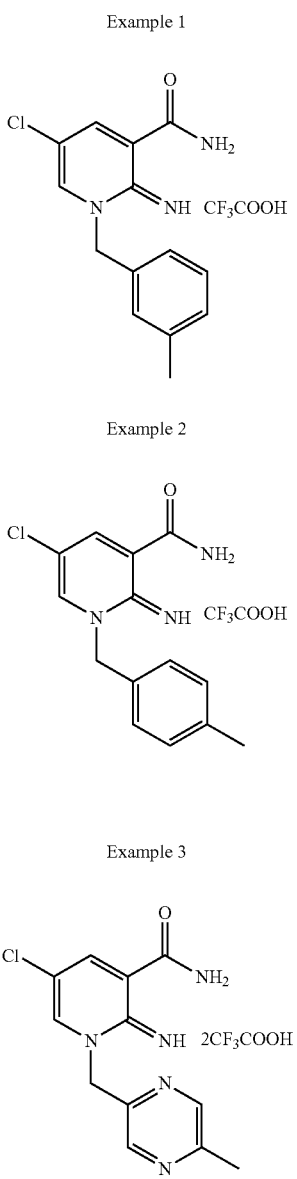
Example 2
Example 3
Example 4
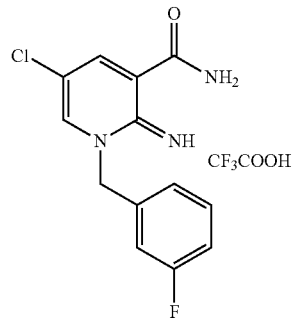 [SMILES: N=c1c(C(N)=O)cc(Cl)cn1Cc1cccc(F)c1 ; "CF3COOH"]

TABLE 3-continued
Example 5
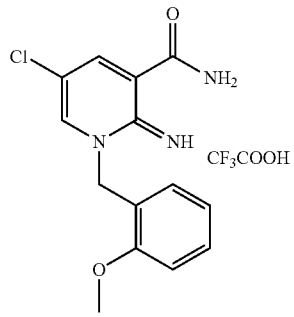 [SMILES: COc1ccccc1Cn1cc(Cl)cc(C(N)=O)c1=N ; "CF3COOH"]
Example 6
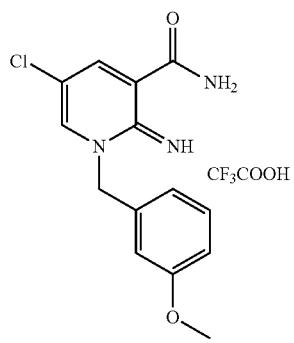 [SMILES: COc1cccc(Cn2cc(Cl)cc(C(N)=O)c2=N)c1 ; "CF3COOH"]
Example 7
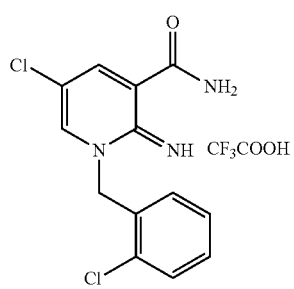 [SMILES: N=c1c(C(N)=O)cc(Cl)cn1Cc1ccccc1Cl ; "CF3COOH"]
Example 8
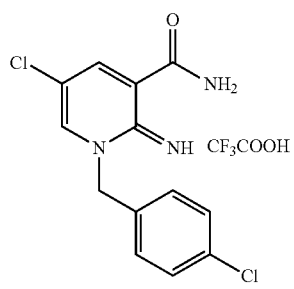 [SMILES: N=c1c(C(N)=O)cc(Cl)cn1Cc1ccc(Cl)cc1 ; "CF3COOH"]
Example 9
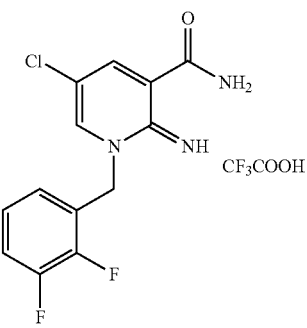 [SMILES: N=c1c(C(N)=O)cc(Cl)cn1Cc1cccc(F)c1F ; "CF3COOH"]
Example 10
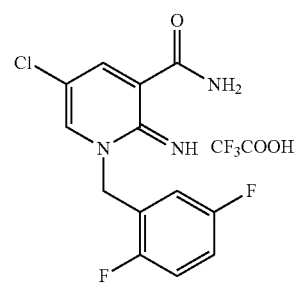 [SMILES: N=c1c(C(N)=O)cc(Cl)cn1Cc1cc(F)ccc1F ; "CF3COOH"]
Example 11
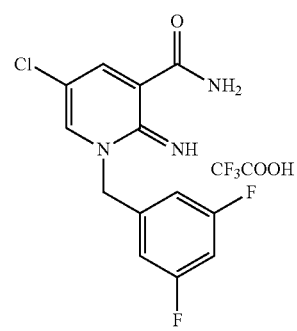 [SMILES: N=c1c(C(N)=O)cc(Cl)cn1Cc1cc(F)cc(F)c1 ; "CF3COOH"]
Example 12
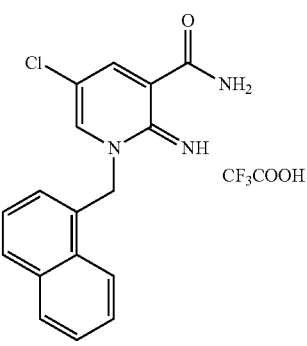 [SMILES: N=c1c(C(N)=O)cc(Cl)cn1Cc1cccc2ccccc12 ; "CF3COOH"]

TABLE 3-continued
Example 13
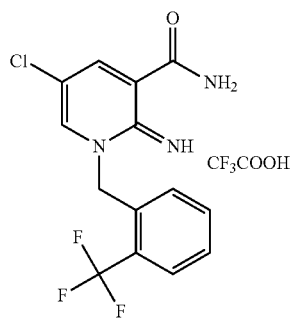 [SMILES: N=c1c(C(N)=O)cc(Cl)cn1Cc1ccccc1C(F)(F)F ; "CF3COOH"]
Example 14
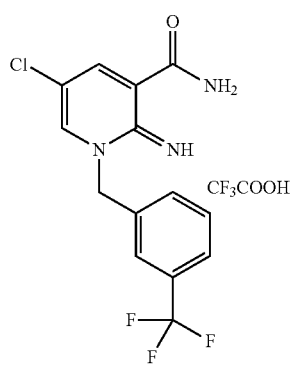 [SMILES: N=c1c(C(N)=O)cc(Cl)cn1Cc1cccc(C(F)(F)F)c1 ; "CF3COOH"]
Example 15
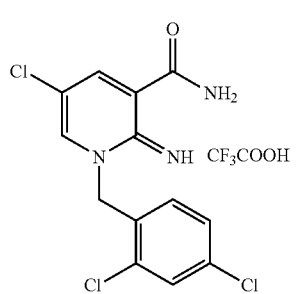 [SMILES: N=c1c(C(N)=O)cc(Cl)cn1Cc1ccc(Cl)cc1Cl ; "CF3COOH"]
Example 16
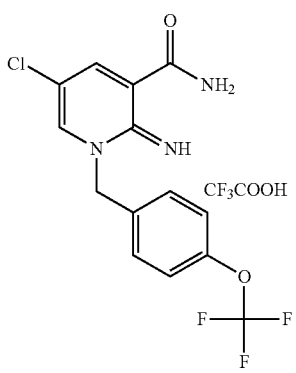 [SMILES: N=c1c(C(N)=O)cc(Cl)cn1Cc1ccc(OC(F)(F)F)cc1 ; "CF3COOH"]
TABLE 3-continued
Example 17
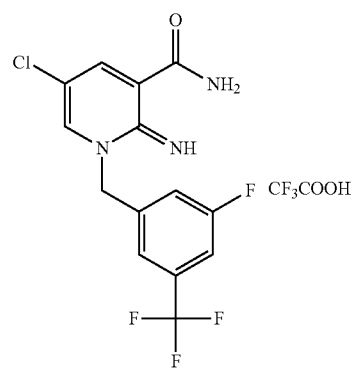 [SMILES: N=c1c(C(N)=O)cc(Cl)cn1Cc1cc(F)cc(C(F)(F)F)c1 ; "CF3COOH"]
Example 18
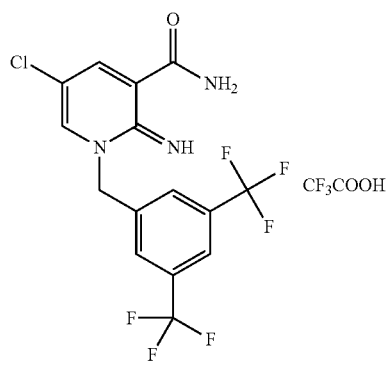 [SMILES: N=c1c(C(N)=O)cc(Cl)cn1Cc1cc(C(F)(F)F)cc(C(F)(F)F)c1 ; "CF3COOH"]
Example 19
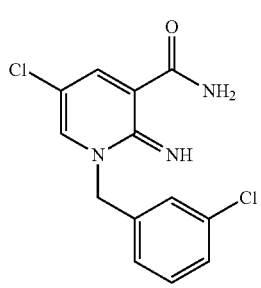 [SMILES: N=c1c(C(N)=O)cc(Cl)cn1Cc1cccc(Cl)c1]
Example 20
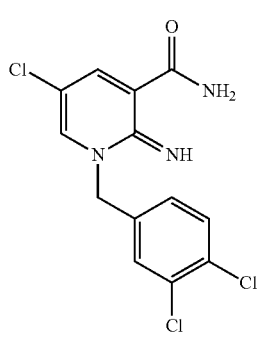 [SMILES: N=c1c(C(N)=O)cc(Cl)cn1Cc1ccc(Cl)c(Cl)c1]

TABLE 3-continued
Example 21
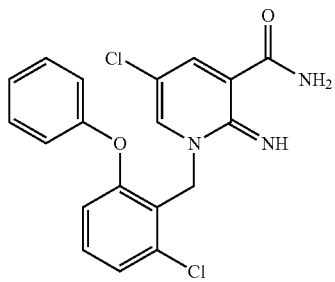 [SMILES: N=c1c(C(N)=O)cc(Cl)cn1Cc1c(Cl)cccc1Oc1ccccc1]
Example 22
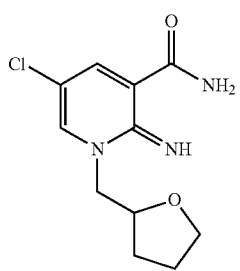 [SMILES: N=c1c(C(N)=O)cc(Cl)cn1CC1CCCO1]
Example 23
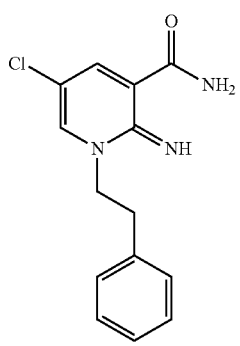 [SMILES: N=c1c(C(N)=O)cc(Cl)cn1CCc1ccccc1]
Example 24
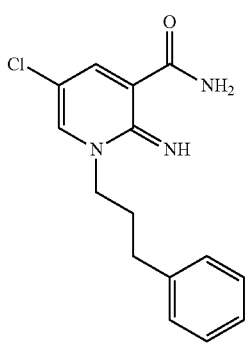 [SMILES: N=c1c(C(N)=O)cc(Cl)cn1CCCc1ccccc1]
TABLE 3-continued
Example 25
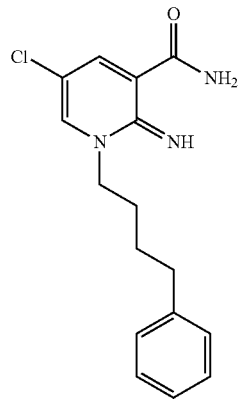 [SMILES: N=c1c(C(N)=O)cc(Cl)cn1CCCCc1ccccc1]
Example 26
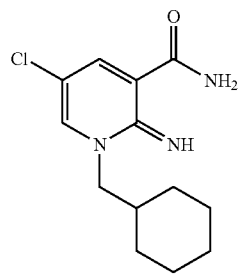 [SMILES: N=c1c(C(N)=O)cc(Cl)cn1CC1CCCCC1]
Example 27
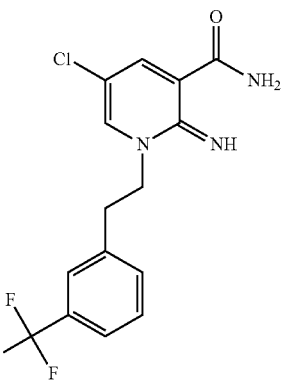
Example 28
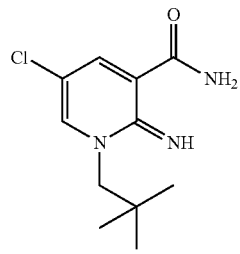 [SMILES: CC(C)(C)Cn1cc(Cl)cc(C(N)=O)c1=N]

TABLE 3-continued
Example 29
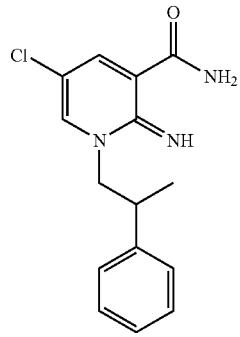 [SMILES: CC(Cn1cc(Cl)cc(C(N)=O)c1=N)c1ccccc1]
Example 30
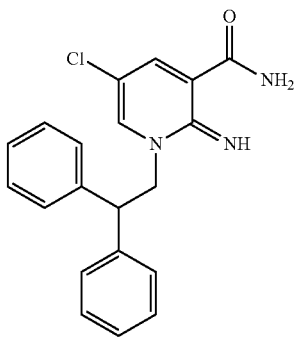 [SMILES: N=c1c(C(N)=O)cc(Cl)cn1CC(c1ccccc1)c1ccccc1]
Example 31
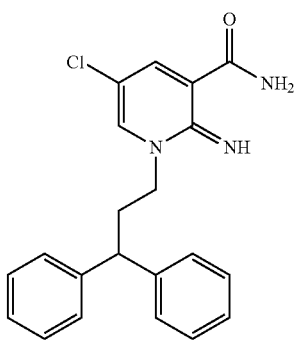 [SMILES: N=c1c(C(N)=O)cc(Cl)cn1CCC(c1ccccc1)c1ccccc1]
Example 32
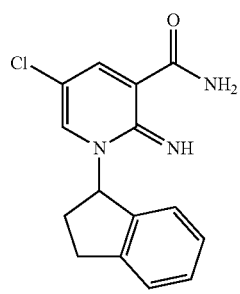 [SMILES: N=c1c(C(N)=O)cc(Cl)cn1C1CCc2ccccc21]
TABLE 3-continued
Example 33
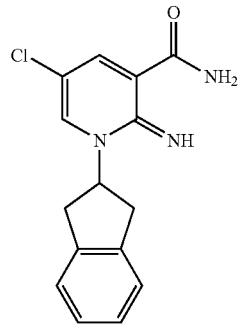 [SMILES: N=c1c(C(N)=O)cc(Cl)cn1C1Cc2ccccc2C1]
Example 34
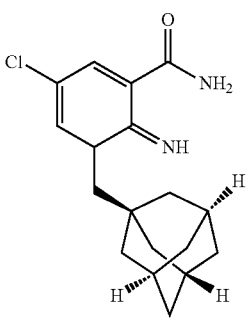 [SMILES: N=C1C(C(N)=O)=CC(Cl)=CC1C[C@]12C[C@H]3C[C@H](C[C@H](C3)C1)C2]
Example 35
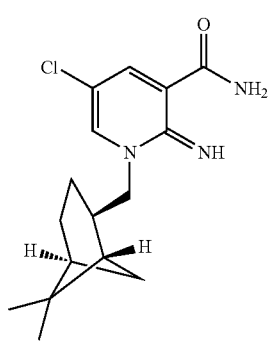 [SMILES: CC1(C)[C@H]2CC[C@@H](Cn3cc(Cl)cc(C(N)=O)c3=N)[C@@H]1C2]
Example 36
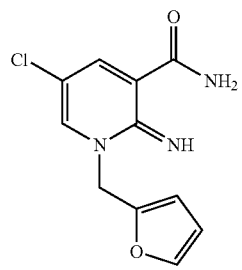 [SMILES: N=c1c(C(N)=O)cc(Cl)cn1Cc1ccco1]

TABLE 3-continued
Example 37
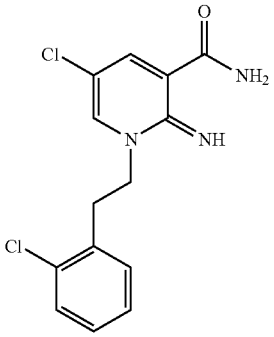 [SMILES: N=c1c(C(N)=O)cc(Cl)cn1CCc1ccccc1Cl]
Example 38
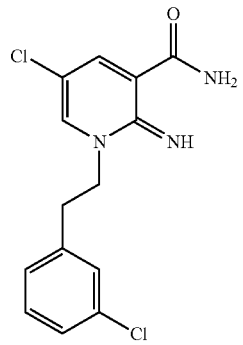 [SMILES: N=c1c(C(N)=O)cc(Cl)cn1CCc1cccc(Cl)c1]
Example 39
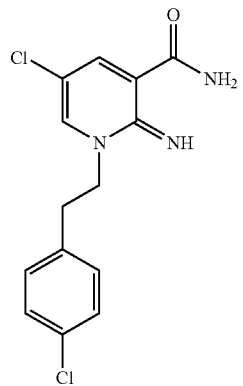 [SMILES: N=c1c(C(N)=O)cc(Cl)cn1CCc1ccc(Cl)cc1]
Example 40
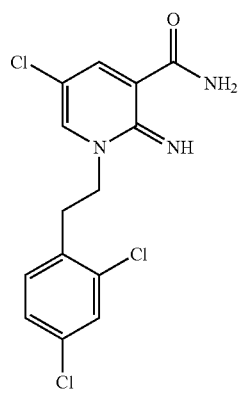 [SMILES: N=c1c(C(N)=O)cc(Cl)cn1CCc1ccc(Cl)cc1Cl]
TABLE 3-continued
Example 41
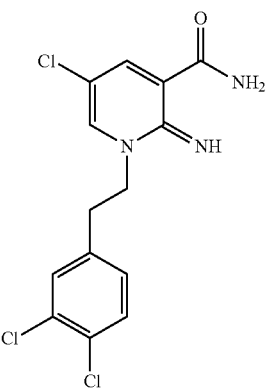 [SMILES: N=c1c(C(N)=O)cc(Cl)cn1CCc1ccc(Cl)c(Cl)c1]
Example 42
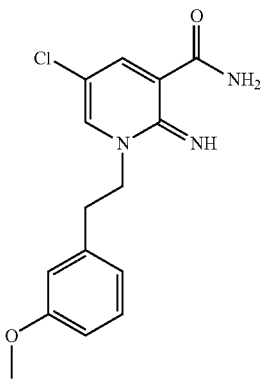 [SMILES: COc1cccc(CCn2cc(Cl)cc(C(N)=O)c2=N)c1]
Example 43
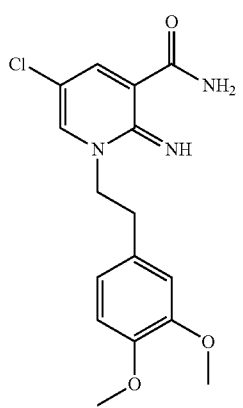 [SMILES: COc1ccc(CCn2cc(Cl)cc(C(N)=O)c2=N)cc1OC]

TABLE 3-continued
Example 44
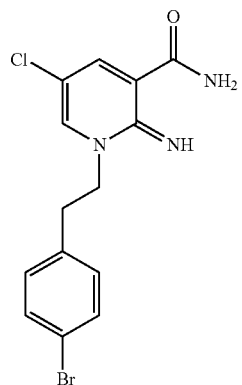 [SMILES: N=c1c(C(N)=O)cc(Cl)cn1CCc1ccc(Br)cc1]
Example 45
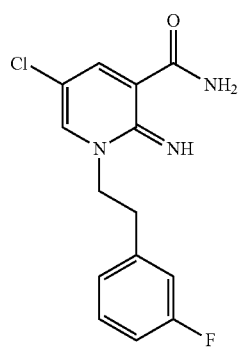 [SMILES: N=c1c(C(N)=O)cc(Cl)cn1CCc1cccc(F)c1]
Example 46
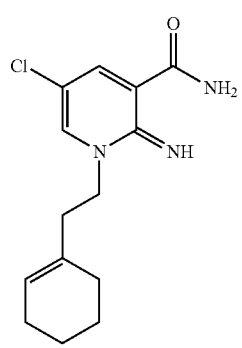 [SMILES: N=c1c(C(N)=O)cc(Cl)cn1CCC1=CCCCC1]
Example 47
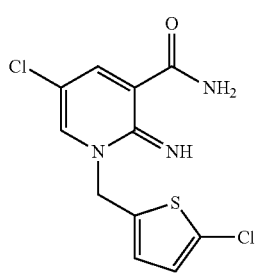 [SMILES: N=c1c(C(N)=O)cc(Cl)cn1Cc1ccc(Cl)s1]
TABLE 3-continued
Example 48
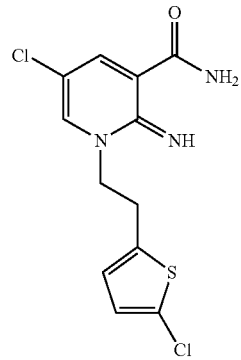 [SMILES: N=c1c(C(N)=O)cc(Cl)cn1CCc1ccc(Cl)s1]
Example 49
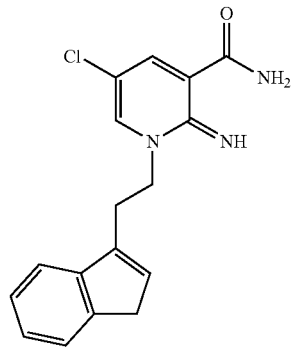 [SMILES: N=c1c(C(N)=O)cc(Cl)cn1CCC1=CCc2ccccc21]
Example 50
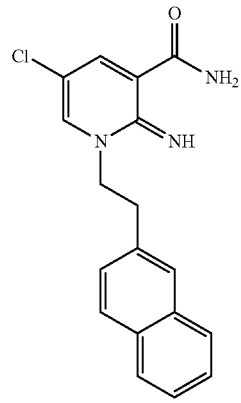 [SMILES: N=c1c(C(N)=O)cc(Cl)cn1CCc1ccc2ccccc2c1]
Example 51
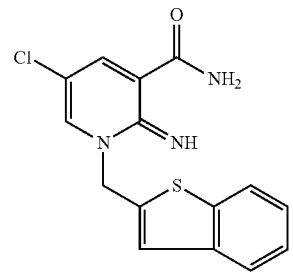 [SMILES: N=c1c(C(N)=O)cc(Cl)cn1Cc1cc2ccccc2s1]

TABLE 3-continued
Example 52
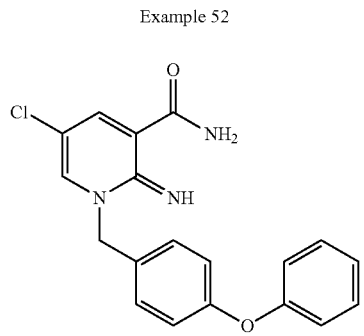
Example 53
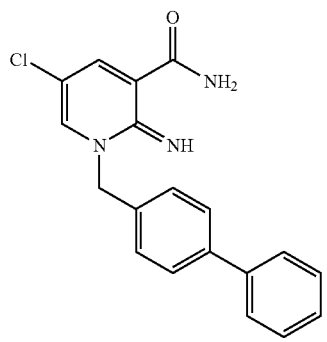 [SMILES: N=c1c(C(N)=O)cc(Cl)cn1Cc1ccc(-c2ccccc2)cc1]
Example 54
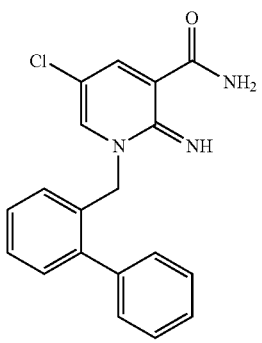 [SMILES: N=c1c(C(N)=O)cc(Cl)cn1Cc1ccccc1-c1ccccc1]
Example 55
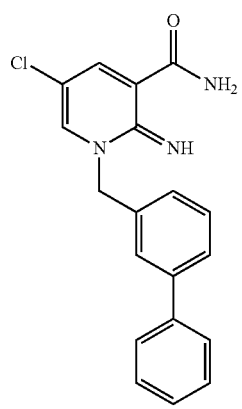 [SMILES: N=c1c(C(N)=O)cc(Cl)cn1Cc1cccc(-c2ccccc2)c1]
TABLE 3-continued
Example 56
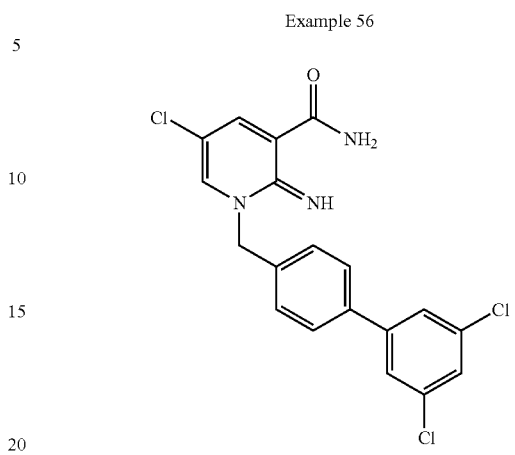
Example 57
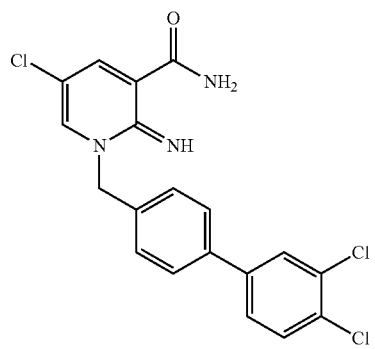 [SMILES: N=c1c(C(N)=O)cc(Cl)cn1Cc1ccc(-c2ccc(Cl)c(Cl)c2)cc1]
Example 58
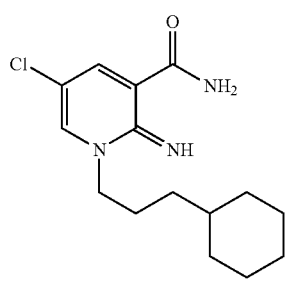 [SMILES: N=c1c(C(N)=O)cc(Cl)cn1CCCC1CCCCC1]
Example 59
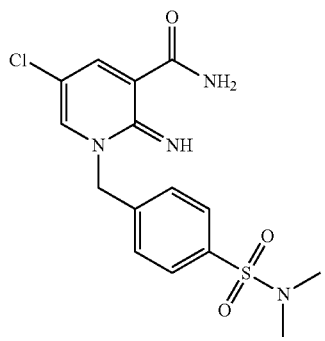 [SMILES: CN(C)S(=O)(=O)c1ccc(Cn2cc(Cl)cc(C(N)=O)c2=N)cc1]

TABLE 3-continued
Example 60
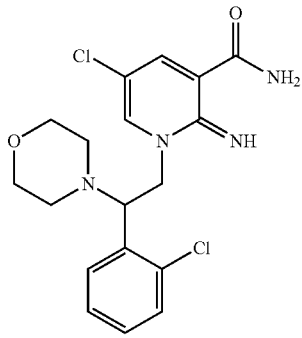 [SMILES: N=c1c(C(N)=O)cc(Cl)cn1CC(c1ccccc1Cl)N1CCOCC1]
Example 61
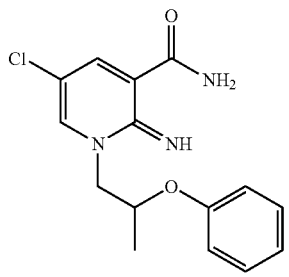 [SMILES: CC(Cn1cc(Cl)cc(C(N)=O)c1=N)Oc1ccccc1]
Example 62
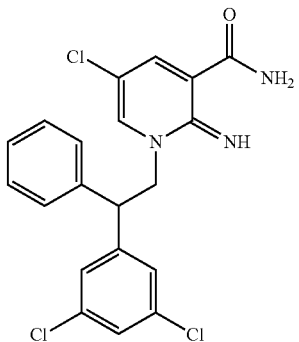 [SMILES: N=c1c(C(N)=O)cc(Cl)cn1CC(c1ccccc1)c1cc(Cl)cc(Cl)c1]
Example 63
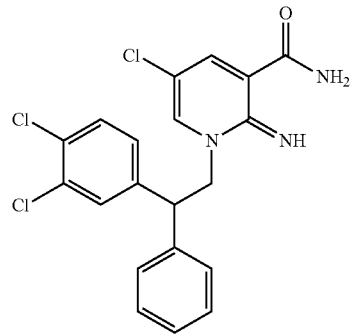 [SMILES: N=c1c(C(N)=O)cc(Cl)cn1CC(c1ccccc1)c1ccc(Cl)c(Cl)c1]
TABLE 3-continued
Example 64
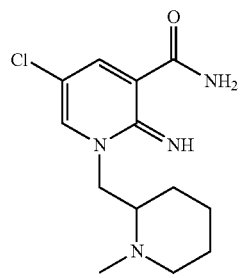 [SMILES: CN1CCCCC1Cn1cc(Cl)cc(C(N)=O)c1=N]
Example 65
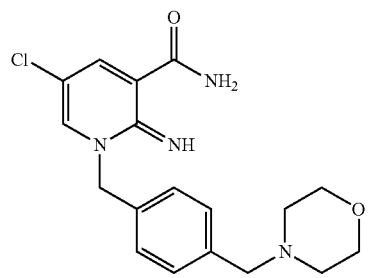 [SMILES: N=c1c(C(N)=O)cc(Cl)cn1Cc1ccc(CN2CCOCC2)cc1]
Example 66
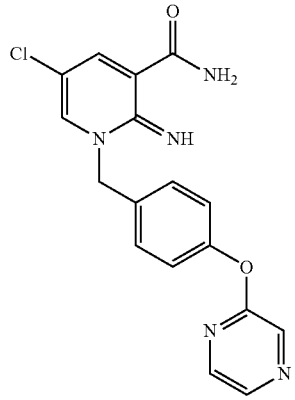 [SMILES: N=c1c(C(N)=O)cc(Cl)cn1Cc1ccc(Oc2cnccn2)cc1]
Example 67
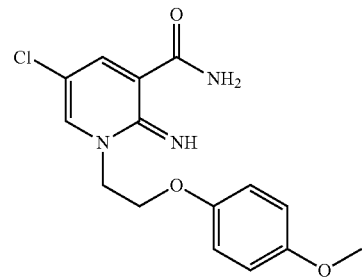 [SMILES: COc1ccc(OCCn2cc(Cl)cc(C(N)=O)c2=N)cc1]

TABLE 3-continued
Example 68
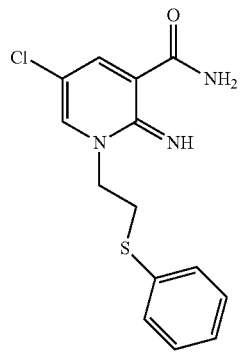 [SMILES: N=c1c(C(N)=O)cc(Cl)cn1CCSc1ccccc1]
Example 69
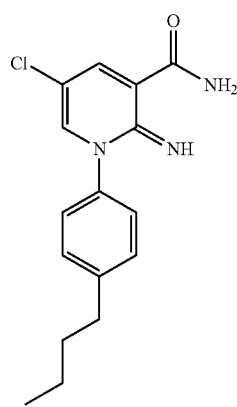 [SMILES: CCCCc1ccc(-n2cc(Cl)cc(C(N)=O)c2=N)cc1]
Example 70
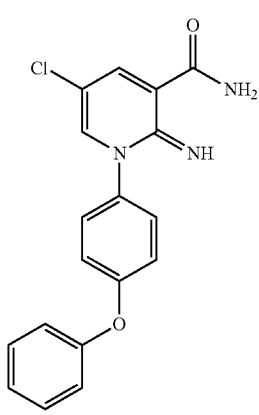 [SMILES: N=c1c(C(N)=O)cc(Cl)cn1-c1ccc(Oc2ccccc2)cc1]
TABLE 3-continued
Example 71
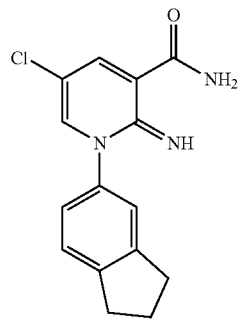 [SMILES: N=c1c(C(N)=O)cc(Cl)cn1-c1ccc2c(c1)CCC2]
Example 72
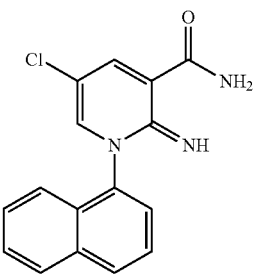 [SMILES: N=c1c(C(N)=O)cc(Cl)cn1-c1cccc2ccccc12]
Example 73
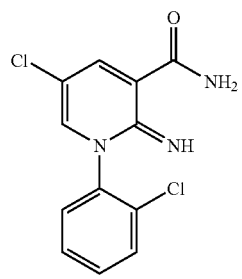 [SMILES: N=c1c(C(N)=O)cc(Cl)cn1-c1ccccc1Cl]
Example 74
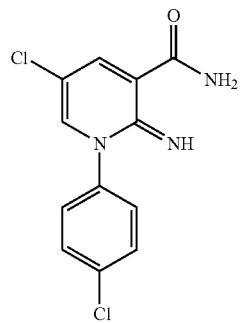 [SMILES: N=c1c(C(N)=O)cc(Cl)cn1-c1ccc(Cl)cc1]

TABLE 3-continued
Example 75
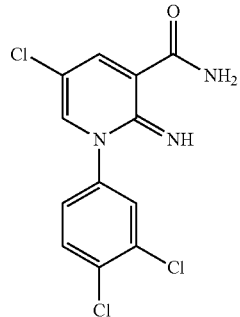 [SMILES: N=c1c(C(N)=O)cc(Cl)cn1-c1ccc(Cl)c(Cl)c1]
Example 76
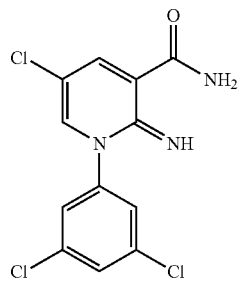 [SMILES: N=c1c(C(N)=O)cc(Cl)cn1-c1cc(Cl)cc(Cl)c1]
Example 77
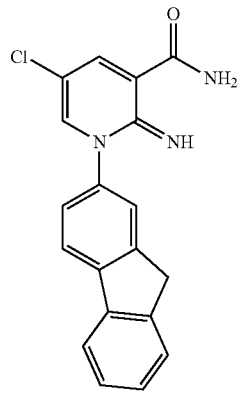 [SMILES: N=c1c(C(N)=O)cc(Cl)cn1-c1ccc2c(c1)Cc1ccccc1-2]
Example 78
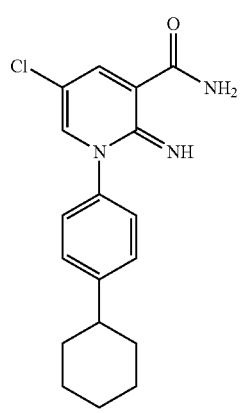 [SMILES: N=c1c(C(N)=O)cc(Cl)cn1-c1ccc(C2CCCCC2)cc1]
TABLE 3-continued
Example 79
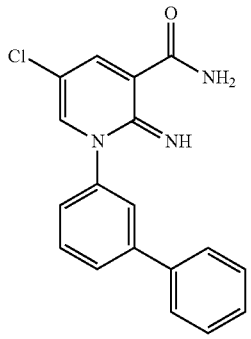 [SMILES: N=c1c(C(N)=O)cc(Cl)cn1-c1cccc(-c2ccccc2)c1]
Example 80
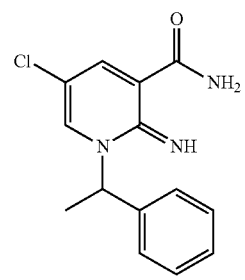 [SMILES: CC(c1ccccc1)n1cc(Cl)cc(C(N)=O)c1=N]
Example 81
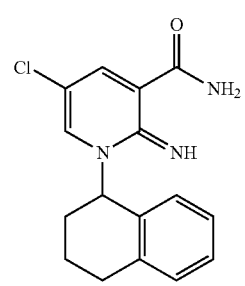 [SMILES: N=c1c(C(N)=O)cc(Cl)cn1C1CCCc2ccccc21]
Example 82
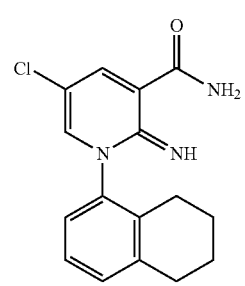 [SMILES: N=c1c(C(N)=O)cc(Cl)cn1-c1cccc2c1CCCC2]

TABLE 3-continued
Example 83
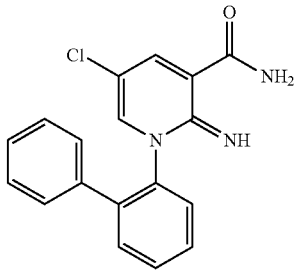 [SMILES: N=c1c(C(N)=O)cc(Cl)cn1-c1ccccc1-c1ccccc1]
Example 84
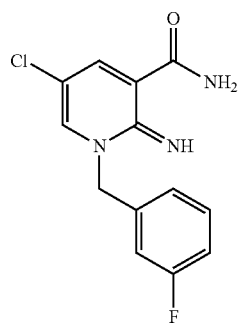 [SMILES: N=c1c(C(N)=O)cc(Cl)cn1Cc1cccc(F)c1]
Example 85
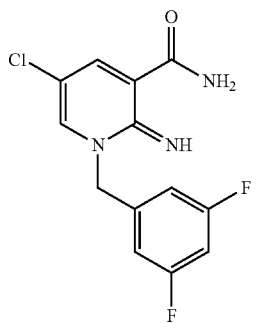 [SMILES: N=c1c(C(N)=O)cc(Cl)cn1Cc1cc(F)cc(F)c1]
Example 86
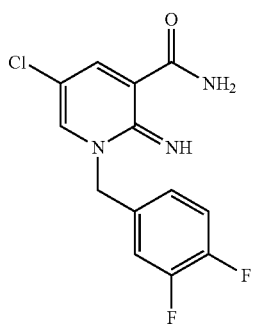 [SMILES: N=c1c(C(N)=O)cc(Cl)cn1Cc1ccc(F)c(F)c1]
TABLE 3-continued
Example 87
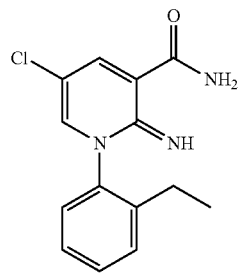 [SMILES: CCc1ccccc1-n1cc(Cl)cc(C(N)=O)c1=N]
Example 88
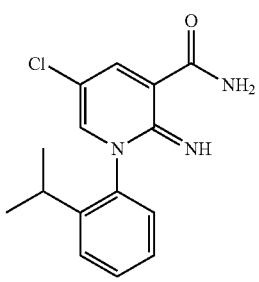 [SMILES: CC(C)c1ccccc1-n1cc(Cl)cc(C(N)=O)c1=N]
Example 89
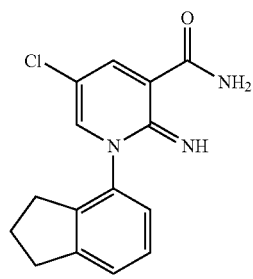 [SMILES: N=c1c(C(N)=O)cc(Cl)cn1-c1cccc2c1CCC2]
Example 90
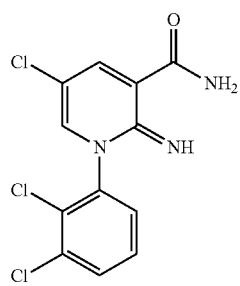 [SMILES: N=c1c(C(N)=O)cc(Cl)cn1-c1cccc(Cl)c1Cl]

TABLE 3-continued
Example 91
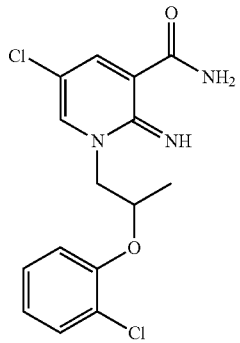 [SMILES: CC(Cn1cc(Cl)cc(C(N)=O)c1=N)Oc1ccccc1Cl]
Example 92
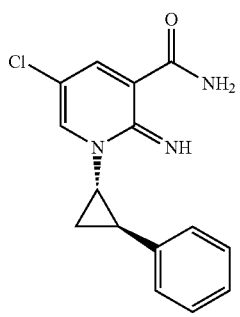 [SMILES: N=c1c(C(N)=O)cc(Cl)cn1[C@H]1C[C@@H]1c1ccccc1]
Example 93
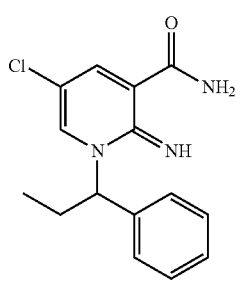 [SMILES: CCC(c1ccccc1)n1cc(Cl)cc(C(N)=O)c1=N]
Example 94
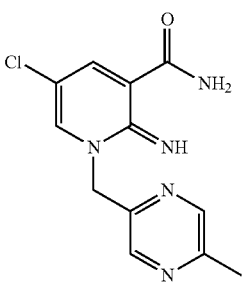 [SMILES: Cc1cnc(Cn2cc(Cl)cc(C(N)=O)c2=N)cn1]
TABLE 3-continued
Example 95
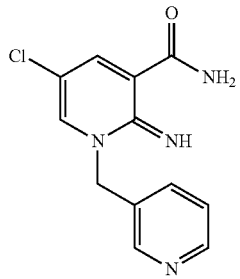 [SMILES: N=c1c(C(N)=O)cc(Cl)cn1Cc1cccnc1]
Example 96
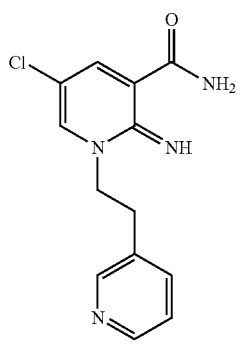 [SMILES: N=c1c(C(N)=O)cc(Cl)cn1CCc1cccnc1]
Example 97
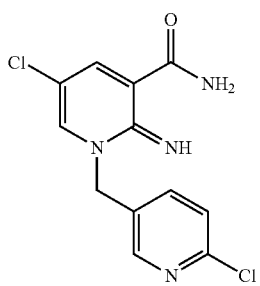 [SMILES: N=c1c(C(N)=O)cc(Cl)cn1Cc1ccc(Cl)nc1]
Example 98
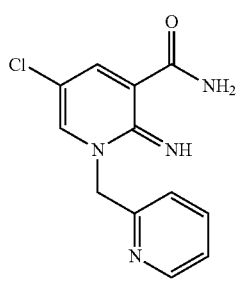 [SMILES: N=c1c(C(N)=O)cc(Cl)cn1Cc1ccccn1]

TABLE 3-continued
Example 99
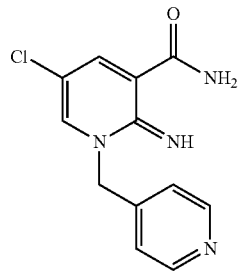 [SMILES: N=c1c(C(N)=O)cc(Cl)cn1Cc1ccncc1]
Example 100
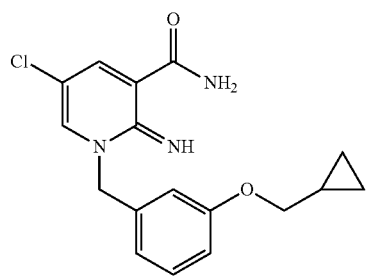 [SMILES: N=c1c(C(N)=O)cc(Cl)cn1Cc1cccc(OCC2CC2)c1]
Example 101
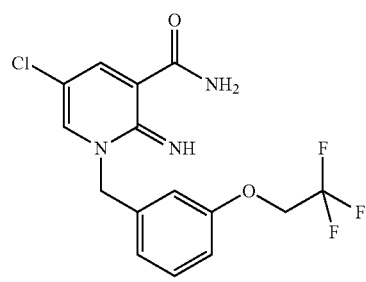 [SMILES: N=c1c(C(N)=O)cc(Cl)cn1Cc1cccc(OCC(F)(F)F)c1]
Example 102
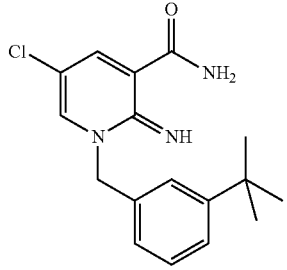 [SMILES: CC(C)(C)c1cccc(Cn2cc(Cl)cc(C(N)=O)c2=N)c1]
TABLE 3-continued
Example 103
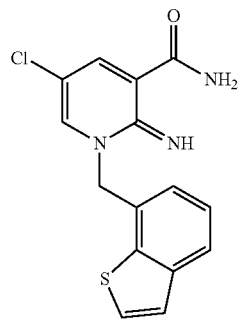 [SMILES: N=c1c(C(N)=O)cc(Cl)cn1Cc1cccc2ccsc12]
Example 104
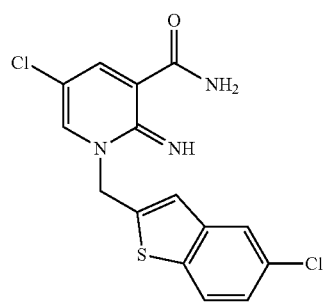 [SMILES: N=c1c(C(N)=O)cc(Cl)cn1Cc1cc2cc(Cl)ccc2s1]
Example 105
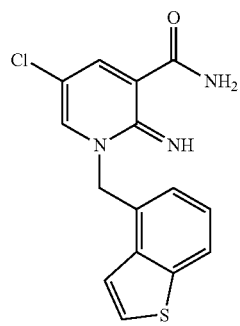 [SMILES: N=c1c(C(N)=O)cc(Cl)cn1Cc1cccc2sccc12]
Example 106
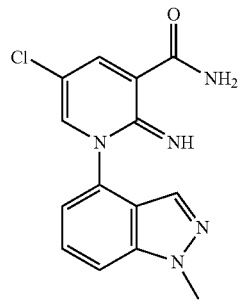 [SMILES: Cn1ncc2c(-n3cc(Cl)cc(C(N)=O)c3=N)cccc21]

TABLE 3-continued
Example 107
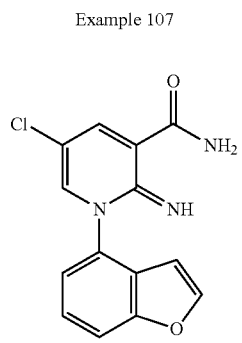
Example 108
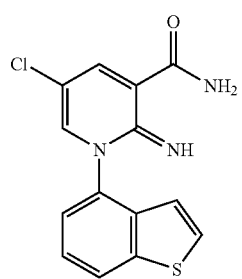 [SMILES: N=c1c(C(N)=O)cc(Cl)cn1-c1cccc2sccc12]
Example 109
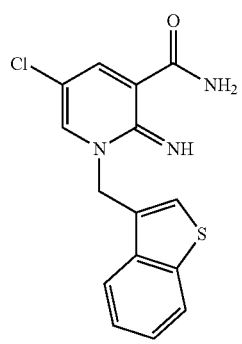 [SMILES: N=c1c(C(N)=O)cc(Cl)cn1Cc1csc2ccccc12]
Example 110
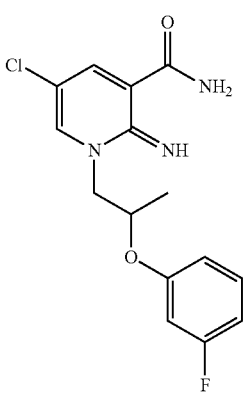 [SMILES: CC(Cn1cc(Cl)cc(C(N)=O)c1=N)Oc1cccc(F)c1]
TABLE 3-continued
Example 111
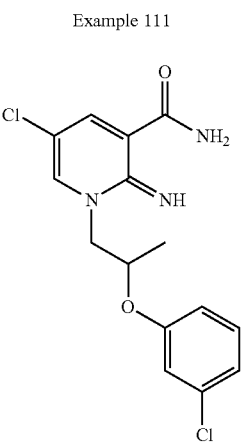
Example 112
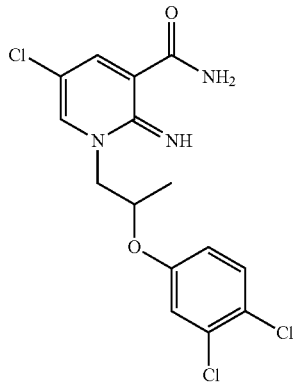 [SMILES: CC(Cn1cc(Cl)cc(C(N)=O)c1=N)Oc1ccc(Cl)c(Cl)c1]
Example 113
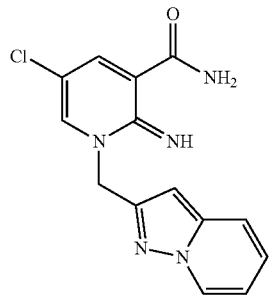 [SMILES: N=c1c(C(N)=O)cc(Cl)cn1Cc1cc2ccccn2n1]
Example 114
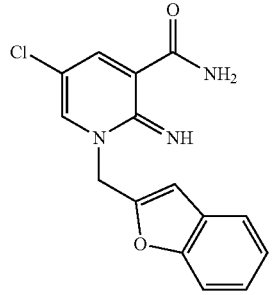 [SMILES: N=c1c(C(N)=O)cc(Cl)cn1Cc1cc2ccccc2o1]

TABLE 3-continued
Example 115
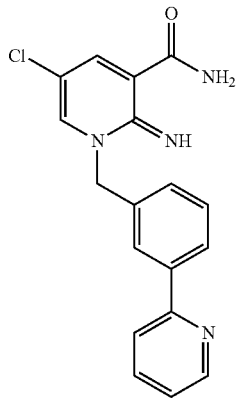 [SMILES: N=c1c(C(N)=O)cc(Cl)cn1Cc1cccc(-c2ccccn2)c1]
Example 116
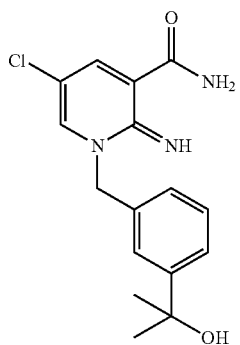 [SMILES: CC(C)(O)c1cccc(Cn2cc(Cl)cc(C(N)=O)c2=N)c1]
Example 117
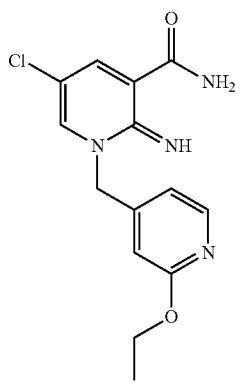 [SMILES: CCOc1cc(Cn2cc(Cl)cc(C(N)=O)c2=N)ccn1]
Example 118
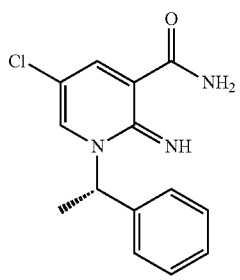 [SMILES: C[C@@H](c1ccccc1)n1cc(Cl)cc(C(N)=O)c1=N]
TABLE 3-continued
Example 119
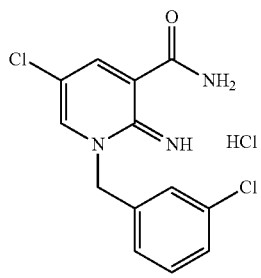 [SMILES: N=c1c(C(N)=O)cc(Cl)cn1Cc1cccc(Cl)c1 ; Cl]
Example 120
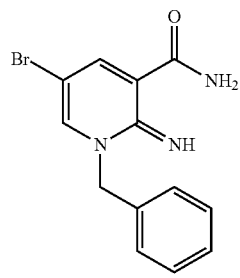 [SMILES: N=c1c(C(N)=O)cc(Br)cn1Cc1ccccc1]
Example 121
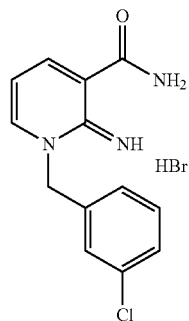 [SMILES: N=c1c(C(N)=O)cccn1Cc1cccc(Cl)c1 ; Br]
Example 122
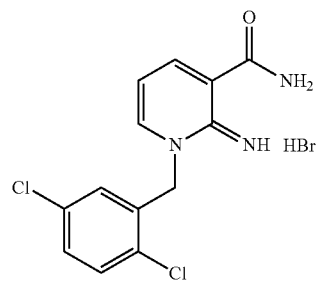 [SMILES: N=c1c(C(N)=O)cccn1Cc1cc(Cl)ccc1Cl ; Br]

TABLE 3-continued
Example 123
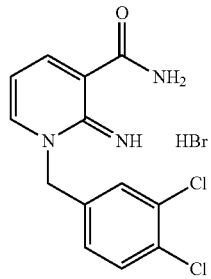 [SMILES: N=c1c(C(N)=O)cccn1Cc1ccc(Cl)c(Cl)c1 ; Br]
Example 124
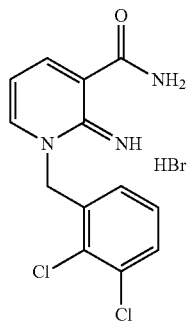 [SMILES: N=c1c(C(N)=O)cccn1Cc1cccc(Cl)c1Cl ; Br]
Example 125
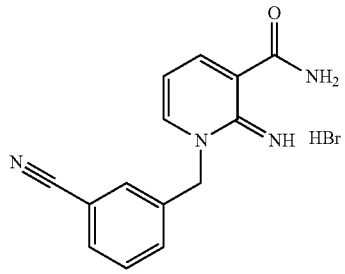 [SMILES: N#Cc1cccc(Cn2cccc(C(N)=O)c2=N)c1 ; Br]
Example 126
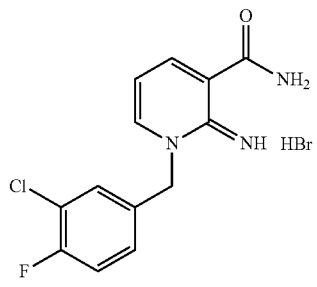 [SMILES: N=c1c(C(N)=O)cccn1Cc1ccc(F)c(Cl)c1 ; Br]
TABLE 3-continued
Example 127
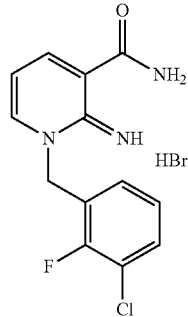
Example 128
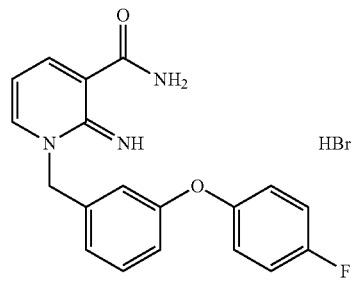 [SMILES: N=c1c(C(N)=O)cccn1Cc1cccc(Oc2ccc(F)cc2)c1 ; Br]
Example 129
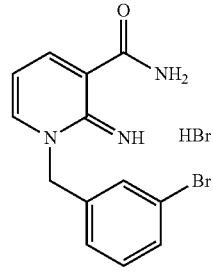 [SMILES: N=c1c(C(N)=O)cccn1Cc1cccc(Br)c1 ; Br]
Example 130
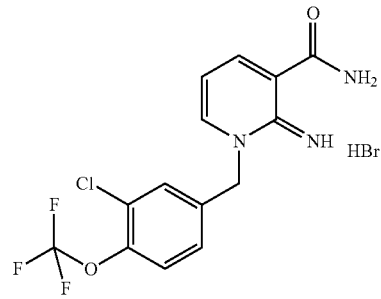 [SMILES: N=c1c(C(N)=O)cccn1Cc1ccc(OC(F)(F)F)c(Cl)c1 ; Br]

TABLE 3-continued
Example 131
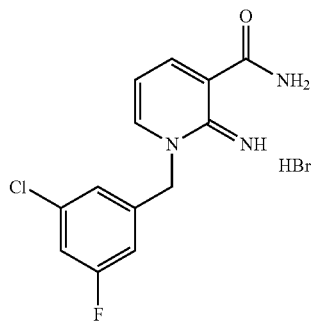 [SMILES: N=c1c(C(N)=O)cccn1Cc1cc(F)cc(Cl)c1 ; Br]
Example 132
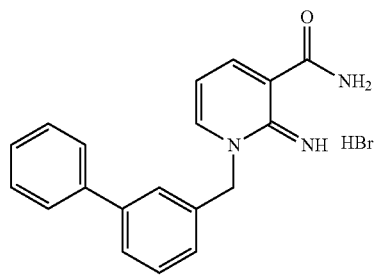 [SMILES: N=c1c(C(N)=O)cccn1Cc1cccc(-c2ccccc2)c1 ; Br]
Example 133
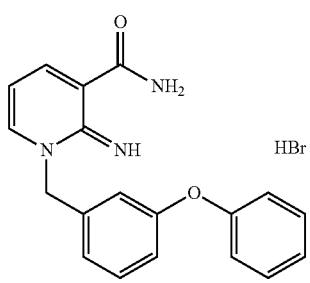 [SMILES: N=c1c(C(N)=O)cccn1Cc1cccc(Oc2ccccc2)c1 ; Br]
Example 134
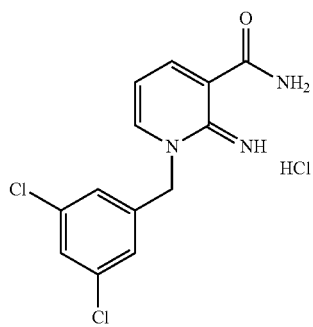 [SMILES: N=c1c(C(N)=O)cccn1Cc1cc(Cl)cc(Cl)c1 ; Cl]
TABLE 3-continued
Example 135
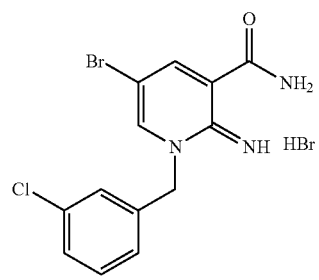 [SMILES: N=c1c(C(N)=O)cc(Br)cn1Cc1cccc(Cl)c1 ; Br]
Example 136
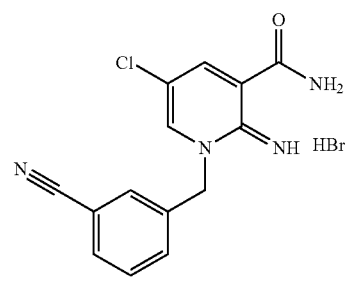 [SMILES: N#Cc1cccc(Cn2cc(Cl)cc(C(N)=O)c2=N)c1 ; Br]
Example 137
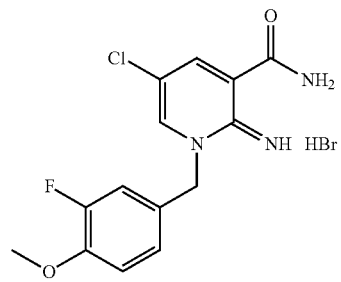 [SMILES: COc1ccc(Cn2cc(Cl)cc(C(N)=O)c2=N)cc1F ; Br]
Example 138
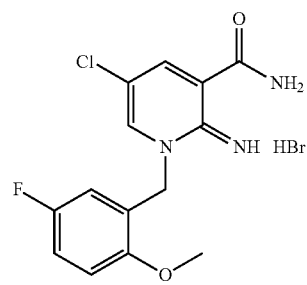 [SMILES: COc1ccc(F)cc1Cn1cc(Cl)cc(C(N)=O)c1=N ; Br]

TABLE 3-continued
Example 139
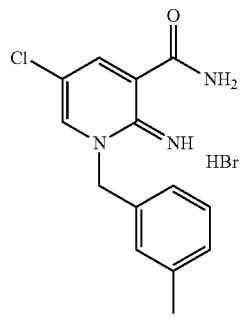 [SMILES: Cc1cccc(Cn2cc(Cl)cc(C(N)=O)c2=N)c1 ; Br]
Example 140
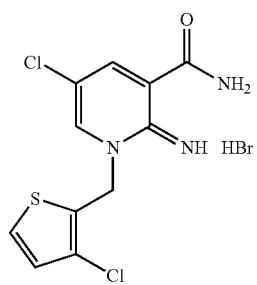 [SMILES: N=c1c(C(N)=O)cc(Cl)cn1Cc1sccc1Cl ; Br]
Example 141
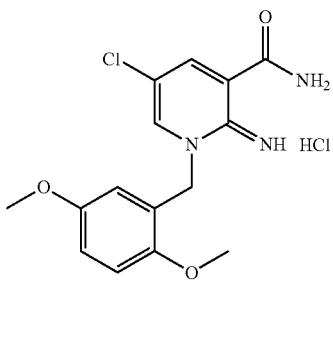 [SMILES: COc1ccc(OC)c(Cn2cc(Cl)cc(C(N)=O)c2=N)c1 ; Cl]
Example 142
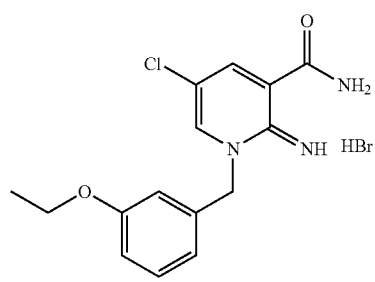 [SMILES: CCOc1cccc(Cn2cc(Cl)cc(C(N)=O)c2=N)c1 ; Br]
TABLE 3-continued
Example 143
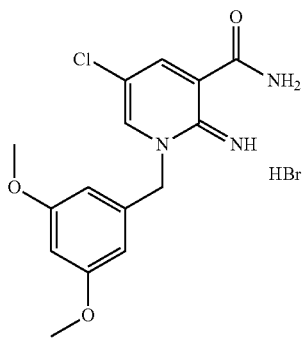 [SMILES: COc1cc(Cn2cc(Cl)cc(C(N)=O)c2=N)cc(OC)c1 ; Br]
Example 144
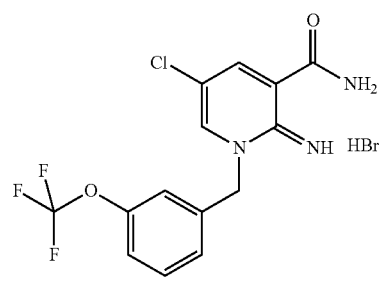 [SMILES: N=c1c(C(N)=O)cc(Cl)cn1Cc1cccc(OC(F)(F)F)c1 ; Br]
Example 145
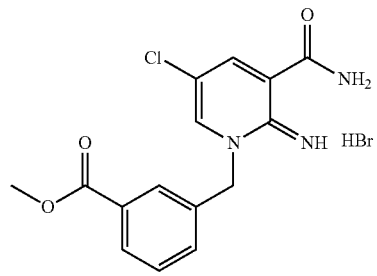 [SMILES: COC(=O)c1cccc(Cn2cc(Cl)cc(C(N)=O)c2=N)c1 ; Br]
Example 146
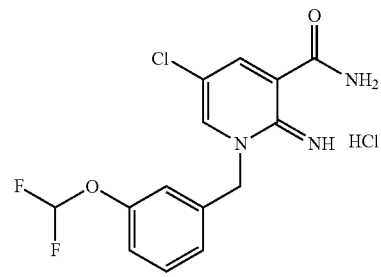 [SMILES: N=c1c(C(N)=O)cc(Cl)cn1Cc1cccc(OC(F)F)c1 ; Cl]

TABLE 3-continued
Example 147
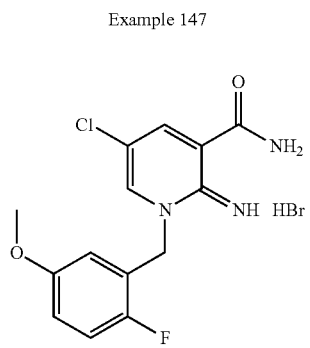
Example 148
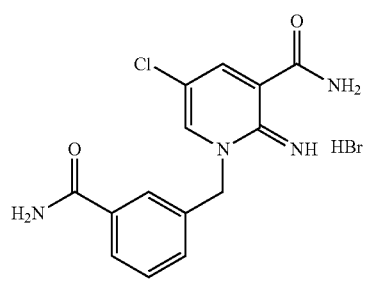
Example 149
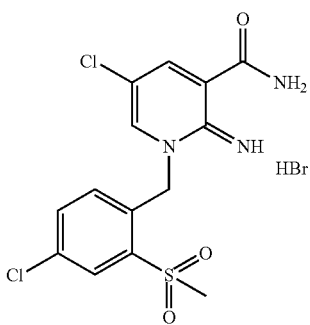 [SMILES: CS(=O)(=O)c1cc(Cl)ccc1Cn1cc(Cl)cc(C(N)=O)c1=N ; Br]
Example 150
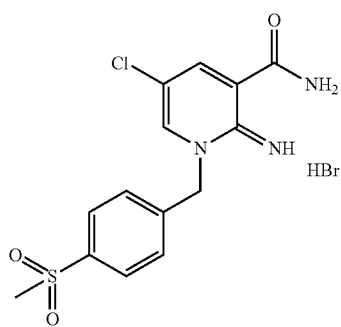 [SMILES: CS(=O)(=O)c1ccc(Cn2cc(Cl)cc(C(N)=O)c2=N)cc1 ; Br]
TABLE 3-continued
Example 151
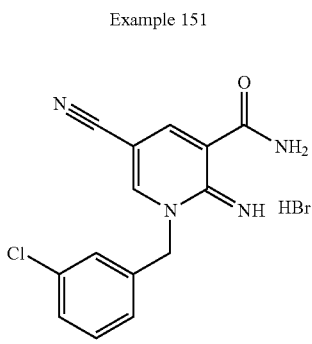
Example 152
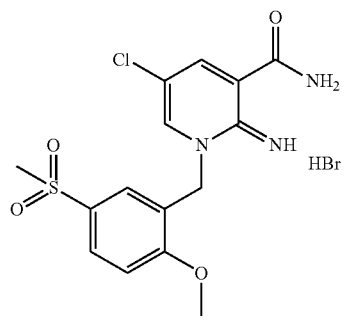 [SMILES: COc1ccc(S(C)(=O)=O)cc1Cn1cc(Cl)cc(C(N)=O)c1=N ; Br]
Example 153
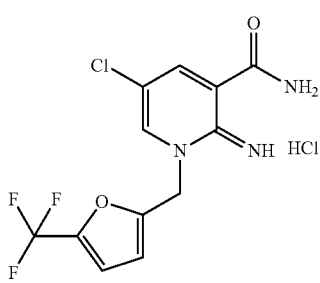 [SMILES: N=c1c(C(N)=O)cc(Cl)cn1Cc1ccc(C(F)(F)F)o1 ; Cl]
Example 154
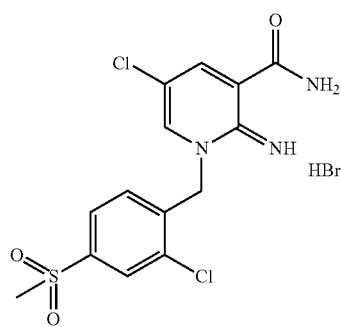 [SMILES: CS(=O)(=O)c1ccc(Cn2cc(Cl)cc(C(N)=O)c2=N)c(Cl)c1 ; Br]

TABLE 3-continued
Example 155
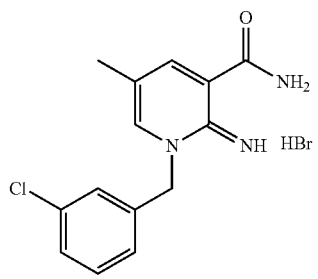 [SMILES: Cc1cc(C(N)=O)c(=N)n(Cc2cccc(Cl)c2)c1 ; Br]
Example 156
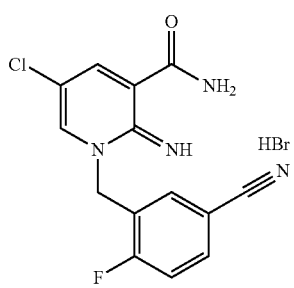 [SMILES: N#Cc1ccc(F)c(Cn2cc(Cl)cc(C(N)=O)c2=N)c1 ; Br]
Example 157
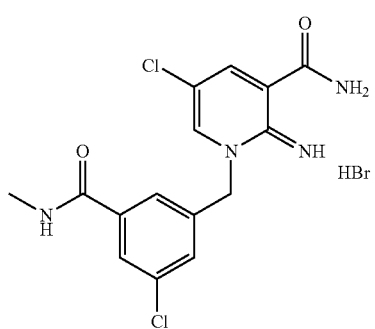 [SMILES: CNC(=O)c1cc(Cl)cc(Cn2cc(Cl)cc(C(N)=O)c2=N)c1 ; Br]
Example 158
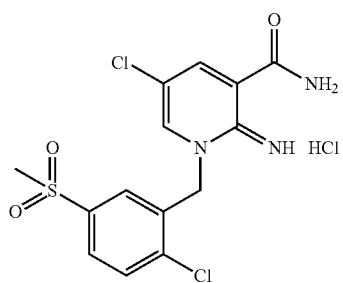 [SMILES: CS(=O)(=O)c1ccc(Cl)c(Cn2cc(Cl)cc(C(N)=O)c2=N)c1 ; Cl]
TABLE 3-continued
Example 159
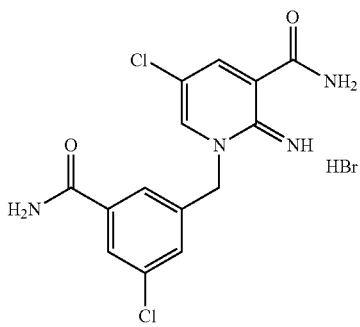 [SMILES: N=c1c(C(N)=O)cc(Cl)cn1Cc1cc(Cl)cc(C(N)=O)c1 ; Br]
Example 160
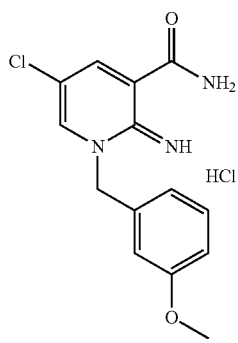 [SMILES: COc1cccc(Cn2cc(Cl)cc(C(N)=O)c2=N)c1 ; Cl]
Example 161
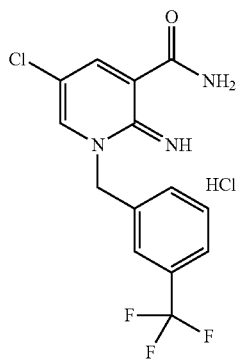 [SMILES: N=c1c(C(N)=O)cc(Cl)cn1Cc1cccc(C(F)(F)F)c1 ; Cl]
Example 162
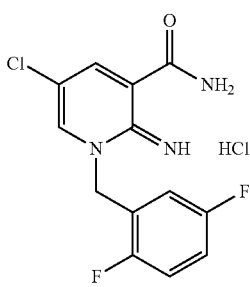 [SMILES: N=c1c(C(N)=O)cc(Cl)cn1Cc1cc(F)ccc1F ; Cl]

TABLE 3-continued
Example 163
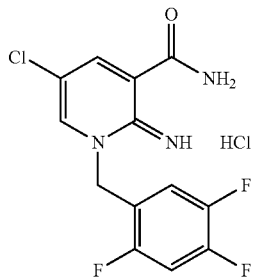 [SMILES: N=c1c(C(N)=O)cc(Cl)cn1Cc1cc(F)c(F)cc1F ; Cl]
Example 164
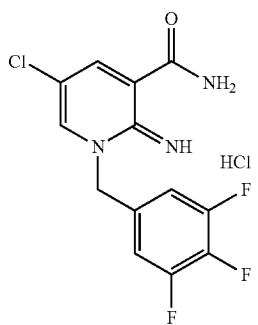 [SMILES: N=c1c(C(N)=O)cc(Cl)cn1Cc1cc(F)c(F)c(F)c1 ; Cl]
Example 165
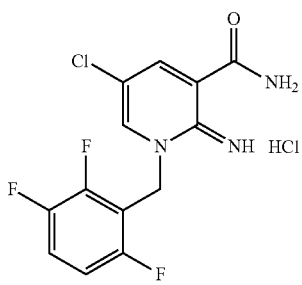 [SMILES: N=c1c(C(N)=O)cc(Cl)cn1Cc1c(F)ccc(F)c1F ; Cl]
Example 166
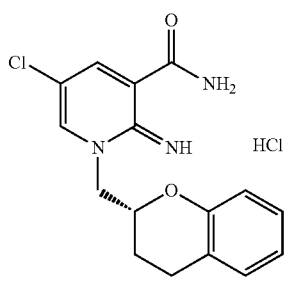 [SMILES: N=c1c(C(N)=O)cc(Cl)cn1C[C@H]1CCc2ccccc2O1 ; Cl]
TABLE 3-continued
Example 167
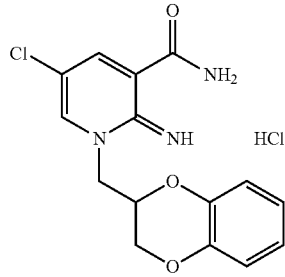 [SMILES: N=c1c(C(N)=O)cc(Cl)cn1CC1COc2ccccc2O1 ; Cl]
Example 168
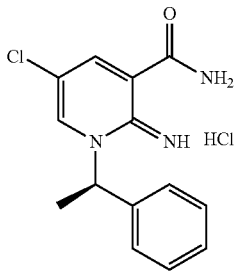 [SMILES: C[C@H](c1ccccc1)n1cc(Cl)cc(C(N)=O)c1=N ; Cl]
Example 169
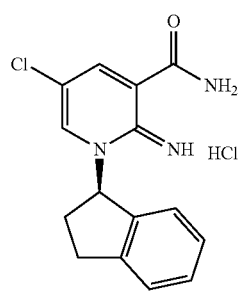 [SMILES: N=c1c(C(N)=O)cc(Cl)cn1[C@@H]1CCc2ccccc21 ; Cl]
Example 170
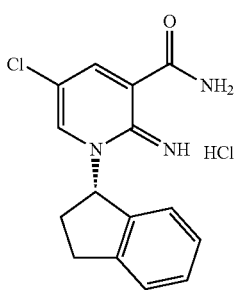 [SMILES: N=c1c(C(N)=O)cc(Cl)cn1[C@H]1CCc2ccccc21 ; Cl]

TABLE 3-continued
Example 171
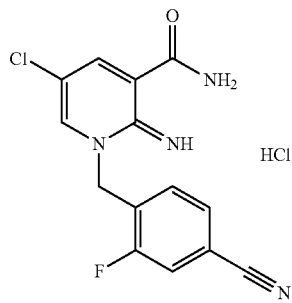 [SMILES: N#Cc1ccc(Cn2cc(Cl)cc(C(N)=O)c2=N)c(F)c1 ; Cl]
HCl
Example 172
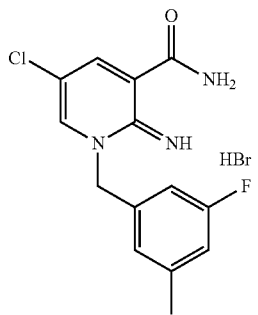 [SMILES: Cc1cc(F)cc(Cn2cc(Cl)cc(C(N)=O)c2=N)c1 ; Br]
HBr
Example 173
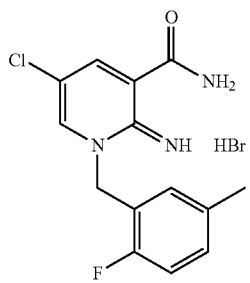 [SMILES: Cc1ccc(F)c(Cn2cc(Cl)cc(C(N)=O)c2=N)c1 ; Br]
HBr
Example 174
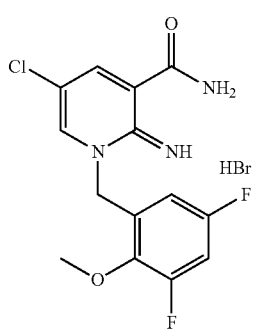 [SMILES: COc1c(F)cc(F)cc1Cn1cc(Cl)cc(C(N)=O)c1=N ; Br]
HBr
TABLE 3-continued
Example 175
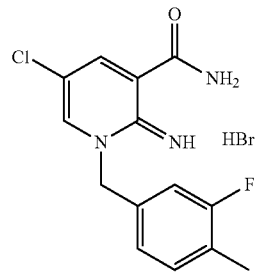 [SMILES: Cc1ccc(Cn2cc(Cl)cc(C(N)=O)c2=N)cc1F ; Br]
HBr
Example 176
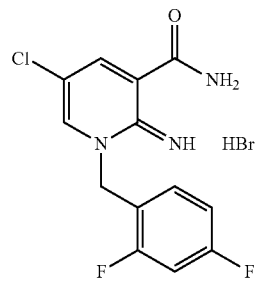 [SMILES: N=c1c(C(N)=O)cc(Cl)cn1Cc1ccc(F)cc1F ; Br]
HBr
Example 177
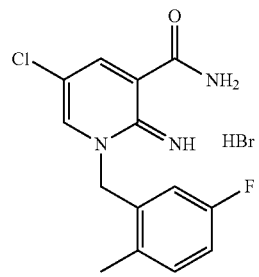 [SMILES: Cc1ccc(F)cc1Cn1cc(Cl)cc(C(N)=O)c1=N ; Br]
HBr
Example 178
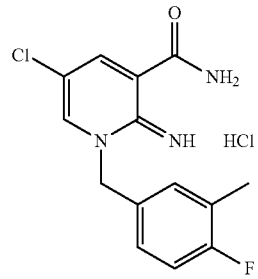 [SMILES: Cc1cc(Cn2cc(Cl)cc(C(N)=O)c2=N)ccc1F ; Cl]
HCl
Example 179
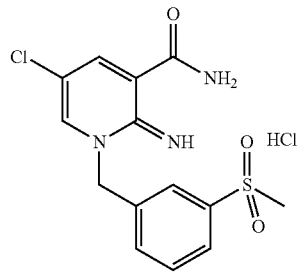 [SMILES: CS(=O)(=O)c1cccc(Cn2cc(Cl)cc(C(N)=O)c2=N)c1 ; Cl]
HCl TABLE 3-continued
Example 180
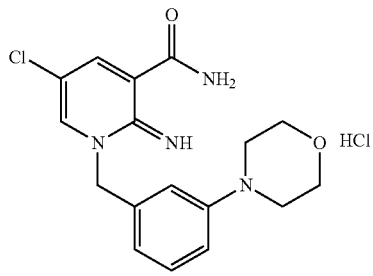 [SMILES: N=c1c(C(N)=O)cc(Cl)cn1Cc1cccc(N2CCOCC2)c1 ; Cl]
Example 181
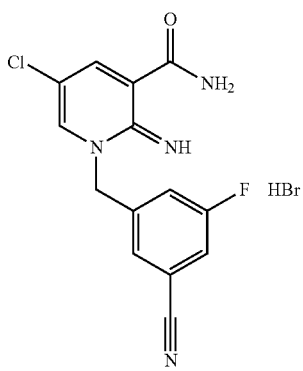 [SMILES: N#Cc1cc(F)cc(Cn2cc(Cl)cc(C(N)=O)c2=N)c1 ; Br]
Example 182
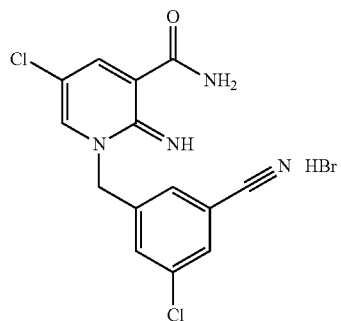 [SMILES: N#Cc1cc(Cl)cc(Cn2cc(Cl)cc(C(N)=O)c2=N)c1 ; Br]
Example 183
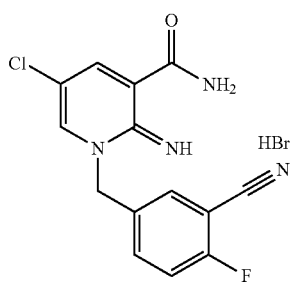 [SMILES: N#Cc1cc(Cn2cc(Cl)cc(C(N)=O)c2=N)ccc1F ; Br]
TABLE 3-continued
Example 184
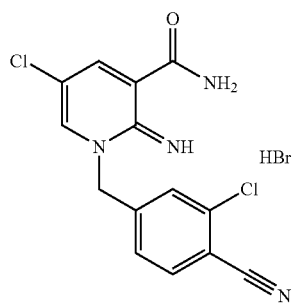 [SMILES: N#Cc1ccc(Cn2cc(Cl)cc(C(N)=O)c2=N)cc1Cl ; Br]
Example 185
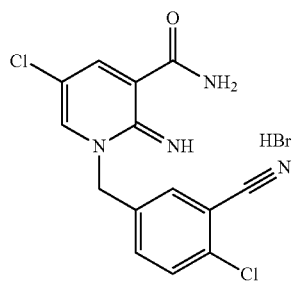 [SMILES: N#Cc1cc(Cn2cc(Cl)cc(C(N)=O)c2=N)ccc1Cl ; Br]
Example 186
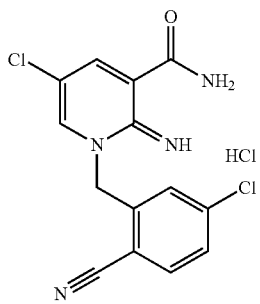 [SMILES: N#Cc1ccc(Cl)cc1Cn1cc(Cl)cc(C(N)=O)c1=N ; Cl]
Example 187
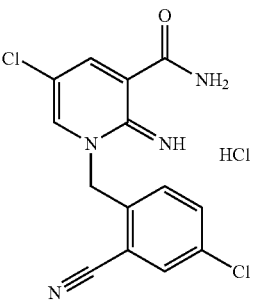 [SMILES: N#Cc1cc(Cl)ccc1Cn1cc(Cl)cc(C(N)=O)c1=N ; Cl]

TABLE 3-continued

Example 188

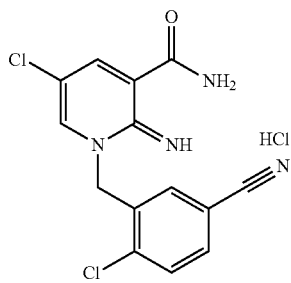 [SMILES: N#Cc1ccc(Cl)c(Cn2cc(Cl)cc(C(N)=O)c2=N)c1 ; Cl]

Example 189

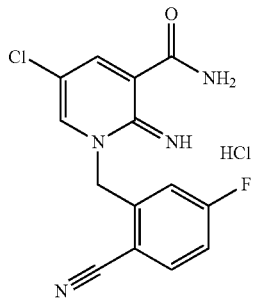 [SMILES: N#Cc1ccc(F)cc1Cn1cc(Cl)cc(C(N)=O)c1=N ; Cl]

Experimental Example 1

Measurement of $\alpha_{1D}$ Receptor Binding Inhibitory Activity

Genetic manipulation methods described below are based on the methods described in Maniatis et al., Molecular Cloning, Cold Spring Harbor Laboratory, 1989, the protocol appended to a reagent and the like.

(i) Preparation of Human Adrenaline $\alpha_{1D}$ Receptor Expression Plasmid

Adrenaline $\alpha_{1D}$ receptor gene was cloned from human liver CDNA by the PCR method. PCR reaction was performed by Gene Amp PCR System 9700 (Applied Biosystems) with 50 μmol each of the primer set 5'-CCGACGGC-CGCTAGCGAGATGACTTTCCGCGATCTCCTGAGCGTC-3' [SEQ ID NO: 1] and 5'-GCTCTGGGTACCTTAAATATCG-GTCTCCCGTAGGTTGC-3' [SEQ ID NO: 2] prepared in reference to the base sequence of the adrenaline $\alpha_{1D}$ receptor gene reported by DEBRA A. et al. (J. Pharamacol. Exp. Ter., 272, 134-142 (1995)), 200 ng of human brain hippocampus cDNA library (Takara Shuzo Co., Ltd.) as a template and TaKaRa LA-Taq DNA Polymerase (Takara Shuzo Co., Ltd.) (reaction conditions: 45 cycles of 94° C. for 15 sec, 68° C. for 3.5 min).

The PCR fragment obtained above was digested with restriction enzymes NheI (Takara Shuzo Co., Ltd.) and Kpn I (Takara Shuzo Co., Ltd.) and applied to agarose gel electrophoresis to recover DNA fragments. The DNA fragments was ligated with animal cell expression plasmid, pcDNA3.1/Zeo (Invitrogen) digested with NheI and Kpn I, by DNA Ligation Kit Ver.2 (Takara Shuzo Co., Ltd.), and transformed the competent cells of Escherichia coli JM109 to obtain plasmid, pcDNA3.1/Zeo-Adre$\alpha_{1D}$.

(ii) Introduction of Human Adrenaline $\alpha_{1D}$ Receptor Expression Plasmid into CHO-K1 Cells and Preparation of Membrane Fraction CHO-K1 cells passage cultured in HmF12 medium (Invitrogen) containing 10% fetal bovine serum (TRACE SCIENCETIFIC) in a 150 cm² culture flask (Corning Coaster) were detached with 0.5 g/L trypsin-0.2 g/L EDTA (Invitrogen), and the cells were washed with D-PBS(−) (Invitrogen) and centrifuged (1000 rpm, 5 min). Then, using Gene Pulser II (Bio-Rad), DNA was introduced into the cells under the following conditions. 1×10⁷ cells suspended in D-PBS(−) (700 μl) and 10 μg of pcDNA3.1/Zeo-Adre$\alpha_{1D}$ were added in a 0.4 cm gap cuvette (BioRad), and electroporation was performed under voltage 0.25 kV, capacitance 960 μF. The cells were cultured in HamF12 medium containing 10% fetal bovine serum and 250 μg/mL Zeocin (Invitrogen) and the Zeocin resistance clones were selected.

Plurality of Zeocin resistance clones were selected and cultured in a cell culture flask (150 cm²) until semiconfluent, and the cellular membrane fraction was prepared as follows.

The semiconfluent cells were detached with 0.02% EDTA containing D-PBS(−) and recovered by centrifugation. The cells were suspended in membrane preparation buffer (10 mM NaHCO₃ pH 7.4, protease inhibitor cocktail (Roche)) and disrupted by 3 times of treatment in a polytron homogenizer (model PT-3100, KINEMATICA AG) at 20000 rpm for 20 seconds. After disruption, the cells were centrifuged at 2000 rpm for 10 min and the supernatant containing membrane fractions was obtained. The supernatant was centrifuged using an ultracentrifuge (model L8-70M, rotor 70 Ti, Beckman Instruments) at 30000 rpm for 1 hr to obtain a precipitate containing membrane fractions. The obtained membrane fraction of each clone was subjected to the binding experiment shown below.

The membrane fraction (20 μg/well) [³H] prazosin (2.5 nM, PerkinElmer Lifescience), as a ligand, were diluted with a binding assay buffer (50 mM Tris-HCl, 10 mM MgCl₂, 0.5% BSA, protease inhibitor cocktail pH 7.5) and added to a 96 well microplate, and reacted at room temperature for 1 hr. For the measurement of non-specific binding, phentolamine (Sigma) was further added to 10 μM. Then, the reaction mixture was filtered and transferred to unifilter GF/C (PerkinElmer Lifescience) by using a cell harvester (PerkinElmer Lifescience). The filter was washed 3 times with ice-cooled 50 mM Tris buffer (pH 7.5). After drying the filter, MicroScinti 0 (PerkinElmer Lifescience) was added to the filter and the radioactivity was measured by TopCount (PerkinElmer Lifescience). Membrane fractions for compound evaluation shown below were prepared by the same method as mentioned previously from the clone that showed the most superior S/B value (total binding radioactivity/non-specific binding radioactivity) in the binding measurement using the membrane fractions.

(iii) Evaluation of Example Compound

The membrane fraction (20 μg/well), the compound and [³H] prazosin (2.5 nM, PerkinElmer Lifescience) were diluted with a binding assay buffer, added to a 96 well microplate, and reacted at room temperature for 1 hr. For the measurement of non-specific binding, phentolamine (Sigma), which is a cold ligand, was further added to 10 μM. Then, the reaction mixture was filtered and transferred to unifilter GF/C (PerkinElmer Lifescience) by using a cell harvester (PerkinElmer Lifescience). The filter was washed 3 times with cooled 50 mM Tris buffer (pH 7.5). After drying the filter, MicroScinti 0 (PerkinElmer Lifescience) was added to the filter and the radioactivity was measured by TopCount (PerkinElmer Lifescience).

The concentration of the compound necessary for decreasing the amount of binding of [$^3$H]-prazosin to the membrane fraction to 50% (IC$_{50}$) was calculated by GlaphPad Prism Ver3.2 (GlaphPad Software).

The results measured by the above-mentioned method ($\alpha_{1D}$ receptor binding inhibitory rate at 1 µM) are shown in Table 4.

TABLE 4

| test compound (Example No.) | binding inhibitory rate (%) |
|---|---|
| 19 | 99.1 |
| 20 | 100.5 |
| 23 | 81.8 |
| 26 | 75.7 |
| 32 | 93.9 |
| 149 | 96.0 |
| 151 | 69.5 |
| 156 | 91.8 |
| 168 | 94.7 |
| 169 | 100.3 |
| 181 | 95.4 |
| 182 | 99.2 |

Experimental Example 2

$\alpha_1$ Receptor Stimulation-Induced Contraction of Isolated Bladder Muscle of Bladder Outlet Obstruction (BOO) Model Rat (i) 7-week-old male Wistar rats (CLEA Japan, Inc., Tokyo) were used. BOO rat was prepared according to publications (Hashimoto T, Nagabukuro H and Doi T: Effects of the selective acetylcholinesterase inhibitor TAK-802 on the voiding behavior and bladder mass increase in rats with partial bladder outlet obstruction. J Urol. 174: 1137-41., 2005.). After pentobarbital (50 mg/kg i.p., Dainippon Sumitomo Pharma Co., Ltd., Osaka) anesthesia, A lower middle abdominal incision was made to expose the bladder. The prostate was detached, the urethra was ligated along with a glass rod having an outer diameter of 1.2 mm, and the glass rod was removed to prepare partial obstruction of the urethra. An animal less the ligation procedure alone was used as a sham surgery rat. After the surgery, the abdomen was sutured, and penicillin (2000 IU/rat, penicillin G potassium, MEIJI SEIKA KAISHA, LTD., Tokyo) was subcutaneously administered. An animal after 2 to 4 weeks from obstruction surgery was used.

(ii) Contractile Responses of Isolated Bladder Muscle (1) Preparation of Bladder Muscle Specimen BOO model rat or sham surgery rat was sacrificed by decaptation, and the bladder was isolated. Muscle strips (length 7-10 mm in the longitudinal direction, width about 3 mm) were prepared from the bladder except bladder trigone (4-6 specimen from each bladder).

(2) Measurement of Tension

The prepared bladder muscle specimens were hung in a Magnus bath aerated with 95% O$_2$-5% CO$_2$ gas and filled with modified Krebs solution. The contraction tension was measured by an isometric strain transducer (TSD125C, Biopac systems, Santa Barbara, Calif., USA) and recorded in the hard disc of PC (ThinkCentre, IBM, USA) via an amplifier (DA100C, Biopac systems) and a multichannel data analysis apparatus (MP100A-CE, Biopac systems). For uptaking the data, a dedicated software (Acqknowledge 3.8.1., Biopac systems) was used and the sampling interval was set to 0.2 second (5 Hz). The specimens were hung with a load of about 1 g and, after an equilibration time of 1 hr or longer, the following experiment was performed.

Phenylephrine ($10^{-8}$-$10^{-4}$ mol/L) was cumulatively treated at a 3-fold common ratio, and the change of the tension was observed. After the completion of the experiment, contraction was induced with a 100 mmol/L KCl-modified Krebs solution.

(3) Data Analysis

The change of tension due to phenylephrine stimulation was evaluated by the two methods shown below [% KCl method and standard deviation (Stddev) method].

(3-1) % KCl Method

The maximum tension of each concentration with cumulative treatment with phenylephrine was measured for one minute immediately before completion of the observation time. In addition, the maximum tension for one minute immediately before phenylephrine treatment and for one minute immediately before 100 mmol/L KCl treatment, and the maximum tension of 100 mmol/L KCl-induced contraction were measured. The change of tension at each phenylephrine concentration (maximum tension after treatment at each concentration—maximum tension before drug treatment) was calculated, and standardized based on 100 mmol/L KCl-induced contraction tension (maximum tension after 100 mmol/L KCl treatment—maximum tension before treatment).

(3-2) Stddev Method

The standard deviation was measured for 3 minutes immediately before phenylephrine treatment, and for 3 minutes immediately before completion of the observation time of each concentration with cumulative treatment, and the difference between them (standard deviation after treatment at each concentration—standard deviation before drug treatment) was calculated, and the level of contractile response accompanying sustained and rhythmic fluctuation was numerically converted.

Figure 2:
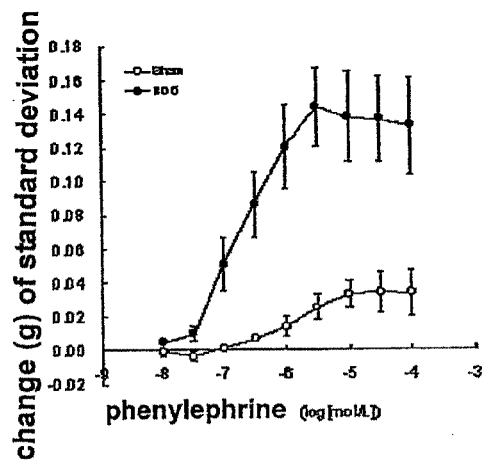
FIG. 2 a graph showing phenylephrine-induced contraction of the bladder muscles isolated from pseudo-operation (Sham) and BOO model rats.
Figure 2:
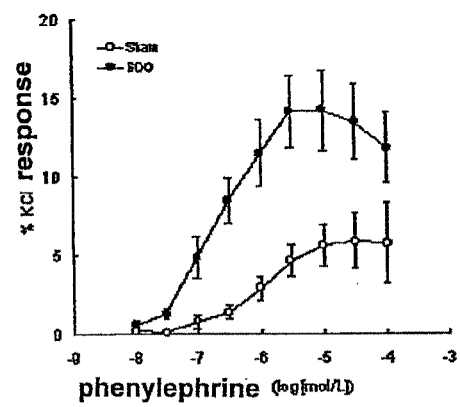

(iii) $\alpha_1$ Receptor Stimulation-Induced Contraction of Isolated Bladder Muscle of BOO Model Rat The isolated bladder muscle specimens were cumulatively treated with phenylephrine. As a result, a contractile response accompanying remarkably high, sustained and rhythmic fluctuation was observed in a concentration-dependent manner in BOO model rats as compared to sham surgery rats (see FIGS. 1 and 2).

Experimental Example 3

Effect of SNAP-8719 on $\alpha_1$ Receptor Stimulation-Induced Contraction of Isolated Bladder Muscle of Bladder Outlet Obstruction (BOO) Model Rat (i) Seven-week-old male Wistar rats (CLEA Japan, Inc., Tokyo) were used. BOO rat was prepared according to publications (Hashimoto T, Nagabukuro H and Doi T: Effects of the selective acetylcholinesterase inhibitor TAK-802 on the voiding behavior and bladder mass increase in rats with partial bladder outlet obstruction. J Urol. 174: 1137-41., 2005.). After pentobarbital (50 mg/kg i.p., Dainippon Sumitomo Pharma Co., Ltd., Osaka) anesthesia, a lower middle abdominal incision was made to expose the bladder. The prostate was detached, the urethra was ligated along with a glass rod having an outer diameter of 1.2 mm, and the glass rod was removed to prepare partial obstruction of the urethra. After the surgery, the abdomen was sutured, and penicillin (2000 IU/rat, penicillin G potassium, MEIJI SEIKA KAISHA, LTD., Tokyo) was subcutaneously administered. An animal after 2 to 4 weeks from obstruction surgery was used.

(ii) Contractile Responses of Isolated Bladder Muscle
(1) Preparation of Bladder Muscle Specimen BOO model rat was sacrificed by decaptation, and the bladder was isolated. Muscle strips (length 7-10 mm in the longitudinal direction, width about 3 mm) were prepared from the bladder except bladder trigone (4-6 specimen from each bladder).

(2) Measurement of Tension

The prepared bladder muscle specimens were hung in a Magnus bath aerated with 95% $O_2$-5% $CO_2$ gas and filled with modified Krebs solution. The contraction tension was measured by an isometric strain transducer (TSD125C, Biopac systems, Santa Barbara, Calif., USA) and recorded in the hard disc of PC (ThinkCentre, IBM, USA) via an amplifier (DA100C, Biopac systems) and a multichannel data analysis apparatus (MP100A-CE, Biopac systems). For uptaking the data, a dedicated software (Acqknowledge 3.8.1., Biopac systems) was used and the sampling interval was set to 0.2 second (5 Hz). The specimens were hung with a load of about 1 g and, after an equilibration time of 1 hr or longer, the following experiment was performed.

The specimens were treated with phenylephrine (3 μmol/L) to induce contraction. After the contractile response was stabilized (>20 min), the specimens were treated with the vehicle 0-4 times at 30 min intervals, and then treated with SNAP-8719 (1 μmol/L), and the tension was observed for 30 minutes.

(3) Data Analysis

The standard deviation was measured for 5 minutes immediately before phenylephrine treatment and for 5 minutes after the contraction was stabilized after treatment (immediately before completion of the about 20 min observation time) and the difference was taken as 100%. The standard deviation was measured for 5 minutes immediately before completion of observation time (30 min) after the SNAP-8719 treatment, and the inhibition rate was calculated. In the vehicle treatment group, the variation rate of phenylephrine-induced contraction was calculated every time the specimens were repeatedly treated with the vehicle, and the inhibition rate of SNAP-8719 was adjusted based on the variation rate of the corresponding vehicle treatment group.

(iii) Action of SNAP-8719 on $\alpha_1$ Receptor Stimulation-Induced Contraction of Isolated Bladder Muscle of BOO Model Rat After the phenylephrine-induced contraction was stabilized, the specimens were treated with the vehicle 0-4 times at 30 min intervals, treated with SNAP-8719 (1 μmol/L), and the variation in the contraction tension in 30 min was observed. As a result, the inhibition rates of SNAP-8719 were 51.2±12.4, 47.4±9.1, 66.6±8.7, 36.3±9.4 and 8.7±32.3% (vehicle adjusted value after treatment with vehicle 0-4 times, average value ± standard error, factor number N=5–8). This suggests that the 4th and 5th treatments in cumulative treatment with a drug may not allow accurate evaluation of the inhibitory effect. Therefore, the evaluation by cumulative treatment with a drug was performed for up to 3 concentrations at 30 min intervals.

Experimental Example 4

Effect of Various Drugs on $\alpha_1$ Receptor Stimulation-Induced Contraction of Isolated Bladder Muscle of Bladder Outlet Obstruction (BOO) Model Rat (i) Seven-week-old male Wistar rats (CLEA Japan, Inc., Tokyo) were used. BOO rat was prepared according to publications (Hashimoto T, Nagabukuro H and Doi T: Effects of the selective acetylcholinesterase inhibitor TAK-802 on the voiding behavior and bladder mass increase in rats with partial bladder outlet obstruction. J Urol. 174: 1137-41., 2005.). After pentobarbital (50 mg/kg i.p., Dainippon Sumitomo Pharma Co., Ltd., Osaka) anesthesia, a lower middle abdominal incision was made to expose the bladder. The prostate was detached, the urethra was ligated along with a glass rod having an outer diameter of 1.2 mm, and the glass rod was removed to prepare partial obstruction of the urethra. After the surgery, the abdomen was sutured, and penicillin (2000 IU/rat, penicillin G potassium, MEIJI SEIKA KAISHA, LTD., Tokyo) was subcutaneously administered. An animal after 2 to 4 weeks from obstruction surgery was used.

(ii) Contractile Responses of Isolated Bladder Muscle
(1) Preparation of Bladder Muscle Specimen BOO model rat was sacrificed by decaptation, and the bladder was isolated. Muscle strips (length 7-10 mm, width about 3 mm) in the longitudinal direction were prepared from the bladder except bladder trigone (4-6 specimen from each bladder).

(2) Measurement of Tension

The prepared bladder muscle specimens were hung in a Magnus bath aerated with 95% $O_2$-5% $CO_2$ gas and filled with modified Krebs solution. The contraction tension was measured by an isometric strain transducer (TSD125C, Biopac systems, Santa Barbara, Calif., USA) and recorded in the hard disc of PC (ThinkCentre, IBM, USA) via an amplifier (DA100C, Biopac systems) and a multichannel data analysis apparatus (MP100A-CE, Biopac systems). For uptaking the data, a dedicated software (Acqknowledge 3.8.1., Biopac systems) was used and the sampling interval was set to 0.2 second (5 Hz). The specimens were hung with a load of about 1 g and, after an equilibration time of 1 hr or longer, the following experiment was performed.

The specimens were treated with phenylephrine (3 μmol/L) to induce contraction. After the contractile response was stabilized (>20 min), the specimens were cumulatively treated 3 times with a drug at a 10-fold common ratio and 30 min intervals, and the variation in the tension was observed.

(3) Data Analysis

The variation in the tension due to $\alpha_1$ receptor stimulation was evaluated by the two methods shown below [average method and standard deviation (Stddev) method].

(3-1) Average Method

The average tension for one minute was measured immediately before phenylephrine treatment and after the contraction was stabilized after the treatment (immediately before completion of about 20 min observation time), and the difference was taken as 100%. The average tension for one minute was measured immediately before completion of observation time (30 min) after treatment with a drug at each concentration, and the inhibition rate of the drug at each concentration was calculated. In the vehicle treatment group, the variation rate of phenylephrine-induced contraction was calculated every time the specimens were treated 3 times with lo the solvent, and the inhibition rate of the drug at each concentration was adjusted based on the variation rate of the corresponding vehicle treatment group. The concentration ($IC_{50}$) necessary for inhibiting the average tension by 50% by preclinical package (SAS Institute Japan, Ver. 5.0) was calculated based on the inhibition rate at each concentration.

(3-2) Stddev Method

The standard deviation was measured immediately before phenylephrine treatment and for 5 min after the contraction was stabilized after treatment (immediately before completion of the about 20 min observation time) and the difference was taken as 100%. The standard deviation was measured for 5 min immediately before completion of observation time (30 min) after the treatment with the drug at each concentration, and the inhibition rate of the drug at each concentration was calculated. In the vehicle treatment group, the variation rate of phenylephrine-induced contraction was calculated every time the specimens were treated 3 times with the vehicle, and the inhibition rate of the drug at each concentration was adjusted based on the variation rate of the corresponding vehicle treatment group. The concentration ($IC_{30}$ value) necessary for inhibiting the contractile responses accompanying sustained and rhythmic fluctuation by 30% by preclinical package (SAS Institute Japan, Ver. 5.0) was calculated based on the inhibition rate at each concentration.

Figure 3:
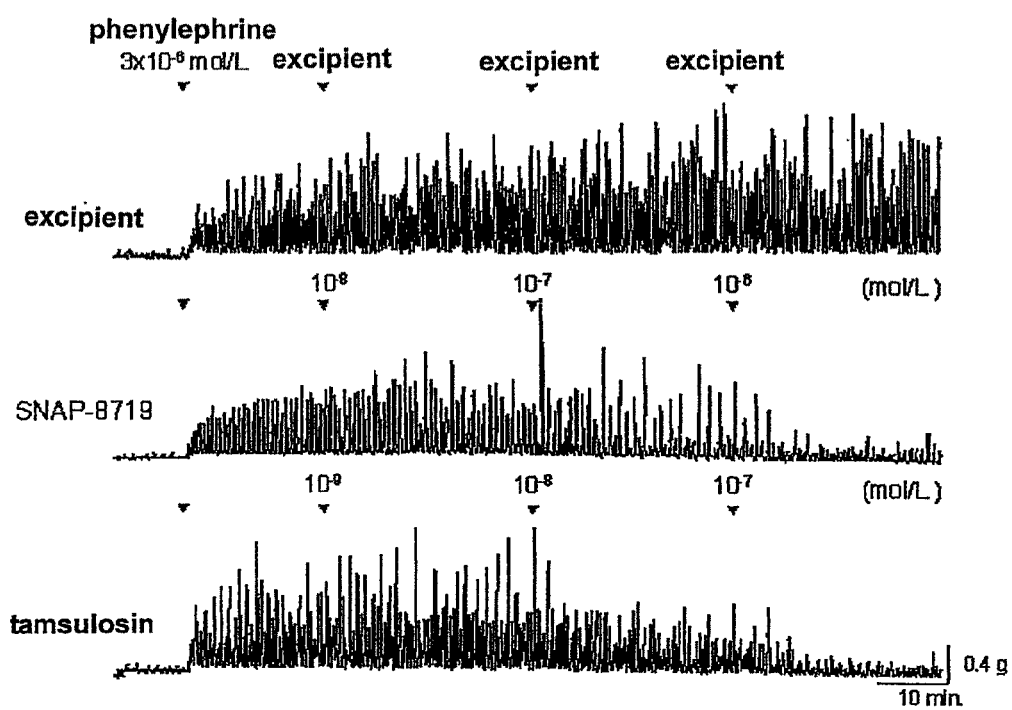
FIG. 3 is a drawing showing effects of various drugs on the $\alpha_1$ receptor stimulation-induced contraction of the bladder muscle isolated from BOO model rat.

(iii) Inhibition of Known Compound having $\alpha_{1D}$ Receptor Antagonistic Action on Phenylephrine-Induced Contraction The effect of known compounds having various $\alpha_{1D}$ receptor antagonistic actions on the rhythmic contractile response induced by the addition of phenylephrine (3 μmol/L) was evaluated by the average method and Stddev method. As a result, tamsulosin and naftopidil used as therapeutic drugs for BPH both inhibited the phenylephrine-induced contractile responses. SNAP-8719 and BMY7378, which are selective $\alpha_{1D}$ receptor antagonists, both inhibited the phenylephrine-induced contractile responses (FIG. 3 and Table 5). From the following achievements, the phenylephrine-induced contraction inhibitory effect was considered to have occurred via an $\alpha_{1D}$ receptor.

TABLE 5

Effect of various drugs on $\alpha_1$ receptor stimulation-induced contraction of isolated bladder muscle of BOO model rat

| Compounds | Inhibitory effect on phenylephrine-induced contraction | |
|---|---|---|
| | $IC_{30}$ (stddev method)) nmol/L | $IC_{50}$ (average method) nmol/L |
| Tamsulosin | 9.4 | 34 |
| Naftopidil | 3800 | 1500 |
| SNAP-8719 | 180 | 360 |
| BMY 7378 | 89 | 270 |

As for $\alpha_{1D}$ receptor antagonistic actions such as tamsulosin[1], naftopidil[1], SNAP-8719[2] and BMY 7378[3], see the following references.

1) Takei, R., Ikegaki, I., Shibata, K. et al.: Naftopidil, a novel alpha1-adrenoceptor antagonist, displays selective inhibition of canine prostatic pressure and high affinity binding to cloned human alpha1-adrenoceptors. Jpn. J. Pharmacol., 79: 447, 1999
2) Konkel, M. J., Wetzel, J. M., Cahir, M. et al.: Synthesis and structure-activity relationship of fluoro analogues of 8-{2-[4-(4-methoxyphenyl)piperazin-1-yl]ethyl}-8-azaspiro[4.5]decane-7,9-dione as selective alpha(1d)-adrenergic receptor antagonists. J. Med. Chem., 48: 3076, 2005
3) Leonardi, A., Barlocco, D., Montesano, F. et al.: Synthesis, screening, and molecular modeling of new potent and selective antagonists at the alpha 1d adrenergic receptor. J. Med. Chem., 47: 1900, 2004

Formulation Example 1

| (1) compound of Example 1 | 10 mg |
|---|---|
| (2) lactose | 60 mg |
| (3) cornstarch | 35 mg |
| (4) hydroxypropylmethylcellulose | 3 mg |
| (5) magnesium stearate | 2 mg |

A mixture of the compound (10 mg) obtained in Example 1, lactose (60 mg) and cornstarch (35 mg) is granulated using 10 wt % aqueous hydroxypropylmethylcellulose solution (0.03 mL, 3 mg as hydroxypropylmethylcellulose), dried at 40° C. and passed through a sieve. The obtained granules are mixed with magnesium stearate (2 mg), and the mixture is compressed. The obtained core tablet is coated with a sugar coating of a suspension of saccharose, titanium dioxide, talc and gum arabic in water. The coated tablet is polished with beeswax to give a coated tablet.

Formulation Example 2

| (1) compound of Example 1 | 10 mg |
|---|---|
| (2) lactose | 70 mg |
| (3) cornstarch | 50 mg |
| (4) soluble starch | 7 mg |
| (5) magnesium stearate | 3 mg |

The compound (10 mg) obtained in Example 1 and magnesium stearate (3 mg) are granulated with an aqueous soluble starch solution (0.07 mL, 7 mg as soluble starch), dried, and mixed with lactose (70 mg) and cornstarch (50 mg). The mixture is compressed to give a tablet.

INDUSTRIAL APPLICABILITY

The compound (I) of the present invention has a superior selective $\alpha_{1D}$ receptor antagonistic action, and is useful as an agent for the prophylaxis or treatment of a lower urinary tract disease and the like. According to the screening method of the present invention, moreover, screening for an agent for the prophylaxis or treatment of a lower urinary tract disease, which antagonizes $\alpha_{1D}$ adrenergic receptor, can be performed rapidly and conveniently.

This application is based on a patent application No. 2006-287957 filed in Japan, the contents of which are incorporated in full herein by this reference.

The invention claimed is:

1. A compound represented by the formula

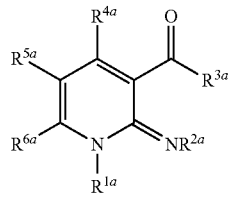

wherein
$R^{1a}$ is a benzyl group optionally having 1 to 3 substituents selected from (i) a halogen atom, (ii) a $C_{1-6}$ alkoxy group optionally substituted by halogen atom(s), (iii) a $C_{1-6}$ alkyl group optionally substituted by halogen atom(s), (iv) an aminosulfonyl group, (v) a di-N,N-$C_{1-6}$ alkylaminosulfonyl group, (vi) a sulfonyl group optionally substituted by a $C_{1-3}$ alkyl group, (vii) a cyano group and (viii) an acyl group optionally substituted by substituent(s) selected from an amino group, a hydroxyl group and a $C_{1-3}$ alkyl group;

$R^{2a}$ is a hydrogen atom;

$R^{3a}$ is an amino group;

$R^{4a}$ is a hydrogen atom;

$R^{5a}$ is a halogen atom, a hydrogen atom, a methyl group, a cyano group or a methoxy group; and $R^{6a}$ is a hydrogen atom, excluding 5-chloro-1,2-dihydro-2-imino-1-phenylmethyl-3-pyridinecarboxamide, 5-bromo-1,2-dihydro-2-imino-1-phenylmethyl-3-pyridinecarboxamide, or a salt thereof.

2. A compound represented by the formula

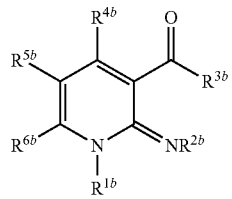

wherein
$R^{1b}$ is $C_{1-6}$ alkyl;

$R^{2b}$ is a hydrogen atom, a hydrocarbon group optionally having substituent(s), an acyl group or a heterocyclic group optionally having substituent(s);

$R^{3b}$ is a hydrocarbon group optionally having substituent(s), a heterocyclic group optionally having substituent(s), an amino group optionally having substituent(s) or a thiol group optionally having a substituent;

$R^{4b}$ is a hydrogen atom, a halogen atom, a cyano group, an acyl group, a heterocyclic group optionally having substituent(s), an amino group optionally having substituent(s), a hydroxyl group optionally having a substituent or a thiol group optionally having a substituent;

$R^{5b}$ is a hydrogen atom, a halogen atom, a cyano group, a hydrocarbon group optionally having substituent(s), an acyl group, an amino group optionally having substituent(s), a hydroxyl group optionally having a substituent or a thiol group optionally having a substituent; and $R^{6b}$ is a hydrogen atom excluding 5-bromo-1,2-dihydro-2-imino-1-butyl-3-pyridinecarboxamid, 5-chloro-1,2-dihydro-2-imino-1-butyl-3-pyridinecarboxamide, 5-bromo-1,2-dihydro-2-imino-1-methyl-3-pyridinecarboxamide, and 5-chloro-1,2-dihydro-2-imino-1-methyl-3-pyridinecarboxamide, or a salt thereof.

3. A compound represented by the formula

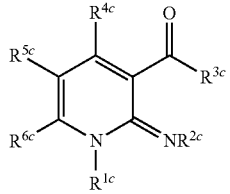

wherein
$R^{1c}$ is a phenyl group having 1 to 3 substituents selected from (i) a halogen atom, (ii) a $C_{1-6}$ alkoxy group optionally substituted by halogen atoms (s), (iii) a $C_{1-6}$ alkyl group substituted by halogen atom(s), (iv) a $C_{3-8}$ cycloalkyl group, (v) a $C_{6-14}$ aryl group, and (vi) a $C_{6-14}$ aryloxy group;

$R^{2c}$ is a hydrogen atom;
$R^{3c}$ is an group;
$R^{4c}$ is a hydrogen atom;
$R^{5c}$ is a halogen atom; and
$R^{6c}$ is a hydrogen atom, or a salt thereof.

4. A compound represented by the formula

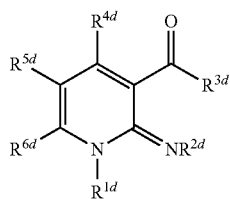

wherein
$R^{1d}$ is
(1) a 5- to 8-membered aromatic heterocyclic group containing, besides carbon atom, 1 to 4 hetero atoms selected from a nitrogen atom, a sulfur atom and an oxygen atom, which optionally has 1 to 3 substituents selected from a halogen atom and a $C_{6-14}$ aryl group, and is optionally condensed with a benzene ring,
(2) a $C_{3-8}$ cycloalkyl group optionally condensed with a benzene ring,
(3) the formula $-CR^{1da'}R^{1db'}R^{1dc'}$ wherein $R^{1da'}$ is a hydrogen atom; $R^{1db'}$ is a alkyl $C_{1-3}$ alkyl group; $R^{1dc'}$ is an aryl group optionally having 1 to 3 substituents selected from (i) a halogen atom, (ii) a $C_{1-6}$ alkoxy group optionally substituted by halogen atom(s), (iii) a $C_{1-6}$ alkyl group optionally substituted by halogen atom(s), (iv) an aminosulfonyl group, (v) a di-N,N-$C_{1-6}$ alkylaminosulfonyl group, (vi) a sulfonylroup optionally substituted by a $C_{1-3}$ alkyl group, (vii) a cyano group, and (viii) an acyl group,
(4) the formula $-CH_2R^{1dd'}$ wherein $R^{1dd'}$ is (1) a cycloalkyl group optionally substituted by, hydroxyl group(s), or (2) a naphthyl group optionally having 1 to 3 substituents selected from (i) a halogen atom, (ii) a $C_{1-6}$ alkoxy group optionally substituted by halogen atom(s), (iii) a $C_{1-6}$ alkyl group optionally substituted by halogen atom(s), (iv) an aminosulfonyl group, (v) a di-N,N- $C_{1-6}$ alkylaminosulfonyl group, (vi) a sulfonyl group optionally having a $C_{1-3}$ alkyl group, (vii) a cyano group, and (viii) an acyl group,
(5) the formula $-(CH_2)_n-R^{1dc'}$ wherein n is an integer of 2 to 5, $R^{1dc'}$ is
1) a cycloalkyl group optionally substituted by hydroxyl group(s),
2) a cycloalkenyl group optionally substituted by hydroxyl group(s),
3) an aryl group optionally having 1 to 3 substituents selected from (i) a halogen atom, (ii) a $C_{1-6}$ alkoxy group optionally substituted by halogen atom(s), (iii) a $C_{1-6}$ alkyl group optionally substituted by halogen atom(s), (iv) an aminosulfonyl group, (v) a di-N,N-$C_{1-6}$ alkylaminosulfonyl group, (vi) a sulfonyl group optionally substituted by a $C_{1-3}$ alkyl group, (vii) a cyano group, and (viii) an acyl group,
4) an aryloxy group optionally having 1 to 3 substituents selected from (i) a halogen atom, (ii) a $C_{1-6}$ alkoxy group optionally substituted by halogen atom(s), (iii) a $C_{1-6}$ alkyl group optionally substituted by halogen atom(s), (iv) an aminosulfonyl group, (v) a di-N,N-$C_{1-6}$ alkylaminosulfonyl group, (vi) a sulfonyl group optionally substituted by a $C_{1-3}$ alkyl group, (vii) a cyano group, and (viii) an acyl group, or
5) a thiol group optionally substituted by an aryl group optionally having 1 to 3substituents selected from a halogen atom, (ii) a $C_{1-6}$ alkoxy group optionally substituted by halogen atom(s), (iii) a $C_{1-6}$ alkyl group optionally substituted by halogen atom(s), (iv) an aminosulfonyl group, (v) a di-N,N-$C_{1-6}$ alkylaminosulfonyl group, (vi) a sulfonyl group optionally substituted by a $C_{1-3}$ alkyl group, (vii) a cyano group, and (viii) an acyl group, and $(CH_2)_n$ optionally has a $C_{1-3}$ alkyl group),
(6) an indenyl group optionally having substituent(s) selected from a halogen atom, a cyano group, a methylsulfonyl group and an acyl group,
(7) a naphthyl group optionally having substituent(s) selected from a halogen atom, a cyano group, a methylsulfonyl group and an acyl group, or
(8) a fluorenyl group optionally having substituent(s) selected from a halogen atom, a cyano group, a methylsulfonyl group and an acyl group;

$R^{2d}$ is a hydrogen atom;
$R^{3d}$ is an amino group;
$R^{4d}$ is a hydrogen atom;
$R^{5d}$ is a halogen atom, a hydrogen atom, a methyl group, a cyano group or a methoxy group; and
$R^{6d}$ is a hydrogen atom, or a salt thereof.

5. A compound selected from the group consisting of 5-chloro-1-(3-chlorobenzyl)-2-imino-1,2-dihydropyridine-3-carboxamide, 5-chloro-1-(3,4-dichlorobenzyl)-2-imino-1,2-dihydropyridine-3-carboxamide, 5-chloro-1-[(5-chloro-2-thienyl)methyl]1-2-imino-1,2-dihydropyridine-3-carboxamide, 5-chloro-2-imino-1-(1-naphthyl)-1,2-dihydropyridine-3-carboxamide, 5-chloro-1-[(1R)-2,3-dihydro-1H-inden-1-yl]-2-imino-1,2-dihydropyridine-3-carboxamide, 5-chloro-2-imino-1- [(1R)- 1-phenylethyl]-1,2-dihydropyridine-3-carboxamide, 1- (3-chlorobenzyl)-5-cyano-2-imino-1,2-dihydropyridine-3-carboxamide, 5-chloro-1- (3-chloro-5-cyanobenzyl)-2-imino-1,2-dihydropyridine-3-carboxamide, 5-chloro-1- (5-cyano-2-fluorobenzyl)-2-imino-1,2-dihydropyridine-3-carboxamide, 5-chloro-1-(3-cyano-5-fluorobenzyl)-2-imino-1,2-dihydropyridine-3-carboxamide, 5-chloro-2-imino-1-(2,4,5-trifluorobenzyl)-1,2-dihydropyridine-3-carboxamide, 5-chloro-2-imino-1-[3-(methylsulfonyl)benzyl]-1,2-dihydropyridine-3-carboxamide and 5-chloro-1-(3-cyanobenzyl)-2-imino-1,2-dihydropyridine-3-carboxamide, or a salt thereof.

6. A pharmaceutical agent comprising a compound of any of claims 1,2,3,4, and 5 or a salt thereof.

7. A method of preventing or treating a lower urinary tract disease, comprising administering an effective amount of a compound represented by the formula

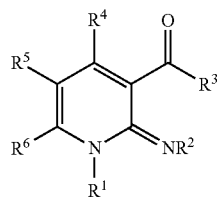

wherein
R¹ is a hydrogen atom, a hydrocarbon group optionally having substituent(s), an acyl group or a heterocyclic group optionally having substituent(s);
R² is a hydrogen atom, a hydrocarbon group optionally having substituent(s), an acyl group or a heterocyclic group optionally having substituent(s);
R³ is a hydrogen atom, a hydrocarbon group optionally having substituent(s), a heterocyclic group optionally having substituent(s), an amino group optionally having substituent(s), a hydroxyl group optionally having a substituent or a thiol group optionally having a substituent;
R⁴ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent;
R⁵ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent; and
R⁶ is a hydrogen atom, a halogen atom, a cyano group, a hydrocarbon group optionally having substituent(s), an acyl group or a heterocyclic group optionally having substituent(s), or a salt thereof, to a mammal.

8. A screening method for an agent having an $\alpha_{1D}$ adrenergic receptor antagonistic action for the prophylaxis or treatment of a lower urinary tract disease, which comprises measuring the tension of the bladder smooth muscle of a bladder outlet obstruction rat, wherein the agent comprises a compound represented by the formula

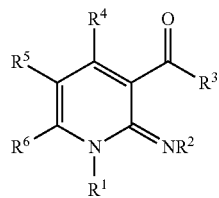

wherein
R¹ is a hydrogen atom, a hydrocarbon group optionally having substituent(s), an acyl group or a heterocyclic group optionally having substituent(s);
R² is a hydrogen atom, a hydrocarbon group optionally having substituent(s), an acyl group or a heterocyclic group optionally having substituent(s);
R³ is a hydrogen atom, a hydrocarbon group optionally having substituent(s), a heterocyclic group optionally having substituent(s), an amino group optionally having substituent(s), a hydroxyl group optionally having a substituent or a thiol group optionally having a substituent;
R⁴ is a hydrogen atom, a halogen atom, a cyano group, a hydrocarbon group optionally having substituent(s), an acyl group, a heterocyclic group optionally having substituent(s), an amino group optionally having substituent(s), hydroxyl group optionally having a substituent or a thiol group optionally having a substituent;
R⁵ is a hydrogen atom, a halogen atom, a cyano group, a hydrocarbon group optionally having substituent(s), an acyl group, a heterocyclic group optionally having substituent(s), an amino group optionally having substituent(s), a hydroxyl group optionally having a substituent or a thiol group optionally having a substituent; and
R⁶ is a hydrogen atom, a halogen atom, a cyano group, a hydrocarbon group optionally having substituent(s), an acyl group or a heterocyclic group optionally having substituent(s), or a salt thereof.

9. The screening method of claim 8, comprising adding a drug having an $\alpha_1$ adrenergic receptor agonistic activity to induce or enhance rhythmic contractile responses of the bladder smooth muscle of the bladder outlet obstruction rat, administering, at predetermined time intervals, an agent having an $\alpha_{1D}$ adrenergic receptor antagonistic action for the prophylaxis or treatment of a lower urinary tract disease, measuring changes in the contraction tension in a given predetermined time for each administration, and evaluating an inhibitory effect of the agent on the rhythmic contractile responses in the bladder smooth muscle based on the inconsistency in the level of changes in the obtained contraction tension.

10. The screening method of claim 9, comprising defining the time from the addition of the drug having an $\alpha_1$ adrenergic receptor agonistic activity to the start of the measurement of the changes in the contraction tension, or limiting the administration frequency of the agent having an $\alpha_{1D}$ adrenergic receptor antagonistic action for the prophylaxis or treatment of a lower urinary tract disease, so as to remove a contraction component irrelevant to the $\alpha_{1D}$ adrenergic receptor, which increases with the lapse of time after the addition of the drug.

* * * * *

UNITED STATES PATENT AND TRADEMARK OFFICE
CERTIFICATE OF CORRECTION

| | | |
|---|---|---|
| PATENT NO. | : 8,470,859 B2 | Page 1 of 1 |
| APPLICATION NO. | : 12/446960 | |
| DATED | : June 25, 2013 | |
| INVENTOR(S) | : Masato Yoshida et al. | |

It is certified that error appears in the above-identified patent and that said Letters Patent is hereby corrected as shown below:

In the Claims

Claim 2, Column 160, Lines 40-41: delete "5-bromo-1,2-dihydro-2-imino-1-butyl-3-pyridinecarboxamid," and insert -- 5-bromo-1,2-dihydro-2-imino-1-butyl-3-pyridinecarboxamide --

Claim 3, Column 161, Line 2: delete "$R^{3c}$ is an group;" and insert -- $R^{3c}$ is an amino group; --

Claim 4, Column 161, Line 29: delete "$R^{1db'}$ is a alkyl $C_{1-3}$ alkyl group;" and insert -- $R^{1db'}$ is a $C_{1-3}$ alkyl group; --

Claim 4, Column 161, Line 39: delete "optionally substituted by, hydroxyl group(s), or" and insert -- optionally substituted by hydroxyl group(s), or --

Claim 4, Column 162, Line 4: delete "optionally having 1 to 3substituents selected from a" and insert -- optionally having 1 to 3 substituents selected from (i) a --

Claim 5, Column 162, Lines 37-38: delete "5-chloro-1-[(5-chloro-2-thienyl)methyl]1-2-imino-1,2-di-hydropyridine-3-carboxamide," and insert -- 5-chloro-1-[(5-chloro-2-thienyl)methyl]-2-imino-1,2-dihydropyridine-3-carboxamide --

Claim 5, Column 162, Lines 44-45: delete "5-chloro-2-imino-1-[(1R)- 1-phenylethyl]-1,2-dihydropyridine-3-carboxamide" and insert -- 5-chloro-2-imino-1-[(1R)-1-phenylethyl]-1,2-dihydropyridine-3-carboxamide --

Claim 5, Column 162, Lines 46-47: delete "1- (3-chlorobenzyl)-5-cyano-2-imino-1,2-dihydropyripyridine-3-carboxamide" and insert -- 1-(3-chlorobenzyl)-5-cyano-2-imino-1,2-dihydropyripyridine-3-carboxamide --

Claim 5, Column 162, Lines 48-49: delete "5-chloro-1- (3-chloro-5-cyanobenzyl)-2-imino-1,2-dihydro-3-pyridinecarboxamide" and insert -- 5-chloro-1-(3-chloro-5-cyanobenzyl)-2-imino-1,2-dihydropyridine-3-carboxamide --

Claim 5, Column 162, Lines 50-51: delete "5-chloro-1- (5-cyano-2-fluorobenzyl)-2-imino-1,2-di hydropyridine-3-carboxamide" and insert -- 5-chloro-1-(5-cyano-2-fluorobenzyl)-2-imino-1,2-dihydropyridine-3-carboxamide --

Claim 8, Column 164, Lines 18-19: delete "an amino group optionally having substituent(s), hydroxyl group optionally having a substituent or" and insert -- an amino group optionally having substituent(s), a hydroxyl group optionally having a substituent or --

Signed and Sealed this
Eighth Day of April, 2014

Michelle K. Lee
*Deputy Director of the United States Patent and Trademark Office*